(12) United States Patent
Shimizu et al.

(10) Patent No.: US 9,883,675 B2
(45) Date of Patent: *Feb. 6, 2018

(54) METHOD FOR CONTROLLING PESTS

(71) Applicant: SUMITOMO CHEMICAL COMPANY, LIMITED, Tokyo (JP)

(72) Inventors: Chie Shimizu, Tokyo (JP); Masashi Kamezaki, Takarazuka (JP); Yoshihiko Nokura, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/764,380

(22) PCT Filed: Jan. 30, 2014

(86) PCT No.: PCT/JP2014/052151
§ 371 (c)(1),
(2) Date: Jul. 29, 2015

(87) PCT Pub. No.: WO2014/119679
PCT Pub. Date: Aug. 7, 2014

(65) Prior Publication Data
US 2015/0366208 A1    Dec. 24, 2015

(30) Foreign Application Priority Data
Jan. 31, 2013  (JP) .................. 2013-016548

(51) Int. Cl.
| A01N 43/78 | (2006.01) |
| A01N 43/90 | (2006.01) |
| A01N 47/02 | (2006.01) |
| A01N 25/00 | (2006.01) |
| A01N 43/52 | (2006.01) |
| A01N 43/76 | (2006.01) |
| C07D 235/18 | (2006.01) |
| C07D 263/57 | (2006.01) |
| C07D 277/66 | (2006.01) |

(52) U.S. Cl.
CPC ............ *A01N 47/02* (2013.01); *A01N 25/00* (2013.01); *A01N 43/52* (2013.01); *A01N 43/76* (2013.01); *A01N 43/78* (2013.01); *A01N 43/90* (2013.01); *C07D 235/18* (2013.01); *C07D 263/57* (2013.01); *C07D 277/66* (2013.01)

(58) Field of Classification Search
None
See application file for complete search history.

(56) References Cited

U.S. PATENT DOCUMENTS

| 2011/0039843 A1 | 2/2011 | Iwakoshi et al. |
| 2012/0015975 A1 | 1/2012 | Takahashi et al. |
| 2012/0196891 A1 | 8/2012 | Iwakoshi |
| 2013/0090353 A1 | 4/2013 | Iwakoshi et al. |
| 2015/0148308 A1 | 5/2015 | Suzuki et al. |
| 2015/0166573 A1 | 6/2015 | Takahashi et al. |
| 2015/0181880 A1 | 7/2015 | Takahashi et al. |

FOREIGN PATENT DOCUMENTS

| CN | 102006776 A | 4/2011 |
| CN | 102414195 A | 4/2012 |
| CN | 102686585 A | 9/2012 |
| EP | 2274983 A1 | 1/2011 |
| EP | 2952099 A1 | 12/2015 |
| EP | 2952100 A1 | 12/2015 |
| EP | 2962565 A1 | 1/2016 |
| JP | 2004-34438 A | 2/2004 |
| JP | 2009-280574 A | 12/2009 |
| JP | 2010-275301 A | 12/2010 |
| JP | 2011-79774 A | 4/2011 |
| WO | WO 2010/125985 A1 | 11/2010 |
| WO | WO 2011/043404 A1 | 4/2011 |
| WO | WO 2012/074135 A1 | 6/2012 |
| WO | WO 2012/086848 A1 | 6/2012 |
| WO | WO 2013/018928 A1 | 2/2013 |
| WO | WO 2013/180194 A1 | 12/2013 |
| WO | WO 2013/187422 A1 | 12/2013 |
| WO | WO 2013/187424 A1 | 12/2013 |
| WO | WO 2013/187425 A1 | 12/2013 |

(Continued)

OTHER PUBLICATIONS

Extended European Search Report dated Jun. 15, 2016, for European Application No. 14745744.4.
Second Chinese Office Action and Search Report dated Jan. 16, 2017, for Chinese Application No. 201480018833.9, including an English translation.
Australian Office Action, dated Feb. 28, 2017, for Australian Application No. 2014213394.

(Continued)

*Primary Examiner* — Alton Pryor
(74) *Attorney, Agent, or Firm* — Birch, Stewart, Kolasch & Birch, LLP

(57) ABSTRACT

The present invention provides a method for controlling pests which comprises applying a compound of formula (1):

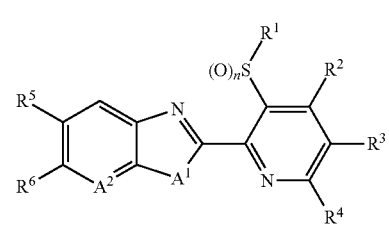

(1)

wherein each of symbols are the same as defined in the Description, or N-oxide thereof to plant seeds,
which has an excellent controlling efficacy on pests.

27 Claims, No Drawings

(56) References Cited

FOREIGN PATENT DOCUMENTS

| WO | WO 2013/187426 A1 | 12/2013 |
|---|---|---|
| WO | WO 2013/191113 A1 | 12/2013 |
| WO | WO 2014/104407 A1 | 7/2014 |
| WO | WO 2014/125651 A1 | 8/2014 |

OTHER PUBLICATIONS

Hisano et al., "Synthesis of Benzoxazoles, Benzothiazoles and Benzimidazoles and Evaluation of Their Antifungal, Insecticidal and Herbicidal Activities," Chemical and Pharmaceutical Bulletin, vol. 30, No. 8, 1982, pp. 2996-3004.
International Preliminary Report on Patentability and Written Opinion of the International Searching Authority (Forms PCT/IB/373 and PCT/ISA/237) for International Application No. PCT/JP2014/052151, dated Aug. 4, 2015.
International Search Report (Form PCT/ISA/210) for International Application No. PCT/JP2014/052151, dated Apr. 8, 2014.
First Office Action and Search Report (including an English translation thereof) issued in the corresponding Chinese Patent Application No. 201480018833.9 dated May 16, 2016.
Reason for Refusal (including an English translation thereof) issued in the corresponding Japanese Patent Application No. 2014-559750 dated Jul. 11, 2017.
Chinese Rejection Decision (including an English translation thereof) issued in the corresponding Chinese Patent Application No. 201480018833.9 dated Sep. 8, 2017.

METHOD FOR CONTROLLING PESTS

TECHNICAL FIELD

This application claims priority to and the benefit of Japanese Patent Application No. 2013-016548, filed Jan. 31, 2013, the entire contents of which is incorporated herein by reference.

The present invention relates to a method for controlling pests.

BACKGROUND ART

Hitherto, many compounds have been known as active ingredients in a method for controlling pests (for example, see Non-Patent Literature-1).

RELATED ART DOCUMENTS

Non-Patent Documents

[Non-Patent Literature-1]: The Pesticide Manual-15th edition, published by British Crop Protection Council (BCPC), ISBN 978-1-901396-18-8

SUMMARY OF INVENTION

Problems to be Solved by Invention

An object of the present invention is to provide a method for controlling pests having an excellent control efficacy on pests.

Means to Solve Problems

The present inventors have intensively studied to find out a method for controlling pests having an excellent control efficacy on pests. As a result, they have found that an application of a compound represented by the following the formula (1) to plant seeds can control pests.

Specifically, the present invention includes:
Item 1.

A method for controlling pests which comprises applying a compound represented by formula (1) or N-oxide thereof to plant seeds:
the formula (1):

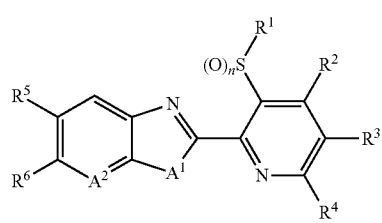

(1)

wherein
$A^1$ represents —$NR^7$—, an oxygen atom, or a sulfur atom;
$A^2$ represents a nitrogen atom or =$CR^8$—;
$R^1$ represents a C1-C6 alkyl group which may be substituted with one or more atoms or groups selected from Group X;
$R^2$, $R^3$ and $R^4$ are the same or different to each other and each independently represent a C1-C6 alkyl group which may be substituted with one or more atoms or groups selected from Group X, a —$OR^{10}$ group, a —$C(OR^{10})_3$ group, a —$S(O)_mR^{10}$ group, a —$S(O)_2NR^{10}R^{11}$ group, a —$NR^{10}R^{11}$ group, a —$NR^{10}CO_2R^{11}$ group, a —$NR^{10}C(O)R^{11}$ group, a —$CO_2R^{10}$ group, a —$C(O)R^{10}$ group, a —$C(O)NR^{10}R^{11}$ group, a —$SF_5$ group, a cyano group, a nitro group, a halogen atom, or a hydrogen atom;
$R^5$ and $R^6$ are the same or different to each other and each independently represent a C1-C6 alkyl group which may be substituted with one or more atoms or groups selected from Group X, a —$OR^{10}$ group, a —$S(O)_mR^{10}$ group, a —$S(O)_2NR^{10}R^{11}$ group, a —$NR^{10}R^{11}$ group, a —$NR^{10}CO_2R^{11}$ group, a —$NR^{10}C(O)R^{11}$ group, a —$CO_2R^{10}$ group, a —$C(O)R^{10}$ group, a —$C(O)NR^{10}R^{11}$ group, —$OC(O)R^{10}$, a —$SF_5$ group, a —SH group, a cyano group, a nitro group, a halogen atom, or a hydrogen atom, except for a case in which $R^5$ and $R^6$ are both hydrogen atoms;
$R^7$ represents a C1-C6 alkyl group which may be substituted with one or more atoms or groups selected from Group W, a —$CO_2R^{10}$ group, a —$C(O)R^{10}$ group, a —$CH_2CO_2R^{10}$ group, a C3-C6 cycloalkyl group, or a hydrogen atom;
$R^8$ represents a C1-C6 alkyl group which may be substituted with one or more halogen atoms, a —$OR^{10}$ group, a —$S(O)_mR^{10}$ group, a —$NR^{10}R^{11}$ group, a —$CO_2R^{10}$ group, a —$C(O)R^{10}$ group, a cyano group, a nitro group, a halogen atom, or a hydrogen atom;
$R^{10}$ and $R^{11}$ are the same or different to each other and each independently represent a C1-C6 alkyl group which may be substituted with one or more atoms or groups selected from Group X or a hydrogen atom, except for a —$S(O)_mR^{10}$ group wherein m is 1 or 2 and $R^{10}$ is a hydrogen atom;
m independently represents 0, 1 or 2; and
n represents 0, 1 or 2;
Group X comprising:
  a C1-C6 alkoxy group which may be substituted with one or more halogen atoms,
  a C3-C6 cycloalkyl group which may be substituted with one or more halogen atoms or one or more C1-C3 alkyl groups,
  a cyano group,
  a hydroxy group, and
  a halogen atom;
Group W comprising:
  a C1-C6 alkoxy group which may be substituted with one or more halogen atoms,
  a C3-C6 cycloalkyl group which may be substituted with one or more halogen atoms,
  a hydroxy group,
  a halogen atom, and
  a cyano group.
Item 2.

The method for controlling pests according to Item 1, in the compound represented by the formula (1) or N-oxide thereof,
$R^1$ is a C1-C6 alkyl group which may be substituted with one or more atoms or groups selected from Group Y;
$R^2$ and $R^4$ are hydrogen atoms;
$R^3$ is a C1-C3 alkyl group which may be substituted with one or more halogen atoms, a —$C(OR^{10})_3$ group, a halogen atom, or a hydrogen atom;
$R^5$ is a C1-C3 alkyl group which may be substituted with one or more halogen atoms, a —$OR^{10}$ group, a —$S(O)_mR^{10}$ group, a —$CO_2R^{10}$ group, a —$SF_5$ group, or a halogen atom;
$R^6$ is a —$OR^{10}$ group, a —$NR^{10}R^{11}$ group, a —$CO_2R^{10}$ group, a —$C(O)NR^{10}R^{11}$ group, —$OC(O)R^{10}$, a cyano group, a halogen atom, or a hydrogen atom;

R$^7$ is a C1-C6 alkyl group which may be substituted with one or more halogen atoms, a —CH$_2$CO$_2$R$^{10}$ group, a C3-C6 cycloalkyl group, or a hydrogen atom, R$^8$ is a C1-C3 alkyl group which may be substituted with one or more halogen atoms, a —OR$^{10}$ group, a —S(O)$_m$R$^{10}$ group, a cyano group, a halogen atom, or a hydrogen atom;

R$^{10}$ and R$^{11}$ are the same or different to each other and each independently represent a C1-C3 alkyl group which may be substituted with one or more halogen atoms or a hydrogen atom, except for a —S(O)$_m$R$^{10}$ group wherein m is 1 or 2 and R$^{10}$ is a hydrogen atom; and Group Y comprising:
a C3-C6 cycloalkyl group which may be substituted with one or more halogen atoms and
a halogen atom.

Item 3.

The method for controlling pests according to Item 1, wherein in the compound represented by the formula (1) or N-oxide thereof, R$^1$ is a C1-C3 alkyl group which may be substituted with one or more halogen atoms;

R$^2$ and R$^4$ are hydrogen atoms;

R$^3$ is a C1-C3 alkyl group which may be substituted with one or more halogen atoms, a —C(OR$^{10}$)$_3$ group, a halogen atom, or a hydrogen atom;

R$^5$ is a C1-C3 alkyl group which may be substituted with one or more halogen atoms, a —OR$^{10}$ group, a —S(O)$_m$R$^{10}$ group, or a halogen atom;

R$^6$ is a cyano group, a —NR$^{10}$R$^{11}$ group, a halogen atom, or a hydrogen atom;

R$^7$ is a C1-C6 alkyl group which may be substituted with one or more halogen atoms;

R$^8$ is a —S(O)$_m$R$^{10}$ group, a cyano group, a halogen atom, or a hydrogen atom; and R$^{10}$ and R$^{11}$ are the same or different to each other and each independently represent a C1-C3 alkyl group which may be substituted with one or more halogen atoms.

Item 4.

The method for controlling pests according to Item 1, wherein in the compound represented by the formula (1) or N-oxide thereof:

R$^1$ is an ethyl group;

R$^2$ and R$^4$ are hydrogen atoms;

R$^3$ is a C1-C3 alkyl group which may be substituted with one or more halogen atoms, a —C(OR$^{10}$)$_3$ group, a halogen atom, or a hydrogen atom;

R$^5$ is a C1-C3 haloalkyl group, a —OR$^{20}$ group, a —S(O)$_m$R$^{20}$ group, or a halogen atom;

R$^6$ is a cyano group, a —NR$^{10}$R$^{11}$ group, a halogen atom, or a hydrogen atom;

R$^7$ is a C1-C6 alkyl group which may be substituted with one or more halogen atoms;

R$^8$ is a —S(O)$_m$R$^{10}$ group, a cyano group, a halogen atom, or a hydrogen atom;

R$^{10}$ and R$^{11}$ are the same or different to each other and each independently represent a C1-C3 alkyl group which may be substituted with one or more halogen atoms; and R$^{20}$ is a C1-C3 haloalkyl group.

Item 5.

The method for controlling pests according to any one of Items 1 to 4, wherein in the compound represented by the formula (1) or N-oxide thereof, A$^1$ is —NR$^7$—.

Item 6.

The method for controlling pests according to any one of Items 1 to 4, wherein in the compound represented by the formula (1) or N-oxide thereof, A$^1$ is an oxygen atom.

Item 7.

The method for controlling pests according to any one of Items 1 to 4, wherein in the compound represented by the formula (1) or N-oxide thereof, A$^1$ is a sulfur atom.

Item 8.

The method for controlling pests according to Item 1, wherein the compound represented by the formula (1) or N-oxide thereof is a compound represented by the formula (1-2) or N-oxide thereof;

the formula (1-2):

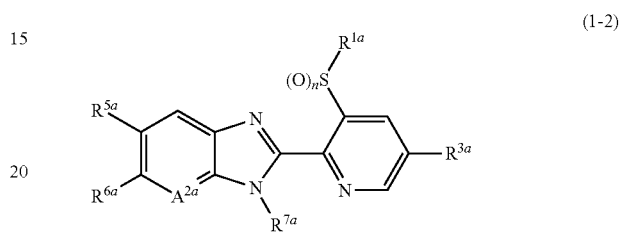

wherein

R$^{1a}$ represents a C1-C3 alkyl group;

A$^{2a}$ represents a nitrogen atom or =CR$^{8a}$—;

R$^{3a}$ represents a C1-C3 alkyl group which may be substituted with one or more halogen atoms, a —C(OR$^{10a}$)$_3$ group, a halogen atom, or a hydrogen atom;

R$^{5a}$ represents a C1-C3 haloalkyl group, a —OR$^{20a}$ group, a —S(O)$_m$R$^{20a}$ group, or a halogen atom;

R$^{6a}$ represents a cyano group, a —NR$^{10a}$R$^{11a}$ group, a halogen atom, or a hydrogen atom;

R$^{7\ a}$ represents a C1-C6 alkyl group which may be substituted with one or more halogen atoms;

R$^{8a}$ represents a —S(O)$_m$R$^{10a}$ group, a cyano group, a halogen atom, or a hydrogen atom;

R$^{10\ a}$ and R$^{11\ a}$ are the same or different to each other and each independently represent a C1-C3 alkyl group which may be substituted with one or more halogen atoms;

R$^{20a}$ represents a C1-C3 haloalkyl group;

m independently represents 0, 1 or 2; and n represents 0, 1 or 2.

Item 9.

The method for controlling pests according to Item 1, wherein the compound represented by the formula (1) or N-oxide thereof is a compound represented by the formula (1-3) or N-oxide thereof;

the formula (1-3):

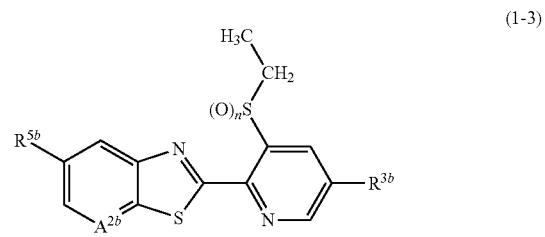

wherein

A$^{2b}$ represents a nitrogen atom or =CR$^{8b}$—;

R$^{3b}$ represents a C1-C3 alkyl group which may be substituted with one or more halogen atoms, a —C(OR$^{10b}$)$_3$ group, a halogen atom, or a hydrogen atom;

$R^{5b}$ represents a C1-C3 haloalkyl group, a —$OR^{20b}$ group, a —$S(O)_mR^{20b}$ group, or a halogen atom;

$R^{8b}$ represents a —$S(O)_mR^{10b}$ group, a cyano group, a halogen atom, or a hydrogen atom;

$R^{10b}$ independently represents a C1-C3 alkyl group which may be substituted with one or more halogen atoms;

$R^{20b}$ represents a C1-C3 haloalkyl group;

m independently represents 0, 1 or 2; and n represents 0, 1 or 2.

Item 10.

The method for controlling pests according to Item 1, wherein in the compound represented by the formula (1-3) or N-oxide thereof, $R^{3b}$ is a halogen atom or a hydrogen atom;

$R^{5b}$ is a C1-C3 perfluoroalkyl group, a —$OR^{30b}$ group, or a —$S(O)_mR^{30b}$ group;

$R^{30b}$ is a C1-C3 perfluoroalkyl group; and $R^{8b}$ is a halogen atom or a hydrogen atom.

Item 11.

The method for controlling pests according to Item 1, wherein the compound represented by the formula (1) or N-oxide thereof is a compound represented by the formula (1-4) or N-oxide thereof;

the formula (1-4):

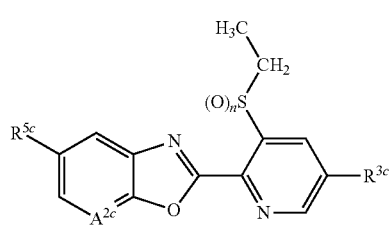

wherein $A^{2c}$ represents a nitrogen atom or =$CR^{8c}$—;

$R^{3c}$ represents a C1-C3 alkyl group which may be substituted with one or more halogen atoms, a —$C(OR^{10c})_3$ group, a halogen atom, or a hydrogen atom;

$R^{5c}$ represents a C1-C3 haloalkyl group, a —$OR^{20c}$ group, a —$S(O)_mR^{20c}$ group, or a halogen atom;

$R^{8c}$ represents a —$S(O)_mR^{10c}$ group, a cyano group, a halogen atom, or a hydrogen atom;

$R^{10c}$ independently represents a C1-C3 alkyl group which may be substituted with one or more halogen atoms;

$R^{20c}$ represents a C1-C3 haloalkyl group;

m independently represents 0, 1 or 2; and n represents 0, 1 or 2.

Item 12.

The method for controlling pests according to Item 11, wherein in the compound represented by the formula (1-4) or N-oxide thereof, $R^{3c}$ is a halogen atom or a hydrogen atom;

$R^{5c}$ is a C1-C3 perfluoroalkyl group, a —$OR^{30c}$ group, or a —$S(O)_mR^{30c}$ group, $R^{30c}$ is a C1-C3 perfluoroalkyl group, and $R^{8c}$ is a halogen atom or a hydrogen atom.

Item 13.

A plant seed containing an effective amount of a compound represented by formula (1) or N-oxide thereof:

the formula (1):

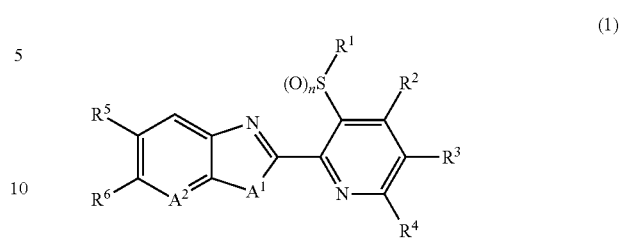

wherein $A^1$ represents —$NR^7$—, an oxygen atom, or a sulfur atom;

$A^2$ represents a nitrogen atom or —$CR^8$—;

$R^1$ represents a C1-C6 alkyl group which may be substituted with one or more atoms or groups selected from Group X;

$R^2$, $R^3$ and $R^4$ are the same or different to each other and each independently represent a C1-C6 alkyl group which may be substituted with one or more atoms or groups selected from Group X, a —$OR^{10}$ group, a —$C(OR^{10})_3$ group, a —$S(O)_mR^{10}$ group, a —$S(O)_2NR^{10}R^{11}$ group, a —$NR^{10}R^{11}$ group, a —$NR^{10}CO_2R^{11}$ group, a —$NR^{10}C(O)R^{11}$ group, a —$CO_2R^{10}$ group, a —$C(O)R^{10}$ group, a —$C(O)NR^{10}R^{11}$ group, a —$SF_5$ group, a cyano group, a nitro group, a halogen atom, or a hydrogen atom;

$R^5$ and $R^6$ are the same or different to each other and each independently represent a C1-C6 alkyl group which may be substituted with one or more atoms or groups selected from Group X, a —$OR^{10}$ group, a —$S(O)_mR^{10}$ group, a —$S(O)_2NR^{10}R^{11}$ group, a —$NR^{10}R^{11}$ group, a —$NR^{10}CO_2R^{11}$ group, a —$NR^{10}C(O)R^{11}$ group, a —$CO_2R^{10}$ group, a —$C(O)R^{10}$ group, a —$C(O)NR^{10}R^{11}$ group, —$OC(O)R^{10}$, a —$SF_5$ group, a —SH group, a cyano group, a nitro group, a halogen atom, or a hydrogen atom, except for a case in which $R^5$ and $R^6$ are both hydrogen atoms;

$R^7$ represents a C1-C6 alkyl group which may be substituted with one or more atoms or groups selected from Group W, a —$CO_2R^{10}$ group, a —$C(O)R^{10}$ group, a —$CH_2CO_2R^{10}$ group, a C3-C6 cycloalkyl group, or a hydrogen atom;

$R^8$ represents a C1-C6 alkyl group which may be substituted with one or more halogen atoms, a —$OR^{10}$ group, a —$S(O)_mR^{10}$ group, a —$NR^{10}R^{11}$ group, a —$CO_2R^{10}$ group, a —$C(O)R^{10}$ group, a cyano group, a nitro group, a halogen atom, or a hydrogen atom;

$R^{10}$ and $R^{11}$ are the same or different to each other and each independently represent a C1-C6 alkyl group which may be substituted with one or more atoms or groups selected from Group X or a hydrogen atom, except for a —$S(O)_mR^{10}$ group wherein m is 1 or 2 and $R^{10}$ is a hydrogen atom;

m independently represents 0, 1 or 2; and n represents 0, 1 or 2;

Group X comprising:

a C1-C6 alkoxy group which may be substituted with one or more halogen atoms, a C3-C6 cycloalkyl group which may be substituted with one or more halogen atoms or one or more C1-C3 alkyl groups, a cyano group, a hydroxy group, and a halogen atom;

Group W comprising:

a C1-C6 alkoxy group which may be substituted with one or more halogen atoms, a C3-C6 cycloalkyl group which may be substituted with one or more halogen atoms,
a hydroxy group,
a halogen atom, and
a cyano group.

Item 14.

The plant seed according to Item 13, in the compound represented by the formula (1) or N-oxide thereof,
$R^1$ is a C1-C6 alkyl group which may be substituted with one or more atoms or groups selected from Group Y;
$R^2$ and $R^4$ are hydrogen atoms;
$R^3$ is a C1-C3 alkyl group which may be substituted with one or more halogen atoms, a —C(OR$^{10}$)$_3$ group, a halogen atom, or a hydrogen atom;
$R^5$ is a C1-C3 alkyl group which may be substituted with one or more halogen atoms, a —OR$^{10}$ group, a —S(O)$_m$R$^{10}$ group, a —CO$_2$R$^{10}$ group, a —SF$_5$ group, or a halogen atom;
$R^6$ is a —OR$^{10}$ group, a —NR$^{10}$R$^{11}$ group, a —CO$_2$R$^{10}$ group, a —C(O)NR$^{10}$R$^{11}$ group, —OC(O)R$^{11}$, a cyano group, a halogen atom, or a hydrogen atom;
$R^7$ is a C1-C6 alkyl group which may be substituted with one or more halogen atoms, a —CH$_2$CO$_2$R$^{10}$ group, a C3-C6 cycloalkyl group, or a hydrogen atom,
$R^8$ is a C1-C3 alkyl group which may be substituted with one or more halogen atoms, a —OR$^{10}$ group, a —S(O)$_m$R$^{10}$ group, a cyano group, a halogen atom, or a hydrogen atom;
$R^{11}$ and $R^{10}$ are the same or different to each other and each independently represent a C1-C3 alkyl group which may be substituted with one or more halogen atoms or a hydrogen atom, except for a —S(O)$_m$R$^{11}$ group wherein m is 1 or 2 and $R^{10}$ is a hydrogen atom; and
Group Y comprising:
a C3-C6 cycloalkyl group which may be substituted with one or more halogen atoms and
a halogen atom.

Item 15.

The plant seed according to Item 13, wherein in the compound represented by the formula (1) or N-oxide thereof,
$R^1$ is a C1-C3 alkyl group which may be substituted with one or more halogen atoms;
$R^2$ and $R^4$ are hydrogen atoms;
$R^3$ is a C1-C3 alkyl group which may be substituted with one or more halogen atoms, a —C(OR$^{10}$)$_3$ group, a halogen atom, or a hydrogen atom;
$R^5$ is a C1-C3 alkyl group which may be substituted with one or more halogen atoms, a —OR$^{10}$ group, a —S(O)$_m$R$^{10}$ group, or a halogen atom;
$R^6$ is a cyano group, a —NR$^{10}$R$^{11}$ group, a halogen atom, or a hydrogen atom;
$R^7$ is a C1-C6 alkyl group which may be substituted with one or more halogen atoms;
$R^8$ is a —S(O)$_m$R$^{10}$ group, a cyano group, a halogen atom, or a hydrogen atom; and
$R^{10}$ and $R^{11}$ are the same or different to each other and each independently represent a C1-C3 alkyl group which may be substituted with one or more halogen atoms.

Item 16.

The plant seed according to Item 13, wherein in the compound represented by the formula (1) or N-oxide thereof:
$R^1$ is an ethyl group;
$R^2$ and $R^4$ are hydrogen atoms;
$R^3$ is a C1-C3 alkyl group which may be substituted with one or more halogen atoms, a —C(OR$^{10}$)$_3$ group, a halogen atom, or a hydrogen atom;

$R^5$ is a C1-C3 haloalkyl group, a —OR$^{20}$ group, a —S(O)$_m$ R$^{20}$ group, or a halogen atom;
$R^6$ is a cyano group, a —NR$^{10}$R$^{11}$ group, a halogen atom, or a hydrogen atom;
$R^7$ is a C1-C6 alkyl group which may be substituted with one or more halogen atoms;
$R^8$ is a —S(O)$_m$R$^{10}$ group, a cyano group, a halogen atom, or a hydrogen atom;
$R^{10}$ and $R^{11}$ are the same or different to each other and each independently represent a C1-C3 alkyl group which may be substituted with one or more halogen atoms; and
$R^{20}$ is a C1-C3 haloalkyl group.

Item 17.

The plant seed according to any one of Items 13 to 16, wherein in the compound represented by the formula (1) or N-oxide thereof,
$A^1$ is —NR$^7$—.

Item 18.

The plant seed according to any one of Items 13 to 16, wherein in the compound represented by the formula (1) or N-oxide thereof,
$A^1$ is an oxygen atom.

Item 19.

The plant seed according to any one of Items 13 to 16, wherein in the compound represented by the formula (1) or N-oxide thereof,
$A^1$ is a sulfur atom.

Item 20.

The plant seed according to Item 13, wherein the compound represented by the formula (1) or N-oxide thereof is a compound represented by the formula (1-2) or N-oxide thereof;
the formula (1-2):

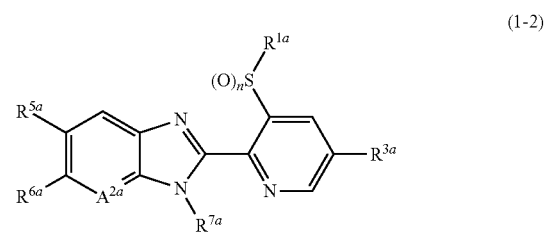

(1-2)

wherein
$R^{1a}$ represents a C1-C3 alkyl group;
$A^{2a}$ represents a nitrogen atom or =CR$^{8a}$—;
$R^{3a}$ represents a C1-C3 alkyl group which may be substituted with one or more halogen atoms, a —C(OR$^{10a}$)$_3$ group, a halogen atom, or a hydrogen atom;
$R^{5a}$ represents a C1-C3 haloalkyl group, a —OR$^{20a}$ group, a —S(O)$_m$R$^{20a}$ group, or a halogen atom;
$R^{6a}$ represents a cyano group, a —NR$^{10a}$R$^{11a}$ group, a halogen atom, or a hydrogen atom;
$R^{7a}$ represents a C1-C6 alkyl group which may be substituted with one or more halogen atoms;
$R^{8a}$ represents a —S(O)$_m$R$^{10a}$ group, a cyano group, a halogen atom, or a hydrogen atom;
$R^{10a}$ and $R^{11a}$ are the same or different to each other and each independently represent a C1-C3 alkyl group which may be substituted with one or more halogen atoms;
$R^{20a}$ represents a C1-C3 haloalkyl group;
m independently represents 0, 1 or 2; and
n represents 0, 1 or 2.

Item 21.

The plant seed according to Item 13, wherein the compound represented by the formula (1) or N-oxide thereof is a compound represented by the formula (1-3) or N-oxide thereof;

the formula (1-3):

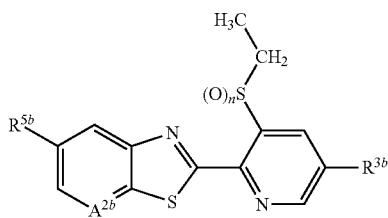

wherein
$A^{2b}$ represents a nitrogen atom or $=CR^{8b}$—;
$R^{3b}$ represents a C1-C3 alkyl group which may be substituted with one or more halogen atoms, a —C(OR$^{10b}$)$_3$ group, a halogen atom, or a hydrogen atom;
$R^{5b}$ represents a C1-C3 haloalkyl group, a —OR$^{20b}$ group, a —S(O)$_m$R$^{20b}$ group, or a halogen atom;
$R^{8b}$ represents a —S(O)$_m$R$^{10b}$ group, a cyano group, a halogen atom, or a hydrogen atom;
$R^{10b}$ independently represents a C1-C3 alkyl group which may be substituted with one or more halogen atoms;
$R^{20b}$ represents a C1-C3 haloalkyl group;
m independently represents 0, 1 or 2; and
n represents 0, 1 or 2.

Item 22.
The plant seed according to Item 21, wherein in the compound represented by the formula (1-3) or N-oxide thereof,
$R^{3b}$ is a halogen atom or a hydrogen atom;
$R^{5b}$ is a C1-C3 perfluoroalkyl group, a —OR$^{30b}$ group, or a —S(O)$_m$R$^{30b}$ group;
$R^{30b}$ is a C1-C3 perfluoroalkyl group; and
$R^{8b}$ is a halogen atom or a hydrogen atom.

Item 23.
The plant seed according to Item 21, wherein the compound represented by the formula (1) or N-oxide thereof is a compound represented by the formula (1-4) or N-oxide thereof;
the formula (1-4):

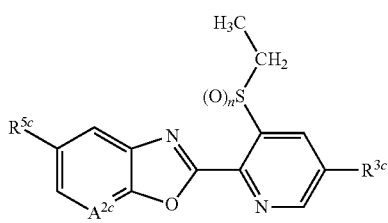

wherein
$A^{2c}$ represents a nitrogen atom or $=CR^{8c}$—;
$R^{3c}$ represents a C1-C3 alkyl group which may be substituted with one or more halogen atoms, a —C(OR$^{10c}$)$_3$ group, a halogen atom, or a hydrogen atom;
$R^{5c}$ represents a C1-C3 haloalkyl group, a —OR$^{20c}$ group, a —S(O)$_m$R$^{20c}$ group, or a halogen atom;

$R^{8c}$ represents a —S(O)$_m$R$^{10c}$ group, a cyano group, a halogen atom, or a hydrogen atom;
$R^{10c}$ independently represents a C1-C3 alkyl group which may be substituted with one or more halogen atoms;
$R^{20c}$ represents a C1-C3 haloalkyl group;
m independently represents 0, 1 or 2; and
n represents 0, 1 or 2.

Item 24.
The plant seed according to Item 23, wherein in the compound represented by the formula (1-4) or N-oxide thereof,
$R^{3c}$ is a halogen atom or a hydrogen atom;
$R^{5c}$ is a C1-C3 perfluoroalkyl group, a —OR$^{30c}$ group, or a —S(O)$_m$R$^{30c}$ group,
$R^{30c}$ is a C1-C3 perfluoroalkyl group, and
$R^{8c}$ is a halogen atom or a hydrogen atom.

Item 25.
The method for controlling pests according to any one items 1 to 12 wherein the compound represented by formula (1) or N-oxide thereof is applied in an amount of 0.01 to 1.000 g per 10 kg seed.

Item 26.
The method for controlling pests according to any one items 1 to 12 or 25, wherein the plant seed is a seed of corn, cotton, soybean, beet, colza, Japanese radish or rice.

Item 27.
The method for controlling pests according to any one items 13 to 24, wherein the plant seed is a seed of corn, cotton, soybean, beet, colza, Japanese radish or rice.

The present invention can control pests.

Mode for Carrying Out the Invention

The method for controlling pests of the present invention comprises applying the above-mentioned compound represented by formula (1) to plant seeds to be protected (hereinafter, referred to as "Present fused heterocyclic compound").

For the present fused heterocyclic compound, "N-oxide" includes a compound wherein one or more ring-constituting nitrogen atoms in one or more the heterocyclic moieties are oxidized. The heterocyclic moieties which may form N-oxide includes, for example, the pyridine ring moiety.

For example, the nitrogen atom of the pyridine ring moiety of the formula (1) may be N-oxide (N→O).

Further, for example, in the formula (1), $A^2$ may be N-oxide (N→O).

The examples of each group as used herein are explained as follows.

In the following "Ca-Cb", "a" means the smallest number of the carbon atoms and "b" means the largest number of carbon atoms.

The term "Ca-Cb alkyl group" as used herein represents a straight- or branched-chain hydrocarbon group having "a" to "b" carbon atoms.

The term "Ca-Cb haloalkyl group represents a straight- or branched-chain hydrocarbon group having "a" to "b" carbon atoms, wherein one or more hydrogen atoms attached to the carbon atoms are replaced with one or more halogen atoms. When two or more halogen atoms are attached to the carbon atoms, the halogen atoms may be the same or different.

The term "Ca-Cb alkoxy group" represents a straight- or branched-chain alkyl-O— group having "a" to "b" carbon atoms.

The term "Ca-Cb cycloalkyl group" represents a saturated cyclic hydrocarbon group having "a" to "b" carbon atoms.

In "which may be substituted with one or more atoms or groups selected from Group X" as used herein, when substituted with two or more atoms or groups selected from Group X, the atoms or groups selected from Group X may be the same or different to each other.

In "which may be substituted with one or more atoms or groups selected from Group Y" as used herein, when substituted with two or more atoms or groups selected from Group Y, the atoms or groups selected from Group Y may be the same or different to each other.

In "which may be substituted with one or more atoms or groups selected from Group W" as used herein, when substituted with two or more atoms or groups selected from Group W, the atoms or groups selected from Group W may be the same or different to each other.

In "which may be substituted with one or more halogen atoms" as used herein, when substituted with two or more halogen atoms, the halogen atoms may be the same or different to each other.

In "which may be substituted with one or more C1-C3 alkyl groups" as used herein, when substituted with two or more C1-C3 alkyl groups, the C1-C3 alkyl groups may be the same or different to each other.

In the present fused heterocyclic compound, the term "halogen atom" includes a fluorine atom, a chlorine atom, a bromine atom, and an iodine atom.

In the present fused heterocyclic compound, "a C1-C6 alkyl group which may be substituted with one or more (for example, 1 to 7, 1 to 5, or 1 to 3) atoms or groups selected from Group X" represents a straight- or branched-chain saturated hydrocarbon group having 1 to 6 carbon atoms, wherein one or more hydrogen atoms attached to the carbon atoms may optionally be replaced with one or more atoms or groups selected from Group X. When substituted with two or more atoms or groups selected from Group X, the atoms or groups selected from Group X may be the same or different to each other.

Examples of "a C1-C6 alkyl group which may be substituted with one or more atoms or groups selected from Group X" include methyl group, ethyl group, propyl group, isopropyl group, butyl group, isobutyl group, sec-butyl group, tert-butyl group, pentyl group, neopentyl group, hexyl group, methoxymethyl group, ethoxymethyl group, propyloxymethyl group, isopropyloxymethyl group, butyloxymethyl group, sec-butyloxymethyl group, tert-butyloxymethyl group, 2-methoxyethyl group, 2-ethoxyethyl group, 2-propyloxyethyl group, 2-isopropyloxyethyl group, 2-butyloxyethyl group, 2-sec-butyloxyethyl group, 2-tert-butyloxyethyl group, trifluoromethyl group, trichloromethyl group, 2-fluoroethyl group, 2,2-difluoroethyl group, 2,2,2-trifluoroethyl group and pentafluoroethyl group, 2-hydroxyethyl group, cyclopropylmethyl group, 1-methylcyclopropylmethyl group, 2,2-difluorocyclopropylmethyl group, trimethoxymethyl group, triethoxymethyl group etc. Examples of subgroups such as "a C1-C3 alkyl group which may be substituted with one or more atoms or groups selected from Group X" may be selected from the above, depending on the indicated number of carbon atom.

In the present fused heterocyclic compound, "a C1-C6 alkyl group which may be substituted with one or more (for example, 1 to 7, 1 to 5, or 1 to 3) halogen atoms" represents a straight- or branched-chain hydrocarbon group having 1 to 6 carbon atoms, wherein one or more hydrogen atoms attached to the carbon atoms may optionally be replaced with one or more halogen atoms. When substituted with two or more halogen atoms, the halogen atoms may be the same or different to each other.

Examples of "a C1-C6 alkyl group which may be substituted with one or more halogen atoms" include methyl group, ethyl group, propyl group, isopropyl group, butyl group, isobutyl group, sec-butyl group, tert-butyl group, pentyl group, neopentyl group, hexyl group, trifluoromethyl group, trichloromethyl group, 2-fluoroethyl group, 2,2-difluoroethyl group, 2,2,2-trifluoroethyl group, and pentafluoroethyl group, heptafluoroisopropyl group etc. Examples of subgroups such as "a C1-C3 alkyl group which may be substituted with one or more halogen atoms" may be selected from the above, depending on the indicated number of carbon atom.

In the present fused heterocyclic compound, examples of "a C1-C6 alkyl group which may be substituted with one or more (for example, 1 to 7, 1 to 5, or 1 to 3) atoms or groups selected from Group W" include methyl group, ethyl group, propyl group, isopropyl group, butyl group, isobutyl group, sec-butyl group, tert-butyl group, pentyl group, neopentyl group, hexyl group, trifluoromethyl group, trichloromethyl group, 2-fluoroethyl group, 2,2-difluoroethyl group, 2,2,2-trifluoroethyl group, pentafluoroethyl group, methoxymethyl group, ethoxymethyl group, propyloxymethyl group, isopropyloxymethyl group, butyloxymethyl group, sec-butyloxymethyl group, isobutyloxymethyl group, tert-butyloxymethyl group, methoxyethyl group, ethoxyethyl group, propyloxyethyl group, isopropyloxyethyl group, butyloxyethyl group, sec-butyloxyethyl group, isobutyloxyethyl group, tert-butyloxyethyl group etc. When substituted with two or more atoms or groups selected from Group W, the atoms or groups selected from Group W may be the same or different to each other.

In the present fused heterocyclic compound, examples of "a C1-C6 alkyl group which may be substituted with one or more atoms or groups selected from Group Y" include methyl group, ethyl group, propyl group, isopropyl group, butyl group, isobutyl group, sec-butyl group, tert-butyl group, pentyl group, neopentyl group, hexyl group, trifluoromethyl group, trichloromethyl group, 2-fluoroethyl group, 2,2-difluoroethyl group, 2,2,2-trifluoroethyl group and pentafluoroethyl group, cyclopropylmethyl group, 1-methylcyclopropylmethyl group, 2,2-difluorocyclopropylmethyl group etc. Examples of subgroups are selected from the above, depending on the indicated number of carbon atom.

In the present fused heterocyclic compound, examples of "a C1-C6 alkoxy group which may be substituted with one or more (for example, 1 to 7, 1 to 5, or 1 to 3) halogen atoms" includes methoxy group, trifluoromethoxy group, ethoxy group, 2,2,2-trifluoroethoxy group, propyloxy group, isopropyloxy group, butyloxy group, isobutyloxy group, sec-butyloxy group, tert-butyloxy group, pentyloxy group, and hexyloxy group.

In the present fused heterocyclic compound, examples of "a C3-C6 cycloalkyl group which may be substituted with one or more (for example, 1 to 7, 1 to 5, or 1 to 3) halogen atoms" include cyclopropyl group, 2,2-difluorocyclopropyl group, 2,2-dichlorocyclopropyl group, 2,2-dibromocyclopropyl group, cyclobutyl group, cyclopentyl group, and cyclohexyl group.

In the present fused heterocyclic compound, examples of "a C3-C6 cycloalkyl group which may be substituted with one or more (for example, 1 to 7, 1 to 5, or 1 to 3) halogen atoms or one or more (for example, 1 to 7, 1 to 5, or 1 to 3) C1-C3 alkyl groups" include cyclopropyl group, 1-methylcyclopropyl group, 2-methylcyclopropyl group, 1-fluorocyclopropyl group, 2,2-difluorocyclopropyl group, 2,2-dichlorocyclopropyl group, 2,2-dibromocyclopropyl group, cyclobutyl group, cyclopentyl group, and cyclohexyl group.

In the present fused heterocyclic compound, the term "a C1-C3 haloalkyl group" represents a straight- or branched-chain hydrocarbon group having 1 to 3 carbon atoms, wherein one or more hydrogen atoms attached to the carbon atoms are replaced with one or more (for example, 1 to 7, 1 to 5, or 1 to 3) halogen atoms. When substituted with two or more halogen atoms, the halogen atoms may be the same or different to each other.

Examples of "a C1-C3 haloalkyl group" include fluoromethyl group, chloromethyl group, bromomethyl group, iodo ethyl group, difluoromethyl group, dichloromethyl group, trifluoromethyl group, chlorodifluoromethyl group, bromodifluoromethyl group, trichloromethyl group, 2-fluoroethyl group, 2-chloroethyl group, 2-bromoethyl group, 2,2-difluoroethyl group, 2,2,2-trifluoroethyl group, pentafluoroethyl group, heptafluoropropyl group, heptafluoroisopropyl group etc.

In the present fused heterocyclic compound, examples of "C1-C3 alkyl group" include methyl group, ethyl group, propyl group, and isopropyl group.

In the present fused heterocyclic compound, examples of "C1-C3 perfluoroalkyl group" include trifluoromethyl group, pentafluoroethyl group, heptafluoropropyl group, and heptafluoroisopropyl group.

Examples of the present fused heterocyclic compound include as follows.

The compound represented by the formula (1), wherein
$R^1$ is a C1-C6 alkyl group which may be substituted with one or more atoms or groups selected from Group Y;
$R^2$ and $R^4$ are hydrogen atoms;
$R^3$ is a C1-C3 alkyl group which may be substituted with one or more halogen atoms, a —$C(OR^{10})_3$ group, a halogen atom, or a hydrogen atom;
$R^5$ is a C1-C3 alkyl group which may be substituted with one or more halogen atoms, a —$OR^{10}$ group, a —$S(O)_mR^{10}$ group, a —$CO_2R^{10}$ group, a —$SF_5$ group, or a halogen atom;
$R^6$ is a —$OR^{10}$ group, a —$NR^{10}R^{11}$ group, a —$CO_2R^{10}$ group, a —$C(O)NR^{10}R^{11}$ group, —$OC(O)R^{10}$, a cyano group, a halogen atom, or a hydrogen atom;
$R^7$ is a C1-C6 alkyl group which may be substituted with one or more halogen atoms, a —$CH_2CO_2R^{10}$ group, a C3-C6 cycloalkyl group, or a hydrogen atom;
$R^8$ is a C1-C3 alkyl group which may be substituted with one or more halogen atoms, a —$OR^{10}$ group, a —$S(O)_mR^{10}$ group, a cyano group, a halogen atom, or a hydrogen atom;
$R^{10}$ and $R^{11}$ are the same or different to each other and each independently represent a C1-C3 alkyl group which may be substituted with one or more halogen atoms or a hydrogen atom, except for a —$S(O)_mR^{10}$ group wherein m is 1 or 2 and $R^{10}$ is a hydrogen atom; and
Group Y comprising:
a C3-C6 cycloalkyl group which may be substituted with one or more halogen atoms and
a halogen atom; or N-oxide thereof.

The compound represented by the formula (1), wherein
$R^1$ is a C1-C3 alkyl group which may be substituted with one or more halogen atoms;
$R^2$ and $R^4$ are hydrogen atoms;
$R^3$ is a C1-C3 alkyl group which may be substituted with one or more halogen atoms, a —$C(OR^{10})_3$ group, a halogen atom, or a hydrogen atom;
$R^5$ is a C1-C3 alkyl group which may be substituted with one or more halogen atoms, a —$OR^{10}$ group, a —$S(O)_mR^{10}$ group, or a halogen atom;
$R^6$ is a cyano group, a —$NR^{10}R^{11}$ group, a halogen atom, or a hydrogen atom;
$R^7$ is a C1-C6 alkyl group which may be substituted with one or more halogen atoms;
$R^8$ is a —$S(O)_mR^{10}$ group, a cyano group, a halogen atom, or a hydrogen atom; and
$R^{10}$ and $R^{11}$ are the same or different to each other and each independently represent a C1-C3 alkyl group which may be substituted with one or more halogen atoms; or N-oxide thereof.

The compound represented by the formula (1), wherein
$R^1$ is an ethyl group;
$R^2$ and $R^4$ are hydrogen atoms;
$R^3$ is a C1-C3 alkyl group which may be substituted with one or more halogen atoms, a —$C(OR^{10})_3$ group, a halogen atom, or a hydrogen atom;
$R^5$ is a C1-C3 haloalkyl group, a —$OR^{20}$ group, a —$S(O)_m R^{20}$ group, or a halogen atom;
$R^6$ is a cyano group, a —$NR^{10}R^{11}$ group, a halogen atom, or a hydrogen atom;
$R^7$ is a C1-C6 alkyl group which may be substituted with one or more halogen atoms;
$R^8$ is a —$S(O)_mR^{10}$ group, a cyano group, a halogen atom, or a hydrogen atom;
$R^{10}$ and $R^{11}$ are the same or different to each other and each independently represent a C1-C3 alkyl group which may be substituted with one or more halogen atoms; and
$R^{20}$ is a C1-C3 haloalkyl group; or N-oxide thereof.

The compound represented by the formula (1), wherein $A^1$ is —$NR^7$—; or N-oxide thereof.

The compound represented by the formula (1), wherein
$A^1$ is —$NR^7$—;
$R^1$ is a C1-C6 alkyl group which may be substituted with one or more atoms or groups selected from Group Y;
$R^2$ and $R^4$ are hydrogen atoms;
$R^3$ is a C1-C3 alkyl group which may be substituted with one or more halogen atoms, a —$C(OR^{10})_3$ group, a halogen atom, or a hydrogen atom;
$R^5$ is a C1-C3 alkyl group which may be substituted with one or more halogen atoms, a —$OR^{10}$ group, a —$S(O)_mR^{10}$ group, a —$CO_2R^{10}$ group, a —$SF_5$ group, or a halogen atom;
$R^6$ is a —$OR^{10}$ group, a —$NR^{10}R^{11}$ group, a —$CO_2R^{10}$ group, a —$C(O)NR^{10}R^{11}$ group, —$OC(O)R^{10}$, a cyano group, a halogen atom, or a hydrogen atom;
$R^7$ is a C1-C6 alkyl group which may be substituted with one or more halogen atoms, a —$CH_2CO_2R^{10}$ group, a C3-C6 cycloalkyl group, or a hydrogen atom;
$R^8$ is a C1-C3 alkyl group which may be substituted with one or more halogen atoms, a —$OR^{10}$ group, a —$S(O)_mR^{10}$ group, a cyano group, a halogen atom, or a hydrogen atom;
$R^{10}$ and $R^{11}$ are the same or different to each other and each independently represent a C1-C3 alkyl group which may be substituted with one or more halogen atoms or a hydrogen atom, except for a —$S(O)_mR^{10}$ group wherein m is 1 or 2 and $R^{10}$ is a hydrogen atom; and
Group Y comprising:
a C3-C6 cycloalkyl group which may be substituted with one or more halogen atoms, and
a halogen atom; or N-oxide thereof.

The compound represented by the formula (1), wherein
$A^1$ is —$NR^7$—;
$R^1$ is a C1-C3 alkyl group which may be substituted with one or more halogen atoms;
$R^2$ and $R^4$ are hydrogen atoms;
$R^3$ is a C1-C3 alkyl group which may be substituted with one or more halogen atoms, a —$C(OR^{10})_3$ group, a halogen atom, or a hydrogen atom;

$R^5$ is a C1-C3 alkyl group which may be substituted with one or more halogen atoms, a —$OR^{10}$ group, a —$S(O)R^{10}$ group, or a halogen atom;

$R^6$ is a cyano group, a —$NR^{10}R^{11}$ group, a halogen atom, or a hydrogen atom;

$R^7$ is a C1-C6 alkyl group which may be substituted with one or more halogen atoms;

$R^8$ is a —$S(O)_mR^{10}$ group, a cyano group, a halogen atom, or a hydrogen atom; and $R^{10}$ and $R^{11}$ are the same or different to each other and each independently represent a C1-C3 alkyl group which may be substituted with one or more halogen atoms; or N-oxide thereof.

The compound represented by the formula (1), wherein
$A^1$ is —$NR^7$—;
$R^1$ is an ethyl group;
$R^2$ and $R^4$ are hydrogen atoms;
$R^3$ is a C1-C3 alkyl group which may be substituted with one or more halogen atoms, a —$C(OR^{10})_3$ group, a halogen atom, or a hydrogen atom;
$R^5$ is a C1-C3 haloalkyl group, a —$OR^{20}$ group, a —$S(O)_m R^{20}$ group, or a halogen atom;
$R^6$ is a cyano group, a —$NR^{10}R^{11}$ group, a halogen atom, or a hydrogen atom,
$R^7$ is a C1-C6 alkyl group which may be substituted with one or more halogen atoms;
$R^8$ is a —$S(O)_mR^{10}$ group, a cyano group, a halogen atom, or a hydrogen atom;
$R^{10}$ and $R^{11}$ are the same or different to each other and each independently represent a C1-C3 alkyl group which may be substituted with one or more halogen atoms; and
$R^{20}$ is a C1-C3 haloalkyl group; or N-oxide thereof.

The compound represented by the formula (1), wherein $A^1$ is an oxygen atom; or N-oxide thereof.

The compound represented by the formula (1), wherein
$A^1$ is an oxygen atom;
$R^1$ is a C1-C6 alkyl group which may be substituted with one or more atoms or groups selected from Group Y;
$R^2$ and $R^4$ are hydrogen atoms;
$R^3$ is a C1-C3 alkyl group which may be substituted with one or more halogen atoms, a —$C(OR^{10})_3$ group, a halogen atom, or a hydrogen atom;
$R^5$ is a C1-C3 alkyl group which may be substituted with one or more halogen atoms, a —$OR^{10}$ group, a —$S(O)_mR^{10}$ group, a —$CO_2R^{10}$ group, a —$SF_5$ group, or a halogen atom;
$R^6$ is a —$OR^{10}$ group, a —$NR^{10}R^{11}$ group, a —$CO_2R^{10}$ group, a —$C(O)NR^{10}R^{11}$ group, —$OC(O)R^{10}$, a cyano group, a halogen atom, or a hydrogen atom;
$R^7$ is a C1-C6 alkyl group which may be substituted with one or more halogen atoms, a —$CH_2CO_2R^{10}$ group, a C3-C6 cycloalkyl group, or a hydrogen atom;
$R^8$ is a C1-C3 alkyl group which may be substituted with one or more halogen atoms, a —$OR^{10}$ group, a —$S(O)_mR^{10}$ group, a cyano group, a halogen atom, or a hydrogen atom;
$R^{10}$ and $R^{11}$ are the same or different to each other and each independently represent a C1-C3 alkyl group which may be substituted with one or more halogen atoms or a hydrogen atom, except for a —$S(O)_mR^{10}$ group wherein m is 1 or 2 and $R^{10}$ is a hydrogen atom; and
Group Y comprising:
a C3-C6 cycloalkyl group which may be substituted with one or more halogen atoms, and
a halogen atom; or N-oxide thereof.

The compound represented by the formula (1), wherein
$A^1$ is an oxygen atom;
$R^1$ is a C1-C3 alkyl group which may be substituted with one or more halogen atoms;
$R^2$ and $R^4$ are hydrogen atoms;
$R^3$ is a C1-C3 alkyl group which may be substituted with one or more halogen atoms, —$C(OR^{10})_3$ group, a halogen atom, or a hydrogen atom;
$R^5$ is a C1-C3 alkyl group which may be substituted with one or more halogen atoms, a —$OR^{10}$ group, a —$S(O)_mR^{10}$ group, or a halogen atom;
$R^6$ is a cyano group, a —$NR^{10}R^{11}$ group, a halogen atom, or a hydrogen atom;
$R^7$ is a C1-C6 alkyl group which may be substituted with one or more halogen atoms;
$R^8$ is a —$S(O)R^{10}$ group, a cyano group, a halogen atom, or a hydrogen atom; and
$R^{10}$ and $R^{11}$ are the same or different to each other and each independently represent a C1-C3 alkyl group which may be substituted with one or more halogen atoms; or N-oxide thereof.

The compound represented by the formula (1), wherein
$A^1$ is a sulfur atom;
$R^1$ is an ethyl group;
$R^2$ and $R^4$ are hydrogen atoms;
$R^3$ is a C1-C3 alkyl group which may be substituted with one or more halogen atoms, a —$C(OR^{10})_3$ group, a halogen atom, or a hydrogen atom;
$R^5$ is a C1-C3 haloalkyl group, a —$OR^{20}$ group, a —$S(O)_mR^{20}$ group, or a halogen atom;
$R^6$ is a cyano group, a —$NR^{10}R^{11}$ group, a halogen atom, or a hydrogen atom;
$R^7$ is a C1-C6 alkyl group which may be substituted with one or more halogen atoms;
$R^8$ is a —$S(O)_mR^{10}$ group, a cyano group, a halogen atom, or a hydrogen atom;
$R^{10}$ and $R^{11}$ are the same or different to each other and each independently represent a C1-C3 alkyl group which may be substituted with one or more halogen atoms; and
$R^{20}$ is a C1-C3 haloalkyl group; or N-oxide thereof.

The compound represented by the formula (1), wherein $A^1$ is a sulfur atom; or N-oxide thereof.

The compound represented by the formula (1), wherein
$A^1$ is a sulfur atom;
$R^1$ is a C1-C6 alkyl group which may be substituted with one or more atoms or groups selected from Group Y;
$R^2$ and $R^4$ are hydrogen atoms,
$R^3$ is a C1-C3 alkyl group which may be substituted with one or more halogen atoms, a —$C(OR^{10})_3$ group, a halogen atom, or a hydrogen atom;
$R^5$ is a C1-C3 alkyl group which may be substituted with one or more halogen atoms, a —$OR^{10}$ group, a —$S(O)_mR^{10}$ group, a —$CO_2R^{10}$ group, a —$SF_5$ group, or a halogen atom;
$R^6$ is a —$OR^{10}$ group, a —$NR^{10}R^{11}$ group, a —$CO_2R^{10}$ group, a —$C(O)NR^{10}R^{11}$ group, —$OC(O)R^{10}$, a cyano group, a halogen atom, or a hydrogen atom;
$R^7$ is a C1-C6 alkyl group which may be substituted with one or more halogen atoms, a —$CH_2CO_2R^{10}$ group, a C3-C6 cycloalkyl group, or a hydrogen atom;
$R^8$ is a C1-C3 alkyl group which may be substituted with one or more halogen atoms, a —$OR^{11}$ group, a —$S(O)_mR^{10}$ group, a cyano group, a halogen atom, or a hydrogen atom;
$R^{10}$ and $R^{11}$ are the same or different to each other and each independently represent a C1-C3 alkyl group which may be substituted with one or more halogen atoms or a hydrogen atom, except for a —$S(O)_mR^{10}$ group wherein m is 1 or 2 and $R^{10}$ is a hydrogen atom; and
Group Y comprising:
a C3-C6 cycloalkyl group which may be substituted with one or more halogen atoms, and
a halogen atom; or N-oxide thereof.

The compound represented by the formula (1), wherein
$A^1$ is a sulfur atom;
$R^1$ is a C1-C3 alkyl group which may be substituted with one or more halogen atoms;
$R^2$ and $R^4$ are hydrogen atoms;
$R^3$ is a C1-C3 alkyl group which may be substituted with one or more halogen atoms, a —$C(OR^{10})_3$ group, a halogen atom, or a hydrogen atom;
$R^5$ is a C1-C3 alkyl group which may be substituted with one or more halogen atoms, a —$OR^{10}$ group, a —$S(O)_mR^{10}$ group, or a halogen atom;
$R^6$ is a cyano group, a —$NR^{10}R^{11}$ group, a halogen atom, or a hydrogen atom;
$R^7$ is a C1-C6 alkyl group which may be substituted with one or more halogen atoms;
$R^8$ is a —$S(O)_mR^{10}$ group, a cyano group, a halogen atom, or a hydrogen atom; and
and $R^{10}$ are the same or different to each other and each independently represent a C1-C3 alkyl group which may be substituted with one or more halogen atoms; or N-oxide thereof.

The compound represented by the formula (1), wherein
$A^1$ is a sulfur atom;
$R^1$ is an ethyl group;
$R^2$ and $R^4$ are hydrogen atoms;
$R^3$ is a C1-C3 alkyl group which may be substituted with one or more halogen atoms, a —$C(OR^{10})_3$ group, a halogen atom, or a hydrogen atom;
$R^5$ is a C1-C3 haloalkyl group, a —$OR^{10}$ group, a —$S(O)_mR^{10}$ group, or a halogen atom;
$R^6$ is a cyano group, a —$NR^{10}R^{11}$ group, a halogen atom, or a hydrogen atom;
$R^7$ is a C1-C6 alkyl group which may be substituted with one or more halogen atoms;
$R^8$ is a —$S(O)_mR^{10}$ group, a cyano group, a halogen atom, or a hydrogen atom;
$R^{10}$ and $R^{11}$ are the same or different to each other and each independently represent a C1-C3 alkyl group which may be substituted with one or more halogen atoms; and
$R^{20}$ is a C1-C3 haloalkyl group; or N-oxide thereof.

The compound represented by the formula (1-2):

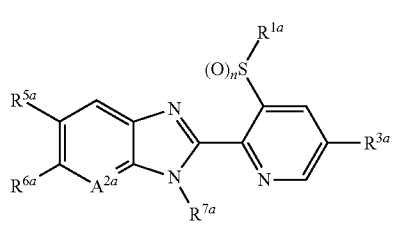

(1-2)

wherein
$R^{1a}$ represents a C1-C3 alkyl group;
$A^{2a}$ represents a nitrogen atom or $=CR^{8a}—$;
$R^{3a}$ represents a C1-C3 alkyl group which may be substituted with one or more halogen atoms, a —$C(OR^{10a})_3$ group, a halogen atom, or a hydrogen atom;
$R^{5a}$ represents a C1-C3 haloalkyl group, a —$OR^{20a}$ group, a —$S(O)_mR^{20a}$ group, or a halogen atom;
$R^{6a}$ represents a cyano group, a —$NR^{10a}R^{11a}$ group, a halogen atom, or a hydrogen atom;
$R^{7a}$ represents a C1-C6 alkyl group which may be substituted with one or more halogen atoms;
$R^{8a}$ represents a —$S(O)_mR^{10a}$ group, a cyano group, a halogen atom, or a hydrogen atom;

$R^{10a}$ and $R^{11a}$ are the same or different to each other and each independently represent a C1-C3 alkyl group which may be substituted with one or more halogen atoms;
$R^{20a}$ represents a C1-C3 haloalkyl group;
m independently represents 0, 1 or 2; and
n represents 0, 1 or 2; or N-oxide thereof.

The compound represented by the formula (1-3):

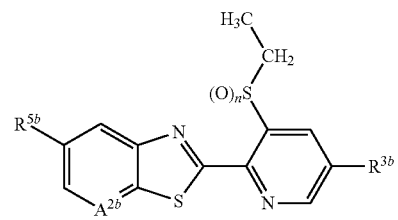

(1-3)

wherein
$A^{2b}$ represents a nitrogen atom or $=CR^{8b}—$;
$R^{3b}$ represents a C1-C3 alkyl group which may be substituted with one or more halogen atoms, a —$C(OR^{10b})_3$ group, a halogen atom, or a hydrogen atom;
$R^{5b}$ represents a C1-C3 haloalkyl group, a —$OR^{20b}$ group, a —$S(O)_mR^{20b}$ group, or a halogen atom;
$R^{8b}$ represents a —$S(O)_mR^{10b}$ group, a cyano group, a halogen atom, or a hydrogen atom;
$R^{10b}$ independently represents a C1-C3 alkyl group which may be substituted with one or more halogen atoms;
$R^{20b}$ represents a C1-C3 haloalkyl group;
m independently represents 0, 1 or 2; and
n represents 0, 1 or 2; or N-oxide thereof.

The compound represented by the formula (1-3), wherein
$R^{3b}$ is a halogen atom or a hydrogen atom;
$R^{5b}$ is a C1-C3 perfluoroalkyl group, a —$OR^{30b}$ group, or a —$S(O)_mR^{30b}$ group;
$R^{30b}$ is a C1-C3 perfluoroalkyl group; and
$R^{8b}$ is a halogen atom or a hydrogen atom; or N-oxide thereof.

The compound represented by the formula (1-4):

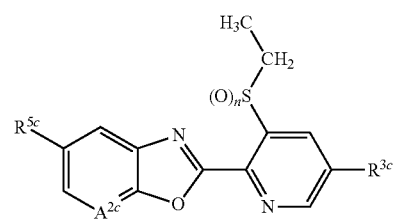

(1-4)

wherein
$A^{2c}$ represents a nitrogen atom or $=CR^{8c}—$;
$R^{3c}$ represents a C1-C3 alkyl group which may be substituted with one or more halogen atoms, a —$C(OR^{10c})_3$ group, a halogen atom, or a hydrogen atom;
$R^{5c}$ represents a C1-C3 haloalkyl group, a —$OR^{20c}$ group, a —$S(O)_mR^{20c}$ group, or a halogen atom;
$R^{8c}$ represents a —$S(O)_mR^{10c}$ group, a cyano group, a halogen atom, or a hydrogen atom;
$R^{10c}$ independently represents a C1-C3 alkyl group which may be substituted with one or more halogen atoms;
$R^{20c}$ represents a C1-C3 haloalkyl group;
m independently represents 0, 1 or 2; and
n represents 0, 1 or 2; or N-oxide thereof.

The compound represented by the formula (1-4), wherein
$R^{3c}$ is a halogen atom or a hydrogen atom;
$R^{5c}$ is a C1-C3 perfluoroalkyl group, a —$OR^{30c}$ group, or a —$S(O)_m R^{30c}$ group;
$R^{30c}$ is a C1-C3 perfluoroalkyl group; and
$R^{8c}$ is a halogen atom or a hydrogen atom; or N-oxide thereof.

Formula (1):

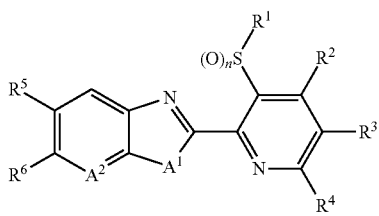

(1)

The compound represented by the formula (1), wherein $A^1$ is —$NR^7$—, and $R^7$ is a C1-C6 alkyl group which may be substituted with one or more halogen atoms, or a hydrogen atom; or N-oxide thereof.

The compound represented by the formula (1), wherein $A^1$ is —$NR^7$—, and $R^7$ is a methyl group, an ethyl group, or a propyl group; or N-oxide thereof.

The compound represented by the formula (1), wherein $A^1$ is —$NR^7$—, and $R^7$ is a methyl group; or N-oxide thereof.

The compound represented by the formula (1), wherein $A^1$ is —$NR^7$ and $R^7$ is a hydrogen atom; or N-oxide thereof.

The compound represented by the formula (1), wherein $A^2$ is a nitrogen atom; or N-oxide thereof.

The compound represented by the formula (1), wherein $A^2$ is =$N(\rightarrow O)$—: (N-oxide).

The compound represented by the formula (1), wherein $A^2$ is =$CR^8$—; or N-oxide thereof.

The compound represented by the formula (1), wherein $A^2$ is =$CR^8$—, and $R^8$ is a C1-C3 alkoxy group, a C1-C3 alkylsulfonyl group, a halogen atom, or a hydrogen atom; or N-oxide thereof.

The compound represented by the formula (1), wherein $A^2$ is =$CR^8$—, and $R^8$ is a C1-C3 alkoxy group; or N-oxide thereof.

The compound represented by the formula (1), wherein $A^2$ is =$CR^8$—, and $R^8$ is a C1-C3 alkylsulfonyl group; or N-oxide thereof.

The compound represented by the formula (1), wherein $A^2$ is =$CR^8$—, and $R^8$ is a halogen atom; or N-oxide thereof.

The compound represented by the formula (1), wherein $A^2$ is =$CH$—; or N-oxide thereof.

The compound represented by the formula (1), wherein $A^1$ is —$NR^7$—, and $A^2$ is a nitrogen atom; or N-oxide thereof.

The compound represented by the formula (1), wherein $A^1$ is —$NR^7$—, and $A^2$ is =$N(\rightarrow O)$—: (N-oxide).

The compound represented by the formula (1), wherein $A^1$ is —$NR^7$—, and $A^2$ is =$CR^8$—; or N-oxide thereof.

The compound represented by the formula (1), wherein $A^1$ is —$NR^7$ and $A^2$ is =$CH$—; or N-oxide thereof.

The compound represented by the formula (1), wherein $A^1$ is an oxygen atom, and $A^2$ is a nitrogen atom; or N-oxide thereof.

The compound represented by the formula (1), wherein $A^1$ is an oxygen atom, and $A^2$ is =$N(O)$—: (N-oxide).

The compound represented by the formula (1), wherein $A^1$ is an oxygen atom, and $A^2$ is =$CR^8$—; or N-oxide thereof.

The compound represented by the formula (1), wherein $A^1$ is an oxygen atom, and $A^2$ is =$CH$—; or N-oxide thereof.

The compound represented by the formula (1), wherein $A^1$ is a sulfur atom, and $A^2$ is a nitrogen atom; or N-oxide thereof.

The compound represented by the formula (1), wherein $A^1$ is a sulfur atom, and $A^2$ is =$N(O)$—: (N-oxide).

The compound represented by the formula (1), wherein $A^1$ is a sulfur atom, and $A^2$ is =$CR^8$—; or N-oxide thereof.

The compound represented by the formula (1), wherein $A^1$ is a sulfur atom, and $A^2$ is =$CH$—; or N-oxide thereof.

The compound represented by the formula (1), wherein $R^1$ is a C1-C6 alkyl group which may be substituted with one or more halogen atoms or a C3-C6 cycloalkyl group which may be substituted with one or more halogen atoms; or N-oxide thereof.

The compound represented by the formula (1), wherein $R^1$ is a C1-C3 alkyl group which may be substituted with one or more halogen atoms; or N-oxide thereof.

The compound represented by the formula (1), wherein $R^1$ is a methyl group, an ethyl group, or a propyl group, an isopropyl group, a trifluoromethyl group, a 2,2,2-trifluoroethyl group, a cyclopropyl group, or a cyclopropylmethyl group; or N-oxide thereof.

The compound represented by the formula (1), wherein $R^1$ is an ethyl group or a cyclopropylmethyl group; or N-oxide thereof.

The compound represented by the formula (1), wherein $R^1$ is a methyl group; or N-oxide thereof;

The compound represented by the formula (1), wherein $R^1$ is an ethyl group; or N-oxide thereof.

The compound represented by the formula (1), wherein $R^1$ is a propyl group; or N-oxide thereof.

The compound represented by the formula (1), wherein $R^1$ is an isopropyl group; or N-oxide thereof.

The compound represented by the formula (1), wherein $R^3$ is a C1-C6 alkyl group which may be substituted with one or more atoms or groups selected from Group X, a halogen atom, or a hydrogen atom; or N-oxide thereof.

The compound represented by the formula (1), wherein $R^3$ is a C1-C3 alkyl group which may be substituted with one or more halogen atoms, a —$C(OR^{10})_3$ group, a halogen atom, or a hydrogen atom; or N-oxide thereof.

The compound represented by the formula (1), wherein $R^3$ is a C1-C3 alkyl group which may be substituted with one or more halogen atoms or a hydrogen atom; or N-oxide thereof.

The compound represented by the formula (1), wherein $R^3$ is a C1-C3 alkyl group which may be substituted with one or more halogen atoms; or N-oxide thereof.

The compound represented by the formula (1), wherein $R^3$ is a —$C(OR^{10})_3$ group; or N-oxide thereof.

The compound represented by the formula (1), wherein $R^3$ is a halogen atom; or N-oxide thereof.

The compound represented by the formula (1), wherein $R^3$ is a hydrogen atom; or N-oxide thereof.

The compound represented by the formula (1), wherein $R^3$ is a methyl group, a trifluoromethyl group, a pentafluoroethyl group, a hexafluoropropyl group, a hexafluoroisopropyl group, a trimethoxymethyl group, a triethoxymethyl group, a fluorine atom, a chlorine atom, a bromine atom, an iodine atom, or a hydrogen atom; or N-oxide thereof.

The compound represented by the formula (1), wherein $R^3$ is a trifluoromethyl group; or N-oxide thereof.

The compound represented by the formula (1), wherein $R^3$ is a trimethoxymethyl group, or N-oxide thereof;

The compound represented by the formula (1), wherein $R^2$ and $R^4$ are both hydrogen atoms; or N-oxide thereof.

The compound represented by the formula (1), wherein $R^2$ and $R^4$ are both hydrogen atoms, and $R^3$ is a C1-C3 alkyl group which may be substituted with one or more halogen atoms, a —C(OR$^{10}$)$_3$ group, a halogen atom, or a hydrogen atom; or N-oxide thereof.

The compound represented by the formula (1), wherein $R^2$ and $R^4$ are both hydrogen atoms, and $R^3$ is a hydrogen atom; or N-oxide thereof.

The compound represented by the formula (1), wherein $R^2$ and $R^4$ are both hydrogen atoms, and is a trifluoromethyl group; or N-oxide thereof.

The compound represented by the formula (1), wherein $R^2$ and $R^4$ are both hydrogen atoms, and $R^3$ is a trimethoxymethyl group; or N-oxide thereof.

The compound represented by the formula (1), wherein $R^5$ is a C1-C3 alkyl group which may be substituted with one or more halogen atoms, a —OR$^{10}$ group, a —S(O)$_m$R$^{10}$ group, a —CO$_2$R$^{10}$ group, a —SF$_5$ group, or a halogen atom; or N-oxide thereof.

The compound represented by the formula (1), wherein a C1-C3 alkyl group which may be substituted with one or more halogen atoms, a —OR$^{10}$ group, a —S(O)$_m$R$^{10}$ group, or a halogen atom; or N-oxide thereof.

The compound represented by the formula (1), wherein $R^5$ is a C1-C3 haloalkyl group, a C1-C3 haloalkoxy group, a C1-C3 haloalkylsulfonyl group, a C1-C3 haloalkylsulfinyl group, a C1-C3 haloalkylsulfonyl group, or a halogen atom; or N-oxide thereof.

The compound represented by the formula (1), wherein $R^5$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom; or N-oxide thereof.

The compound represented by the formula (1), wherein $R^5$ is a C1-C3 perfluoroalkyl group; or N-oxide thereof.

The compound represented by the formula (1), wherein $R^5$ is a C1-C3 perfluoroalkoxy group; or N-oxide thereof.

The compound represented by the formula (1), wherein $R^5$ is a C1-C3 perfluoroalkylsulfanyl group, a C1-C3 perfluoroalkylsulfinyl group, or a C1-C3 perfluoroalkylsulfonyl group; or N-oxide thereof.

The compound represented by the formula (1), wherein $R^5$ is a halogen atom; or N-oxide thereof.

The compound represented by the formula (1), wherein $R^5$ is a trifluoromethyl group, —CF$_2$CF$_3$, —CF$_2$CF$_2$CF$_3$, —CF(CF$_3$)$_2$, —OCF$_3$, —OCF$_2$CF$_3$, —SCF$_3$, —S(O)CF$_3$, —S(O)$_2$CF$_3$, —SCF$_2$CF$_3$, —S(O)CF$_2$CF$_3$, —S(O)$_2$CF$_2$CF$_3$, —SF$_5$, a fluorine atom, a chlorine atom, a bromine atom, or a iodine atom; or N-oxide thereof.

The compound represented by the formula (1), wherein $R^5$ is a trifluoromethyl group; or N-oxide thereof.

The compound represented by the formula (1), wherein $R^5$ is —CF$_2$CF$_2$; or N-oxide thereof.

The compound represented by the formula (1), wherein $R^5$ is —SCF$_2$; or N-oxide thereof.

The compound represented by the formula (1), wherein $R^5$ is —S(O)CF$_3$; or N-oxide thereof.

The compound represented by the formula (1), wherein $R^5$ is —S(O)$_2$CF$_3$; or N-oxide thereof.

The compound represented by the formula (1), wherein $R^6$ is a —OR$^{10}$ group, a —NR$^{10}$R$^{11}$ group, a —CO$_2$R$^{10}$ group, a —C(O)NR$^{10}$R$^{11}$ group, a cyano group, a halogen atom, or a hydrogen atom; or N-oxide thereof.

The compound represented by the formula (1), wherein $R^6$ is a cyano group, a —NR$^{10}$R$^{11}$ group, a halogen atom, or a hydrogen atom; or N-oxide thereof.

The compound represented by the formula (1), wherein $R^6$ is a hydrogen atom; or N-oxide thereof.

The compound represented by the formula (1), wherein $R^5$ is a C1-C3 haloalkyl group, a C1-C3 haloalkoxy group, a C1-C3 haloalkylsulfanyl group, a C1-C3 haloalkylsulfinyl group, a C1-C3 haloalkylsulfonyl group, or a halogen atom, and $R^6$ is a hydrogen atom; or N-oxide thereof.

The compound represented by the formula (1), wherein $R^5$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom, and $R^6$ is a hydrogen atom; or N-oxide thereof.

The compound represented by the formula (1), wherein $R^5$ is a C1-C3 perfluoroalkyl group, and $R^6$ is a hydrogen atom; or N-oxide thereof.

The compound represented by the formula (1), wherein $R^5$ is a C1-C3 perfluoroalkoxy group, and $R^6$ is a hydrogen atom; or N-oxide thereof.

The compound represented by the formula (1), wherein $R^5$ is a C1-C3 perfluoroalkylsulfanyl group, a C1-C3 perfluoroalkylsulfinyl group, or a C1-C3 perfluoroalkylsulfonyl group, and $R^6$ is a hydrogen atom; or N-oxide thereof.

The compound represented by the formula (1), wherein
$A^1$ is —NR$^7$—;
$R^7$ is a methyl group;
$A^2$ is a nitrogen atom;
$R^1$ is a C1-C3 alkyl group which may be substituted with one or more halogen atoms;
$R^2$ and $R^4$ are both hydrogen atoms;
$R^3$ is a C1-C3 alkyl group which may be substituted with one or more halogen atoms, a —C(OR$^{10}$)$_3$ group, a halogen atom, or a hydrogen atom;
$R^5$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom, and
$R^6$ is a hydrogen atom;
or N-oxide thereof.

The compound represented by the formula (1), wherein
$A^1$ is —NR$^7$—;
$R^7$ is a methyl group;
$A^2$ is =N(→O)—;
$R^1$ is a C1-C3 alkyl group which may be substituted with one or more halogen atoms;
$R^2$ and $R^4$ are both hydrogen atoms;
$R^3$ is a C1-C3 alkyl group which may be substituted with one or more halogen atoms, a —C(OR$^{10}$)$_3$ group, a halogen atom, or a hydrogen atom;
$R^5$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom; and
$R^6$ is a hydrogen atom; (N-oxide).

The compound represented by the formula (1), wherein
$A^1$ is —NR$^7$—;
$R^7$ is a methyl group;
$A^2$ is =CR$^8$—;
$R^8$ is a C1-C3 alkoxy group, a C1-C3 alkylsulfanyl group, a halogen atom, or a hydrogen atom;

$R^1$ is a C1-C3 alkyl group which may be substituted with one or more halogen atoms;

$R^2$ and $R^4$ are both hydrogen atoms;

$R^3$ is a C1-C3 alkyl group which may be substituted with one or more halogen atoms, a —C(OR$^{10}$)$_3$ group, a halogen atom, or a hydrogen atom;

$R^5$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom, and $R^6$ is a hydrogen atom;

or N-oxide thereof.

The compound represented by the formula (1), wherein $A^1$ is an oxygen atom;

$A^2$ is a nitrogen atom;

$R^1$ is a C1-C3 alkyl group which may be substituted with one or more halogen atoms;

$R^2$ and $R^4$ are both hydrogen atoms;

$R^3$ is a C1-C3 alkyl group which may be substituted with one or more halogen atoms, a —C(OR$^{10}$)$_3$ group, a halogen atom, or a hydrogen atom;

$R^5$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom, and $R^6$ is a hydrogen atom;

or N-oxide thereof.

The compound represented by the formula (1), wherein $A^1$ is an oxygen atom;

$A^2$ is =N(→O)—;

$R^1$ is a C1-C3 alkyl group which may be substituted with one or more halogen atoms;

$R^2$ and $R^4$ are both hydrogen atoms;

$R^3$ is a C1-C3 alkyl group which may be substituted with one or more halogen atoms, a —C(OR$^{10}$)$_3$ group, a halogen atom, or a hydrogen atom;

$R^5$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom, and $R^6$ is a hydrogen atom (N-oxide).

The compound represented by the formula (1), wherein $A^1$ is an oxygen atom;

$A^2$ is =CR$^8$—;

$R^8$ is a C1-C3 alkoxy group, a C1-C3 alkylsulfanyl group, a halogen atom, or a hydrogen atom;

$R^1$ is a C1-C3 alkyl group which may be substituted with one or more halogen atoms;

$R^2$ and $R^4$ are both hydrogen atoms;

$R^3$ is a C1-C3 alkyl group which may be substituted with one or more halogen atoms, a —C(OR$^{10}$)$_3$ group, a halogen atom, or a hydrogen atom;

$R^5$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom; and $R^6$ is a hydrogen atom;

or N-oxide thereof.

The compound represented by the formula (1-2), wherein $A^{2a}$ is a nitrogen atom; or N-oxide thereof.

The compound represented by the formula (1-2), wherein $A^{2a}$ is =N(→O)—: (N-oxide).

The compound represented by the formula (1-2), wherein $A^{2a}$ is =CR$^{8a}$—; or N-oxide thereof.

The compound represented by the formula (1-2), wherein $A^{2a}$ is =CH—; or N-oxide thereof.

The compound represented by the formula (1-2), wherein $R^{1a}$ is a methyl group; or N-oxide thereof.

The compound represented by the formula (1-2), wherein $R^{1a}$ is an ethyl group; or N-oxide thereof.

The compound represented by the formula (1-2), wherein $R^{1a}$ is a propyl group; or N-oxide thereof.

The compound represented by the formula (1-2), wherein $R^{1a}$ is an isopropyl group; or N-oxide thereof.

The compound represented by the formula (1-2), wherein $R^{3a}$ is a hydrogen atom; or N-oxide thereof.

The compound represented by the formula (1-2), wherein $R^{3a}$ is a trifluoromethyl group; or N-oxide thereof.

The compound represented by the formula (1-2), wherein $R^{5a}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom, and $R^{6a}$ is a hydrogen atom; or N-oxide thereof.

The compound represented by the formula (1-2), wherein $R^{5a}$ is a trifluoromethyl group, and $R^{6a}$ is a hydrogen atom; or N-oxide thereof.

The compound represented by the formula (1-2), wherein $R^{5a}$ is —CF$_2$CF$_3$, and $R^{6a}$ is a hydrogen atom; or N-oxide thereof.

The compound represented by the formula (1-2), wherein $R^{5a}$ is —SCF$_3$, and $R^{6a}$ is a hydrogen atom; or N-oxide thereof.

The compound represented by the formula (1-2), wherein $R^{5a}$ is —S(O)CF$_3$, and $R^{6a}$ is a hydrogen atom; or N-oxide thereof.

The compound represented by the formula (1-2), wherein $R^{5a}$ is —S(O)$_2$CF$_3$, and $R^{6a}$ is a hydrogen atom; or N-oxide thereof.

The compound represented by the formula (1-2), wherein $A^{2a}$ is a nitrogen atom;

$R^{1a}$ is an ethyl group;

$R^{3a}$ is a hydrogen atom;

$R^{5a}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom; and $R^{6a}$ is a hydrogen atom;

or N-oxide thereof.

The compound represented by the formula (1-2), wherein $A^{2a}$ is =N(→O)—;

$R^{1a}$ is an ethyl group;

$R^{3a}$ is a hydrogen atom;

$R^{5a}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom; and $R^{6a}$ is a hydrogen atom: (N-oxide).

The compound represented by the formula (1-2), wherein $A^{2a}$ is =CR$^{8a}$—;

$R^8$ is a C1-C3 alkoxy group, a C1-C3 alkylsulfanyl group, a halogen atom, or a hydrogen atom;

$R^{1a}$ is an ethyl group;

$R^{3a}$ is a hydrogen atom;

$R^{5a}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom; and $R^{6a}$ is a hydrogen atom;

or N-oxide thereof.

The compound represented by the formula (1-2), wherein $A^{2a}$ is a nitrogen atom;

$R^{1a}$ is an ethyl group;

$R^{3a}$ is a trifluoromethyl group;

$R^{5a}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom; and $R^{6a}$ is a hydrogen atom;

or N-oxide thereof.

The compound represented by the formula (1-2), wherein
$A^{2a}$ is =N(→O)—;
$R^{1a}$ is an ethyl group;
$R^{3a}$ is a trifluoromethyl group;
$R^{5a}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom, and
$R^{6a}$ is a hydrogen atom: (N-oxide).

The compound represented by the formula (1-2), wherein
$A^{2a}$ is =$CR^{8a}$—;
$R^8$ is a C1-C3 alkoxy group, a C1-C3 alkylsulfanyl group, a halogen atom, or a hydrogen atom;
$R^{1a}$ is an ethyl group;
$R^{3a}$ is a trifluoromethyl group;
$R^{5a}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom; and
$R^{6a}$ is a hydrogen atom;
or N-oxide thereof.

The compound represented by the formula (1-3), wherein $A^{2b}$ is a nitrogen atom; or N-oxide thereof.

The compound represented by the formula (1-3), wherein $A^{2b}$ is =N(→O)—: (N-oxide).

The compound represented by the formula (1-3), wherein $A^{2b}$ is =$CR^8$—; or N-oxide thereof.

The compound represented by the formula (1-3), wherein $A^{2b}$ is =CH—; or N-oxide thereof.

The compound represented by the formula (1-3), wherein $R^{3b}$ is a hydrogen atom; or N-oxide thereof.

The compound represented by the formula (1-3), wherein $R^{3b}$ is a trifluoromethyl group; or N-oxide thereof.

The compound represented by the formula (1-3), wherein $R^{5b}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom; or N-oxide thereof.

The compound represented by the formula (1-3), wherein $R^{5b}$ is a trifluoromethyl group; or N-oxide thereof.

The compound represented by the formula (1-3), wherein $R^{5b}$ is —$CF_2CF_3$; or N-oxide thereof.

The compound represented by the formula (1-3), wherein $R^{5b}$ is —$SCF_3$; or N-oxide thereof.

The compound represented by the formula (1-3), wherein $R^{5b}$ is —$S(O)CF_3$; or N-oxide thereof.

The compound represented by the formula (1-3), wherein $R^{5b}$ is —$S(O)_2CF_3$; or N-oxide thereof.

The compound represented by the formula (1-3), wherein
$A^{2b}$ is a nitrogen atom;
$R^{3b}$ is a hydrogen atom;
$R^{5b}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom;
or N-oxide thereof.

The compound represented by the formula (1-3), wherein
$A^{2b}$ is =N(→O)—;
$R^{3b}$ is a hydrogen atom; and
$R^{5b}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom: (N-oxide).

The compound represented by the formula (1-3), wherein
$A^{2b}$ is =$CR^{8b}$—;
$R^8$ is a C1-C3 alkoxy group, a C1-C3 alkylsulfanyl group, a halogen atom, or a hydrogen atom;
$R^{3b}$ is a hydrogen atom;
$R^{5b}$ a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom;
or N-oxide thereof.

The compound represented by the formula (1-3), wherein
$A^{2b}$ is a nitrogen atom;
$R^{3b}$ is a trifluoromethyl group;
$R^{5b}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom; or N-oxide thereof.

The compound represented by the formula (1-3), wherein
$A^{2b}$ is =N(→O)—;
$R^{3b}$ is a trifluoromethyl group;
$R^{5b}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom (N-oxide).

The compound represented by the formula (1-3), wherein
$A^{2b}$ is =$CR^{8b}$—;
$R^8$ is a C1-C3 alkoxy group, a C1-C3 alkylsulfanyl group, a halogen atom, or a hydrogen atom;
$R^{3b}$ is a trifluoromethyl group;
$R^{5b}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom;
or N-oxide thereof.

The compound represented by the formula (1-4), wherein $A^{2c}$ is a nitrogen atom; or N-oxide thereof.

The compound represented by the formula (1-4), wherein $A^{2c}$ is =N(=O)—: (N-oxide).

The compound represented by the formula (1-4), wherein $A^{2c}$ is =$CR^{8c}$—; or N-oxide thereof.

The compound represented by the formula (1-4), wherein $A^{2c}$ is =CH—; or N-oxide thereof.

The compound represented by the formula (1-4), wherein $R^{3c}$ is a hydrogen atom; or N-oxide thereof.

The compound represented by the formula (1-4), wherein $R^{3c}$ is a trifluoromethyl group; or N-oxide thereof.

The compound represented by the formula (1-4), wherein $R^{5c}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom, and $R^6c$ is a hydrogen atom; or N-oxide thereof.

The compound represented by the formula (1-4), wherein $R^{5c}$ is a trifluoromethyl group; or N-oxide thereof.

The compound represented by the formula (1-4), wherein $R^{5c}$ is —$CF_2CF_3$; or N-oxide thereof.

The compound represented by the formula (1-4), wherein $R^{5c}$ is —$SCF_3$; or N-oxide thereof.

The compound represented by the formula (1-4), wherein $R^{5c}$ is —$S(O)CF_3$; or N-oxide thereof.

The compound represented by the formula (1-4), wherein $R^{5c}$ is —$S(O)_2CF_3$, or N-oxide thereof.

The compound represented by the formula (1-4), wherein
$A^{2c}$ is a nitrogen atom;
$R^{3c}$ is a hydrogen atom;

$R^{5c}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom;
or N-oxide thereof.

The compound represented by the formula (1-4), wherein
$A^{2c}$ is =N(O)—;
$R^{3c}$ is a hydrogen atom; and
$R^{5c}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom: (N-oxide).

The compound represented by the formula (1-4), wherein
$A^{2c}$ is =$CR^{8c}$—;
$R^8$ is a C1-C3 alkoxy group, C1-C3 alkylsulfanyl group, a halogen atom, or a hydrogen atom;
$R^{3c}$ is a hydrogen atom;
$R^{5c}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom;
or N-oxide thereof.

The compound represented by the formula (1-4), wherein
$A^{2c}$ is a nitrogen atom;
$R^{3c}$ is a trifluoromethyl group; and
$R^{5c}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom;
or N-oxide thereof.

The compound represented by the formula (1-4), wherein
$A^{2c}$ is =N(→O)—;
$R^{3c}$ is a trifluoromethyl group; and
$R^{5c}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom: (N-oxide).

The compound represented by the formula (1-4), wherein
$A^{2c}$ is =$CR^{8c}$—;
$R^8$ is a C1-C3 alkoxy group, a C1-C3 alkylsulfanyl group, a halogen atom, or a hydrogen atom;
$R^{3c}$ is a trifluoromethyl group; and
$R^{5c}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom;
or N-oxide thereof.

Next, a process for preparing the present fused heterocyclic compound is explained.

The present fused heterocyclic compound and intermediate compounds can be prepared, for example, according to the below-mentioned (Process 1) to (Process 24).

(Process 1)

A present fused heterocyclic compound of formula (1) wherein n is 1 or 2 can be prepared by oxidizing a present fused heterocyclic compound of formula (1) wherein n is 0.

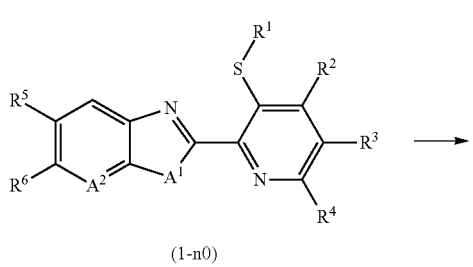

(1-n0)

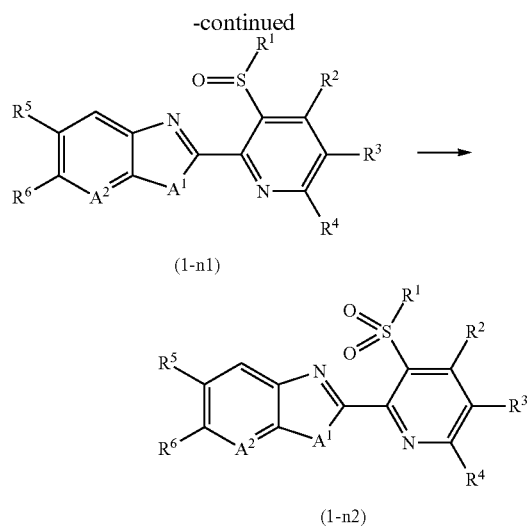

(1-n1)

(1-n2)

[wherein, each symbol is the same as defined in formula (1)]

A present fused heterocyclic compound of formula (1-n1) (when n is 1 in the formula (1)) can be prepared by oxidizing a present fused heterocyclic compound (1-n0) (when n is 0 in the formula (1)) with an oxidizing agent.

The reaction is usually carried out in the presence of a solvent.

Examples of the solvent to be used in the reaction include aliphatic hydrogenated hydrocarbons such as dichloromethane and chloroform; alcohols such as methanol and ethanol; acetic acid; water; and mixed solvents thereof.

Examples of the oxidizing agent to be used include sodium periodate and m-chloroperoxybenzoic acid.

In the reaction, the oxidizing agent is used usually within a range of 1 to 3 molar ratio(s) as opposed to 1 mole of the present fused heterocyclic compound (1-n0). Preferably, the oxidizing agent is used within a range of 1 to 1.2 molar ratio(s) as opposed to 1 mole of the present fused heterocyclic compound (1-n0).

The reaction temperature is usually within a range of −20 to 80° C. The reaction period of the reaction is usually within a range of 0.1 to 12 hours.

When the reaction is completed, the reaction mixtures are extracted with organic solvent(s), and the resulting organic layers are, if necessary, worked up (for example, washing with an aqueous solution of a reducing agent (such as sodium sulfite and sodium thiosulfate) and/or an aqueous solution of a base (such as sodium hydrogen carbonate), drying and concentration) to isolate the present fused heterocyclic compound (1-n1). The isolated present fused heterocyclic compound (1-n1) may be further purified, for example, by chromatography and recrystallization.

A present fused heterocyclic compound of formula (1-n2) (when n is 2 in the formula (1)) can be prepared by oxidizing the present fused heterocyclic compound of formula (1-n1) (when n is 1 in the formula (1)).

The reaction is usually carried out in the presence of a solvent.

Examples of the solvent to be used in the reaction include aliphatic hydrogenated hydrocarbons such as dichloromethane and chloroform; alcohols such as methanol and ethanol; acids such as acetic acid; water; and mixed solvents thereof.

Examples of the oxidizing agent to be used include m-chloroperoxybenzoic acid and hydrogen peroxide.

In the reaction, the oxidizing agent is used usually within a range of 1 to 4 molar ratio(s) as opposed to 1 mole of the present fused heterocyclic compound (1-n1). Preferably, the oxidizing agent is used within a range of 1 to 2 molar ratio(s) as opposed to 1 mole of the present fused heterocyclic compound (1-n1).

The reaction temperature is usually within a range of −20 to 120° C. The reaction period of the reaction is usually within a range of 0.1 to 12 hours.

When the reaction is completed, the reaction mixtures are extracted with organic solvent(s), and the resulting organic layers are, if necessary, worked up (for example, washing with an aqueous solution of a reducing agent (such as sodium sulfite and sodium thiosulfate), an aqueous solution of a base (such as sodium hydrogen carbonate), drying and concentration) to isolate the present fused heterocyclic compound (1-n2). The isolated present fused heterocyclic compound (1-n2) may be further purified, for example, by chromatography and recrystallization.

Also, the present fused heterocyclic compound of formula (1-n2) (when n is 2 in the formula (1)) can be prepared by oxidizing the present fused heterocyclic compound (1-n0) (when n is 0 in the formula (1)) with an oxidizing agent in one step (one-pot).

The reaction is usually carried out in the presence of a solvent.

Examples of the solvent to be used in the reaction include aliphatic hydrogenated hydrocarbons such as dichloromethane and chloroform; alcohols such as methanol and ethanol; acids such as acetic acid; water; and mixed solvents thereof.

Examples of the oxidizing agent to be used include m-chloroperoxybenzoic acid and hydrogen peroxide.

The reaction may be also carried out, if necessary, in the presence of a catalyst.

Examples of the catalyst to be used include sodium tungstate.

In the reaction, the oxidizing agent is used usually within a range of 2 to 5 molar ratio(s), and the catalyst is used usually within a range of 0.01 to 0.5 molar ratio(s), as opposed to 1 mole of the present fused heterocyclic compound (1-n0). Preferably, the oxidizing agent is used usually within a range of 2 to 3 molar ratio(s), and the catalyst is used usually within a range of 0.01 to 0.5 molar ratio(s), as opposed to 1 mole of the present fused heterocyclic compound (1-n0).

The reaction temperature is usually within a range of 0 to 120° C. The reaction period of the reaction is usually within a range of 0.1 to 12 hours.

When the reaction is completed, the reaction mixtures are extracted with organic solvent(s), and the resulting organic layers are, if necessary, worked up (for example, washing with an aqueous solution of a reducing agent (such as sodium sulfite and sodium thiosulfate) and/or an aqueous solution of a base (such as sodium hydrogen carbonate), drying and concentration) to isolate the present fused heterocyclic compound (1-n2). The isolated present fused heterocyclic compound (1-n2) may be further purified, for example, by chromatography and recrystallization.

(Process 2)

A present fused heterocyclic compound can be prepared by reacting an intermediate compound (M1) with an intermediate compound (M2) or an intermediate compound (M18) to afford an intermediate compound (M3), followed by performing an intermolecular condensation of the obtained intermediate compound (M3). In this reaction, a production of the intermediate compound (M3) and an intermolecular condensation thereon may be occurred concurrently, resulting in no confirmation of the intermediate compound (M3).

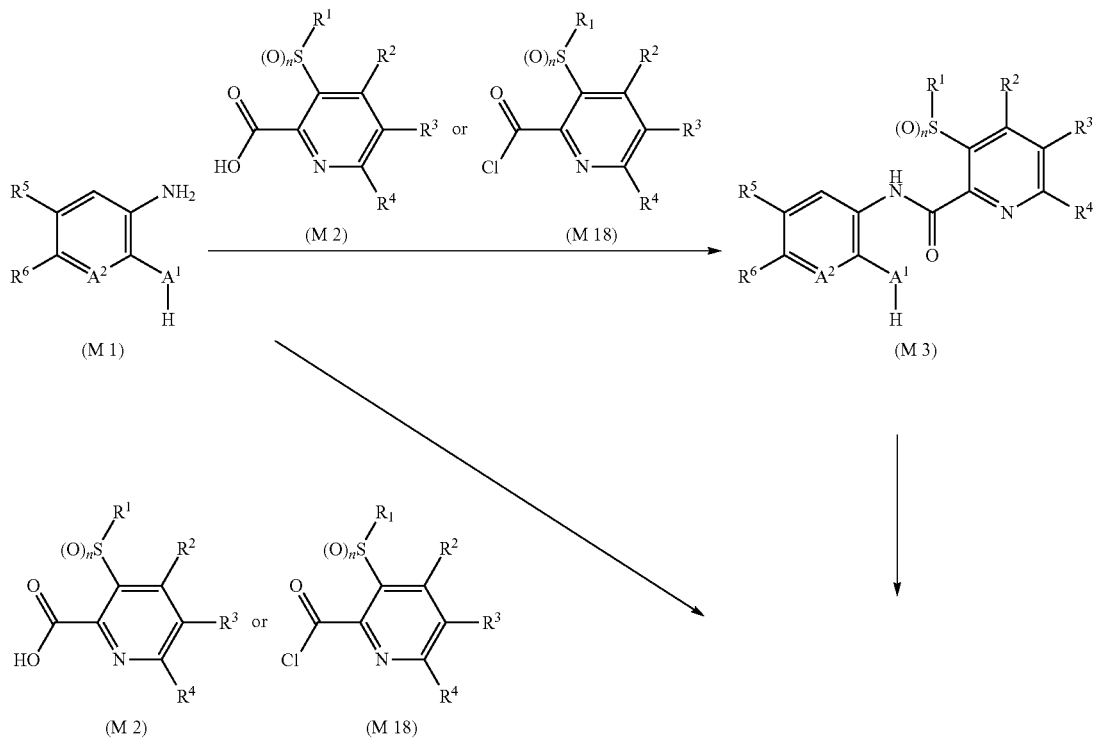

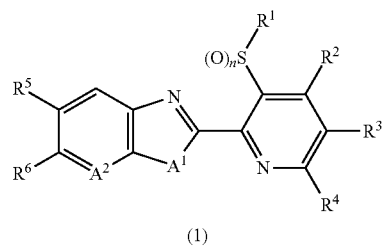

(1)

[wherein, each symbol is the same as defined in the formula (1)]

The intermediate compound (M3) may be prepared by reacting the intermediate compound (M1) with the intermediate compound (M2) in the presence of a condensation agent.

This reaction is usually carried out in the presence of a solvent. Examples of the solvent to be used in the reaction include ethers such as 1,4-dioxane, diethyl ether, tetrahydrofuran (hereinafter, sometimes referred to as THF) and methyl tert-butyl ether; halogenated hydrocarbons such as dichloromethane, chloroform, carbon tetrachloride, 1,2-dichloroethane, chlorobenzene; aromatic hydrocarbons such as toluene, benzene and xylene; esters such as ethyl acetate and butyl acetate; nitriles such as acetonitrile; aprotic polar solvents such as N,N-dimethylformamide (hereinafter, sometimes referred to as DMF), N-methylpyrrolidone (hereinafter, sometimes referred to as NMP), 1,3-dimethyl-2-imidazolidinone and dimethyl sulfoxide (hereinafter, sometimes referred to as DMSO); and nitrogen-containing aromatic compounds such as pyridine and quinoline; and mixed solvents thereof.

The condensation agent to be used include 1-ethyl-3-(3-dimethylaminopropyl)carbodiimide hydrochloride (hereinafter, sometimes referred to as EDC hydrochloride), 1,3-dicyclohexylcarbodiimide. The reaction may be also carried out, if necessary, in the presence of a catalyst.

Examples of the catalyst to be used include 1-hydroxybenzotriazole (hereinafter, sometimes referred to as HOBt).

In the reaction, the intermediate compound (M2) is used usually within a range of 0.5 to 2 molar ratio(s), the condensation agent is used usually within a range of 1 to 5 molar ratio(s), and the catalyst is used usually within a range of 0.01 to 1 molar ratio(s), as opposed to 1 mole of the intermediate compound (M1).

The reaction temperature is usually within a range of 0 to 120° C. The reaction period of the reaction is usually within a range of 0.1 to 24 hours.

When the reaction is completed, the reaction mixtures are added into water and are then extracted with organic solvent(s), and the resulting organic layers are concentrated; the reaction mixtures are added into water and the resulting solids are collected by filtration; or the solids formed in the reaction mixtures are collected by filtration, to isolate the intermediate compound (M3). The isolated intermediate compound (M3) may be further purified, for example, by recrystallization and chromatography.

Also, the intermediate compound (M3) may be prepared by reacting the intermediate compound (M1) with the intermediate compound (M18).

This reaction is usually carried out in the presence of a solvent.

Examples of the solvent to be used in the reaction include ethers such as THF, ethyleneglycol dimethyl ether, methyl tert-butyl ether and 1,4-dioxane; aliphatic hydrocarbons such as hexane, heptane and octane; aromatic hydrocarbons such as toluene and xylene; halogenated hydrocarbons such as chlorobenzene; esters such as ethyl acetate and butyl acetate; nitriles such as acetonitrile; aprotic polar solvents such as DMF, NMP and DMSO; and mixed solvents thereof.

The reaction may be also carried out, if necessary, in the presence of a base.

Examples of the base to be used include alkali metal carbonates such as sodium carbonate and potassium carbonate; tertiary amines such as triethylamine and N,N-diisopropylethylamine; and nitrogen-containing aromatic compounds such as pyridine and 4-dimethylaminopyridine.

In the reaction, the intermediate compound (M18) is used usually within a range of 1 to 3 molar ratio(s), and the base is used usually within a range of 1 to 10 molar ratio(s), as opposed to 1 mole of the intermediate compound (M1).

The reaction temperature is usually within a range of −20 to 100° C. The reaction period of the reaction is usually within a range of 0.1 to 24 hours.

When the reaction is completed, the reaction mixtures are added into water and are extracted with organic solvent(s), and the resulting organic layers are, if necessary, worked up (for example, drying and concentration) to isolate the intermediate compound (M3). The intermediate compound (M3) may be further purified, for example, by chromatography and recrystallization.

The present fused heterocyclic compound (1) can be prepared by performing an intermolecular condensation of the intermediate compound (M3).

The reaction is usually carried out in the presence of a solvent. Examples of the solvent to be used in the reaction include ethers such as 1,4-dioxane, diethyl ether, THF and methyl tert-butyl ether; halogenated hydrocarbons such as dichloromethane, chloroform, carbon tetrachloride, 1,2-dichloroethane and chlorobenzene; aromatic hydrocarbons such as toluene, benzene and xylene; esters such as ethyl acetate and butyl acetate; nitriles such as acetonitrile; aprotic polar solvent such as DMF, NMP, 1,3-dimethyl-2-imidazolidinone and DMSO; nitrogen-containing aromatic compounds such as pyridine and quinoline; and mixed solvents thereof.

In the reaction, if necessary, a condensation agent, an acid, a base or a chlorinating agent may be used.

Examples of the condensation agent to be used include acid anhydrides such as acetic anhydride, trifluoroacetic anhydride; EDC hydrochloride; a mixture of triphenylphosphine, base and carbon tetrachloride or carbon tetrabromide; and a mixture of triphenylphosphine and azodiesters such as diethyl azodicarboxylate.

Examples of the acid to be used include sulfonic acids such as para-toluenesulfonic acid; carboxylic acids such as acetic acid; and polyphosphoric acid.

Examples of the base to be used include pyridine, picoline, 2,6-lutidine and 1,8-diazabicyclo[5.4.0]-7-undecene (hereinafter, sometimes referred to as DEU), nitrogen-containing heterocyclic compounds such as 1,5-diazabicyclo[4.3.0]-5-nonene; tertiary amines such as triethylamine and N,N-diisopropylethylamine; and inorganic bases such as tripotassium phosphate, potassium carbonate and sodium hydride.

Examples of the chlorinating to be used include phosphorus oxychloride.

In the reaction, when a condensation agent is used, the condensation agent is used usually within a range of 1 to 5 molar ratio(s), and when an acid is used, the acid is used usually within a range of 0.1 to 5 molar ratio(s), and when a base is used, the base is used usually within a range of 1 to 5 molar ratio(s), and when a chlorinating agent is used, the chlorinating agent is used usually within a range of 1 to 5 molar ratio(s), as opposed to 1 mole of the intermediate compound (M3).

The reaction temperature is usually within a range of 0 to 200° C. The reaction period of the reaction is usually within a range of 0.1 to 24 hours.

When the reaction is completed, the reaction mixtures are added into water and are then extracted with organic solvent(s), and the resulting organic layers are concentrated; the reaction mixtures are added into water and the resulting solids are collected by filtration; or the solids formed in the reaction mixture are collected by filtration, to afford the present fused heterocyclic compound (1). The isolated the present fused heterocyclic compound (1) may be further purified, for example, by recrystallization and chromatography.

The present fused heterocyclic compound (1) may be prepared in one step (one-pot) by reacting the intermediate compound (M1) with the intermediate compound (M2) in the presence of a condensation agent.

This reaction is usually carried out in the presence of a solvent.

Examples of the solvent to be used in the reaction include ethers such as 1,4-dioxane, diethyl ether, THF, methyl tert-butyl ether; halogenated hydrocarbons such as dichloromethane, chloroform, carbon tetrachloride, 1,2-dichloroethane and chlorobenzene; aromatic hydrocarbons such as toluene, benzene, xylene; esters such as ethyl acetate and butyl acetate; nitriles such as acetonitrile; aprotic polar solvent such as DMF, NMP, 1,3-dimethyl-2-imidazolidinone and DMSO; nitrogen-containing aromatic compounds such as pyridine and quinoline; and mixed solvents thereof.

Examples of the condensation agent to be used include carbodiimides such as EDC hydrochloride and 1,3-dicyclohexylcarbodiimide.

The reaction may be carried out, if necessary, in the presence of a catalyst.

Examples of the catalyst to be used include 1-hydroxybenzotriazole.

In the reaction, the intermediate compound (M2) is used usually within a range of 0.5 to 2 molar ratio(s), the condensation agent is used usually within a range of 1 to 5 molar ratio(s) and the catalyst is used usually within a range of 0.01 to 1 molar ratio(s), as opposed to 1 mole of the intermediate compound (M1).

The reaction temperature is usually within a range of 0 to 200° C. The reaction period of the reaction is usually within a range of 0.1 to 24 hours.

When the reaction is completed, the reaction mixtures are added into water and are then extracted with organic solvent(s), and the resulting organic layers are concentrated; the reaction mixtures are added into water and the resulting solids are collected by filtration; or the solids formed in the reaction mixture are collected by filtration, to isolate the present fused heterocyclic compound (1). The isolated present fused heterocyclic compound (1) may be further purified, for example, by recrystallization and chromatography.

Also, the present fused heterocyclic compound (1) can be prepared in one step (one-pot) by reacting the intermediate compound (M1) with the intermediate compound (M18).

The reaction is usually carried out in the presence or absence of a solvent.

Examples of the solvent to be used in the reaction include ethers such as THF, ethyleneglycol dimethyl ether, methyl text-butyl ether and 1,4-dioxane; aliphatic hydrocarbons such as hexane, heptane and octane; aromatic hydrocarbons such as toluene and xylene; halogenated hydrocarbons such as chlorobenzene; esters such as ethyl acetate and butyl acetate; nitriles such as acetonitrile; aprotic polar solvents such as DMF, NMP and DMSO; and mixed solvents thereof.

The reaction may be also carried out, if necessary, in the presence of a base.

Examples of the base to be used include alkali metal carbonates such as sodium carbonate and potassium carbonate; tertiary amines such as triethylamine and N,N-diisopropylethylamine; and nitrogen-containing aromatic compounds such as pyridine and 4-dimethylaminopyridine.

In the reaction, the intermediate compound (M18) is used usually within a range of 1 to 3 molar ratio(s), and the base is usually within a range of 1 to 10 molar ratio(s), as opposed to 1 mole of the intermediate compound (M1).

The reaction temperature is usually within a range of to 200° C. The reaction period of the reaction is usually within a range of 0.1 to 24 hours.

When the reaction is completed, the reaction mixtures are added into water and are extracted with organic solvent(s), and the resulting organic layers are, if necessary, worked up (for example, drying and concentration) to isolate the present fused heterocyclic compound (1). The isolated present fused heterocyclic compound (1) may be further purified, for example, by chromatography and recrystallization.

(Process 3)

A present fused heterocyclic compound of formula (P20) (when represents a sulfur atom and $A^2$ represents a nitrogen atom in the formula (1)) can be prepared by reacting an intermediate compound (M9) with an intermediate compound (M2) or an intermediate compound (M18) to afford an intermediate compound (M14), followed by reacting the obtained intermediate compound (M14) with a sulfuring agent.

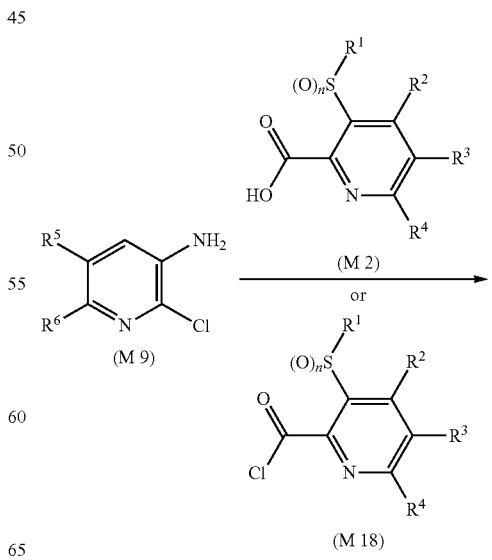

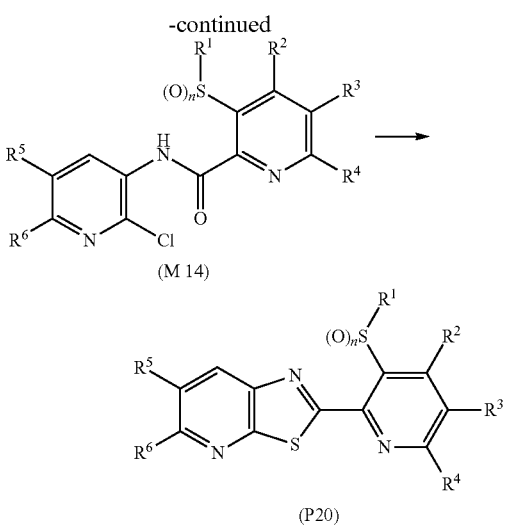

[wherein, each symbol is the same as defined in the formula (1)]

The intermediate compound (M14) can be prepared by reacting the intermediate compound (M9) with the intermediate compound (M2) in the presence of a condensation agent.

The reaction is carried out usually in the presence or absence of a solvent.

Examples of the solvent to be used in the reaction include ethers such as THF, ethyleneglycol dimethyl ether, methyl text-butyl ether and 1,4-dioxane; aliphatic hydrocarbons such as hexane, heptane and octane; aromatic hydrocarbons such as toluene and xylene; halogenated hydrocarbons such as chlorobenzene; esters such as ethyl acetate and butyl acetate; nitriles such as acetonitrile; aprotic polar solvents such as DMF, NMP and DMSO; nitrogen-containing aromatic compounds such as pyridine and quinoline; and mixed solvents thereof.

Examples of the condensation agent to be used include carbodiimides such as EDC hydrochloride and 1,3-dicyclohexylcarbodiimide, and BOP reagent (for example, benzotriazol-1-yloxy-trisdimetylamino phosphonium).

In the reaction, the intermediate compound (M2) is used usually within a range of 1 to 3 molar ratio(s) and the condensation agent is used usually within a range of to 5 molar ratio(s), as opposed to 1 mole of the intermediate compound (M9).

The reaction temperature is usually within a range of 0 to 200° C. The reaction period of the reaction is usually within a range of 0.1 to 24 hours.

When the reaction is completed, the reaction mixtures are added into water and are extracted with organic solvent(s), and the resulting organic layers are, if necessary, worked up (for example, drying and concentration) to isolate the intermediate compound (M14). The isolated intermediate compound (M14) may be further purified, for example, by chromatography and recrystallization.

Also, the intermediate compound (M14) can be prepared by reacting the intermediate compound (M9) with the intermediate compound (M18).

The reaction is carried out usually in the presence or absence of a solvent. If necessary, the reaction may be also carried out in the presence of a base.

Examples of the solvent to be used in the reaction include ethers such as THF, ethyleneglycol dimethyl ether, methyl tert-butyl ether and 1,4-dioxane, aliphatic hydrocarbons such as hexane, heptane and octane; aromatic hydrocarbons such as toluene and xylene; halogenated hydrocarbons such as chlorobenzene, esters such as ethyl acetate and butyl acetate; nitriles such as acetonitrile; aprotic polar solvents such as DMF, NMP and DMSO; nitrogen-containing aromatic compounds such as pyridine and quinoline; and mixed solvents thereof.

Examples of the base to be used include alkali metal carbonates such as sodium carbonate and potassium carbonate; tertiary amines such as triethylamine and N,N-diisopropylethylamine; and nitrogen-containing aromatic compounds such as pyridine and 4-dimethylaminopyridine. In the reaction, the intermediate compound (M18) is used usually within a range of 1 to 3 molar ratio(s), and the base is used usually within a range of 1 to 5 molar ratio(s), as opposed to 1 mole of the intermediate compound (M9).

The reaction temperature is usually within a range of 0 to 200° C. The reaction period of the reaction is usually within a range of 0.1 to 24 hours.

When the reaction is completed, the reaction mixtures are added into water and are extracted with organic solvent(s), and the resulting organic layers are, if necessary, worked up (for example, drying and concentration) to isolate the intermediate compound (M14).

The isolated intermediate compound (M14) may be further purified, for example, by chromatography and recrystallization.

The present fused heterocyclic compound (P20) can be prepared by reacting the intermediate compound (14) with a sulfurizing agent.

The reaction is carried out in the presence or absence of a solvent.

Examples of the solvent to be used in the reaction include ethers such as 1,4-dioxane, diethyl ether, tetrahydrofuran, methyl tert-butyl ether and diglyme; halogenated hydrocarbons such as dichloromethane, chloroform, carbon tetrachloride, 1,2-dichloroethane and chlorobenzene; aromatic hydrocarbons such as toluene, benzene and xylene; nitriles such as acetonitrile; nitrogen-containing aromatic compounds such as pyridine, picoline, lutidine and quinoline; and mixed solvents thereof.

Examples of the sulfurizing agent to be used include phosphorus pentasulfide and Lawesson's reagent (2,4-bis-(4-methoxyphenyl)-1,3-dithia-2,4-diphosphetane-2,4-disulfide).

In the reaction, the sulfurizing agent is used usually within a range of 1 to 3 molar ratio(s) as opposed to 1 mole of the intermediate compound (M14).

The reaction temperature is usually within a range of 0 to 200° C. The reaction period of the reaction is usually within a range of 1 to 24 hours.

When the reaction is completed, the reaction mixtures are added into water and are then extracted with organic solvent(s), and the resulting organic layers are concentrated; the reaction mixtures are added into water and the resulting solids are collected by filtration; or the solids formed in the reaction mixture are collected by filtration, to isolate the present fused heterocyclic compound (P20). The isolated present heterocyclic compound (P20) may be further purified, for example, by recrystallization and chromatography.
(Process 4)

A present fused heterocyclic compound can be prepared by reacting an intermediate compound (M1) with an intermediate compound (M4) in the presence of an oxidizing agent.

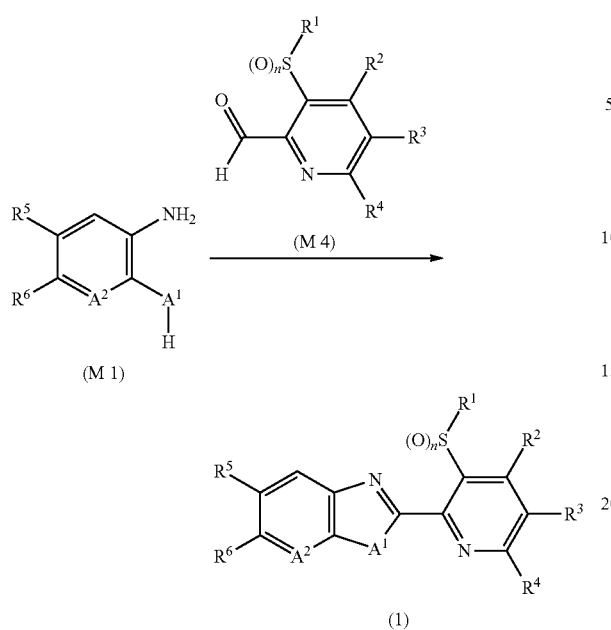

[wherein, each symbol is the same as defined in the formula (1)]

This reaction is usually carried out in the presence of a solvent.

Examples of the solvent to be used in the reaction include alcohols such as methanol and ethanol; ethers such as 1,4-dioxane, diethyl ether, THF and methyl Pert-butyl ether; halogenated hydrocarbons such as dichloromethane, chloroform, carbon tetrachloride, 1,2-dichloroethane and chlorobenzene; aromatic hydrocarbons such as toluene, benzene and xylene; esters such as ethyl acetate and butyl acetate; nitriles such as acetonitrile; aprotic polar solvent such as DMF, NMP, 1,3-dimethyl-2-imidazolidinone and DMSO; nitrogen-containing aromatic compounds such as pyridine and quinoline; and mixed solvents thereof.

The reaction may be also carried out, for necessary, in the presence of an acid.

Examples of the acid to be used in the reaction include sulfonic acids such as paratoluenesulfonic acid; carboxylic acids such as acetic acid; and polyphosphoric acid.

The reaction may be also carried out, if necessary, in the presence of a sulfite.

Examples of the sulfite to be used in the reaction include sulfites such as sodium hydrogen sulfite and sodium bisulfite.

Examples of the oxidizing agent to be used include oxygen (for example, molecular oxygen), copper chloride (II) and DDQ.

In the reaction, the intermediate compound (M4) is used usually within a range of 1 to 2 molar ratio(s), the acid is used usually within a range of 0.1 to 2 molar ratio(s), the sulfites is used usually within a range of 1 to 5 molar ratio(s), and the oxidizing agent is used usually within a range of 1 to 5 molar ratio(s), as opposed to one mole of the intermediate compound (M1).

The reaction temperature is usually within a range of 0 to 200° C. The reaction period of the reaction is usually within a range of 1 to 24 hours.

When the reaction is completed, the reaction mixtures are added into water and are then extracted with organic solvent(s), and the resulting organic layers are concentrated; the reaction mixtures are added into water and the resulting solids are collected by filtration; or the solids formed in the reaction mixture are collected by filtration, to isolate the present fused heterocyclic compound (1). The isolated present heterocyclic compound (1) may be further purified, for example, by recrystallization and chromatography.

(Process 5)

A present fused heterocyclic compound (1) (when n is 0 in the formula (1)) can be prepared by reacting an intermediate compound (M6) with a compound (M7) in the presence of a base.

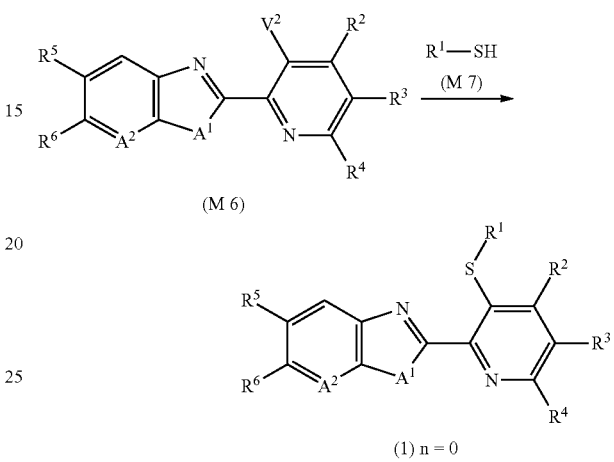

[wherein, $V^2$ represents a halogen atom, and the other symbols are the same as defined in the formula (1)]

This reaction is usually carried out in the presence of a solvent.

Examples of the solvent to be used in the reaction include ethers such as THF, ethyleneglycol dimethyl ether, methyl tert-butyl ether and 1,4-dioxane; aromatic hydrocarbons such as toluene and xylene; nitriles such as acetonitrile; aprotic polar solvents such as DMF, NMP and DMSO; water; and mixed solvents thereof.

Examples of the base to be used include alkali metal carbonates such as sodium carbonate and potassium carbonate; and alkali metal hydrides such as sodium hydride.

In the reaction, the compound (M7) is used usually within a range of 1 to 10 molar ratio(s), and the base is used usually within a range of 1 to 10 molar ratio(s), as opposed to 1 mole of the intermediate compound (M6).

The reaction temperature is usually within a range of 0 to 150° C. The reaction period of the reaction is usually within a range of 0.5 to 24 hours.

When the reaction is completed, the reaction mixtures are extracted with organic solvent(s), and the resulting organic layers are worked up (for example, drying and concentration) to isolate the present fused heterocyclic compound (1) (when n is 0 in the formula (1)). The isolated present fused heterocyclic compound (1) (when n is 0 in the formula (1)) may be further purified, for example, by chromatography and recrystallization.

In the reaction, $V^2$ is preferably a fluorine atom and a chlorine atom.

(Process 6)

An intermediate compound (M6) can be prepared by reacting an intermediate compound (M1) with an intermediate compound (M19) or an intermediate compound (M39) to afford an intermediate compound (M20), followed by performing an intermolecular condensation of the obtained intermediate compound (M20). In this reaction, a production of the intermediate compound (M20) and an intermolecular condensation thereon may be occurred concurrently, resulting in no confirmation of the intermediate compound (M20).

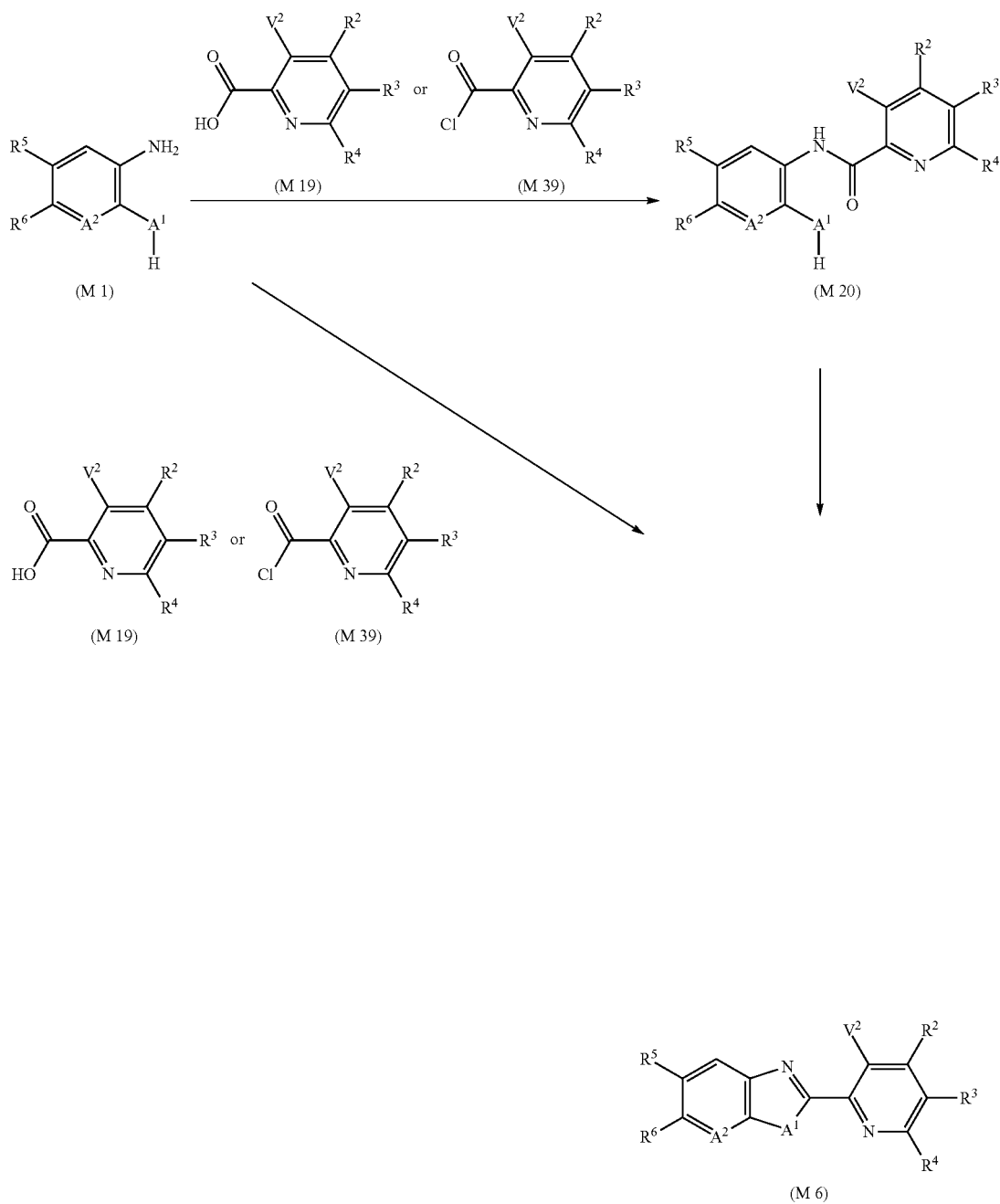

[wherein, $V^2$ represents a halogen atom, and the other each symbol is the same as defined in the formula (1)]

The intermediate compound (M20) can be prepared by using the intermediate compound (M19) instead of the intermediate compound (M2) according to Process 2.

The intermediate compound (M20) can be prepared by using the intermediate compound (M39) instead of the intermediate compound (M18) according to Process 2.

The intermediate compound (M6) can be prepared by using the intermediate compound (M20) instead of the intermediate compound (M3) according to Process 2.

Also, the intermediate compound (M6) can be prepared by using the intermediate compound (M19) instead of the intermediate compound (M2) according to Process 2 in one step (one-pot).

Also, the intermediate compound (M6) can be also prepared by using the intermediate compound (M39) instead of the intermediate compound (M2) according to Process 2 in one step (one-pot).

In the reaction, $V^2$ represents preferably a fluorine atom or a chlorine atom.

(Process 7)

An intermediate compound (M3) (when n is 0 in the formula (M3)) can be prepared by reacting an intermediate compound (M20) with a compound (M7). Also, the obtained intermediate compound (M3) can be performed on intermolecular condensation to afford a present fused heterocyclic compound (1) (when n is 0 in the formula (1)).

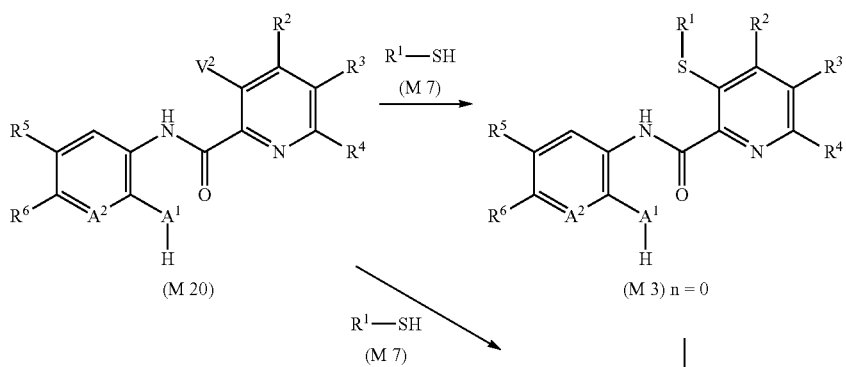

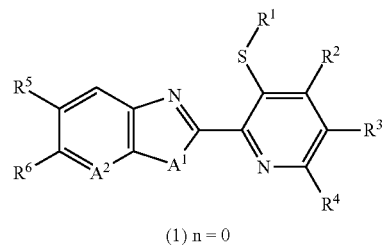

[wherein, $V^2$ represents a halogen atom, and the other each symbol is the same as defined in the formula (1)]

The intermediate compound (M3) (when n is 0 in the formula (M3)) can be prepared by using the intermediate compound (M20) instead of the intermediate compound of formula (M6) according to Process 5.

The present fused heterocyclic compound (1) (when n is in the formula (1)) can be prepared by using the intermediate compound (M3) (when n is 0 in the formula (M3)) instead of the intermediate compound (M3) according to Process 2.

Also, the present fused heterocyclic compound (1) (when n is 0 in the formula (1)) can be also prepared by using the intermediate compound (M20) instead of the intermediate compound (M6) according to Process 5 in one step (one-pot).

In the reaction, $V^2$ represents preferably a fluorine atom or a chlorine atom.

(Process 8)

A present fused heterocyclic compound (1) (when n is 0 in the formula (1)) can be prepared by reacting an intermediate compound (M8) or a disulfide compound thereof, that is, an intermediate compound (M8') with a compound (M17) in the presence of a base.

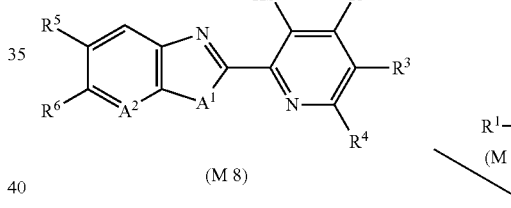

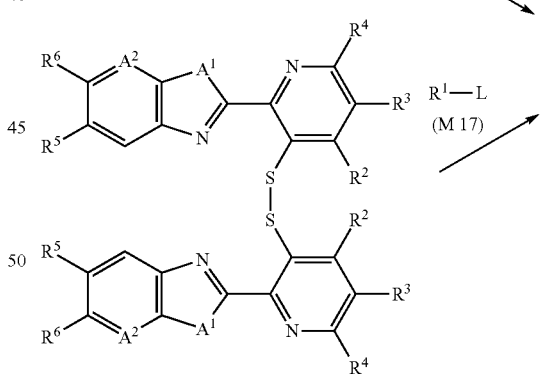

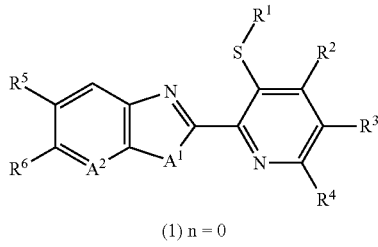

[wherein, L represents a leaving group such as a chlorine atom, a bromine atom, an iodine atom, a trifluoromethanesulfonyloxy group or a methanesulfonyloxy group, and the other each symbol is the same as defined in the formula (1)]

This reaction is usually carried out in the presence of a solvent.

Examples of the solvent to be used in the reaction include ethers such as THF, ethyleneglycol dimethyl ether, methyl tert-butyl ether and 1,4-dioxane; aromatic hydrocarbons such as toluene and xylene; nitriles such as acetonitrile; aprotic polar solvents such as DMF, NMP and DMSO; and mixed solvents thereof.

Examples of the base to be used include an alkali metal or alkaline-earth metal hydrides such as sodium hydride, potassium hydride and calcium hydride; inorganic bases such as sodium carbonate and potassium carbonate; and organic bases such as triethylamine.

When the intermediate compound (M8') being the disulfide compound is used, the reaction is usually carried out in the presence of a reducing agent.

Examples of the reducing agent to be used in the reaction include hydroxymethanesulfinic acid sodium salt (Trade name: Rongalite).

In the reaction, the compound (M17) is used usually within a range of 1 to 10 molar ratio(s), and the base is used usually within a range of 1 to 10 molar ratio(s), as opposed to 1 mole of the intermediate compound (M8). Also, when the intermediate compound (M8') being the disulfide compound is used, the compound (M17) is used usually within a range of 2 to 10 molar ratio(s), the base is used usually within a range of 2 to 10 molar ratio(s), and the reducing agent is used usually within a range of 1 to 5 molar ratio(s), as opposed to 1 mole of the intermediate compound (M8').

The reaction temperature is usually within a range of 0 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present fused heterocyclic compound (1) (when n is 0 in the formula (1)). The isolated present fused heterocyclic compound (1) (when n is 0 in the formula (1)) may be further purified, for example, by chromatography and recrystallization.

(Process 9)

A present fused heterocyclic compound (1) (when n is 0 in the formula (1)) can be prepared by reacting an intermediate compound (M8') with a compound (M17'-1) or a compound (M17'-2).

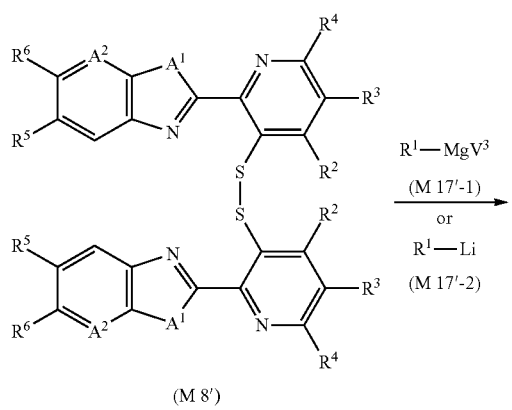

(M 8')

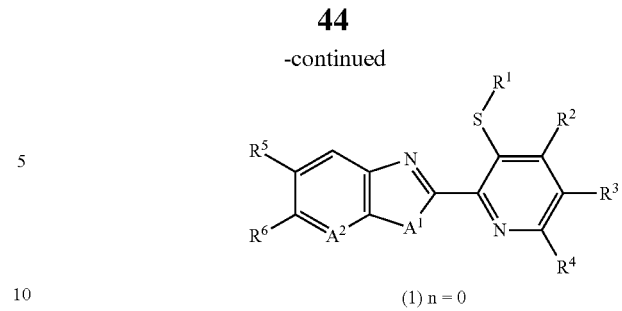

(1) n = 0

[wherein, $V^3$ represents a chlorine atom, a bromine atom or an iodine atom; and the other each symbol is the same as defined in the formula (1)]

This reaction is usually carried out in the presence of a solvent.

Examples of the solvent to be used in the reaction include ethers such as THF, ethyleneglycol dimethyl ether, methyl tert-butyl ether and 1,4-dioxane; aromatic hydrocarbons such as toluene and xylene; nitriles such as acetonitrile; aprotic polar solvents such as DMF, NMP and DMSO; and mixed solvents thereof.

In the reaction, the compound (M17'-1) is used usually within a range of 1 to 2 molar ratio(s) as opposed to 1 mole of the intermediate compound (M8'). Also, when the compound (M17'-2) is used, the compound (M17'-2) is used usually within a range of 1 to 2 molar ratio(s) as opposed to 1 mole of the intermediate compound (M8').

The reaction temperature is usually within a range of −80 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present fused heterocyclic compound (1) (when n is 0 in the formula (1)). The isolated present fused heterocyclic compound (1) (when n is 0 in the formula (1)) may be further purified, for example, by chromatography and recrystallization.

(Process 10)

An intermediate compound (M8) can be prepared by reacting an intermediate compound (MG) with a sulfurizing agent. Also, an intermediate compound (M8') being a disulfide compound can be prepared by oxidizing an intermediate compound (M8).

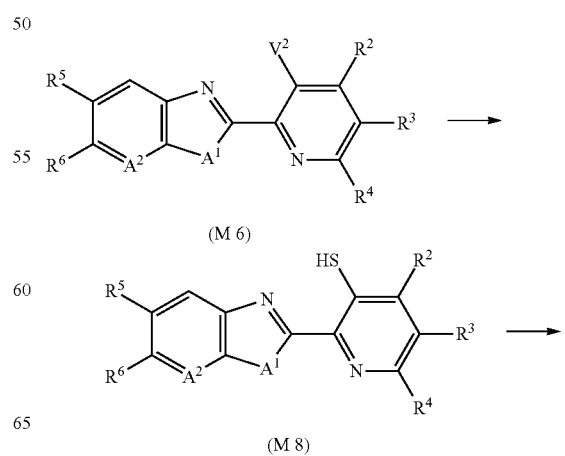

(M 6)

(M 8)

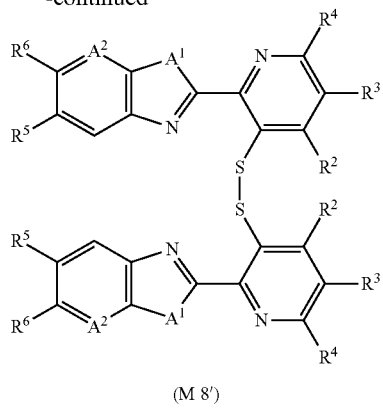

(M 8')

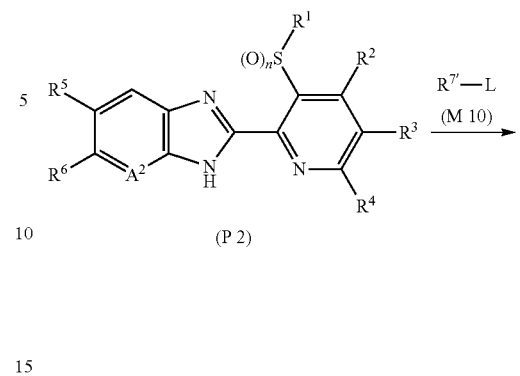

(P 2)

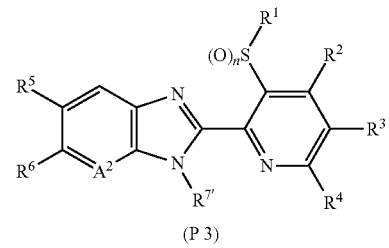

(P 3)

[wherein, V² represents a halogen atom, and the other each symbol is the same as defined in the formula (1)]

The intermediate compound (M8) can be prepared by using sulfides such as sodium sulfide, sodium hydrogen sulfide or hydrogen sulfide instead of the compound (M7) according to Process 5.

In this reaction, the conversion reaction of the intermediate compound (M8) to the intermediate compound (M8') can easily proceed and the intermediate compound (M8') is sometimes formed during a synthesis of the intermediate compound (M8). In the reaction, V² is preferably a fluorine atom or a chlorine atom.

The intermediate compound (M8') can be prepared by reacting two molecules of the intermediate compound (M8) in the presence of an oxidizing agent.

This reaction is usually carried out in the presence of a solvent.

Examples of the solvent to be used in the reaction include water; alcohols such as methanol and ethanol; ethers such as THF, ethyleneglycol dimethyl ether, methyl tert-butyl ether and 1,4-dioxane; aromatic hydrocarbons such as toluene and xylene; nitriles such as acetonitrile; aprotic polar solvents such as DMF, NMP and DMSO; carboxylic acids such as acetic acid; and mixed solvents thereof. Examples of the oxidizing agent to be used include oxygen (such as molecular oxygen), iodine, hydrogen peroxide and potassium ferricyanide.

In the reaction, the oxidizing compound (M8) is used usually within a range of 0.5 to 10 molar ratio(s) as opposed to 1 mole of the intermediate compound (M8).

The reaction temperature is usually within a range of 0 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the intermediate compound (M8'). The obtained intermediate compound (M8') may be further purified, for example, by chromatography and recrystallization.

(Process 11)

A present fused heterocyclic compound (P3) (when $A^1$ represents —NR$^{7'}$— in the formula (1)) can be prepared by reacting a present fused heterocyclic compound (P2) (when $A^1$ represents —NH— in the formula (1)) with a compound (M10) in the presence of a base.

[wherein, R$^{7'}$ represents any group as R$^7$ defined in the formula (1) other than a hydrogen atom, L represents a leaving group such as a chlorine atom, a bromine atom, an iodine atom, a trifluoromethanesulfonyloxy group and a methanesulfonyloxy group; and the other each symbol is the same as defined in the formula (1)]

This reaction is usually carried out in the presence of a solvent.

Examples of the solvent to be used in the reaction include ethers such as THF, ethyleneglycol dimethyl ether, methyl tert-butyl ether and 1,4-dioxane; aromatic hydrocarbons such as toluene and xylene; nitriles such as acetonitrile; aprotic polar solvents such as DMF, NMP and DMSO; and mixed solvents thereof.

Examples of the base to be used include alkali metal or alkaline-earth metal hydrides such as sodium hydride, potassium hydride and calcium hydride; inorganic bases such as sodium carbonate and potassium carbonate; and organic bases such as triethylamine.

In the reaction, the compound (M10) is usually used within a range of 1 to 5 molar ratio(s), and the base is used usually within a range of 1 to 3 molar ratio(s), as opposed to 1 mole of the present fused heterocyclic compound (P2).

The reaction temperature is usually within a range of 0 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present fused heterocyclic compound (P3). The obtained present fused heterocyclic compound (P3) may be further purified, for example, by chromatography and recrystallization.

(Process 12)

An intermediate compound (M2) can be prepared by hydrolyzing an intermediate compound (M37).

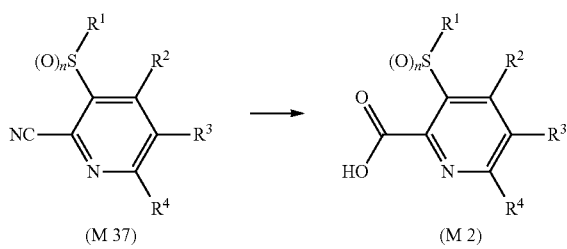

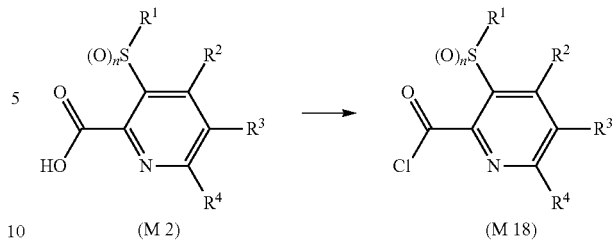

[wherein, each symbol is the same as defined in the formula (1)]

In the case of a hydrolysis with an acid, the reaction is usually carried out by using an aqueous solution of an acid as solvent.

Examples of the acid to be used include mineral acids such as hydrochloric acid, nitric acid, phosphoric acid and sulfuric acid; and organic acids including, for example, organic carboxylic acids such as acetic acid and trifluorocarboxylic acid.

In the reaction, an acid is used usually within a range of 1 to 10 molar ratio(s) as opposed to 1 mole of the intermediate compound (M37).

The reaction temperature is usually within a range of 0 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate intermediate compound (M2). The obtained intermediate compound (M2) may be further purified, for example, by chromatography and recrystallization.

In the case of a hydrolysis with a base, the reaction is usually carried out in a solvent.

Examples of the solvent to be used in the reaction include ethers such as THF, ethyleneglycol dimethyl ether, methyl tert-butyl ether and 1,4-dioxane; alcohols such as methanol and ethanol; water; and mixed solvents thereof.

Examples of the base to be used include alkali metal hydroxides such as sodium hydroxide and potassium hydroxide.

In the reaction, a base is used usually within a range of 1 to 10 molar ratio(s) as opposed to one of the intermediate compound (M37).

The reaction temperature is usually within a range of 0 to 120° C. The reaction period of the reaction is usually within a range of 0.1 to 24 hours.

When the reaction is completed, the reaction solutions are acidified and the reaction mixtures are extracted with organic solvent(s), and the resulting organic layers are worked up (for example, drying and concentration) to isolate the intermediate compound (M2). The isolated intermediate compound (M2) may be further purified, for example, by chromatography and recrystallization.

(Process 13)

An intermediate compound (M18) can be prepared by reacting an intermediate compound (M2) with a chlorinating agent.

[wherein, each symbol is the same as defined in the formula (1)]

This reaction is usually carried out in the presence of a solvent.

Examples of the solvent to be used in the reaction include ethers such as THF, ethyleneglycol dimethyl ether, methyl tert-butyl ether and 1,4-dioxane; aromatic hydrocarbons such as toluene and xylene; aliphatic hydrogenated hydrocarbons such as dichloromethane and chloroform; and mixed solvents thereof.

Examples of the chlorinating agent to be used include sulfonyl chloride, oxalyl dichloride and phosphorus oxychloride.

In the reaction, the chlorinating agent is used usually within a range of 1 to 5 molar ratio(s) as opposed to one of the intermediate compound (M2).

The reaction temperature is usually within a range of 0 to 100° C. The reaction period of the reaction is usually within a range of 0.1 to 24 hours.

When the reaction is completed, the reaction solvents are distilled off to isolate the intermediate compound (M18).

(Process 14)

An intermediate compound (M2), an intermediate compound (M4) or an intermediate compound (M37) can be prepared by reacting an intermediate compound (M19), an interdicted compound (M22) or an intermediate compound (M36) with a compound (M7), if necessary, followed by oxidizing each the obtained intermediate compound.

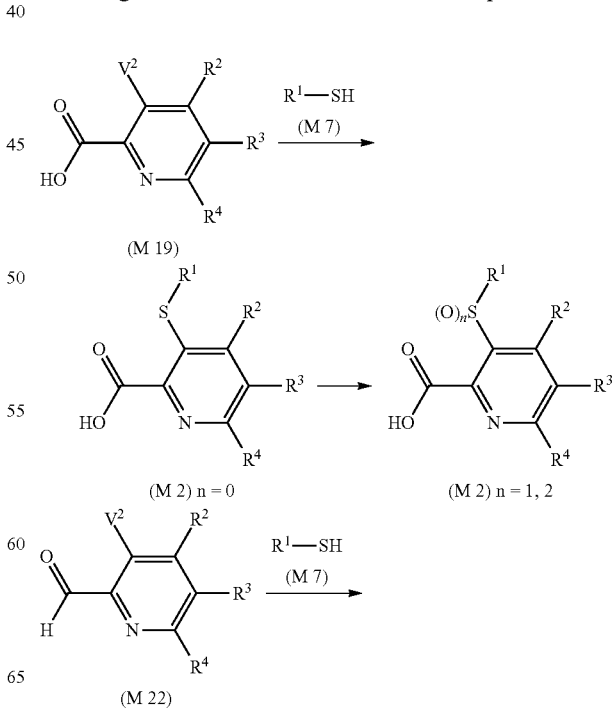

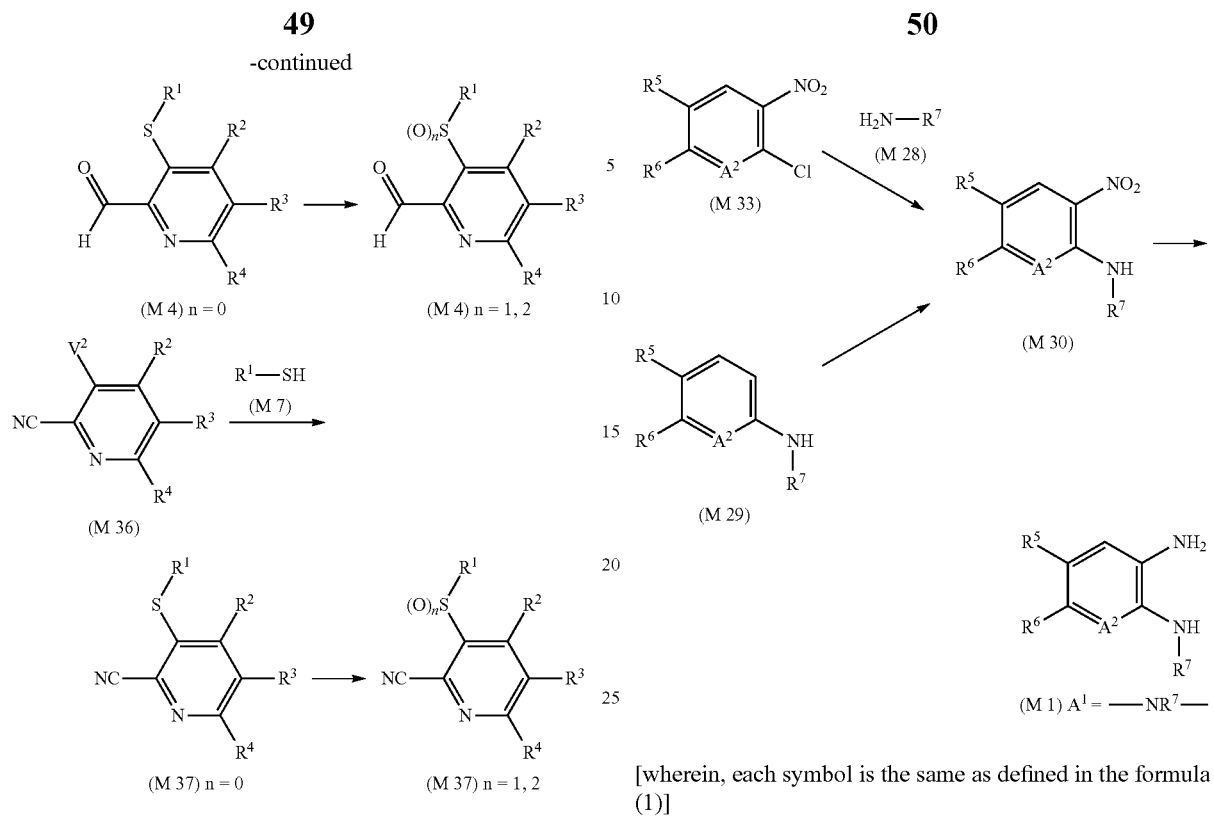

[wherein, each symbol is the same as defined in the formula (1)]

[wherein, $V^2$ represents a halogen atom, and the other each symbol is the same as defined in the formula (1)]

The intermediate compound (M2) (when n is 0) can be prepared by using the intermediate compound (M19) instead of the intermediate compound (M6) according to Process 5.

The intermediate compound (M4) (when n is 0) can be prepared by using the intermediate compound (M22) instead of the intermediate compound (M6) according to Process 5.

The intermediate compound (M37) (when n is 0) can be prepared by using the intermediate compound (M36) instead of the intermediate compound (M6) according to Process 5.

The intermediate compound (M2) (when n is 1 or 2) can be prepared by using the intermediate compound (M2) (when n is 0) instead of the present fused heterocyclic compound (1) (when n is 0) according to Process 1.

The intermediate compound (M4) (when n is 1 or 2) can be prepared by using the intermediate compound (M4) (when n is 0) instead of the present fused heterocyclic compound (1) (when n is 0) according to Process 1.

The intermediate compound (M37) (when n is 1 or 2) can be prepared by using the intermediate compound (M37) (when n is 0) instead of the present fused heterocyclic compound (1) (when n is 0) according to Process 1.

In the reaction, $V^2$ represents preferably a fluorine atom or a chlorine atom.

(Process 15)

An intermediate compound (M30) can be prepared by performing a nitration reaction of an intermediate compound (M29) or by reacting an intermediate compound (M33) with a compound (M28). The obtained intermediate compound (M30) can be reduced to afford an intermediate compound (M1) (when $A^1$ represents —$NR^7$— in the formula (M1)).

The intermediate compound (M30) can be prepared by reacting the intermediate compound (M33) with the compound (M28) in the presence of a base.

This reaction is usually carried out in the presence of a solvent.

Examples of the solvent to be used in the reaction include ethers such as THF, ethyleneglycol dimethyl ether, methyl tert-butyl ether and 1,4-dioxane; aromatic hydrocarbons such as toluene and xylene; nitriles such as acetonitrile; aprotic polar solvents such as DMF, NMP and DMSO; and mixed solvents thereof.

The reaction may be carried out, if necessary, in the presence of a base. Examples of the base to be used include alkali metal hydrides such as sodium hydride; alkali metal carbonates such as sodium carbonate and potassium carbonate; tertiary amines such as triethylamine and N,N-diisopropylethylamine; and nitrogen-containing aromatic compounds such as pyridine and 4-dimethylaminopyridine.

In the reaction, the compound (M28) is used usually within a range of 1 to 10 molar ratio(s), and the base is used usually within a range of 0 to 10 molar ratio(s), as opposed to 1 mole of the intermediate compound (M33).

The reaction temperature is usually within a range of 0 to 150° C. The reaction period of the reaction is usually within a range of 0.5 to 24 hours.

When the reaction is completed, the reaction mixtures are extracted with organic solvent(s), and the resulting organic layers are worked up (for example, drying and concentration) to isolate the intermediate compound (M30). The isolated intermediate compound (M30) may be further purified, for example, by chromatography and recrystallization.

The intermediate compound (M30) can be prepared by reacting the intermediate compound (M29) with a nitrating agent.

This reaction is usually carried out in the presence of a solvent.

Examples of the solvent to be used in the reaction include aliphatic hydrogenated hydrocarbons such as dichloromethane and chloroform; acids such as acetic acid, concentrated sulfuric acid and concentrated nitric acid; water; and mixed solvents thereof.

The nitrating agent to be used in the reaction includes a concentrated nitric acid.

In the reaction, the nitrating agent is used usually within a range of 1 to 3 molar ratio(s) as opposed to 1 mole of the intermediate compound (M29).

The reaction temperature is usually within a range of −10 to 100° C. The reaction period of the reaction is usually within a range of 0.1 to 24 hours.

When the reaction is completed, the reaction mixtures are added into water and are extracted with organic solvent(s), and the resulting organic layers are worked up (for example, drying and concentration) to isolate the intermediate compound (M30). The isolated intermediate compound (M30) may be further purified, for example, by chromatography and recrystallization.

Also, in the case where in the formula (M30), represents a hydrogen atom, the compounds of formula (M30) wherein $R^7$ represents any group other than a hydrogen atom can be prepared by using the intermediate compound (M30) wherein $R^7$ represents a hydrogen atom instead of the compound (P2) according to Process 11.

The intermediate compound (M1) (when $A^1$ represents —$NR^7$—) can be prepared by reacting the intermediate compound (M30) with hydrogen gas in the presence of a catalyst for hydrogenation.

The reaction is carried out under hydrogen atmosphere of usually 1 to 100 atmospheric pressure(s) and usually in the presence of a solvent.

Examples of the solvent to be used in the reaction include ethers such as THF, ethyleneglycol dimethyl ether, methyl tert-butyl ether and 1,4-dioxane; esters such as ethyl acetate and butyl acetate; alcohols such as methanol and ethanol; water; and mixed solvents thereof.

The catalysts for hydrogenation to be used in the reaction include transition metal compounds such as palladium-carbon, palladium hydroxide, raney nickel and platinum oxide.

In the reaction, the hydrogen gas is used usually within a range of 3 molar ratios, and the catalysts for hydrogenation are used usually within a range of 0.001 to 0.5 molar ratio(s), as opposed to 1 mole of the intermediate compound (M30).

The reaction may be carried out, if necessary, in the presence of an acid or a base and the others.

Examples of the acids to be used in the reaction include acids such as acetic acid and hydrochloric acid, and examples of the base to be used include tertiary amines such as triethylamine and magnesium oxide.

The reaction temperature is usually within a range of −20 to 100° C. The reaction period of the reaction is usually within a range of 0.1 to 24 hours.

When the reaction is completed, the reaction mixtures are filtered and, if necessary, are extracted with organic solvent(s), and the resulting organic layers are worked up (for example, drying and concentration) to isolate the intermediate compound (M1) (when $A^1$ represents —$NR^7$—). The isolated intermediate compound (M1) (when $A^1$ represents —$NR^7$—) may be further purified, for example, by chromatography and recrystallization.

Also, the intermediate compound (M30) can be prepared as mentioned below, for example, by acetylating the intermediate compound (M29) to afford the intermediate compound (M29'), followed by performing a nitration reaction of the obtained intermediate compound (M29') to afford the intermediate compound (M30') and further by hydrolyzing the obtained intermediate compound (M30').

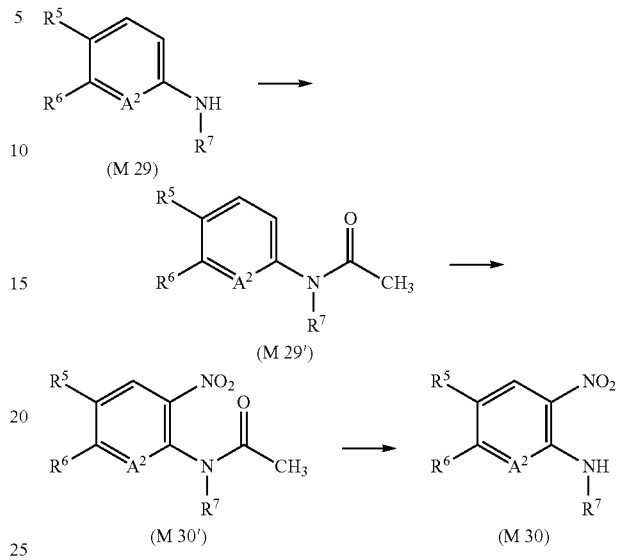

[wherein, each symbol is the same as defined in the formula (1)]

The intermediate compound (M29') can be prepared by reacting the intermediate compound (M29) with an acylating agent.

The reaction is carried out usually in the presence of a solvent or by using the acylating agent as solvent.

Examples of the solvent to be used in the reaction include aliphatic hydrogenated hydrocarbons such as dichloromethane and chloroform; aliphatic hydrogenated hydrocarbons such as dichloromethane and chloroform; ethers such as THF, ethyleneglycol dimethyl ether, methyl tert-butyl ether and 1,4-dioxane; aromatic hydrocarbons such as toluene and xylene; nitriles such as acetonitrile; aprotic polar solvents such as DMF, NMP and DMSO; and mixed solvents thereof. Examples of the acylating agent to be used in the reaction include acetic anhydride and para-acetoxy nitrobenzene.

The reaction may be also carried out, if necessary, in the presence of a base. Examples of the base to be used include tertiary amines such as triethylamine and N,N-diisopropyl-ethylamine; and nitrogen-containing aromatic compounds such as pyridine and 4-dimethylaminopyridine.

In the reaction, the acylating agent is used within a range of 1 or more molar ratio(s), and the base is used usually within a range of 0.1 to 10 molar ratio(s), as opposed to 1 mole of the intermediate compound (M29).

The reaction temperature is usually within a range of 0 to 150° C. The reaction period of the reaction is usually within a range of 0.5 to 24 hours.

When the reaction is completed, the reaction mixtures are extracted with organic solvent(s), and the resulting organic layers are worked up (for example, drying and concentration) to isolate the intermediate compound (M29'). The isolated intermediate compound (M29') may be further purified, for example, by chromatography and recrystallization.

The intermediate compound (M30') can be prepared by using the intermediate compound (M29') instead of the intermediate compound (M29) according to Process 15.

The intermediate compound (M30) can be prepared by hydrolyzing the intermediate compound (M30') in the presence of an acid or a base.

In the case of a hydrolysis with an acid, the reaction is usually carried out by using an aqueous solution of the acid as solvent.

Examples of the acid to be used in the reaction include mineral acids such as hydrochloric acid and sulfuric acid; and organic acid including, for example, organic carboxylic acids such as acetic acid and trifluoroacetic acid.

The reaction temperature is usually within a range of 0 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the intermediate compound (M30).

The isolated intermediate compound (M30) may be further purified, for example, by chromatography and recrystallization.

In the case of a hydrolysis with a base, the reaction is usually carried out in a solvent.

Examples of the solvent to be used in the reaction include ethers such as THF, ethyleneglycol dimethyl ether, methyl tert-butyl ether and 1,4-dioxane; alcohols such as methanol and ethanol; water; and mixed solvents thereof.

Examples of the base to be used include alkali metal hydroxides such as sodium hydroxide and potassium hydroxide; and hydrazine.

In the reaction, the base is used usually within a range of 1 to 10 molar ratio(s) as opposed to 1 mole of the intermediate compound (M30').

The reaction temperature is usually within a range of 0 to 120° C. The reaction period of the reaction is usually within a range of 0.1 to 24 hours.

When the reaction is completed, the reaction solutions are acidified, and the reaction mixtures are extracted with organic solvent(s), and the resulting organic layers are worked up (for example, drying and concentration) to isolate the intermediate compound (M30). The isolated intermediate compound (M30) may be further purified, for example, by chromatography and recrystallization.

(Process 16)

An intermediate compound (M1) (when $A^1$ represents $NR^7$—) can be prepared by brominating an intermediate compound (M29) to afford an intermediate compound (M35), followed by aminating the obtained intermediate compound (M35).

[wherein, each symbol is the same as defined in the formula (1)]

The intermediate compound (M35) can be prepared by reacting the intermediate compound (M29) with a brominating agent.

This reaction is usually carried out in the presence of a solvent.

Examples of the solvent to be used in the reaction include water; acetic acid; ethers such as 1,4-dioxane, diethyl ether and THF; esters such as ethyl acetate and butyl acetate; halogenated hydrocarbons such as dichloromethane, chloroform, carbon tetrachloride and 1,2-dichloroethane; nitriles such as acetonitrile; aprotic polar solvents such as DMF, NMP and DMSO; and mixed solvents thereof.

Examples of the brominating agent to be used include N-bromosuccinimide and bromine.

The brominating agent is used usually within a range of 1 to 3 molar ratio(s) as opposed to 1 mole of the intermediate compound (M29).

The reaction temperature is usually within a range of −10 to 100° C. The reaction period of the reaction is usually within a range of 0.1 to 24 hours.

When the reaction is completed, the reaction mixtures are added into water and are then extracted with organic solvent(s), and the resulting organic layers are concentrated; the reaction mixtures are added into water and the resulting solids are collected by filtration; or the solids formed in the reaction mixture are collected by filtration, to afford the intermediate compound (M35). The isolated intermediate compound (M35) may be further purified, for example, by recrystallization and chromatography.

The intermediate compound (M1) (when $A^1$ represents —$NR^7$—) can be prepared by reacting the intermediate compound (M35) with an aminating agent in the presence of a copper compound.

This reaction is usually carried out in the presence of a solvent.

Examples of the solvent to be used in the reaction include water; alcohols such as methanol and ethanol; ethers such as 1,4-dioxane, diethyl ether and THF; esters such as ethyl acetate and butyl acetate; halogenated hydrocarbons such as dichloromethane, chloroform, carbon tetrachloride and 1,2-dichloroethane; nitriles such as acetonitrile; aprotic polar solvents such as DMF, NMP and DMSO; nitrogen-containing aromatic compounds such as pyridine and quinoline; and mixed solvents thereof.

The aminating agent to be used in the reaction includes ammonia, aqueous ammonia and lithium amide.

The copper compound to be used in the reaction includes copper, copper iodide(I), copper oxide(I), copper oxide(II), acetylacetone copper(II), copper acetate(II) and copper sulfate(II).

The reaction may be also carried out, if necessary, in the presence of a ligand.

Examples of the ligand to be used in the reaction include acetylacetone, salen (N,N'-bis(salicylidene)ethylenediamine) and phenanthroline.

The reaction may be also carried out, if necessary, in the presence of a base.

Examples of the base to be used include nitrogen-containing heterocyclic compounds such as pyridine, picoline, 2,6-lutidine, DBU, 1,5-diazabicyclo[4.3.0]-5-nonene; tertiary amines such as triethylamine and N,N-diisopropylethylamine; and inorganic bases such as tripotassium phosphate, potassium carbonate, cesium carbonate and sodium hydroxide.

The aminating agent is used usually within a range of 1 to 5 molar ratio(s), the copper compound is used usually within a range of 0.02 to 0.5 molar ratio(s), the ligand is used usually within a range of 0.02 to 2 molar ratio(s) and the base is used usually within a range of 1 to 5 molar ratio(s), as opposed to 1 mole of the intermediate compound (M35).

The reaction temperature is usually within a range of to 200° C. The reaction period of the reaction is usually within a range of 0.1 to 48 hours.

When the reaction is completed, the reaction mixtures are added into water and are then extracted with organic solvent(s), and the resulting organic layers are concentrated; the reaction mixtures are added into water and the resulting solids are collected by filtration; or the solids formed in the reaction mixture are collected by filtration, to afford the intermediate compound (M1) (when $A^1$ represents —$NR^7$—). The isolated intermediate compound (M1) (when $A^1$ represents —$NR^7$—) may be further purified, for example, by recrystallization and chromatography.

(Process 17)

An intermediate compound (M1) (when $A^1$ represents an oxygen atom) can be prepared by performing a nitration reaction of an intermediate compound (M31) to afford an intermediate compound (M32), followed by reducing the obtained intermediate compound (M32).

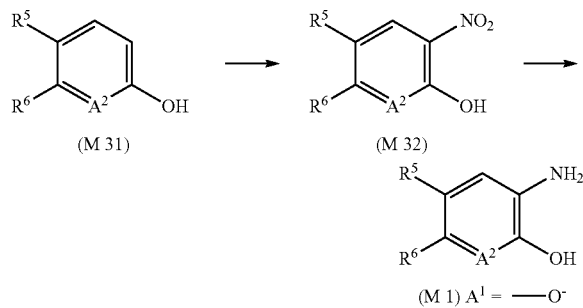

[wherein, each symbol is the same as defined in the formula (1)]

The intermediate compound (M32) can be prepared by using the intermediate compound (M31) instead of the intermediate compound (M29) according to Process 15.

The intermediate compound (M1) (when $A^1$ represents an oxygen atom) can be prepared by using the intermediate compound (M32) instead of the intermediate compound (M30) according to Process 15.

(Process 18)

An intermediate compound (M1) can be prepared by reacting an intermediate compound (M33) with a sulfurizing agent to afford an intermediate compound (M34), followed by reacting the obtained intermediate compound (M34) with a reducing agent.

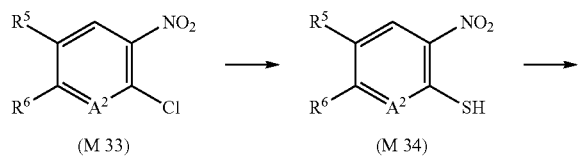

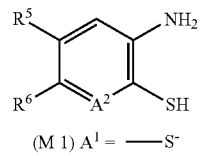

[wherein, each symbol is the same as defined in the formula (1)]

The intermediate compound (M34) can be prepared by reacting the intermediate compound (M33) with a thiourea in the presence of a base.

This reaction is usually carried out in the presence of a solvent.

Examples of the solvent to be used in the reaction include alcohols such as methanol and ethanol; water; and mixed solvents thereof.

Examples of the base to be used include alkali metal hydroxides such as sodium hydroxide and potassium hydroxide.

In the reaction, the thiourea is used usually within a range of 0.5 to 3 molar ratio(s), and the base is used usually within a range of 1 to 10 molar ratio(s), as opposed to 1 mole of the intermediate compound (M33).

The reaction temperature is usually within a range of 0 to 100° C. The reaction period of the reaction is usually within a range of 0.1 to 24 hours.

When the reaction is completed, to the reaction mixtures are added an acid, and the resulting mixtures are extracted with organic solvent(s), and the resulting organic layers are worked up (for example, drying and concentration) to isolate the intermediate compound (M34). The isolated intermediate compound (M34) may be further purified, for example, by chromatography and recrystallization.

The intermediate compound (M1) (when $A^1$ represents a sulfur atom) can be prepared by reacting the intermediate compound (M34) with a reducing agent.

The reduction reaction may be carried out, for example, in the presence of metal powder such as zinc powder; acids such as hydrochloric acid and acetic acid; and water.

This reaction is usually carried out in the presence of a solvent.

Examples of the solvent to be used in the reaction include ethers such as THF, ethyleneglycol dimethyl ether, methyl tert-butyl ether and 1,4-dioxane; esters such as ethyl acetate and butyl acetate; alcohols such as methanol and ethanol; aprotic polar solvents such as DMF, NMP and DMSO; and mixed solvents thereof.

Examples of the reducing agent to be used in the reaction include metal powder such as iron powder, zinc powder and tin dichloride.

In the reaction, the metal powder is used usually within a range of 3 to 10 molar ratio(s) as opposed to 1 mole of the intermediate compound (M34).

The reaction temperature is usually within a range of 0 to 100° C. The reaction period of the reaction is usually within a range of 0.1 to 24 hours.

When the reaction is completed, to the reaction mixtures are added an acid, and the resulting mixtures are extracted with organic solvent(s), and the resulting organic layers are worked up (for example, drying and concentration) to isolate the intermediate compound (M1) wherein $A^1$ represents a sulfur atom. The isolated intermediate compound (M1) wherein $A^1$ represents a sulfur atom may be further purified, for example, by chromatography and recrystallization.

(Process 19)

A compound of formula (1) wherein $R^5$ represents a C1-C6 perfluoroalkyl group, that is, a present fused heterocyclic compound (P7) can be prepared by reacting a compound of formula (1) wherein $R^5$ represents a halogen atom, that is, a present fused heterocyclic compound (P4) with a compound (M11) or a compound (M11') in the presence of a copper compound.

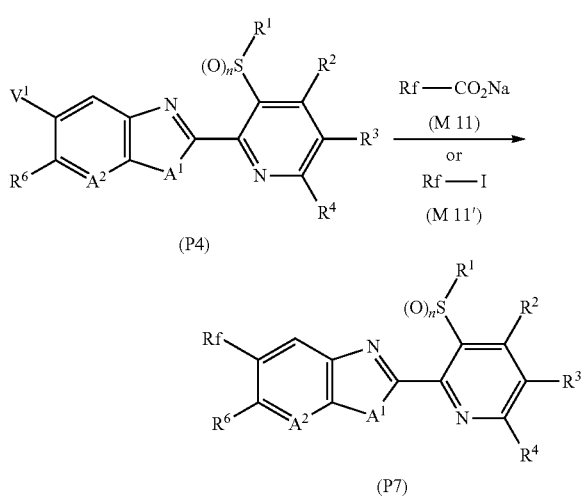

[wherein, $V^1$ represents a halogen atom, Rf represents a C1-C6 perfluoroalkyl group, and the other each symbol is the same as defined in the formula (1)]

This reaction is usually carried out in the presence of a solvent.

Examples of the solvent to be used in the reaction include aromatic hydrocarbons such as toluene and xylene; aprotic polar solvents such as DMF, NMP and DMSO; and mixed solvents thereof. Examples of the copper compound to be used in the reaction include copper and copper iodide(I). When the compound (M11) is used in the reaction, the compound (M11) is used usually within a range of 1 to 10 molar ratio(s), the copper compound is used usually within a range of 0.5 to 10 molar ratio(s), as opposed to 1 mole of the present fused heterocyclic compound (P4).

The reaction temperature is usually within a range of 100 to 200° C. The reaction period of the reaction is usually within a range of 0.5 to 48 hours.

In the reaction, when the intermediate compound (M11') is used, a potassium fluoride may be optionally added. The compound (M11') is used usually within a range of 1 to 10 molar ratio(s), the copper compound is used usually within a range of 0.1 to 10 molar ratio(s), and the potassium fluoride is used usually within a range of 0.1 to 5 molar ratio(s), as opposed to 1 mole of the present fused heterocyclic compound (P4).

The reaction temperature is usually within a range of 0 to 150° C. The reaction period of the reaction is usually within a range of 0.5 to 48 hours.

When the reaction is completed, the resulting mixtures are extracted with organic solvent(s), and the resulting organic layers are worked up (for example, drying and concentration) to isolate the present fused heterocyclic compound (P7). The isolated present fused heterocyclic compound (P7) may be further purified, for example, by chromatography and recrystallization. In the reaction, V1 represents preferably a bromine atom and an iodine atom.

(Process 20)

A present fused heterocyclic compound (P9) (when $R^5$ represents a —SH group in the formula (1)) can be prepared by reacting a present fused heterocyclic compound (P4) with a sulfurizing agent. Also, the present fused heterocyclic compound (P9) can be oxidized to afford a disulfide compound thereof, that is, an intermediate compound (P9').

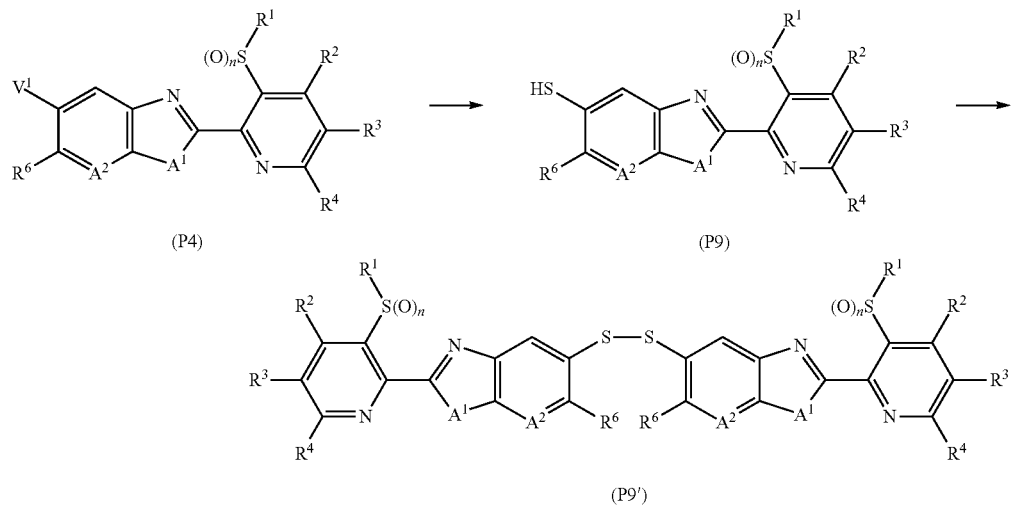

[wherein, $V^1$ represents a halogen atom, and each other symbols are the same as defined in formula (1)]

The present fused heterocyclic compound (P9) can be prepared by reacting the present fused heterocyclic compound (P4) with a thiolating agent in the presence of a catalyst.

This reaction is usually carried out in the presence of a solvent.

Examples of the solvent to be used in the reaction include aromatic hydrocarbons such as toluene and xylene; aprotic polar solvents such as DMF, NMP and DMSO; and mixed solvents thereof.

Examples of the thiolating agent to be used in the reaction include sodium sulfide, sodium sulfide nine hydrates and thiourea.

Examples of the catalyst to be used include copper chloride(I), copper bromide(I) and copper iodide(I).

The reaction may be also carried out, if necessary, in the presence of a ligand.

Examples of the ligand to be used in the reaction include acetylacetone, salen and phenanthroline.

The reaction may be also carried out, if necessary, in the presence of a base.

Examples of the base to be used include inorganic bases such as potassium carbonate, cesium carbonate and tripotassium phosphate; and organic bases such as triethylamine.

In the reaction, the thiolating agent is used usually within a range of 1 to 10 molar ratio(s), the catalyst is used usually within a range of 0.1 to 5 molar ratio(s), the ligand is used usually within a range of 0.1 to 5 molar ratio(s), and the base is used usually within a range of 1 to 2 molar ratio(s), as opposed to 1 mole of the present fused heterocyclic compound (P4).

The reaction temperature is usually within a range of 50 to 200° C. The reaction period of the reaction is usually within a range of 0.5 to 24 hours.

When the reaction is completed, the resulting mixtures are extracted with organic solvent(s), and the resulting organic layers are worked up (for example, drying and concentration) to isolate the present fused heterocyclic compound (P9). The isolated present fused heterocyclic compound (P9) may be further purified, for example, by chromatography and recrystallization. In the reaction, V' represents preferably a bromine atom and an iodine atom.

In this reaction, the conversion reaction of the intermediate compound (P9) to the intermediate compound (P9') can easily proceed and the intermediate compound (P9') is sometimes formed during a synthesis of the intermediate compound (P9).

The intermediate compound (P9') can be prepared by reacting the present fused heterocyclic compound (P9) with an oxidizing agent.

This reaction is usually carried out in the presence of a solvent.

Examples of the solvent to be used in the reaction include water; alcohols such as methanol and ethanol; ethers such as THF, ethyleneglycol dimethyl ether, methyl test-butyl ether and 1,4-dioxane; aromatic hydrocarbons such as toluene and xylene; nitriles such as acetonitrile; aprotic polar solvents such as DMF, NMP and DMSO; carboxylic acids such as acetic acid; and mixed solvents thereof.

Examples of the oxidizing agent to be used include oxygen (for example, molecular oxygen), iodine, hydrogen peroxide and potassium ferricyanide.

In the reaction, the oxidizing agent is used usually within a range of 0.5 to 10 molar ratio(s) as opposed to 1 mole of the present fused heterocyclic compound (P9).

The reaction temperature is usually within a range of 0 to 100° C. The reaction period of the reaction is usually within a range of 0.1 to 24 hours.

When the reaction is completed, the resulting mixtures are extracted with organic solvent(s), and the resulting organic layers are worked up (for example, drying and concentration) to isolate the intermediate compound (P9'). The isolated intermediate compound (P9') may be further purified, for example, by chromatography and recrystallization.

Also, the present fused heterocyclic compound (P9) can be prepared by thioesterifying the present fused heterocyclic compound (P4) to afford the intermediate compound (P9-1), followed by hydrolyzing the obtained intermediate compound (P9-1).

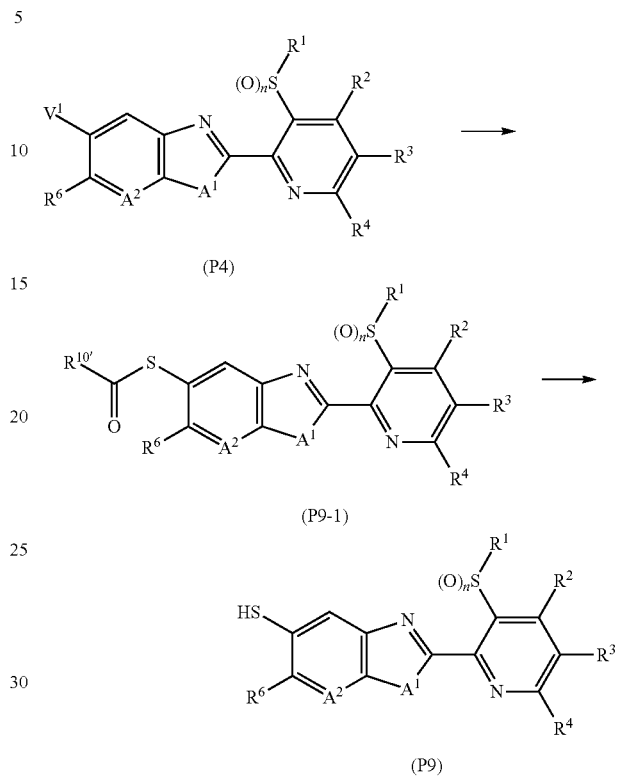

[wherein, $P^{10'}$ represents any group as $R^{10}$ defined in the formula (1) other than a hydrogen atom, and each other symbol is the same as defined in the formula (1)]

The intermediate compound (P9-1) can be prepared by reacting the present fused heterocyclic compound (P4) with a thioesterifying agent in the presence of a base and a catalyst.

This reaction is usually carried out in the presence of a solvent.

Examples of the solvent to be used in the reaction include aromatic hydrocarbons such as toluene and xylene; aprotic polar solvents such as DMF, NMP and DMSO; and mixed solvents thereof.

Examples of the thioesterifying agent include thiobenzoic acid.

Examples of the catalyst to be used include copper chloride(I), copper bromide(I) and copper iodide(I).

The reaction may be carried out, for example, in the presence of a ligand.

Examples of the ligand to be used in the reaction include acetyl acetone, salen and phenanthroline.

Examples of the base to be used include inorganic bases such as potassium carbonate, cesium carbonate, tripotassium phosphate; and organic bases such as triethylamine.

In the reaction, the thioesterifying agent is used usually within a range of 1 to 10 molar ratio(s), the catalyst is used usually within a range of 0.1 to 5 molar ratio(s), the ligand is used usually within a range of 0.1 to 5 molar ratio(s), and the base is used usually within a range of 1 to 2 molar ratio(s), as opposed to 1 mole of the present fused heterocyclic compound (P4).

The reaction temperature is usually within a range of 50 to 200° C. The reaction period of the reaction is usually within a range of 0.5 to 24 hours.

When the reaction is completed, the resulting mixtures are extracted with organic solvent(s), and the resulting organic layers are worked up (for example, drying and concentration) to isolate the intermediate compound (P9-1). The isolated intermediate compound (P9-1) may be further purified, for example, by chromatography and recrystallization.

In the reaction, $V^1$ represents preferably a bromine atom and an iodine atom.

The present fused heterocyclic compound (P9) can be prepared by hydrolyzing the intermediate compound (P9-1).

In the case of a hydrolysis with an acid, the reaction is usually carried out by using an aqueous solution of the acid as solvent.

Examples of the acid to be used in the reaction include mineral acids such as hydrochloric acid, nitric acid, phosphoric acid and sulfuric acid; and organic acid including, for example, organic carboxylic acids such as acetic acid and trifluoroacetic acid.

The reaction temperature is usually within a range of 0 to 100° C. The reaction period of the reaction is usually within a range of 0.1 to 24 hours.

When the reaction is completed, the resulting mixtures are extracted with organic solvent(s), and the resulting organic layers are worked up (for example, drying and concentration) to isolate the present fused heterocyclic compound (P9). The present fused heterocyclic compound (P9) may be further purified, for example, by chromatography and recrystallization.

In the case of a hydrolysis with a base, the reaction is usually carried out in a solvent.

Examples of the solvent to be used in the reaction include ethers such as THF, ethyleneglycol dimethyl ether, methyl tert-butyl ether and 1,4-dioxane; alcohols such as methanol and ethanol; water; and mixed solvents thereof.

Examples of the base to be used include alkali metal hydroxides such as sodium hydroxide and potassium hydroxide.

In the reaction, the base is used usually within a range of 1 to 10 molar ratio(s) as opposed to 1 mole of the intermediate compound (P9-1).

The reaction temperature is usually within a range of 0 to 120° C. The reaction period of the reaction is usually within a range of 0.1 to 24 hours.

When the reaction is completed, the reaction solutions were acidified, the resulting mixtures are extracted with organic solvent(s), and the resulting organic layers are worked up (for example, drying and concentration) to isolate the present fused heterocyclic compound (P9). The present fused heterocyclic compound (P9) may be further purified, for example, by chromatography and recrystallization.

In this reaction, the conversion reaction of the present fused heterocyclic compound (P9) to the intermediate compound (P9') can easily proceed and the intermediate compound (P9') is sometimes formed during a synthesis of the present fused heterocyclic compound (P9).

(Process 21)

A present fused heterocyclic compound (P10-m0) (when $R^5$ represents a $-S(O)_mR^{10}$ group and also m is 0) can be prepared by reacting a present fused heterocyclic compound (P9) or a disulfide compound thereof, that is, an intermediate compound (P9') with a compound (M13).

The present fused heterocyclic compound (P10-m0) (when m is 0) can be oxidized to afford the present fused heterocyclic compound (P10) (when $R^5$ represents a $-S(O)_m R^{10}$ group and also m is 1 or 2).

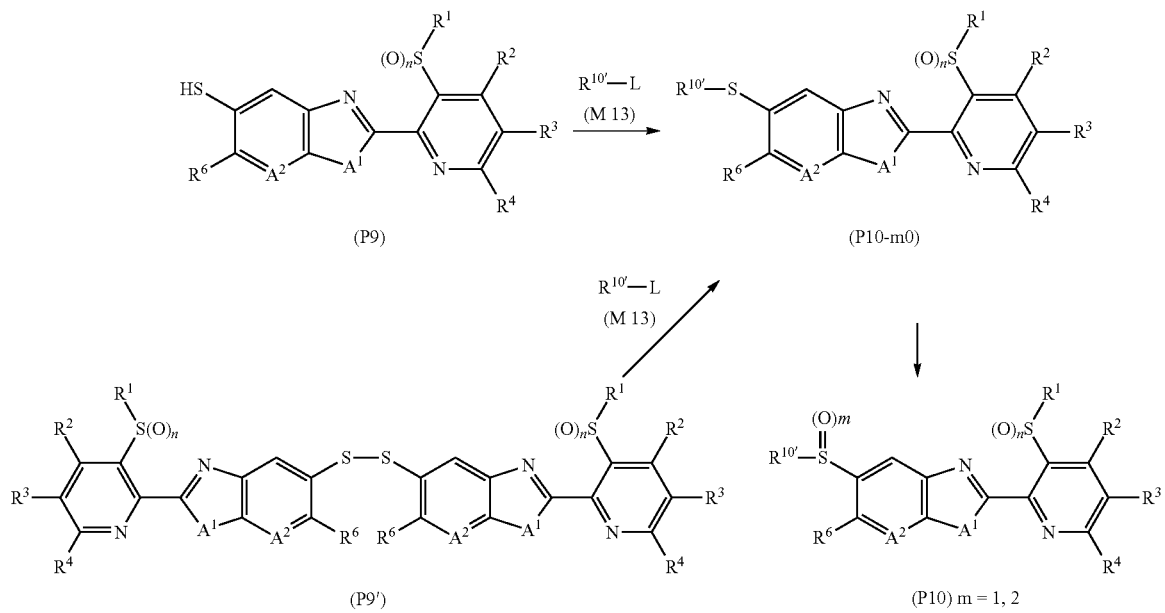

[wherein, $R^{10'}$ represents any group of $R^{10}$ defined in formula (1) other than a hydrogen atom, L represents a leaving group such as a chlorine atom, a bromine atom, an iodine atom, a trifluoromethanesulfonyloxy group and a methanesulfonyloxy group, and each other symbol is the same as defined in the formula (1)]

This reaction is usually carried out in the presence of a solvent.

Examples of the solvent to be used in the reaction include ethers such as THF, ethyleneglycol dimethyl ether, methyl tert-butyl ether and 1,4-dioxane; aromatic hydrocarbons such as toluene and xylene; nitriles such as acetonitrile; aprotic polar solvents such as DMF, NMP and DMSO; and mixed solvents thereof.

Examples of the base to be used include an alkali metal or alkaline-earth metal hydrides such as sodium hydride, potassium hydride and calcium hydride; and inorganic bases such as sodium carbonate, potassium carbonate; and organic bases such as triethylamine.

In the case where the intermediate compound (P9') being disulfide compound is used, the reaction is usually carried out in the presence of a reducing agent.

Examples of the reducing agent to be used in the reaction include hydroxymethanesulfinic acid sodium salt (Trade name: Rongalite).

In the reaction, the compound (M13) is usually used within a range of 1 to 10 molar ratio(s), and the base is usually used within a range of 1 to 10 molar ratio(s), as opposed to 1 mole of the present fused heterocyclic compound (P9).

Also, in the case where the intermediate compound (P9') being disulfide compound is used, the compound (M13) is used usually within a range of 2 to 10 molar ratio(s), the base is used usually within a range of 2 to 10 molar ratio(s), and the reducing agent is used usually within a range of 1 to 5 molar ratio(s), as opposed to 1 mole of the intermediate compound (P9').

The reaction temperature is usually within a range of 0 to 100° C. The reaction period of the reaction is usually within a range of 0.1 to 24 hours.

When the reaction is completed, the resulting mixtures are extracted with organic solvent(s), and the resulting organic layers are worked up (for example, drying and concentration) to isolate the present fused heterocyclic compound (P10-m0) (m is 0). The isolated present fused heterocyclic compound (P10-m0) (m is 0) may be further purified, for example, by chromatography and recrystallization.

Also, among the present fused heterocyclic compound (P10-m0) (when m is 0), the intermediate compound (P9') (when $R^{10'}$ represents a C1-C6 perfluoroalkyl group) can be prepared by reacting the intermediate compound (P9'), a perfluoroalkyl iodide and a reducing agent. This reaction is usually carried out in the presence of a solvent.

Examples of the solvent to be used in the reaction include ethers such as THF, ethyleneglycol dimethyl ether, methyl tert-butyl ether and 1,4-dioxane; aromatic hydrocarbons such as toluene and xylene; nitriles such as acetonitrile; aprotic polar solvents such as DMF, NMP and DMSO; and mixed solvents thereof.

Examples of the reducing agent to be used in the reaction include tetrakis(dimethylamino)ethylene.

Examples of the perfluoroalkyl iodide include trifluoroiodomethane, iodopentafluoroethane and heptafluoro-2-iodopropane.

In the reaction, the perfluoroalkyl iodide is used usually within a range of 2 to 10 molar ratio(s), and the reducing agent is used usually within a range of 1 to 5 molar ratio(s), as opposed to 1 mole of the intermediate compound (P9').

The reaction temperature is usually within a range of –80 to 50° C. The reaction period of the reaction is usually within a range of 0.1 to 24 hours.

When the reaction is completed, the resulting mixtures are extracted with organic solvent(s), and the resulting organic layers are worked up (for example, drying and concentration) to isolate the present fused heterocyclic compound (P10-m0) (when m is 0). The isolated present fused hetero-cyclic compound (P10-m0) (when m is 0) may be further purified, for example, by chromatography and recrystallization.

Among the present fused heterocyclic compound (P10), the present fused heterocyclic compound wherein m is 1 or 2 can be prepared by reacting the present fused heterocyclic compound (P10-m0) (when m is 0) with an oxidizing agent.

This reaction is usually carried out in a solvent.

Examples of the solvent to be used in the reaction include aliphatic hydrogenated hydrocarbons such as dichloromethane and chloroform; alcohols such as methanol and ethanol; carboxylic acids such as acetic acid; water; and mixed solvents thereof.

Examples of the oxidizing agent to be used include m-chloroperoxybenzoic acid or hydrogen peroxide.

The reaction may be also carried out, if necessary, in the presence of a catalyst.

Examples of the catalyst to be used include sodium tungstate.

In the reaction, the oxidizing agent is used usually within a range of 1 to 5 molar ratio(s), and the catalyst is used usually within a range of 0.01 to 0.5 molar ratio(s), as opposed to 1 mole of the present fused heterocyclic compound (P10-m0) (when m is 0).

In the preparation of the compound wherein m is 1, the oxidizing agent is used usually within a range of 0.8 to 1.2 molar ratio(s), and the catalyst is used usually within a range of 0.05 to 0.2 molar ratio(s), as opposed to 1 mole of the present fused heterocyclic compound (P10-m0) when (m is 0). In the preparation of the compound wherein m is 2, the oxidizing agent is used usually within a range of 1.8 to 5 molar ratio(s), and the catalyst is used usually within a range of 0.05 to 0.2 molar ratio(s), as opposed to 1 mole of the present fused heterocyclic compound (P10-m0) (when m is 0).

The reaction temperature is usually within a range of –20 to 120° C. The reaction period of the reaction is usually within a range of 0.1 to 12 hours.

When the reaction is completed, the resulting mixtures are extracted with organic solvent(s), and if necessary, the resulting organic layers are worked up (for example, washing with an aqueous solution of the reducing agent (for example, sodium sulfite, sodium thiosulfate) and/or an aqueous solution of the base (for example, sodium hydrogen carbonate), drying and concentration) to isolate the present fused heterocyclic compound (P10) (when m is 1 or 2). The isolated present fused heterocyclic compound (P10) (when m is 1 or 2) may be further purified, for example, by chromatography and recrystallization.

(Process 22)

A present fused heterocyclic compound (P11) (when $R^5$ represents —OH) can be prepared via an intermediate compound (P11') from the present fused heterocyclic compound (P4).

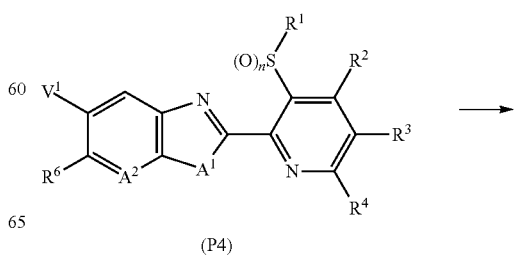

(P4)

-continued

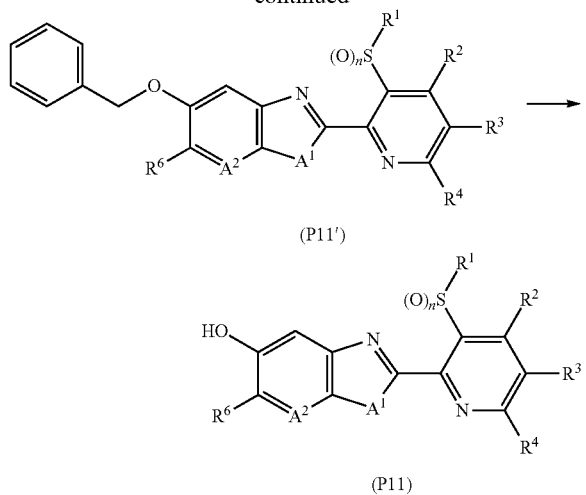

(P11')

(P11)

[wherein, $V^1$ represents a halogen atom and each other symbol is the same as defined in the formula (1)]

The intermediate compound (P11') can be prepared by reacting the present fused heterocyclic compound (P4) with benzyl alcohol in the presence of a base.

The reaction is usually carried out in the presence of a solvent or by using benzyl alcohol as solvent.

Examples of the solvent to be used in the reaction include aromatic hydrocarbons such as toluene and xylene; aprotic polar solvents such as DMF, NMP and DMSO; and mixed solvents thereof. The reaction may be carried out, if necessary, in the presence of a catalyst. Examples of the catalyst to be used include copper halides such as copper chloride(I), copper bromide(I) and copper iodide(I).

The reaction may be also carried out, if necessary, in the presence of a ligand.

Examples of the ligand to be used in the reaction include acetyl acetone, salen and phenanthroline.

The reaction is usually carried out in the presence of a base.

Examples of the base to be used include inorganic bases such as potassium carbonate, cesium carbonate and tripotassium phosphate.

In the reaction, the benzyl alcohol is used usually within a range of 1 to 10 molar ratio(s), the catalyst is used usually within a range of 0.1 to 5 molar ratio(s), the ligand is used usually within a range of 0.1 to 5 molar ratio(s), and the base is used usually within a range of 1 to 2 molar ratio(s), as opposed to 1 mole of the present fused heterocyclic compound (P4).

The reaction temperature is usually within a range of 50 to 200° C. The reaction period of the reaction is usually within a range of 0.5 to 24 hours.

When the reaction is completed, the resulting mixtures are extracted with organic solvent(s), and the resulting organic layers are worked up (for example, drying and concentration) to isolate the intermediate compound (P11').

The isolated intermediate compound (P11') may be further purified, for example, by chromatography and recrystallization.

In the reaction, $V^1$ represents preferably a bromine atom and an iodine atom.

The present fused heterocyclic compound (P11) can be prepared by reacting the intermediate compound (P11') with hydrogen gas in the presence of a catalyst for hydrogenation.

The reaction is carried out under hydrogen atmosphere of usually 1 to 100 atmospheric pressure(s) and usually in the presence of a solvent.

Examples of the solvent to be used in the reaction include ethers such as THF, ethyleneglycol dimethyl ether, methyl tert-butyl ether and 1,4-dioxane; esters such as ethyl acetate and butyl acetate; alcohols such as methanol and ethanol; water; and mixed solvents thereof.

Examples of the catalyst for hydrogenation to be used in the reaction include transition metal compounds such as palladium-carbon, palladium hydroxide, raney nickel and platinum oxide.

In the reaction, the hydrogen gas is used usually within a range of 3 molar ratios, the catalysts for hydrogenation is used usually within a range of 0.001 to 0.5 molar ratio(s), as opposed to 1 mole of the intermediate compound (P11').

The reaction may be also carried out, if necessary, in the presence of an acid or a base and the others.

Examples of the acids to be used in the reaction include organic acids such as acetic acid and inorganic acids such as hydrochloric acid, and examples of the base to be used include tertiary amines such as triethylamine and metal oxide such as magnesium oxide.

The reaction temperature is usually within a range of −20 to 100° C. The reaction period of the reaction is usually within a range of 0.1 to 24 hours.

When the reaction is completed, the reaction mixtures are filtered and, if necessary, are extracted with organic solvent(s), and the resulting organic layers are worked up (for example, drying and concentration) to isolate the present fused heterocyclic compound (P11). The isolated present fused heterocyclic compound (P11) may be further purified, for example, by chromatography and recrystallization.

(Process 23)

A present fused heterocyclic compound (P12) (when $R^5$ represents a —$OR^{10}$ group' in the formula (1)) can be prepared by reacting the present fused heterocyclic compound (P11) with the compound (M13).

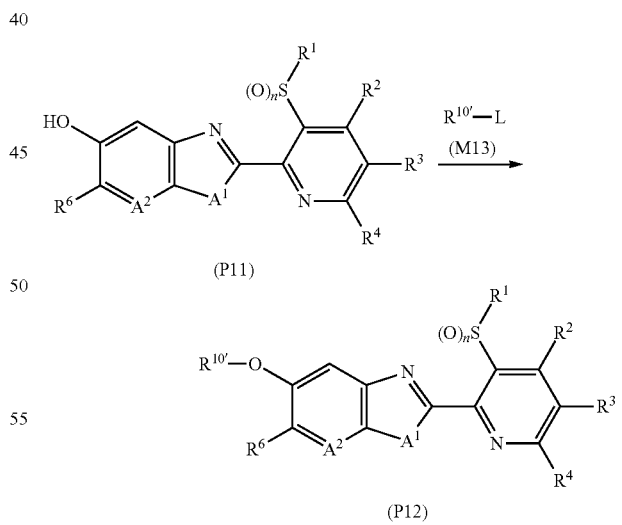

(P11)

(P12)

[wherein, $R^{10'}$ represents any group of $R^{10}$ defined in the formula (1) other than a hydrogen atom, and each other symbol is the same as defined in the formula (1)]

This reaction is usually carried out in the presence of a solvent.

Examples of the solvent to be used in the reaction include ethers such as THF, ethyleneglycol dimethyl ether, methyl tert-butyl ether and 1,4-dioxane; aromatic hydrocarbons such as toluene and xylene; nitriles such as acetonitrile; aprotic polar solvents such as DMF, NMP and DMSO; and mixed solvents thereof.

Examples of the base to be used include inorganic bases including an alkali metal or alkaline-earth metal hydrides such as sodium hydride, potassium hydride and calcium hydride; and an alkali metal or alkaline-earth metal carbonates such as sodium carbonate and potassium carbonate; and organic bases such as triethylamine.

In the reaction, the compound (M13) is used usually within a range of 1 to 10 molar ratio(s) and the base is used usually within a range of 1 to 10 molar ratio(s), as opposed to 1 mole of the present fused heterocyclic compound (P11).

The reaction temperature is usually within a range of 0 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present fused heterocyclic compound (P12). The isolated present fused heterocyclic compound (P12) may be further purified, for example, by chromatography and recrystallization.

Also, among the present fused heterocyclic compound (P12), the present fused heterocyclic compound (P12) (when represents a trifluoromethyl group) can be carried out according to the below-mentioned process.

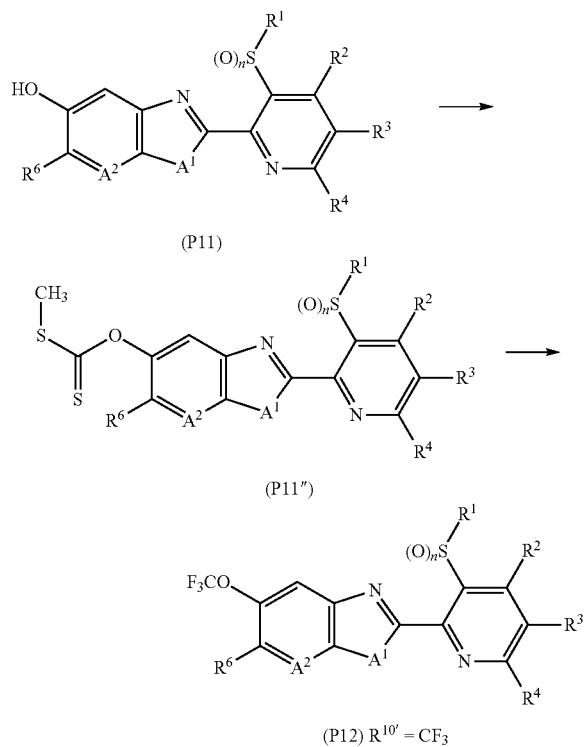

(P11)

(P11")

(P12) $R^{10'} = CF_3$

[wherein, each symbol is the same as defined in the formula (1)]

The intermediate compound (P11") can be prepared by reacting the present fused heterocyclic compound (P11) with a base, carbon disulfide and a methylating agent.

The reaction is carried out in the presence of a solvent.

Examples of the solvent to be used in the reaction include aprotic polar solvents such as DMF, NMP and DMSO.

Examples of the base to be used include alkali metal hydrides such as sodium hydride.

Examples of the methylating agent to be used in the reaction include methyl iodide.

In the reaction, the base is used usually within a range of 1 to 2 molar ratio(s), the carbon dioxide is used usually within a range of 1 to 10 molar ratio(s), and the methylating agent is used usually within a range of 1 to 10 molar ratio(s), as opposed to 1 mole of the present fused heterocyclic compound (P11).

The reaction temperature is usually within a range of 0 to 100° C. The reaction period of the reaction is usually within a range of 0.5 to 24 hours.

When the reaction is completed, the reaction mixtures are extracted with organic solvent(s), and the resulting organic layers are worked up (for example, drying and concentration) to isolate the present fused heterocyclic compound (P11"). The isolated present fused heterocyclic compound (P11") may be further purified, for example, by chromatography and recrystallization.

Among the present fused heterocyclic compound (P12), the present fused heterocyclic compound (P12) (when $R^{10'}$ represents a trifluoroethyl group) can be prepared by reacting the intermediate compound (P11") with a fluorinating agent in the presence of a base.

The reaction is usually carried out in the presence of a solvent.

Examples of the solvent to be used in the reaction include halogenated hydrocarbons such as dichloromethane, chloroform, carbon tetrachloride and 1,2-dichloroethane.

The reaction is carried out in the presence of a base and a fluorinating agent.

Examples of the base to be used include 1,3-dibromo-5,5-dimethylhydantoin.

Examples of the fluorinating agent to be used in the reaction include tetra-n-butylammonium fluoride and hydrogen fluoride pyridine complex.

In the reaction, the base is used usually within a range of 1 to 10 molar ratio(s), and the fluorinating agent is used usually within a range of 1 to 10 molar ratio(s), as opposed to 1 mole of the intermediate compound (P11").

The reaction temperature is usually within a range of −80 to 50° C. The reaction period of the reaction is usually within a range of 0.5 to 24 hours.

When the reaction is completed, the reaction mixtures are extracted with organic solvent(s), and the resulting organic layers are worked up (for example, drying and concentration) to isolate the present fused heterocyclic compound (P12) (when $R^{10'}$ represents a trifluoromethyl group). The isolated present fused heterocyclic compound (P12) (when $R^{10'}$ represents a trifluoromethyl group) may be further purified, for example, by chromatography and recrystallization.

(Process 24)

Among the present fused heterocyclic compounds and the above-mentioned intermediate compounds, a reaction between the compounds that includes a nitrogen-containing heterocyclic part having lone pair electrons on nitrogen atom and an oxidizing agent may optionally afford N-oxide compounds having the oxidized nitrogen atom.

Examples of the nitrogen-containing heterocyclic part include a pyridine ring.

The reaction may be carried out according to the well-known method, and typically, may be carried out by using an oxidizing agent such as m-chloroperoxybenzoic acid and hydrogen peroxide in solvent(s) including halogenated hydrocarbons such as dichloromethane, chloroform and chlorobenzene; alcohols such as methanol and ethanol; carboxylic acids such as acetic acid; water; and mixed solvents thereof.

In the method of the present invention, the present fused heterocyclic compound is applied to plant seeds such that an effective amount of the present fused heterocyclic compound is retained inside and/or on surface of the plant seeds, and the present method can thus control pests that give feeding damage to plants after the plant seeds are germinated.

In the present invention, the present fused heterocyclic compound may be used as itself, but is usually mixed with an inert active carrier, if necessary, with adding surfactants and other auxiliary agents for formulation, to formulate into emulsifiable concentrates, flowables, wettable powders, dust formulations and the others. In the formulation comprising the present fused heterocyclic compound, the amount of the present fused heterocyclic compound is usually within a range of 0.1% to 70% by weight, preferably within a range of 1 to 60% by weight and more preferably within a range of 5 to 50% by weight.

Examples of the inert carrier to be used in the formulation include an inert solid carrier and an inert liquid carrier.

Examples of the above-mentioned inert solid carrier include fine powders or granules of clays (for example, kaolin clay, diatomaceous earth, bentonite, Fubasami clay, or acid white clay), synthetic hydrated silicon oxides, talcs, ceramics, other inorganic minerals (for example, sericite, quartz, sulfur, active carbon, calcium carbonate or hydrated silica) or chemical fertilizers (for example, ammonium sulfate, ammonium phosphate, ammonium nitrate, urea or ammonium chloride) and the others; as well as synthetic resins (for example, polyester resins such as polypropylene, polyacrylonitrile, polymethylmethacrylate and polyethylene terephthalate; nylon resins (for example, nylon-6, nylon-11 and nylon-66); polyamide resins; polyvinyl chloride, polyvinylidene chloride, vinyl chloride-propylene copolymers, and the others).

Examples of the above-mentioned liquid carriers include water; alcohols (for example, methanol, ethanol, isopropyl alcohol, butanol, hexanol, benzyl alcohol, ethylene glycol, propylene glycol or phenoxy ethanol); ketones (for example, acetone, methyl ethyl ketone or cyclohexanone); aromatic hydrocarbons (for example, toluene, xylene, ethyl benzene, dodecyl benzene, phenyl xylyl ethane or methylnaphthalene); aliphatic hydrocarbons (for example, hexane, cyclohexane, kerosene or light oil); esters (for example, ethyl acetate, butyl acetate, isopropyl myristate, ethyl oleate, diisopropyl adipate, diisobutyl adipate or propylene glycol monomethyl ether acetate); nitriles (for example, acetonitrile or isobutyronitrile); ethers (for example, diisopropyl ether, 1,4-dioxane, ethyleneglycol dimethyl ether, diethyleneglycol dimethyl ether, diethylene glycol monomethyl ether, propylene glycol monomethyl ether, dipropylene glycol monomethyl ether or 3-methoxy-3-methyl-1-butanol); acid amides (for example, N,N-dimethylformamide or N,N-dimethylacetamide); halogenated hydrocarbons (for example, dichloromethane, trichloroethane or carbon tetrachloride); sulfoxides (for example, dimethyl sulfoxide); propylene carbonate; and vegetable oils (for example, soybean oil or cottonseed oil).

Examples of the surfactants include nonionic surfactants such as polyoxyethylenated alkyl ethers, polyoxyethylenated alkyl aryl ethers and polyethylene glycol fatty acid esters; and anionic surfactants such as alkyl sulfonates, alkylbenzene sulfonates and alkyl sulfates.

Examples of the other auxiliary agents for formulation include a binder, a dispersant and a stabilizer. Specific examples include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol).

Specific examples of the application form of the present fused heterocyclic compound to seeds of plants may various types of application forms, and include, for example, a spray coating treatment of the present fused heterocyclic compound on the surface of seeds, a smear treatment on the seeds, a coating treatment, a film coating treatment and a pellet coating treatment.

Herein, "plant seed(s)" represent seed(s) of plant in the state before seeding them into a soil or medium where plant grows.

The dose used of the present fused heterocyclic compound to plant seeds may vary depending on the kinds of plants to be treated, the species or the degree of emergence of the pests to be controlled, the dosage form, the timing of seeding, weather conditions and the others. The dose is within the range of usually from 0.01 to 1,000 g, preferably from 0.2 to 200 g, and more preferably from 1 to 10 g. The dose thereof is within the range of usually from 0.01 to 1,000 mg, and preferably from 0.1 to 100 mg per 100 grain of plant seed.

The pests that can be controlled by the method of the present invention includes plant seeds containing an effective amount of the present fused heterocyclic compound or pests that give feeding damage to plants after the plant seeds are germinated. Example of the pest includes harmful insects and specifically includes the followings.

Hemiptera:
Delphacidae (for example, *Laodelphax striatellus, Nilaparvata lugens*, or *Sogatella furcifera*);
Deltocephalidae (for example, *Nephotettix cincticeps*);
Aphididae (for example, *Aphis gossypii, Myzus persicae, Brevicoryne brassicae, Macrosiphum euphorbiae, Aulacorthum solani, Rhopalosiphum padi*);
Pentatomidae (for example, *Nezara antennata, Riptortus clavetus, Leptocorisa chinensis, Eysarcoris parvus*, or *Halyomorpha mista*);
Aleyrodidae (for example, *Trialeurodes vaporariorum, Bemisia tabaci*).

Lepidoptera:
Pyralidae (for example, *Chilo suppressalis, Tryporyza incertulas, Cnaphalocrocis medinalis, Notarcha derogata, Piodia interpunctella, Ostrinia furnacalis* or *Hellula undalis*);
Noctuidae (for example, *Spodoptera litura, Spodoptera exigua, Mythimna separata, Mamestra brassicae, Agrotis ipsilon, Plusia nigrisigna, Trichoplusia* spp., *Heliothis* spp., or *Helicoverpa* spp.);
Pieridae (for example, *Pieris rapae*);
Tortricidae (for example, *Leguminivora glycinivorella, Matsumuraeses azukivora*) and
Yponomeutidae (for example, *Plutella rylostella*).
Thysanoptera: *Frankliniella occidentalis, Thrips palmi, Scirtothrips dorsalis, Thrips tabaci, Frankliniella intonsa*, and the others.

Diptera:
Anthomyiidae (for example, *Delia platura*, or *Delia antiqua*);

Agromyzidae (for example, *Agromyza oryzae, Hydrellia griseola, Liriomyza sativae, Liriomyza trifolii*, or *Chromatomyia horticola*);

Chloropidae (for example, *Chlorops oryzae*); and Drosophilidae.

Coleoptera:

Corn root worms (*Diabrotica* spp.)(for example, *Diabrotica virgifera virgifera*, or *Diabrotica undecimpunctata howardi*);

Scarabaeidae (for example, *Anomala cuprea, Anomala rufocuprea*, or *Popillia japonica*);

Curculionidae (for example, *Sitophilus zeamais, Lissorhoptrus oryzophilus, Echinocnemus squameus*, or *Anthonomus grandis*);

Chrysomelidae (for example, *Oulema oryzae, Aulacophora femoralis, Phyllotreta striolata*, or *Leptinotarsa decemlineata*);

Elateridae (*Agriotes* spp.); and *Paederus fuscipes*.

In the present invention, the Present fused heterocyclic compound can be applied to the below-mentioned plant.

Crops:

corn, rice, wheat, barley, rye, oat, sorghum, cotton, soybean, peanut, buckwheat, beet, colza, sunflower, sugar cane, tobacco, and the others;

Vegetables:

solanaceous vegetables (for example, eggplant, tomato, pimento, pepper or potato), cucurbitaceous vegetables (for example, cucumber, pumpkin, zucchini, water melon or melon), cruciferous vegetables (for example, Japanese radish, white turnip, horseradish, kohlrabi, Chinese cabbage, cabbage, leaf mustard, broccoli, cauliflower), asteraceous vegetables (for example, burdock, crown daisy, artichoke or lettuce), liliaceous vegetables (for example, green onion, onion, garlic or asparagus), ammiaceous vegetables (for example, carrot, parsley, celery or parsnip), chenopodiaceous vegetables (for example, spinach or Swiss chard), lamiaceous vegetables (for example, *Perilla frutescens*, mint or basil).

In particular, the method of the present invention is preferably used as a method for controlling pests in the cultivation of corn, cotton, soybean, beet, colza, Japanese radish.

The above-mentioned "Plants" includes genetically modified plants.

The plant seeds of the present invention contain an effective amount of the present fused heterocyclic compound inside and/or on surface of plant seeds. The effective amount of the present fused heterocyclic compound is usually within the range of 0.01 to 1,000 g, preferably within a range of 0.2 to 200 g and more preferably within a range of 1 to 10 g per 10 kg of plant seeds. Also, the effective amount of the present fused heterocyclic compound is usually within a range of 0.01 to 1,000 mg, preferably within a range of 0.1 to 100 mg per 100 grains of plant seed. The surface of plant seed means to include coating layer that formed on surrounding of plant seeds.

The plant seeds of the present invention may be prepared a method of applying the above-mentioned present fused heterocyclic compound to plant seeds, and may be seeded shortly after the present fused heterocyclic compound is applied to seeds or may be seeded after the plant seeds are kept during the period from an application to a use. Also, before, at or after seeding or after germination or during the growing period, an agent for controlling pests such as insecticide, nematicide, fungicide and herbicide may be applied and also a plowing or a fertilization or the like may be carried out before or simultaneously with seeding.

EXAMPLES

The following Examples including Production example, Formulation examples, Treatment examples and Test examples serve to illustrate the present invention in more detail, which should not intend to limit the present invention.

Production Examples of the present fused heterocyclic compound are shown below.

The following Production examples of the present fused heterocyclic compound should not intend to limit the present fused heterocyclic compound.

Production Example 1 (1)

A mixture of N2-methyl-5-trifluoromethylpyridine-2,3-diamine 0.76 g, 3-fluoropyridine-2-carboaldehyde 0.50 g, sodium hydrogensulfite 0.50 g, and DMF 3 mL was stirred at 120° C. for 8 hr. To the reaction mixture allowed to cool was added saturated aqueous sodium bicarbonate, and the resulting mixture was extracted with ethyl acetate. The organic layer was washed with water, dried over anhydrous magnesium sulfate, and then concentrated under reduced pressure. The resultant residue was treated with silica gel column chromatography to give 2-(3-fluoropyridin-2-yl)-3-methyl-6-trifluoromethyl-3H-imidazo[4,5-b]pyridine (hereinafter referred to as Intermediate compound (M6-2)) 0.43 g.

Intermediate Compound (M6-2)

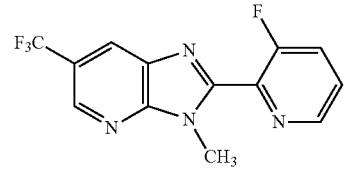 [SMILES: Cn1c(-c2ncccc2F)nc2cc(C(F)(F)F)cnc21]

$^1$H-NMR (CDCl$_3$) δ: 8.75 (1H, d), 8.66-8.63 (1H, m), 8.40 (1H, d), 7.73-7.67 (1H, m), 7.56-7.51 (1H, m), 4.16 (3H, s).

Production Example 1 (2)

To a mixture of Intermediate compound (M6-2) 1.23 g and DMF 3.5 mL at ice temperature was added sodium ethanethiolate 0.48 g, and the resulting mixture was stirred at RT for 2 hr. To the reaction mixture was added water, and the resulting mixture was extracted with ethyl acetate. The organic layer was washed with water, and dried over anhydrous magnesium sulfate, and then concentrated under reduced pressure. The resultant residue was treated with silica gel column chromatography to give 2-(3-ethylsulfanylpyridin-2-yl)-3-methyl-6-trifluoromethyl-3H-imidazo[4,5-b]pyridine (hereinafter referred to as the present fused heterocyclic compound 1) 1.39 g.

Present Fused Heterocyclic Compound 1

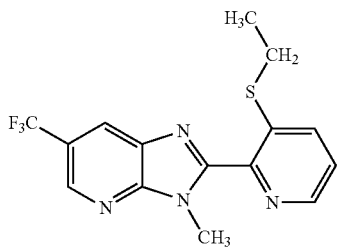 [SMILES: CCSc1cccnc1-c1nc2cc(C(F)(F)F)cnc2n1C]

$^1$H-NMR (CDCl$_3$) δ: 8.73 (1H, d), 8.53 (1H, dd), 8.39 (1H, d), 7.80 (1H, dd), 7.40 (1H, dd), 4.04 (3H, s), 2.97 (2H, q), 1.35 (3H, t).

Production Examples 2, 3

To a mixture of 2-(3-ethylsulfanylpyridin-2-yl)-3-methyl-6-trifluoromethyl-3H-imidazo[4,5-b]pyridine (the present fused heterocyclic compound 1) 0.62 g and chloroform 10 mL at ice temperature was added m-chloroperbenzoic acid (65% or more purity) 0.79 g, and then the resulting mixture was stirred at RT for 5 hr. To the reaction mixture was added saturated aqueous sodium bicarbonate, and the reaction mixture was extracted with chloroform. The organic layer was washed with water, and dried over anhydrous magnesium sulfate, and then concentrated under reduced pressure. The resultant residue was treated with silica gel column chromatography to give 2-(3-ethylsulfinylpyridin-2-yl)-3-methyl-6-trifluoromethyl-3H-imidazo[4,5-b]pyridine (hereinafter referred to as the present fused heterocyclic compound 2) 87 mg, and 2-(3-ethylsulfonylpyridin-2-yl)-3-methyl-6-trifluoromethyl-3H-imidazo[4,5-b]pyridine (hereinafter referred to as the present fused heterocyclic compound 3) 0.49 g.

Present Fused Heterocyclic Compound 2

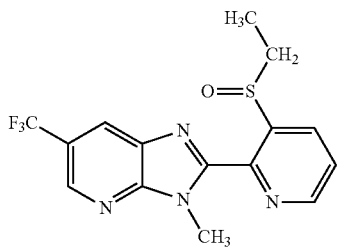 [SMILES: CCS(=O)c1cccnc1-c1nc2cc(C(F)(F)F)cnc2n1C]

$^1$H-NMR (CDCl$_3$) δ: 8.85 (1H, dd), 8.77 (1H, s), 8.67 (1H, dd), 8.34 (1H, s), 7.69 (1H, dd), 4.36 (3H, s), 3.72-3.62 (1H, m), 3.14-3.04 (1H, m), 1.47 (3H, t).

Present Fused Heterocyclic Compound 3

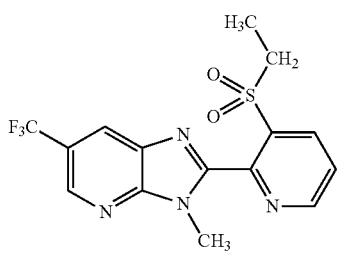

$^1$H-NMR (CDCl$_3$) δ: 9.01 (1H, dd), 8.76 (1H, s), 8.55 (1H, dd), 8.31 (1H, s), 7.74 (1H, dd), 3.88 (3H, s), 3.83 (2H, q), 1.37 (3H, t).

Production Example 4 (1)

A mixture of N2-methyl-5-trifluoromethylpyridine-2,3-diamine 0.70 g, 3-chloro-5-trifluoromethylpyridine-2-carboxylic acid 0.53 g, EDC hydrochloride 0.82 g, HOBt 42 mg, and pyridine 4.5 mL was stirred at 60° C. for 4 hr. To the reaction mixture allowed to cool was added water, and the resulting mixture was extracted with ethyl acetate. The organic layer was washed with water, and dried over anhydrous magnesium sulfate, and then concentrated under reduced pressure to give Intermediate compound (M20-3).

Intermediate Compound (M20-3)

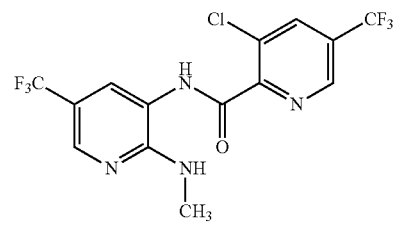

A mixture of the total amount of the resulting Intermediate compound (M20-3), p-toluenesulfonic acid monohydrate 1.04 g, and N-methylpyrrolidinone 4 mL was stirred with heating at 150° C. for 2.5 hr. To the reaction mixture allowed to cool was added saturated aqueous sodium bicarbonate, and the resulting mixture was extracted with ethyl acetate. The organic layer was washed with water, and dried over anhydrous magnesium sulfate, and then concentrated under reduced pressure. The resultant residue was treated with silica gel column chromatography to give 2-(3-chloro-5-trifluoromethylpyridin-2-yl)-3-methyl-6-trifluoromethyl-3H-imidazo[4,5-b]pyridine (hereinafter referred to as Intermediate compound (M6-3)) 0.71 g.

Intermediate Compound (M6-3)

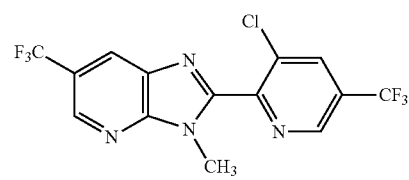 [SMILES: Cn1c(-c2ncc(C(F)(F)F)cc2Cl)nc2cc(C(F)(F)F)cnc21]

$^1$H-NMR (CDCl$_3$) δ: 8.96 (1H, d), 8.79 (1H, d), 8.42 (1H, d), 8.22 (1H, d), 4.02 (3H, s).

Production Example 4 (2)

To a mixture of 2-(3-chloro-5-trifluoromethylpyridin-2-yl)-3-methyl-6-trifluoromethyl-3H-imidazo[4,5-b]pyridine (Intermediate compound (M6-3)) 0.71 g and DMF 4 mL at ice temperature was added sodium ethanethiolate 0.24 g, and the resulting mixture was stirred at RT for 1 hr. To the reaction mixture was added water, and the resulting mixture was extracted with ethyl acetate. The organic layer was washed with water, dried over anhydrous magnesium sulfate, and then concentrated under reduced pressure to give 2-(3-ethylsulfanyl-5-trifluoromethylpyridin-2-yl)-3-methyl- 6-trifluoromethyl-3H-imidazo[4,5-b]pyridine (hereinafter referred to as the present fused heterocyclic compound 4) 0.76 g.

Present Fused Heterocyclic Compound 4

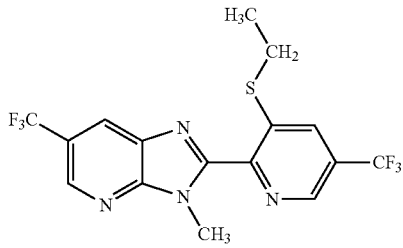

$^1$H-NMR (CDCl$_3$) δ: 8.77 (1H, d), 8.75 (1H, d), 8.43 (1H, d), 7.93 (1H, d), 4.11 (3H, s), 3.02 (2H, q), 1.40 (3H, t).

Production Example 5

To a mixture of 2-(3-ethylsulfanyl-5-trifluoromethylpyridin-2-yl)-3-methyl-6-trifluoromethyl-3H-imidazo[4,5-b]pyridine (the present fused heterocyclic compound 4) 0.61 g and chloroform 10 mL at ice temperature was added m-chloroperbenzoic acid (65% or more purity) 0.66 g, and then the mixture was stirred at RT for 10 hr. To the reaction mixture was added aqueous 10% sodium thiosulfate and saturated aqueous sodium bicarbonate, and the reaction mixture was extracted with chloroform. The organic layer was washed with water, dried over anhydrous magnesium sulfate, and then concentrated under reduced pressure to give 2-(3-ethylsulfonyl-5-trifluoromethylpyridin-2-yl)-3-methyl-6-trifluoromethyl-3H-imidazo[4,5-b]pyridine (hereinafter referred to as the present fused heterocyclic compound 5) 0.62 g.

Present Fused Heterocyclic Compound 5

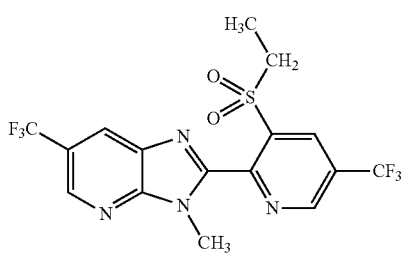

$^1$H-NMR (CDCl$_3$) δ: 9.25 (1H, d), 8.80 (1H, d), 8.79 (1H, d), 8.34 (1H, d), 3.96 (2H, q), 3.94 (3H, s), 1.42 (3H, t).

Production Example 6

A mixture of 2-(3-ethylsulfanyl-pyridin-2-yl)-6-iodo-3-methyl-3H-imidazo[4,5-b]pyridine 835 mg, sodium pentafluoropropionate 2.0 g, copper iodide 2.0 g, NMP 10 mL, and xylene 50 mL was stirred with heating at 150° C. for 0.8 hr. The mixture was allowed to cool to RT, and to the mixture was added aqueous 40% ammonia and saturated aqueous sodium bicarbonate, and the resulting mixture was extracted with ethyl acetate. The organic layer was dried over sodium sulfate, and then concentrated under reduced pressure. The resultant residue was treated with silica gel column chromatography to give 2-(3-ethylsulfanyl-pyridin-2-yl)-3-methyl-6-pentafluoroethyl-3H-imidazo[4,5-b]pyridine (hereinafter referred to as the present fused heterocyclic compound 6) 303 mg.

Present Fused Heterocyclic Compound 6

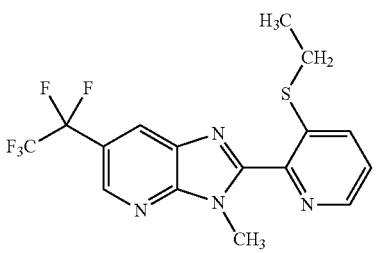 [SMILES: CCSc1cccnc1-c1nc2cc(C(F)(F)C(F)(F)F)cnc2n1C]

$^1$H-NMR (CDCl$_3$) δ: 8.69 (1H, d), 8.52 (1H, dd), 8.40 (1H, d), 7.80 (1H, dd), 7.39 (1H, dd), 4.06 (3H, s), 2.97 (2H, q), 1.34 (3H, t).

Production Examples 7, 8

To a mixture of 2-(3-ethylsulfanyl-pyridin-2-yl)-3-methyl-6-pentafluoroethyl-3H-imidazo[4,5-b]pyridine 254 mg and chloroform 10 mL at ice temperature was added m-chloroperbenzoic acid (65% or more purity) 266 mg. The mixture was allowed to warm to RT, and stirred for 0.5 hr. To the mixture was added saturated aqueous sodium bicarbonate and saturated aqueous sodium thiosulfate, and the mixture was extracted with chloroform. The organic layer was dried over magnesium sulfate, and then concentrated under reduced pressure. The resultant residue was treated with silica gel column chromatography to give 2-(3-ethanesulfinyl-pyridin-2-yl)-3-methyl-6-pentafluoroethyl-3H-imidazo[4,5-b]pyridine (hereinafter referred to as the present fused heterocyclic compound 7) 8 mg and 2-(3-ethanesulfonyl-pyridin-2-yl)-3-methyl-6-pentafluoroethyl-3H-imidazo[4,5-b]pyridine (hereinafter referred to as the present fused heterocyclic compound 8) 235 mg.

Present Fused Heterocyclic Compound 7

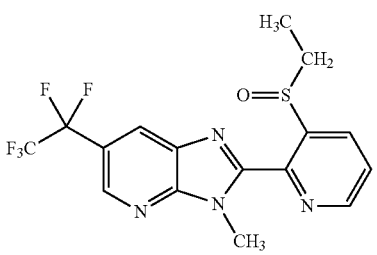 [SMILES: CCS(=O)c1cccnc1-c1nc2cc(C(F)(F)C(F)(F)F)cnc2n1C]

$^1$H-NMR (CDCl$_3$) δ: 8.85 (1H, dd), 8.72 (1H, d), 8.68 (1H, dd), 8.31 (1H, d), 7.69 (1H, dd), 4.36 (3H, s), 3.72-3.61 (1H, m), 3.17-3.06 (1H, m), 1.47 (3H, t).

Present Fused Heterocyclic Compound 8

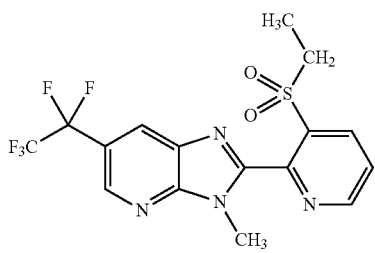 [SMILES: CCS(=O)(=O)c1cccnc1-c1nc2cc(C(F)(F)C(F)(F)F)cnc2n1C]

$^1$H-NMR (CDCl$_3$) δ: 9.00 (1H, dd), 8.72 (1H, d), 8.55 (1H, dd), 8.30 (1H, d), 7.73 (1H, dd), 3.89 (3H, s), 2.84 (2H, q), 1.37 (3H, t).

Production Example 9 (1)

To a mixture of 5-iodo-N2-methyl-pyridine-2,3-diamine 1.9 g and pyridine 6 mL was added EDC hydrochloride 1.28 g, HOBt 86 mg, and 3-chloro-pyridine-2-carboxylic acid 1.3 g, and the mixture was stirred at RT for 9 hr. To the reaction mixture was added water, and the precipitated powder was collected by filtration, and washed with chloroform to give 3-chloro-pyridine-2-carboxylic acid (5-iodo-2-methyl-amino-pyridin-3-yl)-amide (hereinafter referred to as Intermediate compound (M20-7)) 3.6 g.

Intermediate Compound (M20-7)

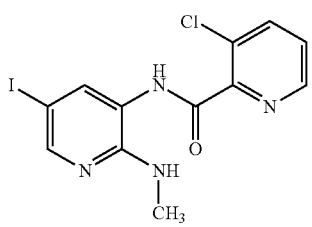 [SMILES: CNc1ncc(I)cc1NC(=O)c1ncccc1Cl]

$^1$H-NMR (DMSO-D$_6$) δ: 9.95 (1H, s), 8.65 (1H, d), 8.15-8.10 (2H, m), 8.00 (1H, d), 7.65 (1H, dd), 6.30 (1H, d), 2.81 (3H, d).

Production Example 9 (2)

A mixture of Intermediate compound (M20-7) 3.4 g, p-toluenesulfonic acid monohydrate 5.8 g, DMF 30 mL, and toluene 120 mL was stirred with heating at 130° C. for 12 hr. The mixture was allowed to cool to RT, and to the mixture was added saturated aqueous sodium bicarbonate, and the resulting mixture was extracted with ethyl acetate. The organic layer was dried over sodium sulfate, and then concentrated under reduced pressure. The resultant residue was treated with silica gel column chromatography to give 2-(3-chloro-pyridin-2-yl)-6-iodo-3-methyl-3H-imidazo[4,5-b]pyridine (hereinafter referred to as Intermediate compound (M6-7)) 2.0 g.

Intermediate Compound (M6-7)

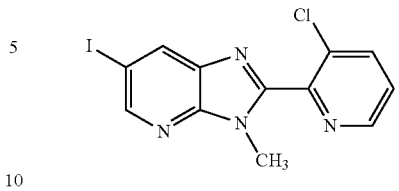

$^1$H-NMR (CDCl$_3$) δ: 8.70 (1H, d), 8.66-8.63 (1H, m), 8.47-8.44 (1H, m), 7.95 (1H, d), 7.45 (1H, dd), 3.90 (3H, s).

Production Example 9 (3)

A mixture of Intermediate compound (M6-7) 2.0 g, sodium ethanethiolate 888 mg, and DMF 45 mL was stirred with heating at 50° C. for 12 hr. The mixture was allowed to cool to RT, and to the mixture was added saturated aqueous sodium bicarbonate, and the resulting mixture was extracted with ethyl acetate. The organic layer was dried over sodium sulfate, and then concentrated under reduced pressure. The resultant residue was treated with silica gel column chromatography to give 2-(3-ethylsulfanyl-pyridin-2-yl)-6-iodo-3-methyl-3H-imidazo[4,5-b]pyridine (hereinafter referred to as the present fused heterocyclic compound 9) 1.0 g.

Present Fused Heterocyclic Compound 9

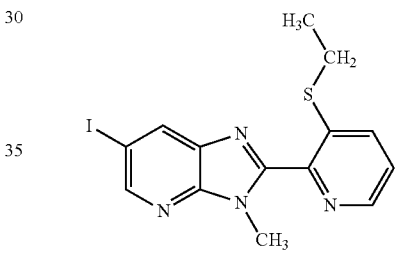

$^1$H-NMR (CDCl$_3$) δ: 8.61 (1H, d), 8.51 (1H, dd), 8.45 (1H, d), 7.76 (1H, dd), 7.37 (1H, dd), 3.96 (3H, s), 2.94 (2H, q), 1.33 (3H, t).

Production Example 10 (1)

A mixture of 3-amino-5-trifluoromethylpyridine-2-thiol 0.45 g, 3-chloro-5-trifluoromethylpyridine-2-carboxylic acid 0.55 g, EDC hydrochloride 0.67 g, HOBt 31 mg, and pyridine 4.5 mL was stirred at 60° C. for 4 hr. The reaction mixture was allowed to cool, and to the reaction mixture was added water, and the resulting mixture was extracted with ethyl acetate. The organic layer was washed with water, and dried over anhydrous magnesium sulfate, and then concentrated under reduced pressure to give Intermediate compound (M20-9).

Intermediate Compound (M20-9)

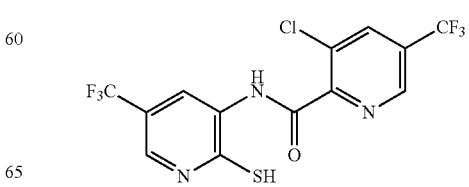

A mixture of the total amount of the resulting Intermediate compound (M20-9), p-toluenesulfonic acid monohydrate 1.04 g, and N-methylpyrrolidinone 3.5 mL was stirred with heating at 150° C. for 2 hr. To the reaction mixture allowed to cool was added saturated aqueous sodium bicarbonate, and the resulting mixture was extracted with ethyl acetate. The organic layer was washed with water, and dried over anhydrous magnesium sulfate, and then concentrated under reduced pressure. The resultant residue was treated with silica gel column chromatography to give 2-(3-chloro-5-trifluoromethylpyridin-2-yl)-6-(trifluoromethyl)thiazolo[5,4-b]pyridine (hereinafter referred to as Intermediate compound (M6-9)) 0.29 g.

Intermediate Compound (M6-9)

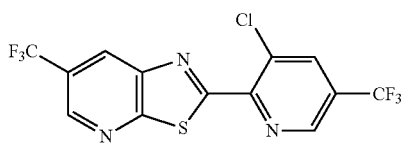 [SMILES: FC(F)(F)c1cnc(-c2nc3cc(C(F)(F)F)cnc3s2)c(Cl)c1]

$^1$H-NMR (CDCl$_3$) δ: 8.94 (1H, d), 8.90 (1H, d), 8.69 (1H, d), 8.19 (1H, d).

Production Example 10 (2)

2-(3-Ethylsulfanyl-5-trifluoromethylpyridin-2-yl)-6-(trifluoromethyl)thiazolo[5,4-b]pyridine (hereinafter referred to as the present fused heterocyclic compound 10) was prepared in a similar manner as described for the preparation of Production example 4 (2) by using Intermediate compound (M6-9) instead of 2-(3-chloro-5-trifluoromethylpyridin-2-yl)-3-methyl-6-trifluoromethyl-3H-imidazo[4,5-b]pyridine (Intermediate compound (M6-3)).

Present Fused Heterocyclic Compound 10

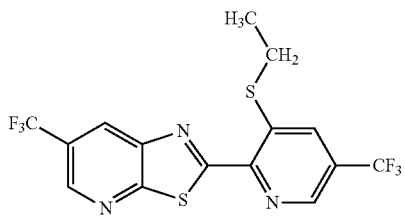 [SMILES: CCSc1cc(C(F)(F)F)cnc1-c1nc2cc(C(F)(F)F)cnc2s1]

$^1$H-NMR (CDCl$_3$) δ: 8.91 (1H, d), 8.70-8.67 (2H, m), 7.91 (1H, s), 3.09 (2H, q), 1.51 (3H, t).

Production Example 11

2-(3-Ethylsulfonyl-5-trifluoromethylpyridin-2-yl)-6-(trifluoromethyl)thiazolo[5,4-b]pyridine (hereinafter referred to as the present fused heterocyclic compound 11) was prepared in a similar manner as described for the preparation of Production example 5 by using 2-(3-ethylsulfanyl-5-trifluoromethylpyridin-2-yl)-6-(trifluoromethyl)thiazolo[5,4-b]pyridine instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).

Present Fused Heterocyclic Compound 11

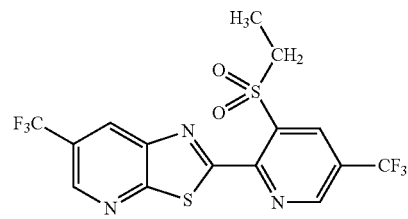 [SMILES: CCS(=O)(=O)c1cc(C(F)(F)F)cnc1-c1nc2cc(C(F)(F)F)cnc2s1]

$^1$H-NMR (CDCl$_3$) δ: 9.19 (1H, d), 8.98 (1H, d), 8.89 (1H, d), 8.61 (1H, d), 4.17 (2H, q), 1.49 (3H, t).

Production Example 12 (1)

A mixture of 3-amino-5-trifluoromethylpyridine-2-thiol 0.45 g, 3-chloropyridine-2-carboxylic acid 0.39 g, EDC hydrochloride 0.67 g, HOBt 31 mg, and pyridine 4 mL was stirred at RT for 12 hr. To the reaction mixture was added water, and the precipitated solid was collected by filtration. The resulting solid was washed with water, and n-hexane, and dried to give 3-chloropyridine-2-carboxylic acid (2-mercapto-5-trifluoromethylpyridin-3-yl)-amide (hereinafter referred to as Intermediate compound (M20-11)) 0.45 g.

Intermediate Compound (M20-11)

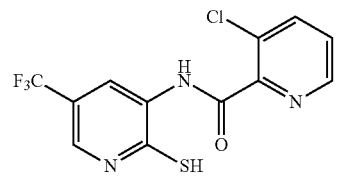 [SMILES: O=C(Nc1cc(C(F)(F)F)cnc1S)c1ncccc1Cl]

Production Example 12 (2)

A mixture of Intermediate compound (M20-11) 0.45 g, p-toluenesulfonic acid monohydrate 0.70 g, and NMP 4 mL was stirred at 150° C. for 2 hr. To the reaction mixture allowed to cool was added saturated aqueous sodium bicarbonate, and the resulting mixture was extracted with ethyl acetate. The organic layer was washed with water, and dried over anhydrous magnesium sulfate, and then concentrated under reduced pressure. The resultant residue was treated with silica gel column chromatography to give 2-(3-chloropyridin-2-yl)-6-(trifluoromethyl)thiazolo[5,4-b]pyridine (hereinafter referred to as Intermediate compound (M6-11)) 0.47 g.

Intermediate Compound (M6-11)

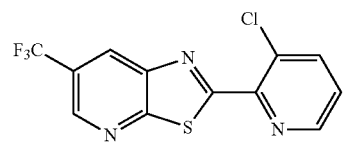 [SMILES: FC(F)(F)c1cnc2sc(-c3ncccc3Cl)nc2c1]

Production Example 12 (3)

2-(3-Ethylsulfanyl-2-yl)-6-(trifluoromethyl)thiazolo[5,4-b]pyridine (hereinafter referred to as the present fused heterocyclic compound 41) was prepared in a similar manner as described for the preparation of Production example 1 (2) by using Intermediate compound (M6-11) instead of 2-(3-fluoropyridin-2-yl)-3-methyl-6-trifluoromethyl-3H-imidazo[4,5-b]pyridine (Intermediate compound (M6-2)).
Present Fused Heterocyclic Compound 41

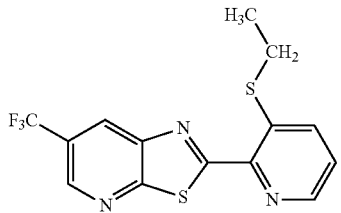 [SMILES: CCSc1cccnc1-c1nc2cc(C(F)(F)F)cnc2s1]

$^1$H-NMR (CDCl$_3$) δ: 8.87 (1H, d), 8.64 (1H, d), 8.48 (1H, dd), 7.76 (1H, dd), 7.37 (1H, dd), 3.06 (2H, q), 1.49 (3H, t).

Production Example 12 (4)

To a mixture of 2-(3-ethylsulfanyl-2-yl)-6-(trifluoromethyl)thiazolo[5,4-b]pyridine 0.36 g and chloroform 5 mL was added m-chloroperbenzoic acid (65% or more purity) 0.56 g, and the resulting mixture was stirred at RT for 12 hr. To the reaction mixture was added aqueous 10% sodium thiosulfate and saturated aqueous sodium bicarbonate, and the mixture was extracted with chloroform. The organic layer was washed with water, dried over anhydrous magnesium sulfate, and then concentrated under reduced pressure to give 2-(3-ethylsulfonyl-2-yl)-6-(trifluoromethyl)thiazolo[5,4-b]pyridine (hereinafter referred to as the present fused heterocyclic compound 12) 0.27 and 2-(3-ethylsulfonyl-2-yl)-6-(trifluoromethyl)thiazolo[5,4-b]pyridine 4-oxide (hereinafter referred to as the present fused heterocyclic compound 22) 91 mg.
Present Fused Heterocyclic Compound 12

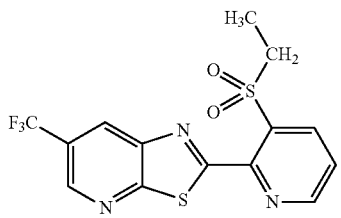 [SMILES: CCS(=O)(=O)c1cccnc1-c1nc2cc(C(F)(F)F)cnc2s1]

$^1$H-NMR (CDCl$_3$) δ: 8.98-8.93 (2H, m), 8.66 (1H, dd), 8.57 (1H, d), 7.69 (1H, dd), 4.13 (2H, q), 1.45 (3H, t).
Present Fused Heterocyclic Compound 22

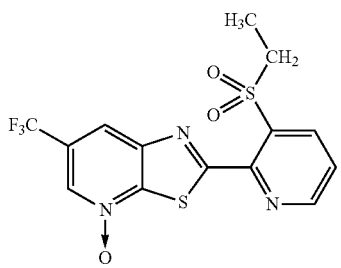 [SMILES: CCS(=O)(=O)c1cccnc1-c1nc2cc(C(F)(F)F)c[n+]([O-])c2s1]

$^1$H-NMR (CDCl$_3$) δ: 8.96 (1H, dd), 8.68 (1H, dd), 8.62 (1H, s), 8.20 (1H, s), 7.74 (1H, dd), 4.06 (2H, q), 1.44 (3H, t).

Production Example 13 (1)

A mixture of 2-(3-ethylsulfanyl-pyridin-2-yl)-6-iodo-3-methyl-3H-imidazo[4,5-b]pyridine 1.1 g, copper iodide 160 mg, sodium sulfide nonahydrate 2.7 g, and DMF 10 mL was stirred at 110° C. for 5 hr. To the reaction mixture was added water, and the resulting mixture was extracted with ethyl acetate. The organic layer was dried over sodium sulfate, and then concentrated under reduced pressure. The resultant residue was treated with silica gel column chromatography to give the compound having the formula:

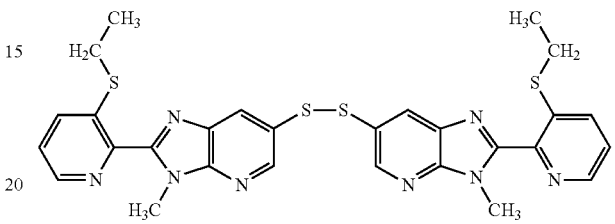

(hereinafter referred to as Intermediate compound (P9'-1)) 710 mg.
Intermediate Compound (P9'-1)
$^1$H-NMR (DMSO-D$_6$) δ: 8.56-8.55 (2H, m), 8.53-8.50 (2H, m), 8.38-8.36 (2H, m), 8.04 (2H, d), 7.61-7.56 (2H, m), 3.87 (6H, brs), 3.00 (4H, q), 1.23-1.16 (6H, m).

Production Example 13 (2)

A mixture of Intermediate compound (P9'-1) 710 mg and DMF 12 mL was cooled to −60° C., and to the mixture was added trifluoroiodomethane 10 g. To the mixture was added dropwise tetrakis(dimethylamino)ethylene 1.2 mL at −40° C. The mixture was allowed to warm to −10° C. and stirred at −10° C. for 5 hr. To the reaction mixture was added water, and the resulting mixture was extracted with ethyl acetate. The organic layer was dried over sodium sulfate, and then concentrated under reduced pressure. The resultant residue was treated with silica gel column chromatography to give 2-(3-ethylsulfanyl-pyridin-2-yl)-3-methyl-6-trifluoromethylsulfanyl-3H-imidazo[4,5-b]pyridine (hereinafter referred to as the present fused heterocyclic compound 13) 530 mg.
Present Fused Heterocyclic Compound 13

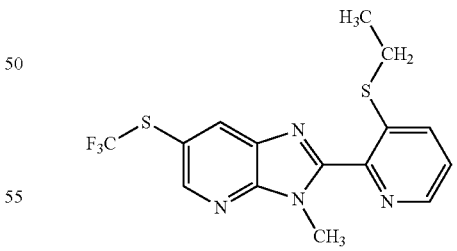

$^1$H-NMR (CDCl$_3$) δ: 8.67 (1H, d), 8.52 (1H, dd), 8.46 (1H, d), 7.79 (1H, dd), 7.39 (1H, dd), 4.03 (3H, s), 2.97 (2H, q), 1.36 (3H, t).

Production Examples 14, 15

A mixture of 2-(3-ethylsulfanyl-pyridin-2-yl)-3-methyl-6-trifluoromethylsulfanyl-3H-imidazo[4,5-b]pyridine (the present fused heterocyclic compound 13) 200 mg, m-chloroperbenzoic acid (65%) or more purity) 230 mg, and chloroform 10 mL was Stirred at ice temperature for 5 hr. To the reaction mixture was added saturated aqueous sodium bicarbonate, and the mixture was extracted with chloroform. The organic layer was dried over sodium sulfate, and then concentrated under reduced pressure. The resultant residue was treated with silica gel column chromatography to give 2-(3-ethylsulfinyl-pyridin-2-yl)-3-methyl-6-trifluoromethylsulfanyl-3H-imidazo[4,5-b]pyridine (hereinafter referred to as the present fused heterocyclic compound 14) 89 mg and 2-(3-ethylsulfonyl-pyridin-2-yl)-3-methyl-6-trifluoromethylsulfanyl-3H-imidazo[4,5-b]pyridine (hereinafter referred to as the present fused heterocyclic compound 15) 130 mg.

Present Fused Heterocyclic Compound 14

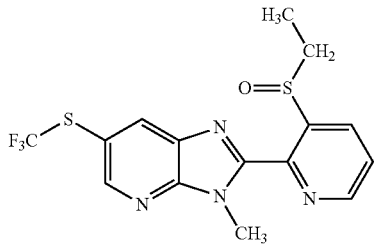 [SMILES: CCS(=O)c1cccnc1-c1nc2cc(SC(F)(F)F)cnc2n1C]

$^1$H-NMR (CDCl$_3$) δ: 8.87-8.83 (1H, m), 8.73-8.64 (2H, m), 8.41 (1H, d), 7.72-7.66 (1H, m), 4.34 (3H, s), 3.72-3.62 (1H, m), 3.17-3.05 (1H, m), 1.47 (3H, t).

Present Fused Heterocyclic Compound 15

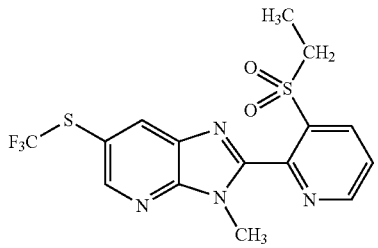

$^1$H-NMR (CDCl$_3$) δ: 9.01-8.98 (1H, m), 8.71 (1H, d), 8.55-8.52 (1H, m), 8.39 (1H, d), 7.72 (1H, dd), 3.90-3.81 (5H, m), 1.36 (3H, t).

Production Example 16

To a mixture of 2-(3-ethylsulfanyl-pyridin-2-yl)-3-methyl-6-trifluoromethylsulfanyl-3H-imidazo[4,5-b]pyridine (the present fused heterocyclic compound 13) 270 mg, sodium tungstate dihydrate 110 mg, and acetonitrile 5 mL was added aqueous 30% hydrogen peroxide 2 mL at 40° C. The mixture was heated to 80° C. and stirred for 24 hr. To the mixture was added saturated aqueous sodium thiosulfate, and then the resulting mixture was extracted with ethyl acetate. The organic layer was dried over sodium sulfate, and then concentrated under reduced pressure. The resultant residue was treated with silica gel column chromatography to give 2-(3-ethylsulfonyl-pyridin-2-yl)-3-methyl-6-trifluoromethylsulfonyl-3H-imidazo[4,5-b]pyridine (hereinafter referred to as the present fused heterocyclic compound 16) 280 mg.

Present Fused Heterocyclic Compound 16

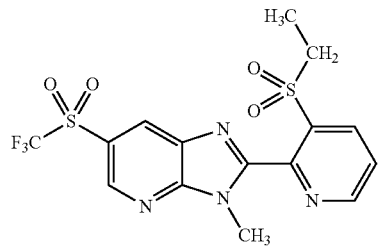 [SMILES: CCS(=O)(=O)c1cccnc1-c1nc2cc(S(=O)(=O)C(F)(F)F)cnc2n1C]

$^1$H-NMR (CDCl$_3$) δ: 9.08 (1H, d), 9.04 (1H, dd), 8.71 (1H, d), 8.57 (1H, dd), 7.79 (1H, dd), 3.93 (3H, s), 3.82 (2H, q), 1.38 (3H, t).

Production Example 17(1)

A mixture of N2-methyl-5-pentafluoroethyl-pyridine-2,3-diamine 590 mg, 3-chloro-5-trifluoromethyl-pyridine-2-carboxylic acid 560 mg, EDC hydrochloride 520 mg, HOBt 35 mg, pyridine 5 mL was stirred at RT for 5 hr. To the reaction mixture was added water, and the resulting mixture was extracted with ethyl acetate. The organic layer was dried over sodium sulfate, and then concentrated under reduced pressure to give Intermediate compound (M20-17).

Intermediate compound (M20-17)

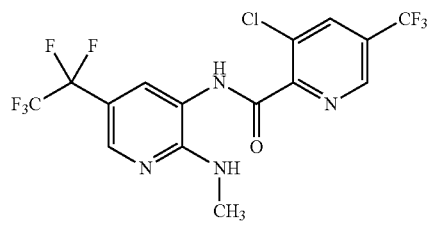 [SMILES: CNc1ncc(C(F)(F)C(F)(F)F)cc1NC(=O)c1ncc(C(F)(F)F)cc1Cl]

The resulting Intermediate compound (M20-17) was dissolved in a mixed solvent of DMF 7.5 mL and toluene 30 mL, and to the resulting mixture was added p-toluenesulfonic acid monohydrate 1.5 g. The mixture was stirred at 160° C. for 6 hr. The reaction mixture allowed to cool to RT, and to the reaction mixture was added saturated aqueous sodium bicarbonate, and then the mixture was extracted with t-butyl methyl ether. The organic layer was dried over sodium sulfate, and then concentrated under reduced pressure. The resultant residue was treated with silica gel column chromatography to give 2-(3-chloro-5-trifluoromethyl-pyridin-2-yl)-3-methyl-6-pentafluoroethyl-3H-imidazo[4,5-b]pyridine (hereinafter referred to as Intermediate compound (M6-17)) 540 mg.

Intermediate Compound (M6-17)

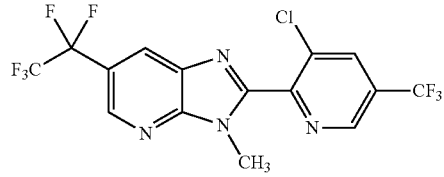 [SMILES: Cn1c(-c2ncc(C(F)(F)F)cc2Cl)nc2cc(C(F)(F)C(F)(F)F)cnc21]

$^1$H-NMR (CDCl$_3$) δ: 8.96 (1H, d), 8.74 (1H, d), 8.40 (1H, d), 8.23 (1H, d), 4.03 (3H, s).

Production Example 17(2)

2-(3-Ethylsulfanyl-5-trifluoromethyl-pyridin-2-yl)-3-methyl-6-pentafluoroethyl-3H-imidazo[4,5-b]pyridine (hereinafter referred to as the present fused heterocyclic compound 17) was prepared in a similar manner as described for the preparation of Production example 1 (2) by using Intermediate compound (M6-17) instead of 2-(3-fluoropyridin-2-yl)-3-methyl-6-trifluoromethyl-3H-imidazo[4,5-b]pyridine (Intermediate compound (M6-2)).

Present Fused Heterocyclic Compound 17

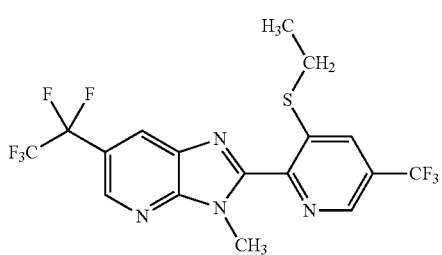

$^1$H-NMR (CDCl$_3$) δ: 8.75 (1H, d), 8.71 (1H, d), 8.42 (1H, d), 7.93 (1H, d), 4.12 (3H, s), 3.03 (2H, q), 1.41 (3H, t).

Production Examples 18, 19

2-(3-Ethylsulfinyl-5-trifluoromethyl-pyridin-2-yl)-3-methyl-6-pentafluoroethyl-3H-imidazo[4,5-b]pyridine (hereinafter referred to as the present fused heterocyclic compound 18) and 2-(3-ethylsulfonyl-5-trifluoromethyl-pyridin-2-yl)-3-methyl-6-pentafluoroethyl-3H-imidazo[4,5-b]pyridine (hereinafter referred to as the present fused heterocyclic compound 19) was prepared in a similar manner as described for the preparation of Production examples 2, 3 by using 2-(3-ethylsulfanyl-5-trifluoromethyl-pyridin-2-yl)-3-methyl-6-pentafluoroethyl-3H-imidazo[4,5-b]pyridine instead of 2-(3-ethylsulfanylpyridin-2-yl)-3-methyl-6-trifluoromethyl-3H-imidazo[4,5-b]pyridine (the present fused heterocyclic compound 1).

Present Fused Heterocyclic Compound 18

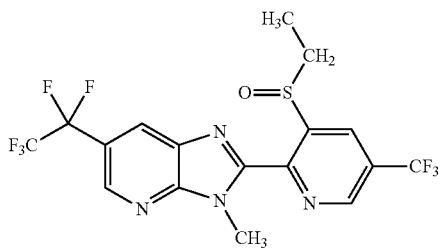 [SMILES: CCS(=O)c1cc(C(F)(F)F)cnc1-c1nc2cc(C(F)(F)C(F)(F)F)cnc2n1C]

$^1$H-NMR (CDCl$_3$) δ: 9.10 (1H, d), 8.94 (1H, d), 8.76 (1H, d), 8.36 (1H, d), 4.41 (3H, s), 3.76-3.66 (1H, m), 3.18-3.07 (1H, m), 1.49 (3H, t).

Present Fused Heterocyclic Compound 19

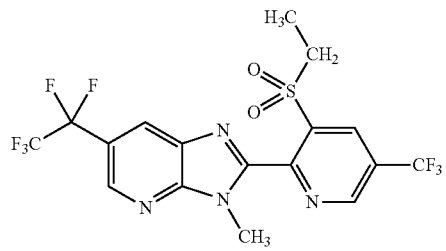 [SMILES: CCS(=O)(=O)c1cc(C(F)(F)F)cnc1-c1nc2cc(C(F)(F)C(F)(F)F)cnc2n1C]

$^1$H-NMR (CDCl$_3$) δ: 9.27 (1H, d), 8.80 (1H, d), 8.76 (1H, s), 8.24 (1H, s), 4.01-3.94 (5H, m), 1.41 (3H, t).

Production Example 20

To a mixture of 2-(2-ethylsulfonyl-pyridin-2-yl)-2-methyl-6-trifluoromethylsulfanyl-3H-imidazo[4,5-b]pyridine 500 mg and chloroform 10 mL at ice temperature was added m-chloroperbenzoic acid (65% or more purity) 429 mg, and the mixture was stirred at RT for 1 hr and at 50° C. for 2 hr. To the reaction mixture was added aqueous sodium thiosulfate and aqueous sodium bicarbonate, and the mixture was extracted with chloroform. The organic layer was dried over sodium sulfate, and then concentrated under reduced pressure. The resultant residue was treated with silica gel column chromatography to give 2-(3-ethylsulfonyl-pyridin-2-yl)-3-methyl-6-trifluoromethylsulfinyl-3H-imidazo[4,5-b]pyridine (hereinafter referred to as the present fused heterocyclic compound 20) 353 mg.

Present Fused Heterocyclic Compound 20

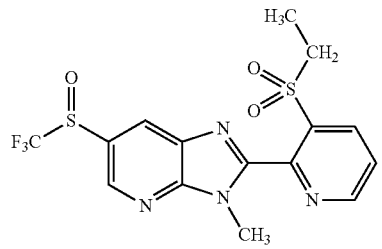 [SMILES: CCS(=O)(=O)c1cccnc1-c1nc2cc(S(=O)C(F)(F)F)cnc2n1C]

$^1$H-NMR (CDCl$_3$) δ: 9.02 (1H, dd), 8.77 (1H, d), 8.60-8.52 (2H, m), 7.75 (1H, dd), 3.91 (3H, s), 3.83 (2H, q), 1.38 (3H, t).

Production Example 21 (1)

To a mixture of 4-iodo-2-nitro-phenylamine 2.0 g, 60% sodium hydride (in oil) 330 mg, DMF 20 mL at ice temperature was added dropwise iodomethane 470 μL. The reaction mixture was allowed to warm to RT, and then stirred for 2 hr. To the reaction mixture was added water, and the resulting mixture was extracted with ethyl acetate. The organic layer was dried over sodium sulfate, and then concentrated under reduced pressure. The resultant residue was treated with silica gel column chromatography to give (4-iodo-2-nitro-phenyl)-methyl-amine 2.0 g.

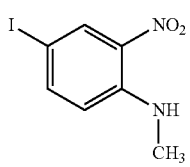

Production Example 21 (2)

A mixture of iron powder 1.7 g, acetic acid 2.2 mL, ethanol 80 mL, and water 25 mL was stirred at 70° C. To the reaction mixture was added dropwise a mixture of (4-iodo-2-nitro-phenyl)-methyl-amine 2.0 g and ethanol 20 mL. After adding dropwise, the mixture was stirred at 70° C. for 6 hr. The reaction mixture was filtered washing with THF. The resulting filtrate was concentrated under reduced pressure. To the resultant residue was added saturated aqueous sodium bicarbonate, and the resulting mixture was extracted with ethyl acetate. The organic layer was dried over sodium sulfate, and then concentrated under reduced pressure. The resultant residue was treated with silica gel column chromatography to give 4-iodo-N1-methyl-benzene-1,2-diamine 1.6 g.

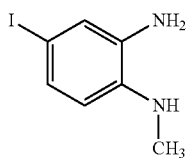

Production Example 21 (3)

A mixture of 4-iodo-N1-methyl-benzene-1,2-diamine 850 mg, 3-chloro-pyridine-2-carboxylic acid 590 mg, EDC hydrochloride 790 mg, HOBt 46 mg, and pyridine 10 mL at 100° C. for 12 hr was stirred. To the reaction mixture was added water, and the resulting mixture was extracted with ethyl acetate. The organic layer was dried over sodium sulfate, and then concentrated under reduced pressure. The resultant residue was treated with silica gel column chromatography to give 2-(3-chloro-pyridin-2-yl)-5-iodo-1-methyl-1H-benzimidazole (hereinafter referred to as Intermediate compound (M6-21)) 930 mg.
Intermediate Compound (M6-21)

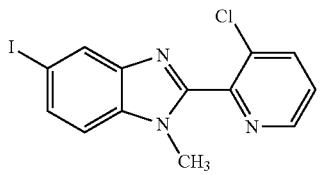 [SMILES: Cn1c(-c2ncccc2Cl)nc2cc(I)ccc21]

Production Example 21 (4)

2-(3-Ethylsulfanyl-pyridin-2-yl)-5-iodo-1-methyl-1H-benzimidazole (hereinafter referred to as the present fused heterocyclic compound 21) was prepared in a similar manner as described for the preparation of Production example 1 (2) by using Intermediate compound (M6-21) instead of 2-(3-fluoropyridin-2-yl)-3-methyl-6-trifluoromethyl-3H-imidazo[4,5-b]pyridine (Intermediate compound (M6-2)).
Present Fused Heterocyclic Compound 21

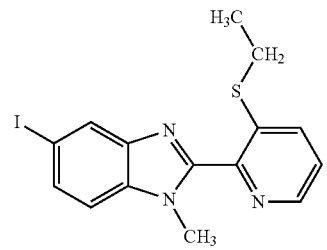 [SMILES: CCSc1cccnc1-c1nc2cc(I)ccc2n1C]

$^1$H-NMR (CDCl$_3$) δ: 8.49 (1H, dd), 8.22 (1H, d), 7.75 (1H, d), 7.62 (1H, dd), 7.35 (1H, dd), 7.21 (1H, d), 3.87 (3H, s), 2.92 (2H, q), 1.32 (3H, t).

Production Example 22 (1)

A mixture of 4-aminophenylsulfurpentafluoride 5.2 g, acetic anhydride 2.7 mL, triethylamine 6.6 mL, and chloroform 20 mL was stirred at RT for 3 hr. To the mixture was added water, and the reaction mixture was extracted with chloroform. The resultant residue was recrystallized by using hexane and ethyl acetate to give 4-acetamidephenyl sulfur pentafluoride 5.4 g.

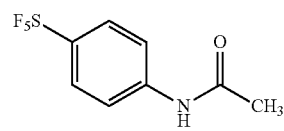

Production Example 22 (2)

To a mixture of 4-acetamidephenyl sulfur pentafluoride 5.4 g and sulfuric acid 15 mL at ice temperature was added dropwise fuming nitric acid 905 mL. After adding dropwise, the mixture was stirred at RT for 3 hr. To ice was poured the reaction mixture, the precipitated crystal was collected by filtration. The crystal was washed with water and dried to give 4-amino-3-nitrophenyl sulfur pentafluoride 5.2 g.

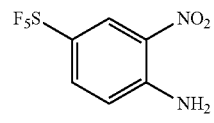

Production Example 22 (3)

To a mixture of 4-amino-3-nitrophenyl sulfur pentafluoride 2.0 g, 60% sodium hydride (in oil) 310 mg and DMF 15 mL at ice temperature was added dropwise iodomethane 447 µL. After adding dropwise, the mixture was stirred at RT for 3 hr. To water was poured the reaction mixture, and then the precipitated solid was collected by filtration. The solid was washed with water and dried to give methyl-(2-nitro-4-pentafluorosulfanyl-phenyl)-amine 2.0 g.

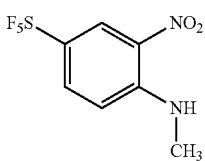

$^1$H-NMR (CDCl$_3$) δ: 8.60 (1H, d), 8.28 (1H, brs), 7.78 (1H, dd), 6.89 (1H, d), 3.10 (3H, d).

Production Example 22 (4)

N1-Methyl-4-pentafluorosulfanyl-benzene-1,2-diamine was prepared in a similar manner as described for the preparation of Production example 21 (2) by using methyl-(2-nitro-4-pentafluorosulfanyl-phenyl)-amine instead of (4-iodo-2-nitro-phenyl)-methyl-amine.

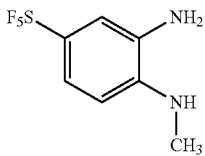

Production Example 22 (5)

3-Chloro-pyridine-2-carboxylic acid (2-methylamino-5-pentafluorosulfanyl-phenyl)-amide (hereinafter referred to as Intermediate compound (M20-23)) was prepared in a similar manner as described for the preparation of Production example 9 (1) by using N1-methyl-4-pentafluorosulfanyl-benzene-1,2-diamine instead of 5-iodo-N2-methyl-pyridine-2,3-diamine.

Intermediate Compound (M20-23)

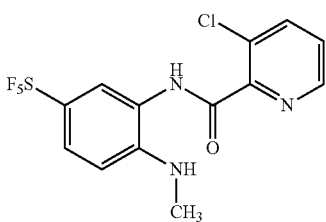

$^1$H-NMR (CDCl$_3$) δ: 9.57 (1H, s), 8.55 (1H, dd), 7.91 (1H, dd), 7.81 (1H, d), 7.59 (1H, dd), 7.50-7.45 (1H, m), 6.71 (1H, d), 4.52 (1H, d), 2.93 (3H, d).

Production Example 22 (6)

To a mixture of Intermediate compound (M20-23) 405 mg and DMF 10 mL, at ice temperature was added sodium ethanethiolate 193 mg, and then the mixture was stirred at RT for 8 hr and at 60° C. for 2 hr. To the reaction mixture was added water, and the resulting mixture was extracted with ethyl acetate. The organic layer was washed with water, and dried over anhydrous magnesium sulfate, and then concentrated under reduced pressure. The resultant residue was treated with silica gel column chromatography to give 2-(3-ethylsulfanyl-5-trifluoromethyl-pyridin-2-yl)-1-methyl-5-pentafluorosulfanyl-1H-benzimidazole (hereinafter referred to as the present fused heterocyclic compound 23) 411 mg.

Present Fused Heterocyclic Compound 23

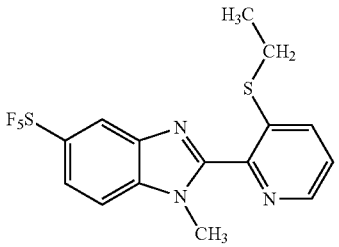

$^1$H-NMR (CDCl$_3$) δ: 8.50 (1H, dd), 8.33 (1H, d), 7.79-7.74 (2H, m), 7.46-7.43 (1H, m), 7.37 (1H, dd), 3.92 (3H, s), 2.94 (2H, q), 1.33 (3H, t).

Production Example 23

2-(3-Ethylsulfonyl-pyridin-2-yl)-1-methyl-5-pentafluorosulfanyl-1H-benzimidazole (hereinafter referred to as the present fused heterocyclic compound 24) was prepared in a similar manner as described for the preparation of Production example 11 by using 2-(3-ethylsulfanyl-pyridin-2-yl)-1-methyl-5-pentafluorosulfanyl-1H-benzimidazole instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).

Present Fused Heterocyclic Compound 24

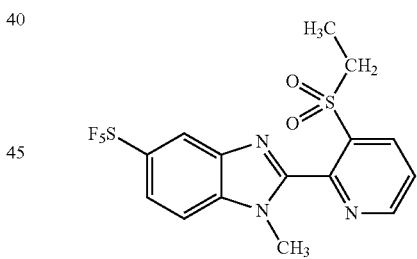

$^1$H-NMR (CDCl$_3$) δ: 8.96 (1H, dd), 8.50 (1H, dd), 8.24 (1H, d), 7.79 (1H, dd), 7.68 (1H, dd), 7.48 (1H, d), 3.82 (2H, q), 3.75 (3H, s), 1.34 (3H, t).

Production Example 24 (1)

3-Chloro-5-trifluoromethyl-pyridine-2-carboxylic acid (5-iodo-2-methylamino-pyridin-3-yl)-amide (hereinafter referred to as Intermediate compound (M20-35)) was prepared in a similar manner as described for the preparation of Production Example 9 (1) by using 3-chloro-5-trifluoromethyl-pyridine-2-carboxylic acid instead of 3-chloro-pyridine-2-carboxylic acid.

Intermediate Compound (M20-35)

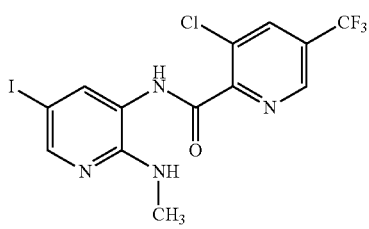 [SMILES: CNc1ncc(I)cc1NC(=O)c1ncc(C(F)(F)F)cc1Cl]

¹H-NMR (CDCl₃) δ: 9.33 (1H, s), 8.80 (1H, d), 8.28 (1H, d), 8.17 (1H, d), 8.00 (1H, d), 4.60 (1H, s), 3.01 (3H, d).

Production Example 24 (2)

2-(3-Chloro-5-trifluoromethyl-pyridin-2-yl)-6-iodo-3-methyl-3H-imidazo[4,5-b]pyridine (hereinafter referred to as Intermediate compound (M6-35)) was prepared in a similar manner as described for the preparation of Production Example 9 (2) by using Intermediate compound (M20-35) instead of 3-chloro-pyridine-2-carboxylic acid (5-iodo-2-methylamino-pyridin-3-yl)-amide (Intermediate compound (M20-7)).

Intermediate Compound (M6-35)

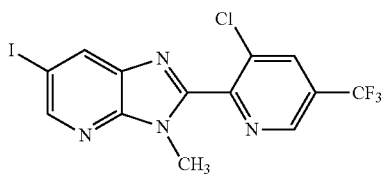

¹H-NMR (CDCl₃) δ: 8.95 (1H, s), 8.68 (1H, s), 8.49 (1H, s), 8.20 (1H, s), 3.95 (3H, s).

Production Example 24 (3)

2-(3-Ethylsulfanyl-5-trifluoromethyl-pyridin-2-yl)-6-iodo-3-methyl-3H-imidazo[4,5-b]pyridine (hereinafter referred to as the present fused heterocyclic compound 42) was prepared in a similar manner, as described for the preparation of Production example 1 (2) by using Intermediate compound (M6-35) instead of 2-(3-fluoropyridin-2-yl)-3-methyl-6-trifluoromethyl-3H-imidazo[4,5-b]pyridine (Intermediate compound (M6-2)).

Present Fused Heterocyclic Compound 42

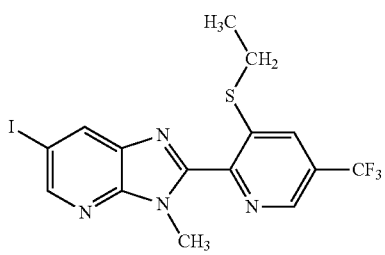 [SMILES: CCSc1cc(C(F)(F)F)cnc1-c1nc2cc(I)cnc2n1C]

¹H-NMR (CDCl₃) δ: 8.73 (1H, s), 8.65 (1H, d), 8.49 (1H, d), 7.91 (1H, s), 4.04 (3H, s), 3.01 (2H, q), 1.39 (3H, t).

Production Example 24 (4)

A mixture of 2-(3-ethylsulfanyl-5-trifluoromethyl-pyridin-2-yl)-6-iodo-3-methyl-3H-imidazo[4,5-b]pyridine 900 mg, thiobenzoic acid 320 μL, copper iodide 45 mg, 1,10-phenanthroline 85 mg, diisopropylethylamine 940 μL, and toluene 25 mL was stirred at 110° C. for 8 hr. To the reaction mixture was added water, and the resulting mixture was extracted with ethyl acetate. The organic layer was dried over sodium sulfate, and then concentrated under reduced pressure. The resultant residue was treated with silica gel column chromatography to give thiobenzoic acid S-[2-(3-ethylsulfanyl-5-trifluoromethyl-pyridin-2-yl)-3-methyl-3H-imidazo[4,5-b]pyridine]ester 990 mg.

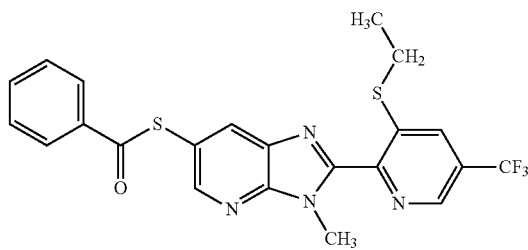 [SMILES: CCSc1cc(C(F)(F)F)cnc1-c1nc2cc(SC(=O)c3ccccc3)cnc2n1C]

¹H-NMR (CDCl₃) δ: 8.74 (1H, s), 8.54 (1H, d), 8.33 (1H, d), 8.07 (2H, dd), 7.92 (1H, s), 7.63 (1H, t), 7.51 (2H, t), 4.10 (3H, s), 3.01 (2H, q), 1.39 (3H, t).

Production Example 24 (5)

A mixture of thiobenzoic acid S-[2-(3-ethylsulfanyl-5-trifluoromethyl-pyridin-2-yl)-3-methyl-3H-imidazo[4,5-b]pyridine]ester 1.8 g, potassium carbonate 1.1 g, and methanol 20 mL was stirred at RT for 4.5 hr. To the reaction mixture was added saturated aqueous ammonium chloride, and the resulting mixture was extracted with ethyl acetate. The organic layer was washed with saturated aqueous sodium bicarbonate, dried over sodium sulfate, and concentrated under reduced pressure to give 2-(3-ethylsulfanyl-5-trifluoromethyl-pyridin-2-yl)-3-methyl-3H-imidazo[4,5-b]pyridine-6-thiol (hereinafter referred to as the present fused heterocyclic compound 43) 1.2 g.

Present Fused Heterocyclic Compound 43

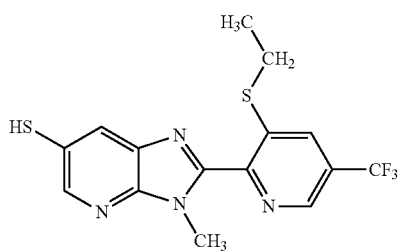 [SMILES: CCSc1cc(C(F)(F)F)cnc1-c1nc2cc(S)cnc2n1C]

¹H-NMR (CDCl₃) δ: 8.73 (1H, s), 8.46 (1H, d), 8.19 (1H, d), 7.90 (1H, s), 4.04 (3H, s), 3.01 (2H, q), 1.39 (3H, t).

Production Example 24 (6)

A mixture of 2-(3-ethylsulfanyl-5-trifluoromethyl-pyridin-2-yl)-3-methyl-3H-imidazo[4,5-b]pyridine-6-thiol 1.2 g, iodine 20 mg, and DMF 30 mL was stirred at RT for 12 hr under air atmosphere. The reaction mixture was concentrated, and the resultant residue was treated with silica gel column chromatography to give a compound having the formula:

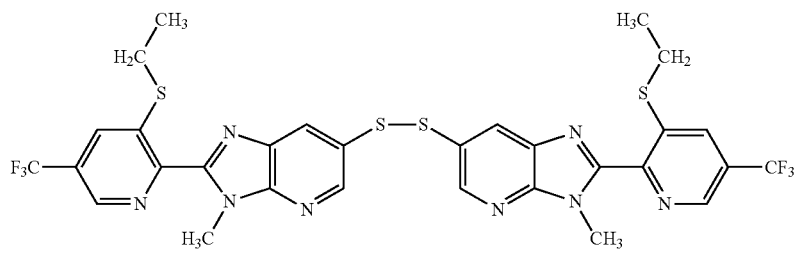 [SMILES: CCSc1cc(C(F)(F)F)cnc1-c1nc2cc(SSc3cnc4c(c3)nc(-c3ncc(C(F)(F)F)cc3SCC)n4C)cnc2n1C]

(hereinafter referred to as Intermediate compound (P9'-4)) 800 mg.

Intermediate Compound (P9'-4)

$^1$H-NMR (CDCl$_3$) δ: 8.73 (2H, s), 8.52 (2H, d), 8.35 (2H, d), 7.91 (2H, d), 4.06 (6H, s), 3.04-2.98 (4H, m), 1.39 (6H, t).

Production Example 24 (7)

2-(3-Ethylsulfanyl-5-trifluoromethyl-pyridin-2-yl)-3-methyl-6-trifluoromethylsulfanyl-3H-imidazo[4,5-b]pyridine (hereinafter referred to as the present fused heterocyclic compound 28) was prepared in a similar manner as described for the preparation of Production example 13 (2) by using Intermediate compound (P9'-4) instead of Intermediate compound (P9'-1).

Present Fused Heterocyclic Compound 28

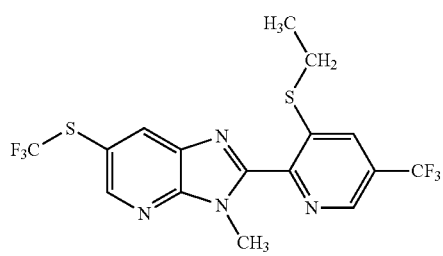 [SMILES: CCSc1cc(C(F)(F)F)cnc1-c1nc2cc(SC(F)(F)F)cnc2n1C]

$^1$H-NMR (CDCl$_3$) δ: 8.75 (1H, d), 8.71 (1H, d), 8.50 (1H, d), 7.93 (1H, d), 4.10 (3H, s), 3.03 (2H, q), 1.41 (3H, t).

Production Example 24 (8)

To a mixture of 2-(3-ethylsulfanyl-5-trifluoromethyl-pyridin-2-yl)-3-methyl-6-trifluoromethylsulfanyl-3H-imidazo[4,5-b]pyridine 299 mg and chloroform 30 mL at ice temperature was added m-chloroperbenzoic acid (65% or more purity) 0.34 g, and the mixture was stirred at ice temperature for 5 hr. To the reaction mixture was added saturated aqueous sodium bicarbonate and saturated aqueous sodium thiosulfate, and the reaction mixture was extracted with chloroform. The organic layer was dried over magnesium sulfate, and then concentrated under reduced pressure. The resultant residue was treated with silica gel column chromatography to give 2-(3-ethylsulfonyl-5-trifluoromethyl-pyridin-2-yl)-3-methyl-6-trifluoromethylsulfanyl-3H-imidazo[4,5-b]pyridine (hereinafter referred to as the present fused heterocyclic compound 44) 0.24 g.

Present Fused Heterocyclic Compound 44

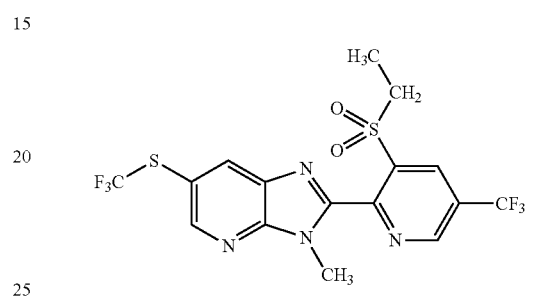

$^1$H-NMR (CDCl$_3$) δ: 9.24 (1H, d), 8.79 (1H, d), 8.74 (1H, d), 8.40 (1H, d), 3.97 (2H, q), 3.93 (3H, s), 1.42 (3H, t).

Production Example 24 (9)

2-(3-Ethylsulfonyl-5-trifluoromethyl-pyridin-2-yl)-3-methyl-6-trifluoromethylsulfonyl-3H-imidazo[4,5-b]pyridine (hereinafter referred to as the present fused heterocyclic compound 25) was prepared in a similar manner as described for the preparation of Production example 16 by using 2-(3-ethylsulfanyl-5-trifluoromethyl-pyridin-2-yl)-3-methyl-6-trifluoromethylsulfanyl-3H-imidazo[4,5-b]pyridine instead of 2-(3-ethylsulfanyl-pyridin-2-yl)-3-methyl-6-trifluoromethylsulfanyl-3H-imidazo[4,5-b]pyridine (the present fused heterocyclic compound 13).

Present Fused Heterocyclic Compound 25

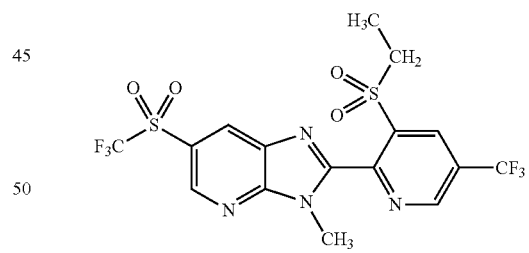

$^1$H-NMR (CDCl$_3$) δ: 9.28 (1H, d), 9.10 (1H, d), 8.80 (1H, d), 8.72 (1H, d), 3.98 (3H, s), 3.93 (2H, q), 1.43 (3H, t).

Production Example 25

A mixture of 2-(3-ethylsulfanyl-pyridin-2-yl)-5-iodo-1-methyl-1H-benzimidazole 340 mg, copper iodide 410 mg, sodium pentafluoropropionate 800 mg, NMP 5 mL, xylene 5 mL was stirred at 160° C. for 5 hr. The reaction mixture was allowed to cool to RT, and then to the reaction mixture was added saturated aqueous sodium bicarbonate and aqueous 28% ammonia, and the mixture was extracted with t-butyl methyl ether. The organic layer was dried over sodium sulfate, and then concentrated under reduced pressure. The resultant residue was treated with silica gel column chromatography to give 2-(3-ethylsulfanyl-pyridin-2-yl)-1-methyl-5-pentafluoroethyl-1H-benzimidazole (hereinafter referred to as the present fused heterocyclic compound 26) 240 mg.

Present Fused Heterocyclic Compound 26

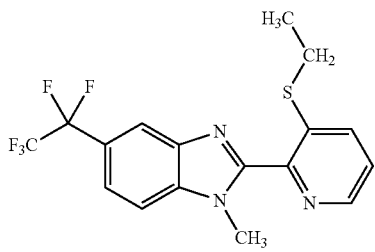 [SMILES: CCSc1cccnc1-c1nc2cc(C(F)(F)C(F)(F)F)ccc2n1C]

$^1$H-NMR (CDCl$_3$) δ: 8.50 (1H, dd), 8.16 (1H, s), 7.77 (1H, dd), 7.57 (1H, d), 7.53 (1H, d), 7.36 (1H, dd), 3.93 (3H, s), 2.94 (2H, q), 1.33 (3H, t).

Production Example 26

2-(3-Ethylsulfonyl pyridin-2-yl)-1-methyl-5-pentafluoroethyl-1H-benzimidazole (hereinafter referred to as the present fused heterocyclic compound 27) was prepared in a similar manner as described for the preparation of Production example 5 by using 2-(3-ethylsulfanyl-pyridin-2-yl)-1-methyl-5-pentafluoroethyl-1H-benzimidazole instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).

Present Fused Heterocyclic Compound 27

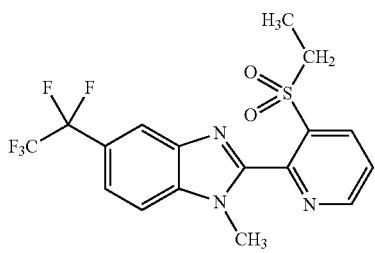 [SMILES: CCS(=O)(=O)c1cccnc1-c1nc2cc(C(F)(F)C(F)(F)F)ccc2n1C]

$^1$H-NMR (CDCl$_3$) δ: 8.98 (1H, dd), 8.53 (1H, dd), 8.06 (1H, s), 7.70 (1H, dd), 7.60 (1H, d), 7.56 (1H, d), 3.86-3.78 (5H, m), 1.34 (3H, t).

Production Example 27

To a mixture of 2-(3-ethylsulfanyl-5-trifluoromethylpyridin-2-yl)-3-methyl-6-trifluoromethylsulfanyl-3H-imidazo[4,5-b]pyridine 0.18 and chloroform 4 mL at ice temperature was added m-chloroperbenzoic acid (65% or more purity) 0.21 g, and the mixture was stirred at ice temperature for 5 min. To the reaction mixture was added saturated aqueous sodium bicarbonate and saturated aqueous sodium thiosulfate, and the reaction mixture was extracted with chloroform. The organic layer was dried over magnesium sulfate, and then concentrated under reduced pressure. The resultant residue was treated with silica gel column chromatography to give 2-(3-ethylsulfanyl-5-trifluoromethylpyridin-2-yl)-3-methyl-6-trifluoromethylsulfanyl-3H-imidazo[4,5-b]pyridine (hereinafter referred to as the present fused heterocyclic compound 29) 0.16 g.

Present Fused Heterocyclic Compound 29

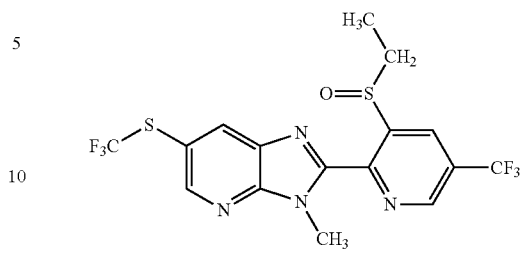

$^1$H-NMR (CDCl$_3$) δ: 9.10-9.07 (1H, m), 8.94-8.91 (1H, m), 8.77-8.74 (1H, m), 8.46-8.44 (1H, m), 4.38 (3H, s), 3.76-3.65 (1H, m), 3.16-3.05 (1H, m), 1.49 (3H, t).

Production Example 28 (1)

3-Chloro-pyridine-2-carboxylic acid (2-methylamino-5-trifluoromethyl-phenyl)-amide (hereinafter referred to as Intermediate compound (M20-29)) was prepared in a similar manner as described for the preparation of Production example 9 (1) by using N1-methyl-4-trifluoromethyl-benzene-1,2-diamine instead of 5-iodo-N2-methyl-pyridine-2,3-diamine.

Intermediate Compound (M20-29)

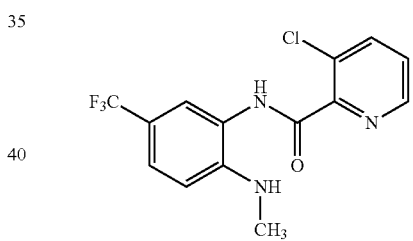

$^1$H-NMR (CDCl$_3$) δ: 9.56 (1H, s), 8.55-8.54 (1H, m), 7.91 (1H, dd), 7.70 (1H, d), 7.49-7.43 (3H, m), 6.79 (1H, d), 2.93 (3H, d).

Production Example 28 (2)

A mixture of Intermediate compound (M20-29) 800 mg, sodium ethanethiolate 350 mg, and DMF 10 mL was stirred at 100° C. for 5 hr. To the reaction mixture was added saturated aqueous sodium bicarbonate, and the resulting mixture was extracted with ethyl acetate. The organic layer was dried over sodium sulfate, and then concentrated under reduced pressure. The resultant residue was treated with silica gel column chromatography to give 2-(3-ethylsulfanyl-pyridin-2-yl)-1-methyl-5-trifluoromethyl-1H-benzimidazole (hereinafter referred to as the present fused heterocyclic compound 30) 410 mg.

Present Fused Heterocyclic Compound 30

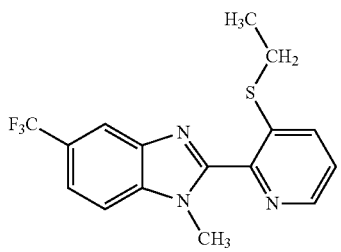

¹H-NMR (CDCl₃) δ: 8.51 (1H, dd), 8.17 (1H, d), 7.78 (1H, dd), 7.61 (1H, dd), 7.52 (1H, d), 7.38 (1H, dd), 3.93 (3H, s), 2.94 (2H, q), 1.33 (3H, t).

Production Examples 29, 30

2-(3-Ethylsulfinyl-pyridin-2-yl)-1-methyl-5-trifluoromethyl-1H-benzimidazole (hereinafter referred to as the present fused heterocyclic compound 31) and 2-(3-ethylsulfonyl-pyridin-2-yl)-1-methyl-5-trifluoromethyl-1H-benzimidazole (hereinafter referred to as the present fused heterocyclic compound 32) were prepared in a similar manner as described for the preparation of Production examples 2, by using 2-(3-ethylsulfanyl-pyridin-2-yl)-1-methyl-5-trifluoromethyl-1H-benzimidazole instead of 2-(3-ethylsulfanylpyridin-2-yl)-3-methyl-6-trifluoromethyl-3H-imidazo[4,5-b]pyridine.

Present Fused Heterocyclic Compound 31

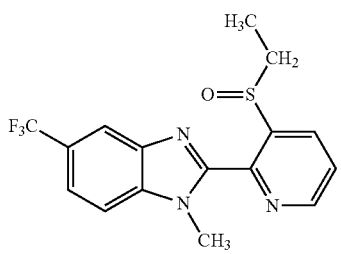

¹H-NMR (CDCl₃) δ: 8.77 (1H, d), 8.61 (1H, d), 8.05 (1H, s), 7.61 (1H, dd), 7.55 (1H, d), 7.48 (1H, d), 4.20 (3H, s), 3.73-3.61 (1H, m), 3.11-3.00 (1H, m), 1.47 (3H, t).

Present Fused Heterocyclic Compound 32

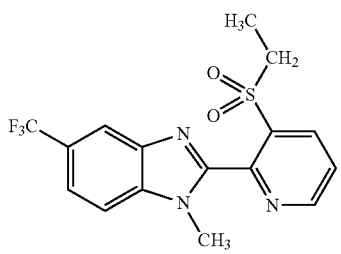

¹H-NMR (CDCl₃) δ: 8.95 (1H, dd), 8.50 (1H, dd), 8.09 (1H, d), 7.66 (1H, dd), 7.61 (1H, d), 7.53 (1H, d), 3.83 (2H, q), 3.75 (3H, s), 1.33 (3H, t).

Production Example 31 (1)

3-Chloro-5-trifluoromethyl-pyridine-2-carboxylic acid (2-methylamino-5-trifluoromethyl-phenyl)-amide (hereinafter referred to as Intermediate compound (M20-31)) was prepared in a similar manner as described for the preparation of Production example 9 (1) by using N1-methyl-4-trifluoromethyl-benzene-1,2-diamine instead of 5-iodo-N2-methyl-pyridine-2,3-diamine and by using 3-chloro-5-trifluoromethylpyridine-2-carboxylic acid instead of 3-chloropyridine-2-carboxylic acid.

Intermediate Compound (M20-31)

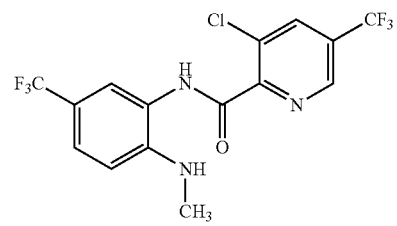 [SMILES: CNc1ccc(C(F)(F)F)cc1NC(=O)c1ncc(C(F)(F)F)cc1Cl]

¹H-NMR (CDCl₃) δ: 9.42 (1H, s), 8.80 (1H, d), 8.16 (1H, d), 7.71 (1H, s), 7.47 (1H, d), 6.81 (1H, d), 4.32 (1H, s), 2.93 (3H, d).

Production Example 31 (2)

2-(3-Ethylsulfanyl-5-trifluoromethyl-pyridin-2-yl)-1-methyl-5-trifluoromethyl-1H-benzimidazole (hereinafter referred to as the present fused heterocyclic compound 33) and 2-ethylsulfanyl-5-trifluoromethyl-pyridine-2-carboxylic acid (2-methylamino-5-trifluoromethyl-phenyl)-amide (hereinafter referred to as Intermediate compound (M3-32)) was prepared in a similar manner as described for the preparation of Production example 28 (2) by using Intermediate compound (M20-31) instead of 3-chloro-pyridine-2-carboxylic acid (2-methylamino-5-trifluoromethyl-phenyl)-amide (Intermediate compound (M20-29)).

Present Fused Heterocyclic Compound 33

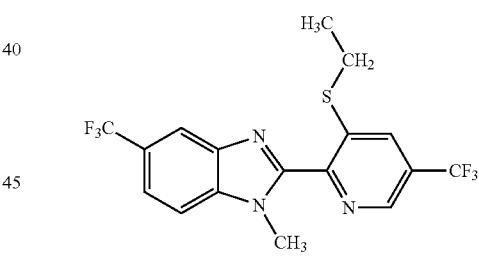

¹H-NMR (CDCl₃) δ: 8.72 (1H, d), 8.21 (1H, d), 7.91 (1H, d), 7.63 (1H, d), 7.54 (1H, d), 4.00 (3H, s), 3.00 (2H, q), 1.38 (3H, t).

Intermediate Compound (M3-32)

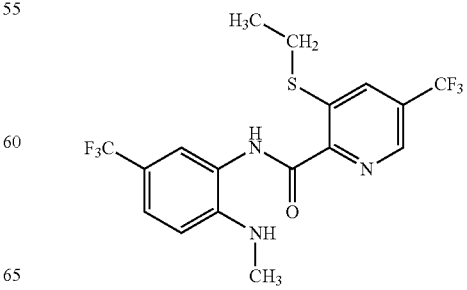

$^1$H-NMR (CDCl$_3$) δ: 9.64 (1H, s), 8.53 (1H, d), 7.86 (1H, s), 7.76 (1H, d), 7.41 (1H, dd), 6.76 (1H, d), 4.35 (1H, d), 2.96 (2H, q), 2.90 (3H, d), 1.44 (3H, t).

Production Examples 32, 33

2-(3-Ethylsulfinyl-5-trifluoromethyl-pyridin-2-yl)-1-methyl-5-trifluoromethyl-1H-benzimidazole (hereinafter referred to as the present fused heterocyclic compound 34) and 2-(3-ethylsulfonyl-5-trifluoromethyl-pyridin-2-yl)-1-methyl-5-trifluoromethyl-1H-benzimidazole (hereinafter referred to as the present fused heterocyclic compound 35) was prepared in a similar manner as described for the preparation of Production examples 2, 3 by using 2-(3-ethylsulfanyl-5-trifluoromethyl-pyridin-2-yl)-1-methyl-5-trifluoromethyl-1H-benzimidazole instead of 2-(3-ethylsulfanylpyridin-2-yl)-3-methyl-6-trifluoromethyl-3H-imidazo[4,5-b]pyridine (the present fused heterocyclic compound 1).

Present Fused Heterocyclic Compound 34

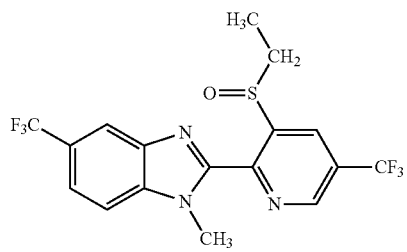 [SMILES: CCS(=O)c1cc(C(F)(F)F)cnc1-c1nc2cc(C(F)(F)F)ccc2n1C]

$^1$H-NMR (CDCl$_3$) δ: 9.05 (1H, d), 8.91 (1H, d), 8.12 (1H, d), 7.67 (1H, dd), 7.60 (1H, d), 4.32 (3H, s), 3.80-3.70 (1H, m), 3.15-3.05 (1H, m), 1.51 (3H, t).

Present Fused Heterocyclic Compound 35

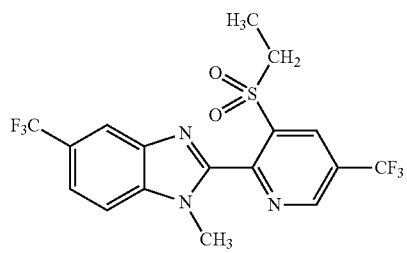

$^1$H-NMR (CDCl$_3$) δ: 9.22 (1H, d), 8.77 (1H, d), 8.10 (1H, d), 7.66 (1H, dd), 7.57 (1H, d), 3.98 (2H, q), 3.84 (3H, s), 1.40 (3H, t).

Production Examples 34, 35

To a mixture of 2-(3-ethylsulfonylpyridin-2-yl)-3-methyl-6-trifluoromethyl-3H-imidazo[4,5-b]pyridine 550 mg and chloroform 15 mL was added m-chloroperbenzoic acid (65% or more purity) 750 mg, and the mixture was heated to reflux for 20 hr. To the reaction mixture was added aqueous 10% sodium thiosulfate, and the reaction mixture was extracted with chloroform. The organic layer was washed with saturated aqueous sodium bicarbonate, and dried over anhydrous magnesium sulfate, and then concentrated under reduced pressure. The resultant residue was treated with silica gel column chromatography to give 2-(3-ethylsulfonyl-1-oxypyridin-2-yl)-3-methyl-6-trifluoromethyl-3H-imidazo[4,5-b]pyridine (hereinafter referred to as the present fused heterocyclic compound 36) 168 mg and 2-(3-ethylsulfonylpyridin-2-yl)-3-methyl-6-trifluoromethyl-3H-imidazo[4,5-b]pyridine 4-oxide (hereinafter referred to as the present fused heterocyclic compound 37) 73 mg.

Present Fused Heterocyclic Compound 36

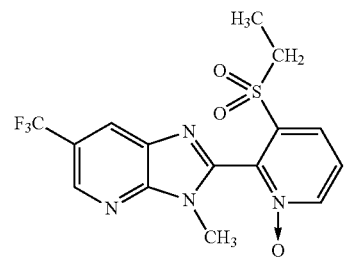 [SMILES: CCS(=O)(=O)c1ccc[n+]([O-])c1-c1nc2cc(C(F)(F)F)cnc2n1C]

$^1$H-NMR (CDCl$_3$) δ: 8.79 (1H, d), 8.54 (1H, dd), 8.33 (1H, d), 7.99 (1H, dd), 7.69 (1H, dd), 3.85-3.74 (4H, m), 3.52-3.42 (1H, m), 1.34 (3H, t).

Present Fused Heterocyclic Compound 37

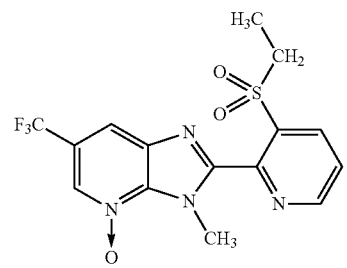 [SMILES: CCS(=O)(=O)c1cccnc1-c1nc2cc(C(F)(F)F)c[n+]([O-])c2n1C]

$^1$H-NMR (CDCl$_3$) δ: 9.03 (1H, dd), 8.53 (1H, dd), 8.47 (1H, d), 7.92 (1H, d), 7.77 (1H, dd), 4.29 (3H, s), 3.69 (2H, q), 1.36 (3H, t).

Production Example 36 (1)

2-(3-Chloro-5-trifluoromethyl-pyridin-2-yl)-5-iodo-1-methyl-1H-benzimidazole (hereinafter referred to as Intermediate compound (M6-41)) was prepared in a similar manner as described for the preparation of Production example 4 (1) by using 4-iodo-N1-methyl-benzene-1,2-diamine instead of N2-methyl-5-trifluoromethylpyridine-2,3-diamine.

Intermediate Compound (M6-41)

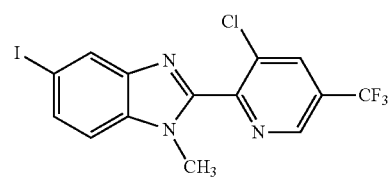 [SMILES: Cn1c(-c2ncc(C(F)(F)F)cc2Cl)nc2cc(I)ccc21]

$^1$H-NMR (CDCl$_3$) δ: 8.92 (1H, d), 8.23 (1H, d), 8.17 (1H, d), 7.66 (1H, dd), 7.23 (1H, d), 3.85 (3H, s).

Production Example 36 (2)

2-(3-Ethylsulfanyl-5-trifluoromethyl-pyridin-2-yl)-5-iodo-1-methyl-1H-benzimidazole (hereinafter referred to as the present fused heterocyclic compound 45) was prepared in a similar manner as described for the preparation of Production example 1 (2) by using Intermediate compound (M6-41) instead of 2-(3-fluoropyridin-2-yl)-3-methyl-6-trifluoromethyl-3H-imidazo[4,5-b]pyridine.

Present Fused Heterocyclic Compound 45

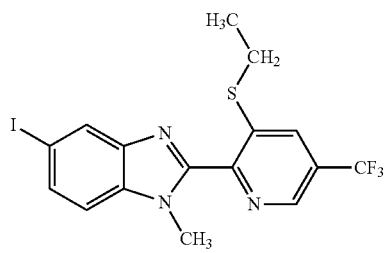 [SMILES: CCSc1cc(C(F)(F)F)cnc1-c1nc2cc(I)ccc2n1C]

Production Example 36 (3)

2-(3-Ethylsulfanyl-5-trifluoromethyl-pyridin-2-yl)-1-methyl-5-pentafluoroethyl-1H-benzimidazole (hereinafter referred to as the present fused heterocyclic compound 38) was prepared in a similar manner as described for the preparation of Production example 25 by using 2-(3-ethylsulfanyl-5-trifluoromethyl-pyridin-2-yl)-5-iodo-1-methyl-1H-benzimidazole instead of 2-(3-ethylsulfanyl-pyridin-2-yl)-5-iodo-1-methyl-1H-benzimidazole.

Present Fused Heterocyclic Compound 38

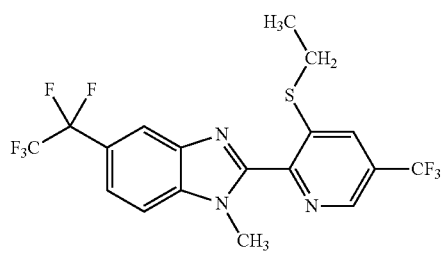

$^1$H-NMR (CDCl$_3$) δ: 8.72 (1H, d), 8.20 (1H, s), 7.91 (1H, d), 7.60 (1H, d), 7.55 (1H, d), 4.00 (3H, s), 3.01 (2H, q), 1.39 (3H, t).

Production Examples 37, 38

2-(3-Ethylsulfinyl-5-trifluoromethyl-pyridin-2-yl)-1-methyl-5-pentafluoroethyl-1H-benzimidazole (hereinafter referred to as the present fused heterocyclic compound 39) and 2-(3-ethylsulfonyl-5-trifluoromethyl-pyridin-2-yl)-1-methyl-5-pentafluoroethyl-1H-benzimidazole (hereinafter referred to as the present fused heterocyclic compound 40) was prepared in a similar manner as described for the preparation of Production examples 2, 3 by using 2-(3-ethylsulfanyl-5-trifluoromethyl-pyridin-2-yl)-1-methyl-5-pentafluoroethyl-1H-benzimidazole instead of 2-(3-ethylsulfanylpyridin-2-yl)-3-methyl-6-trifluoromethyl-3H-imidazo[4,5-b]pyridine.

Present Fused Heterocyclic Compound 39

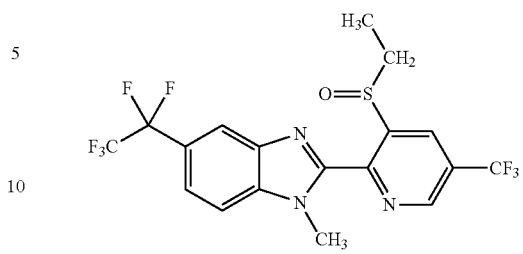

$^1$H-NMR (CDCl$_3$) δ: 9.05 (1H, d), 8.91 (1H, d), 8.10 (1H, s), 7.66-7.60 (2H, m), 4.33 (3H, s), 3.80-3.69 (1H, m), 3.17-3.07 (1H, m), 1.50 (3H, t).

Present Fused Heterocyclic Compound 40

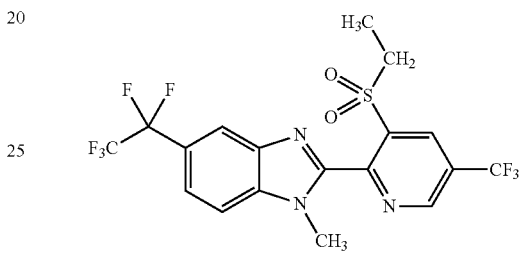

$^1$H-NMR (CDCl$_3$) δ: 9.22 (1H, d), 8.77 (1H, d), 8.08 (1H, s), 7.63 (1H, d), 7.58 (1H, d), 3.99 (2H, q), 3.84 (3H, s), 1.40 (3H, t).

Production Example 39 (1)

To a mixture of methyl-(2-nitro-4-trifluoromethyl-phenyl)-amine 16 g and acetonitrile 200 mL at ice temperature was added N-bromosuccinimide 15 g. The reaction mixture was stirred at RT for 5 hr. To the resulting reaction mixture was added saturated aqueous sodium bicarbonate, and the resulting mixture was extracted with ethyl acetate. The organic layer was dried over magnesium sulfate, and then concentrated under reduced pressure. The resultant residue was treated with silica gel column chromatography to give (2-bromo-6-nitro-4-trifluoromethyl-phenyl)-methyl-amine 15 g.

(2-bromo-6-nitro-4-trifluoromethyl-phenyl)-methyl-amine

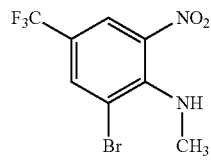

$^1$H-NMR (CDCl$_3$) δ: 8.12 (1H, s), 7.86 (1H, s), 6.48 (1H, brs), 3.07 (3H, d).

Production Example 39 (2)

While a mixture of iron powder 11 g, acetic acid 12 mL, THF 40 mL, and water 10 mL was stirred with heating at 70° C., to the mixture was added dropwise another mixture of (2-bromo-6-nitro-4-trifluoromethyl-phenyl)-methyl-amine 10 g and THF 50 mL. After adding dropwise, the mixture was stirred with heating at 70° C. for 3 hr. The resulting reaction mixture was filtered using Celite™ with washing with THF. The resulting filtrate was concentrated under reduced pressure. To the resultant residue was added aqueous 10% sodium hydroxide, and the resulting mixture was extracted with ethyl acetate. The organic layer was dried over magnesium sulfate, and then concentrated under reduced pressure to give 3-bromo-N2-methyl-5-trifluoromethyl-benzene-1,2-diamine 11 g.

3-Bromo-N2-methyl-5-trifluoromethyl-benzene-1,2-diamine

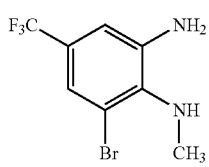

Production Example 39 (3)

3-Chloro-pyridine-2-carboxylic acid (3-bromo-2-methylamino-5-trifluoromethyl-phenyl)-amide (hereinafter referred to as Intermediate compound (M20-43)) was prepared in a similar manner as described for the preparation of Production example 9 (1) by using 3-bromo-N2-methyl-5-trifluoromethyl-benzene-1,2-diamine instead of 5-iodo-N2-methyl-pyridine-2,3-diamine.

Intermediate Compound (M20-43)

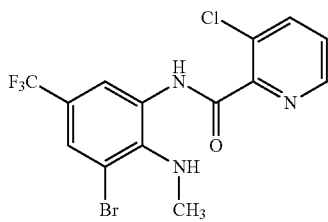

¹H-NMR (CDCl₃) δ: 10.63 (1H, s), 8.77 (1H, d), 8.58 (1H, dd), 7.91 (1H, dd), 7.56 (1H, d), 7.47 (1H, dd), 3.75-3.68 (1H, m), 2.83 (3H, d).

Production Example 39 (4)

2-(3-Ethylsulfanyl-pyridin-2-yl)-7-bromo-1-methyl-5-trifluoromethyl-1H-benzimidazole (hereinafter referred to as the present fused heterocyclic compound 75), 3-ethylsulfanyl-pyridine-2-carboxylic acid (3-bromo-2-methylamino-5-trifluoromethyl-phenyl)-amide (hereinafter referred to as Intermediate compound (M3-42)), and 2-(3-chloro-pyridin-2-yl)-7-bromo-1-methyl-5-trifluoromethyl-1H-benzimidazole (hereinafter referred to as Intermediate compound (M6-43)) were prepared in a similar manner as described for the preparation of Production example 28 (2) by using Intermediate compound (M20-43) instead of Intermediate compound (M20-29).

Present Fused Heterocyclic Compound 75

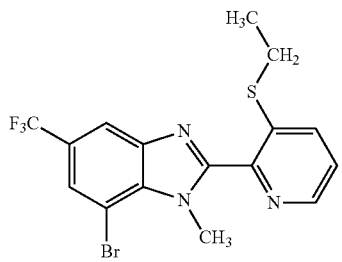 [SMILES: CCSc1cccnc1-c1nc2cc(C(F)(F)F)cc(Br)c2n1C]

¹H-NMR (CDCl₃) δ: 8.54 (1H, dd), 8.08 (1H, d), 7.79 (1H, dd), 7.72 (1H, d), 7.40 (1H, dd), 4.13 (3H, s), 2.94 (2H, q), 1.32 (3H, t).

Intermediate Compound (M3-42)

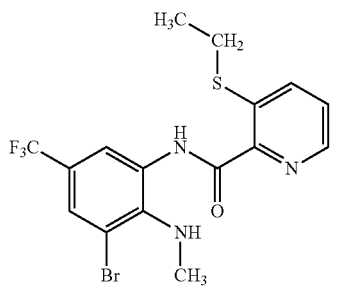 [SMILES: CCSc1cccnc1C(=O)Nc1cc(C(F)(F)F)cc(Br)c1NC]

¹H-NMR (CDCl₃) δ: 10.80 (1H, s), 8.82 (1H, s), 8.38 (1H, dd), 7.74 (1H, d), 7.54 (1H, s), 7.42 (1H, dd), 3.75-3.65 (1H, brm), 2.97 (2H, q), 2.82 (3H, d), 1.45 (3H, t).

Intermediate Compound (MG-43)

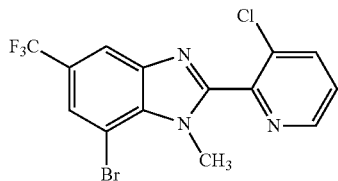 [SMILES: Cn1c(-c2ncccc2Cl)nc2cc(C(F)(F)F)cc(Br)c21]

¹H-NMR (CDCl₃) δ: 8.71 (1H, dd), 8.08 (1H, d), 7.95 (1H, dd), 7.74 (1H, d), 7.47 (1H, dd), 4.09 (3H, s).

Production Example 40

2-(3-Ethylsulfonyl-pyridin-2-yl)-7-bromo-1-methyl-5-trifluoromethyl-1H-benzimidazole (hereinafter referred to as the present fused heterocyclic compound 46) was prepared in a similar manner as described for the preparation of Production example 5 by using 2-(3-ethylsulfanyl-pyridin-2-yl)-7-bromo-1-methyl-5-trifluoromethyl-1H-benzimidazole instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).

Present Fused Heterocyclic Compound 46

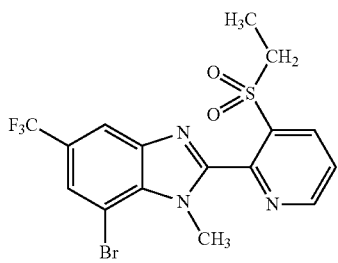 [SMILES: CCS(=O)(=O)c1cccnc1-c1nc2cc(C(F)(F)F)cc(Br)c2n1C]

$^1$H-NMR (CDCl$_2$) δ: 8.99 (1H, dd), 8.51 (1H, dd), 8.00 (1H, d), 7.75 (1H, d), 7.72 (1H, dd), 4.03 (3H, s), 3.73 (2H, q), 1.33 (3H, t).

Production Examples 41, 42

A mixture of 2-(3-ethylsulfanyl-5-trifluoromethylpyridin-2-yl)-3-methyl-6-trifluoromethyl-3H-imidazo[4,5-b]pyridine (the present fused heterocyclic compound 4) 1.0 g, m-chloroperbenzoic acid (65% or more purity) 2.72 g, and chloroform 5 mL was refluxed for 8 hr, and to the mixture was added m-chloroperbenzoic acid (65% or more purity) 2.0 g, and then the mixture was further refluxed for 5 hr. To the reaction mixture allowed to cool was added aqueous 10% sodium thiosulfate, and the reaction mixture was extracted with chloroform. The organic layer was washed with saturated aqueous sodium bicarbonate, dried over anhydrous magnesium sulfate, and then concentrated under reduced pressure to give 2-(3-ethylsulfonyl-5-trifluoromethylpyridin-2-yl)-3-methyl-6-trifluoromethyl-3H-imidazo[4,5-b]pyridine 4-oxide (hereinafter referred to as the present fused heterocyclic compound 48) 362 mg and 2-(3-ethylsulfonyl-1-oxy-5-trifluoromethylpyridin-2-yl)-3-methyl-6-trifluoromethyl-3H-imidazo[4,5-b]pyridine (hereinafter referred to as the present fused heterocyclic compound 51) 45 mg.

Present Fused Heterocyclic Compound 48

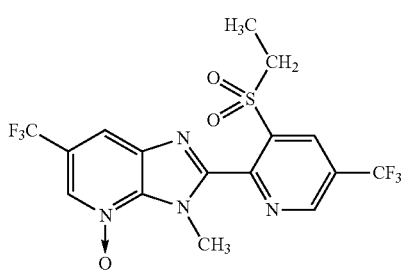 [SMILES: CCS(=O)(=O)c1cc(C(F)(F)F)cnc1-c1nc2cc(C(F)(F)F)c[n+]([O-])c2n1C]

$^1$H-NMR (CDCl$_3$) δ: 9.27 (1H, d), 8.76 (1H, d), 8.49 (1H, d), 7.94 (1H, d), 4.33 (3H, s), 3.80 (2H, q), 1.40 (3H, t).

Present Fused Heterocyclic Compound 51

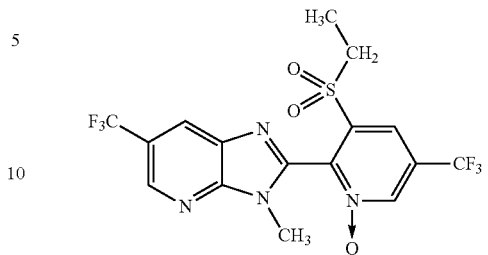

$^1$H-NMR (CDCl$_3$) δ: 8.75 (1H, s), 8.50 (1H, s), 8.12 (1H, s), 7.94 (1H, s), 4.28 (3H, s), 3.75-3.65 (1H, m), 3.55-3.44 (1H, m), 1.38 (3H, t).

Production Example 43 (1)

A mixture of 2-chloro-3-nitro-5-trifluoromethylpyridine 2.60 g, 2,2,2-trifluoroethylamine 0.79 g, N,N-diisopropylethylamine 1.04 g, and N-methyl-2-pyrrolidone 5 mL was stirred at RT for 10 hr. To the reaction mixture was added aqueous 10% citric acid, and the resulting mixture was extracted with ethyl acetate. The organic layer was washed with water, and dried over sodium sulfate, and then concentrated under reduced pressure to give (3-nitro-5-trifluoromethylpyridin-2-yl)-(2,2,2-trifluoroethyl)amine 1.83 g.

(3-Nitro-5-trifluoromethylpyridin-2-yl)-(2,2,2-trifluoroethyl)amine

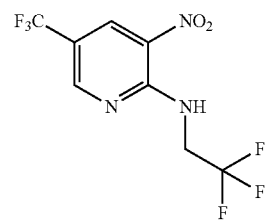 [SMILES: O=[N+]([O-])c1cc(C(F)(F)F)cnc1NCC(F)(F)F]

$^1$H-NMR (CDCl$_3$) δ: 8.72 (1H, d), 8.68 (1H, d), 8.59 (1H, brs), 4.54-4.41 (2H, m).

Production Example 43 (2)

To a mixture of iron powder 2.12 g, ethanol 6 mL, water 4 mL, and acetic acid 0.1 mL was added dropwise another mixture of (3-nitro-5-trifluoromethylpyridin-2-yl)-(2,2,2-trifluoroethyl)amine 1.83 g and ethanol 10 mL at 70° C., and then the resulting mixture was stirred at 70° C. for 1 hr. The reaction mixture allowed to cool was filtered, and then the filtrate was extracted with ethyl acetate and water. The organic layer was washed with water, and dried over sodium sulfate, and then concentrated under reduced pressure to give N2-(2,2,2-trifluoroethyl)-5-trifluoromethylpyridine-2,3-diamine 1.59 g.

N2-(2,2,2-Trifluoroethyl)-5-trifluoromethylpyridine-2,3-diamine

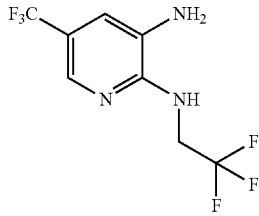

$^1$H-NMR (CDCl$_3$) δ: 8.04-8.02 (1H, m), 7.10-7.07 (1H, m), 4.81 (1H, brs), 4.31-4.20 (2H, m), 3.34 (2H, brs).

Production Example 43 (3)

A mixture of N2-(2,2,2-trifluoroethyl)-5-trifluoromethylpyridine-2,3-diamine 0.52 g, 3-ethylsulfanylpyridine-2-carboxylic acid 0.37 g, EDC hydrochloride 0.46 g, HOBt 27 mg, and pyridine 2 mL was stirred at RT for 3 hr. To the reaction mixture was added aqueous 10% citric acid, and the resulting mixture was extracted with ethyl acetate. The organic layer was washed with water, and dried over sodium sulfate, and then concentrated under reduced pressure to give 3-ethylsulfanylpyridine-2-carboxylic acid [2-(2,2,2-trifluoroethyl)amino-5-trifluoromethylpyridin-3-yl]amide (hereinafter referred to as Intermediate compound (M3-43)) 0.75 g.

Intermediate Compound (M3-43)

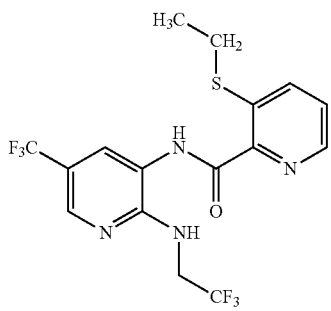 [SMILES: CCSc1cccnc1C(=O)Nc1cc(C(F)(F)F)cnc1NCC(F)(F)F]

Production Example 43 (4)

A mixture of Intermediate compound (M3-43) 0.75 g and acetic acid 5 mL was stirred with heating to reflux for 2 days. The mixture was cooled to RT, and then concentrated under reduced pressure. The crude product was treated with silica gel column chromatography to give 2-(3-ethylsulfanylpyridin-2-yl)-3-(2,2,2-trifluoroethyl)-6-trifluoromethyl-3H-imidazo[4,5-b]pyridine (hereinafter referred to as the present fused heterocyclic compound 65) 0.53 g.

Present Fused Heterocyclic Compound 65

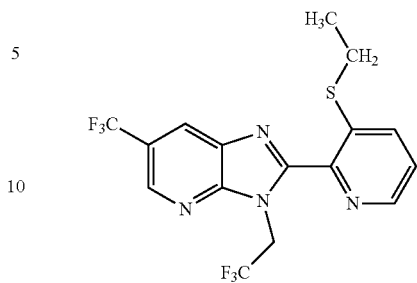

$^1$H-NMR (CDCl$_3$) δ: 8.77-8.74 (1H, m), 8.48 (1H, dd), 8.45-8.42 (1H, m), 7.82 (1H, dd), 7.40 (1H, dd), 5.64 (2H, q), 2.99 (2H, q), 1.35 (3H, t).

Production Example 44 (1)

A mixture of N2-(2,2,2-trifluoroethyl)-5-trifluoromethylpyridine-2,3-diamine 0.52 g, 3-ethylsulfanyl-5-trifluoromethylpyridine-2-carboxylic acid 0.50 g, EDC hydrochloride 0.46 g, HOBt 27 mg, and pyridine 2 mL was stirred at RT for 3 hr. To the reaction mixture was added aqueous 10% citric acid, and the resulting mixture was extracted with ethyl acetate. The organic layer was washed with water, and dried over sodium sulfate, and then concentrated under reduced pressure to give 3-ethylsulfanyl-5-trifluoromethylpyridine-2-carboxylic acid [2-(2,2,2-trifluoroethyl)amino-5-trifluoromethylpyridin-3-yl]amide (hereinafter referred to as Intermediate compound (M3-44)) 0.89 g.

Intermediate Compound (M3-44)

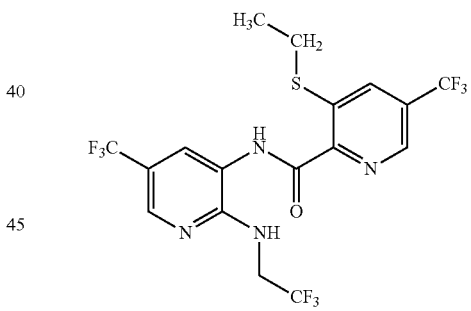

Production Example 44 (2)

A mixture of Intermediate compound (M3-44) 0.89 g, p-toluenesulfonic acid.monohydrate 1.14 g, N-methyl-2-pyrrolidone 10 mL, and xylene 10 mL was heated to reflux for 8 hr with removing water using Dean-Stark apparatus. The reaction mixture was allowed to cool, and then to the reaction mixture was added water, and the resulting mixture was extracted with ethyl acetate. The organic layer was washed with water, and dried over sodium sulfate, and then concentrated under reduced pressure. The crude product was treated with silica gel column chromatography to give 2-(3-ethylsulfanyl-5-trifluoromethylpyridin-2-yl)-3-(2,2,2-trifluoroethyl)-6-trifluoromethyl-3H-imidazo[4,5-b]pyridine (hereinafter referred to as the present fused heterocyclic compound 66) 0.76 g.

Present Fused Heterocyclic Compound 66

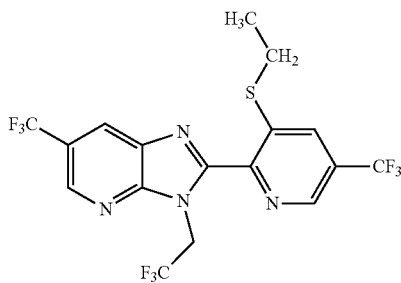 [SMILES: CCSc1cc(C(F)(F)F)cnc1-c1nc2cc(C(F)(F)F)cnc2n1CC(F)(F)F]

$^1$H-NMR (CDCl$_3$) δ: 8.80 (1H, d), 8.70 (1H, d), 8.48 (1H, d), 7.96 (1H, d), 5.67 (2H, q), 3.04 (2H, q), 1.40 (3H, t).

Production Example 45

To a mixture of the present fused heterocyclic compound 65 0.32 g and chloroform 2 mL at ice temperature was added m-chloroperbenzoic acid (65% or more purity) 0.36 g, and then the mixture was allowed to warm to RT, and stirred for 1 hr. To the mixture was added saturated aqueous sodium bicarbonate and saturated aqueous sodium thiosulfate, and the reaction mixture was extracted with chloroform. The organic layer was washed with water, and dried over sodium sulfate, and then concentrated under reduced pressure. The crude product was treated with silica gel column chromatography to give 2-(3-ethylsulfonylpyridin-2-yl)-3-(2,2,2-trifluoroethyl)-6-trifluoromethyl-3H-imidazo[4,5-b]pyridine (hereinafter referred to as the present fused heterocyclic compound 67) 0.32 g.

Present Fused Heterocyclic Compound 67

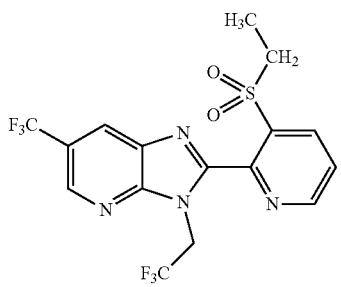 [SMILES: CCS(=O)(=O)c1cccnc1-c1nc2cc(C(F)(F)F)cnc2n1CC(F)(F)F]

$^1$H-NMR (CDCl$_3$) δ: 6.98 (1H, dd), 8.80 (1H, d), 8.59 (1H, dd), 8.37 (1H, d), 7.75 (1H, dd), 5.31 (2H, q), 3.95 (2H, q), 1.40 (3H, t).

Production Example 46

To a mixture of the present fused heterocyclic compound 66 (0.32 g) and chloroform 2 mL at ice temperature was added m-chloroperbenzoic acid (65% or more purity) 0.31 g, and then the mixture was allowed to warm to RT, and stirred for 1 hr. To the mixture was added saturated aqueous sodium bicarbonate and saturated aqueous sodium thiosulfate, and the reaction mixture was extracted with chloroform. The organic layer was washed with water, and dried over sodium sulfate, and then concentrated under reduced pressure. The resulting crude product was washed with hexane to give 2-(3-ethylsulfonyl-5-trifluoromethylpyridin-2-yl)-3-(2,2,2-trifluoroethyl)-6-trifluoromethyl-3H-imidazo[4,5-b]pyridine (hereinafter referred to as the present fused heterocyclic compound 68) 0.28 g.

Present Fused Heterocyclic Compound 68

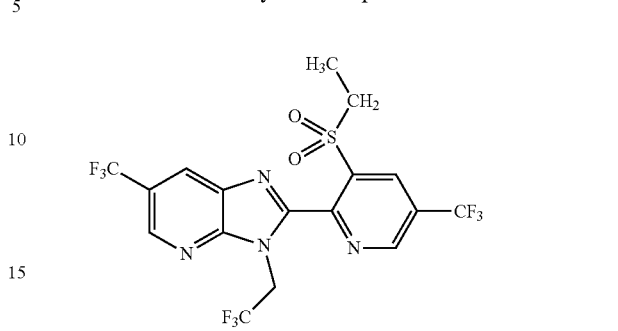

$^1$H-NMR (CDCl$_3$) δ: 9.22 (1H, d), 8.83-8.83 (2H, m), 8.40 (1H, d), 5.36 (2H, q), 4.05 (2H, q), 1.45 (3H, t).

Production Example 47 (1)

A mixture of 2-chloro-5-iodopyridine 20.0 g, sodium pentafluoropropionate 77.8 g, copper iodide (I) 31.8 g, xylene 84 mL, and N-methylpyrrolidone 84 mL was heated to 160° C., and stirred with heating to reflux for 6 hr. The reaction mixture was cooled to RT, and then to the reaction mixture was added water. The mixture was extracted with methyl-tert-butyl ether. The organic layer was dried over sodium sulfate, and then concentrated under reduced pressure to give 2-chloro-5-pentafluoroethylpyridine.

2-Chloro-5-pentafluoroethylpyridine

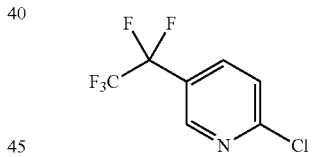

$^1$H-NMR (CDCl$_3$) δ: 8.65-8.62 (1H, m), 7.85-7.81 (1H, m), 7.48-7.44 (1H, m)

Production Example 47 (2)

A mixture of a half amount of 2-chloro-5-pentafluoroethylpyridine prepared in Production example 47 (1), zinc cyanide (II) 14.4 g, tetrakis(triphenylphosphine)palladium 2.42 g, and N-methylpyrrolidone 84 mL was heated to 80° C., and stirred with heating for 2.5 hr. The reaction mixture was cooled to RT, and then to the mixture was added water and methyl-tert-butyl ether. The mixture was filtrated with Celite (Trademark) to remove the resulting precipitate, and the resultant residue was washed with methyl-tert-butyl ether. The filtrate was extracted with methyl-text-butyl ether, and the organic layer was dried over sodium sulfate, and then concentrated under reduced pressure. The crude product was treated with silica gel column chromatography to give 2-cyano-5-pentafluoroethylpyridine 4.19 g.

2-Cyano-5-pentafluoroethylpyridine

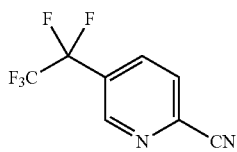 [SMILES: N#Cc1ccc(C(F)(F)C(F)(F)F)cn1]

$^1$H-NMR (CDCl$_3$) δ: 8.97-8.96 (1H, m), 8.12-8.09 (1H, m), 7.90-7.87 (1H, m)

Production Example 47 (3)

A mixture of water 17 mL and concentrated sulfuric acid 17 mL was heated to 100° C., and to the mixture was added dropwise 2-cyano-5-pentafluoroethylpyridine 3.81 g with heating, and then the mixture was stirred at 100° C. for 2.5 hr. The mixture was cooled to RT, and then the reaction mixture was added to iced water. The precipitated solid was collected by filtration, and washed with water. The resulting solid was dried under reduced pressure to give 5-pentafluoropyridine-2-carboxylic acid 3.52 g.

5-Pentafluoropyridine-2-carboxylic acid

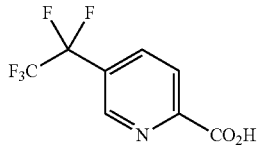 [SMILES: O=C(O)c1ccc(C(F)(F)C(F)(F)F)cn1]

$^1$H-NMR (CDCl$_3$) δ: 8.92-8.88 (1H, m), 8.44-8.39 (1H, m), 8.25-8.20 (1H, m)

Production Example 47 (4)

A mixture of tetramethylpiperidine 5.5 mL and THF 58 mL was cooled to −78° C., and then a solution of 1.6 M n butyllithium in hexane was added dropwise into the mixture. The mixture was allowed to warm to RT, and then stirred for 10 min. The mixture was cooled to −78° C. again, and to the mixture was added dropwise a solution of 5-pentafluoropyridine-2-carboxylic acid 3.52 g in THF, and the mixture was stirred at −78° C. for 1 hr. To the mixture was added dropwise diethyldisulfide 4.0 mL at −78° C. Then the mixture was allowed to warm to RT and was stirred for 1 hr. To the reaction mixture was added 1 N hydrochloric acid, and then to the mixture was added aqueous 5 N sodium hydroxide. The aqueous layer was washed with methyl-tert-butyl ether. To the aqueous layer was added 12 N hydrochloric acid, and the precipitated solid was collected by filtration and dissolved in methyl-tert-butyl ether. The mixture was dried over sodium sulfate, and then concentrated under reduced pressure to give 3-ethylsulfanyl-5-pentafluoroethylpyridine-2-carboxylic acid (hereinafter referred to as Intermediate compound (M2-7)) 1.99 g.

Intermediate Compound (M2-7)

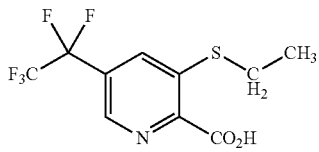 [SMILES: CCSc1cc(C(F)(F)C(F)(F)F)cnc1C(=O)O]

$^1$H-NMR (CDCl$_3$) δ: 8.51-8.50 (1H, m), 7.89-7.87 (1H, m), 3.01 (2H, q), 1.46 (3H, t)

Production Example 47 (5)

A mixture of N2-methyl-5-trifluoromethylpyridine-2,3-diamine 0.50 g, Intermediate compound (M2-7) 0.79 g, EDC hydrochloride 0.37 g, HOBt 35 mg, and pyridine 5 mL was stirred at RT for 3 hr. To the reaction mixture was added water, and the mixture was extracted with methyl-tert-butyl ether. The organic layer was dried over magnesium sulfate, and then concentrated under reduced pressure to give 3-ethylsulfanyl-5-pentafluoroethylpyridine-2-carboxylic acid (2-methylamino-5-trifluoromethylpyridin-3-yl)amide (hereinafter referred to as Intermediate compound (M3-45)).
Intermediate compound (M3-45)

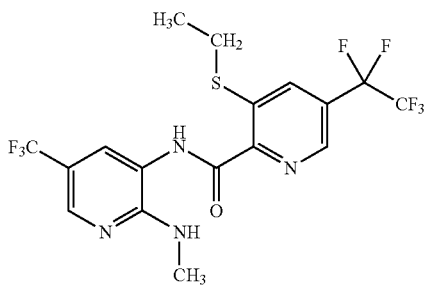 [SMILES: CCSc1cc(C(F)(F)C(F)(F)F)cnc1C(=O)Nc1cc(C(F)(F)F)cnc1NC]

$^1$H-NMR (CDCl$_3$) δ: 9.57 (1H, brs), 8.54-8.52 (1H, m), 8.37-8.35 (1H, m), 7.94-7.92 (1H, m), 7.89-7.87 (1H, m), 4.97 (1H, brs), 3.08 (3H, d), 2.99 (2H, q), 1.45 (3H, t)

A mixture of the total amount of the resulting Intermediate compound (M3-45) and acetic acid 5 mL was heated to 120° C., and stirred with heating to reflux for 3 hr. The mixture was cooled to RT, and then concentrated under reduced pressure. The crude product was treated with silica gel column chromatography to give 2-(3-ethylsulfanyl-5-pentafluoroethylpyridin-2-yl)-3-methyl-6-trifluoromethyl-3H-imidazo[4,5-b]pyridine (hereinafter referred to as the present fused heterocyclic compound 71) 0.77 g.
Present Fused Heterocyclic Compound 71

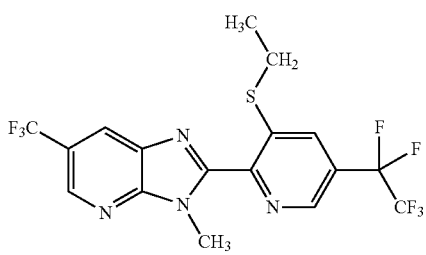

$^1$H-NMR (CDCl$_3$) δ: 8.78-8.76 (1H, m), 8.71-8.69 (1H, m), 8.44-8.42 (1H, m), 7.91-7.89 (1H, m), 4.13 (3H, s), 3.02 (2H, q), 1.39 (3H, t)

Production Example 48

To a mixture of the present fused heterocyclic compound 71 0.47 g and chloroform 10 m at ice temperature was added m-chloroperbenzoic acid (65% or more purity) 0.57 g, and then the mixture was allowed to warm to RT and stirred for 1 hr. To the mixture was added saturated aqueous sodium bicarbonate and saturated aqueous sodium thiosulfate, and the reaction mixture was extracted with chloroform. The organic layer was dried over sodium sulfate, and then concentrated under reduced pressure. The crude product was treated with silica gel column chromatography to give 2-(3-ethylsulfonyl-5-pentafluoroethylpyridin-2-yl)-3-methyl-6-trifluoromethyl-3H-imidazo[4,5-b]pyridine (hereinafter referred to as the present fused heterocyclic compound 72) 0.39 g.
Present Fused Heterocyclic Compound 72

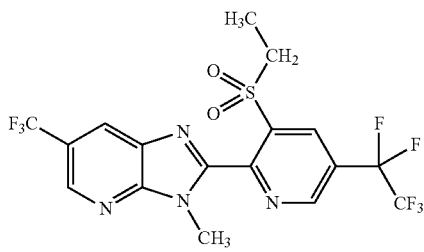 [SMILES: CCS(=O)(=O)c1cc(C(F)(F)C(F)(F)F)cnc1-c1nc2cc(C(F)(F)F)cnc2n1C]

$^1$H-NMR (CDCl$_3$) δ: 9.21-9.19 (1H, m), 8.81-8.79 (1H, m), 8.76-8.75 (1H, m), 8.35-8.33 (1H, m), 3.99-3.93 (5H, m), 1.41 (3H, t)

Production Example 49

A mixture of N2-methyl-5-pentafluoroethylpyridine-2,3-diamine 0.50 g, Intermediate compound (M2-7) 0.62 g, EDC hydrochloride 0.29 g, HOBt 28 mg, and pyridine 4 mL was stirred at RT for 3 hr. To the reaction mixture was added water, and the mixture was extracted with methyl-tert-butyl ether. The organic layer was dried over magnesium sulfate, and then concentrated under reduced pressure to give 3-ethylsulfanyl-5-pentafluoroethylpyridine-2-carboxylic acid (2-methylamino-5-pentafluoroethylpyridin-3-yl)amide (hereinafter referred to as Intermediate compound (M3-46)).
Intermediate Compound (M3-46)

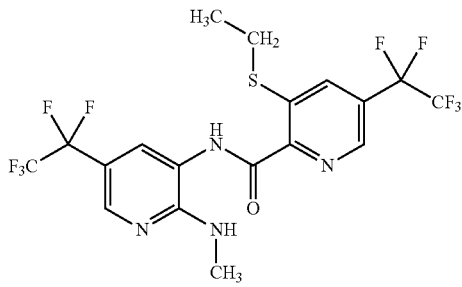 [SMILES: CCSc1cc(C(F)(F)C(F)(F)F)cnc1C(=O)Nc1cc(C(F)(F)C(F)(F)F)cnc1NC]

$^1$H-NMR (CDCl$_3$) δ: 9.59 (1H, brs), 8.54-8.52 (1H, m), 8.32-8.30 (1H, m), 7.89-7.87 (1H, m), 7.85-7.83 (1H, m), 5.04 (1H, brs), 3.09 (3H, d), 2.99 (2H, q), 1.45 (3H, t)

A mixture of the total amount of the resulting Intermediate compound (M3-46) and acetic acid 4 mL was heated to 120° C. and stirred with heating to reflux for 3 hr. The mixture was cooled to RT, and then concentrated under reduced pressure. The crude product was treated with silica gel column chromatography to give 2-(3-ethylsulfanyl-5-pentafluoroethylpyridin-2-yl)-3-methyl-6-pentafluoroethyl-3H-imidazo[4,5-b]pyridine (hereinafter referred to as the present fused heterocyclic compound 73) 0.84 g.
Present Fused Heterocyclic Compound 73

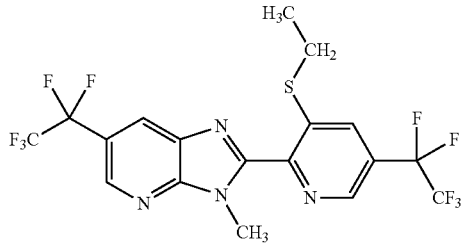 [SMILES: CCSc1cc(C(F)(F)C(F)(F)F)cnc1-c1nc2cc(C(F)(F)C(F)(F)F)cnc2n1C]

$^1$H-NMR (CDCl$_3$) δ: 8.72-8.69 (2H, m), 8.42-8.41 (1H, m), 7.90-7.89 (1H, m), 4.15-4.12 (3H, m), 3.02 (2H, q), 1.40 (3H, t)

Production Example 50

To a mixture of the present fused heterocyclic compound 73 0.54 g and chloroform 11 mL at ice temperature was added m-chloroperbenzoic acid (65% or more purity) 0.59 g, and then the mixture was allowed to warm to RT and stirred for 1 hr. To the mixture was added saturated aqueous sodium bicarbonate and saturated aqueous sodium thiosulfate, and the reaction mixture was extracted with chloroform. The organic layer was dried over sodium sulfate, and then concentrated under reduced pressure.

The crude product was treated with silica gel column chromatography to give 2-(3-ethylsulfonyl-5-pentafluoroethylpyridin-2-yl)-3-methyl-6-pentafluoroethyl-3H-imidazo[4,5-b]pyridine (hereinafter referred to as the present fused heterocyclic compound 74) 0.34 g.
Present Fused Heterocyclic Compound 74

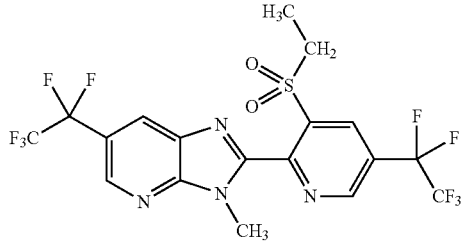 [SMILES: CCS(=O)(=O)c1cc(C(F)(F)C(F)(F)F)cnc1-c1nc2cc(C(F)(F)C(F)(F)F)cnc2n1C]

$^1$H-NMR (CDCl$_3$) δ: 9.21-9.20 (1H, m), 8.77-8.74 (2H, m), 8.32-8.31 (1H, m), 4.00-3.94 (5H, m), 1.41 (3H, t)

Production Example 51

2-(3-Ethylsulfonylpyridin-2-yl)-1-methyl-5-trifluoromethoxy-1H-benzimidazole (hereinafter referred to as the present fused heterocyclic compound 50) was prepared in a similar manner as described for the preparation of Production Example 5 by using 2-(3-ethylsulfanylpyridin-2-yl)-1-methyl-5-trifluoromethoxy-1H-benzimidazole instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).

Present Fused Heterocyclic Compound 50

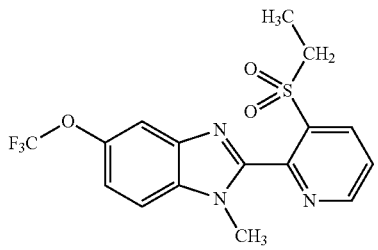 [SMILES: CCS(=O)(=O)c1cccnc1-c1nc2cc(OC(F)(F)F)ccc2n1C]

¹H-NMR (CDCl₃) δ: 8.93 (1H, dd), 8.49 (1H, dd), 7.68-7.62 (2H, m), 7.43 (1H, d), 7.25 (1H, d), 3.84 (2H, q), 3.73 (3H, s), 1.31 (3H, q).

Production Example 52

2-(3-Ethylsulfonylpyridin-2-yl)-5-trifluoromethyl-benzothiazole (hereinafter referred to as the present fused heterocyclic compound 53) was prepared in a similar manner as described for the preparation of Production example 5 by using 2-(3-ethylsulfanylpyridin-2-yl)-5-trifluoromethyl-benzothiazole instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).
Present Fused Heterocyclic Compound 53

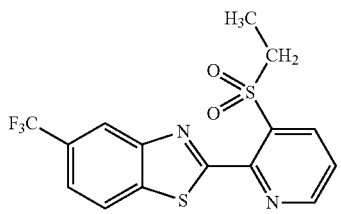 [SMILES: CCS(=O)(=O)c1cccnc1-c1nc2cc(C(F)(F)F)ccc2s1]

¹H-NMR (CDCl₃) δ: 8.92 (1H, dd), 8.65 (1H, dd), 8.37 (1H, s), 8.11 (1H, d), 7.72 (1H, dd), 7.66 (1H, dd), 4.19 (2H, q), 1.45 (3H, t).

Production Example 53

2-(3-Ethylsulfonylpyridin-2-yl)-6-trifluoromethyl-oxazolo[5,4-b]pyridine (hereinafter referred to as the present fused heterocyclic compound 81) was prepared in a similar manner as described for the preparation of Production Example 5 by using 2-(3-ethylsulfanylpyridin-2-yl)-6-trifluoromethyl-oxazolo[5,4-b]pyridine instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).
Present Fused Heterocyclic Compound 81

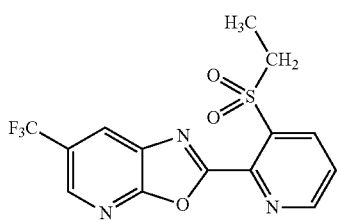 [SMILES: CCS(=O)(=O)c1cccnc1-c1nc2cc(C(F)(F)F)cnc2o1]

¹H-NMR (CDCl₃) δ: 9.06 (1H, dd), 8.79 (1H, d), 8.58 (1H, dd), 8.43 (1H, d), 7.78 (1H, dd), 3.88 (2H, q), 1.44 (3H, t).

Production Example 54

2-(3-Ethylsulfonylpyridin-2-yl)-5-trifluoromethyl-benzoxazole (hereinafter referred to as the present fused heterocyclic compound 85) was prepared in a similar manner as described for the preparation of Production example 5 by using 2-(3-ethylsulfanylpyridin-2-yl)-5-trifluoromethyl-benzoxazole instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).
Present Fused Heterocyclic Compound 85

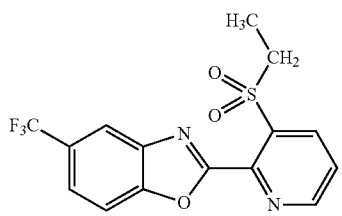 [SMILES: CCS(=O)(=O)c1cccnc1-c1nc2cc(C(F)(F)F)ccc2o1]

¹H-NMR (CDCl₃) δ: 9.03 (1H, dd), 8.60 (1H, dd), 8.16-8.13 (1H, m), 7.82-7.71 (3H, m), 4.01 (2H, q), 1.43 (3H, t).

Production Example 55

To phosphorus oxychloride 2.04 g at ice temperature was added the present fused heterocyclic compound 48 (0.20 g), and the mixture was stirred at 110° C. for 2 hr. The reaction mixture was allowed to cool to RT, and to the reaction mixture at ice temperature was added saturated aqueous sodium bicarbonate, and the resulting mixture was extracted with ethyl acetate. The organic layer was dried over anhydrous magnesium sulfate, and then concentrated under reduced pressure. The resultant residue was treated with silica gel column chromatography to give 5-chloro-2-(3-ethylsulfonyl-5-trifluoromethylpyridin-2-yl)-3-methyl-6-trifluoromethyl-3H-imidazo[4,5-b]pyridine (hereinafter referred to as the present fused heterocyclic compound 89) 0.21 g.
Present Fused Heterocyclic Compound 89

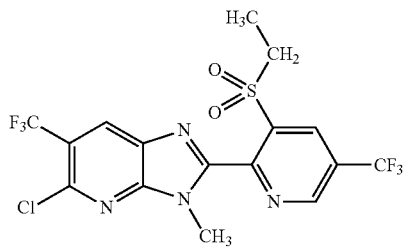 [SMILES: CCS(=O)(=O)c1cc(C(F)(F)F)cnc1-c1nc2cc(C(F)(F)F)c(Cl)nc2n1C]

¹H-NMR (CDCl₃) δ: 9.25 (1H, d), 8.78 (1H, d), 8.43 (1H, s), 3.97-3.87 (5H, m), 1.41 (3H, t).

Production Example 56

To a mixture of the present fused heterocyclic compound 89 (0.20 g) and NMP 0.5 mL was added dimethylamine (in methanol, 2.0 mol/L) 0.3 mL, and the mixture was stirred at RT for 1 hr and at 50° C. for 3 hr. To the reaction mixture allowed to cool to RT was added dimethylamine (in methanol, 2.0 mol/L) 0.3 mL, and the mixture was stirred at 50° C. for 3 hr. To the reaction mixture allowed to cool to RT was added water, and the resulting mixture was extracted with ethyl acetate. The organic layer was dried over anhydrous magnesium sulfate, and then concentrated under reduced pressure. The resultant residue was treated with silica gel column chromatography to give 5-dimethylamino-2-(3-ethylsulfonyl-5-trifluoromethylpyridin-2-yl)-3-methyl-6-trifluoromethyl-3H-imidazo[4,5-b]pyridine (hereinafter referred to as the present fused heterocyclic compound 99) 0.03 g.

Present Fused Heterocyclic Compound 99

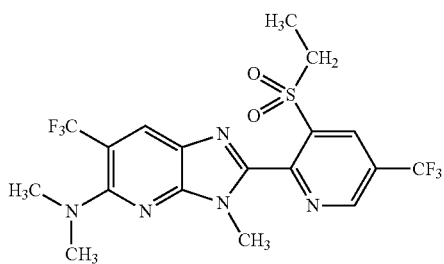 [SMILES: CCS(=O)(=O)c1cc(C(F)(F)F)cnc1-c1nc2cc(C(F)(F)F)c(N(C)C)nc2n1C]

$^1$H-NMR (CDCl$_3$) δ: 9.20 (1H, d), 8.76 (1H, d), 8.26 (1H, s), 4.02 (2H, q), 3.84 (3H, s), 3.04 (6H, s), 1.41 (3H, t).

Production Example 57

7-Cyano-2-(3-ethylsulfonylpyridin-2-yl)-1-methyl-5-trifluoromethyl-1H-benzimidazole (hereinafter referred to as the present fused heterocyclic compound 130) was prepared in a similar manner as described for the preparation of Production example 5 by using 7-cyano-2-(3-ethylsulfanylpyridin-2-yl)-1-methyl-5-trifluoromethyl-1H-benzimidazole instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).

Present Fused Heterocyclic Compound 130

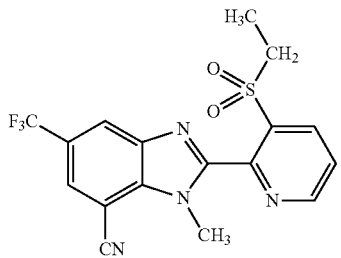 [SMILES: CCS(=O)(=O)c1cccnc1-c1nc2cc(C(F)(F)F)cc(C#N)c2n1C]

$^1$H-NMR (CDCl$_3$) δ: 9.02 (1H, dd), 8.54 (1H, dd), 8.28 (1H, s), 7.95 (1H, s), 7.77 (1H, dd), 4.06 (3H, s), 3.74 (2H, q), 1.35 (3H, t).

Production Example 58

2-(5-Chloro-3-ethylsulfonylpyridin-2-yl)-3-methyl-6-pentafluoroethyl-3H-imidazo[4,5-b]pyridine (hereinafter referred to as the present fused heterocyclic compound 312) was prepared in a similar manner as described for the preparation of Production example 5 by using 2-(5-chloro-3-ethylsulfanylpyridin-2-yl)-3-methyl-6-pentafluoroethyl-3H-imidazo[4,5-b]pyridine instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).

Present Fused Heterocyclic Compound 312

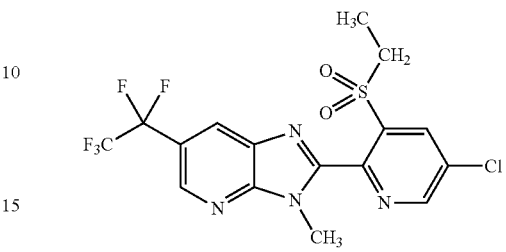

$^1$H-NMR (CDCl$_3$) δ: 8.95 (1H, d), 8.72-8.71 (1H, m), 8.53 (1H, d), 8.30-8.28 (1H, m), 3.94-3.87 (5H, m), 1.40 (3H, t)

To a mixture of the present fused heterocyclic compound 48 (0.30 g), triethylamine 0.14 mL, and acetonitrile 1 mL, trimethylsilyl cyanide 0.35 mL was added, and the mixture was stirred at 110° C. for 3 hr. To the reaction mixture allowed to cool to RT was added water, and the resulting mixture was extracted with ethyl acetate. The organic layer was dried over anhydrous magnesium sulfate, and then concentrated under reduced pressure. The resultant residue was treated with silica gel column chromatography to give 5-cyano-2-(3-ethylsulfonyl-5-trifluoromethylpyridin-2-yl)-3-methyl-6-trifluoromethyl-3H-imidazo[4,5-b]pyridine (hereinafter referred to as the present fused heterocyclic compound 399) 0.23 g.

Present Fused Heterocyclic Compound 399

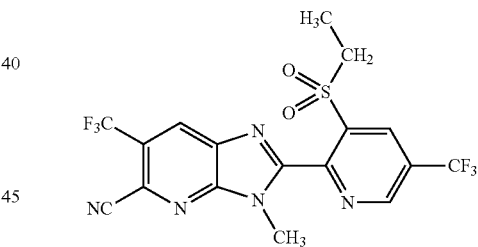

$^1$H-NMR (CDCl$_3$) δ: 9.28 (1H, d), 8.79 (1H, d), 8.48 (1H, s), 3.96 (3H, s), 3.89 (2H, q), 1.42 (3H, t).

Production Example 60

To a mixture of 2-(3-ethylsulfanylpyridin-2-yl)-1-methyl-7-methylsulfanyl-5-trifluoromethyl-1H-benzimidazole 0.11 g and chloroform 5 mL at ice temperature was added m-chloroperbenzoic acid (65% or more purity) 0.32 g, and then the resulting mixture was stirred at RT for 5 hr. The reaction mixture was cooled at ice temperature, and to the mixture was added m-chloroperbenzoic acid (65% or more purity) 0.32 g, and then the mixture was stirred at RT for 3 hr. To the reaction mixture was added aqueous 10% sodium thiosulfate and saturated aqueous sodium bicarbonate, and the reaction mixture was extracted with chloroform. The organic layer was washed with water, dried over anhydrous magnesium sulfate, and then concentrated under reduced pressure to give 2-(3-ethylsulfonylpyridin-2-yl)-1-methyl-7- methylsulfonyl-5-trifluoromethyl-1H-benzimidazole (hereinafter referred to as the present fused heterocyclic compound 404) 0.62 g.

Present Fused Heterocyclic Compound 404

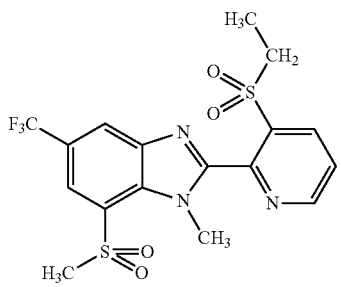 [SMILES: CCS(=O)(=O)c1cccnc1-c1nc2cc(C(F)(F)F)cc(S(C)(=O)=O)c2n1C]

¹H-NMR (CDCl₃) δ: 9.08-8.97 (1H, m), 8.58-8.46 (1H, m), 8.41-8.26 (2H, m), 7.84-7.70 (1H, m), 4.12 (3H, s), 3.72-3.59 (2H, m), 3.33 (3H, s), 1.39-1.22 (3H, m).

Production Example 61

To a mixture of the present fused heterocyclic compound 19 (2.0 g) and chloroform 20 mL at ice temperature was added m-chloroperbenzoic acid (65% or more purity) 3.03 g, and then the mixture was stirred with heating to reflux for 3 hr. The reaction mixture was cooled at ice temperature, and to the mixture was added m-chloroperbenzoic acid (65% or more purity) 3.03 g, and then the mixture was stirred with heating to reflux for 3 hr. The reaction mixture was cooled at ice temperature, and to the mixture was added m-chloroperbenzoic acid (65% or more purity) 3.03 g, and then the mixture was stirred with heating to reflux for 3 hr. To the reaction mixture allowed to cool to RT was added aqueous 10% sodium thiosulfate and saturated aqueous sodium bicarbonate, and the reaction mixture was extracted with chloroform. The organic layer was washed with water, dried over anhydrous magnesium sulfate, and then concentrated under reduced pressure to give 2-(3-ethylsulfonyl-5-trifluoromethyl-pyridin-2-yl)-3-methyl-6-pentafluoroethyl-3H-imidazo[4,5-b]pyridine 4-oxide (hereinafter referred to as the present fused heterocyclic compound 409) 1.10 g.

Present Fused Heterocyclic Compound 409

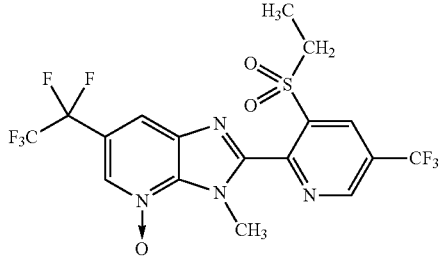 [SMILES: CCS(=O)(=O)c1cc(C(F)(F)F)cnc1-c1nc2cc(C(F)(F)C(F)(F)F)c[n+]([O-])c2n1C]

¹H-NMR (CDCl₃) δ: 9.27 (1H, d), 8.77 (1H, d), 8.45 (1H, 8), 7.92 (1H, s), 4.34 (3H, s), 3.81 (2H, q), 1.40 (3H, t).

Production Example 62

To a mixture of the present fused heterocyclic compound 19 (0.65 g), methanol 6 mL, THF 6 mL, and water 2 mL was added sodium hydroxide 0.54 g, and the mixture was stirred with heating to reflux for 1 day. To the reaction mixture allowed to cool to RT was added water, and the resulting mixture was extracted with ethyl acetate. The organic layer was dried over anhydrous magnesium sulfate, and then concentrated under reduced pressure. The resultant residue was treated with silica gel column chromatography to give 2-(3-ethylsulfonyl-5-trimethoxymethyl-pyridin-2-yl)-3-methyl-6-pentafluoroethyl-3H-imidazo[4,5-b]pyridine (hereinafter referred to as the present fused heterocyclic compound 414) 0.25 g.

Present Fused Heterocyclic Compound 414

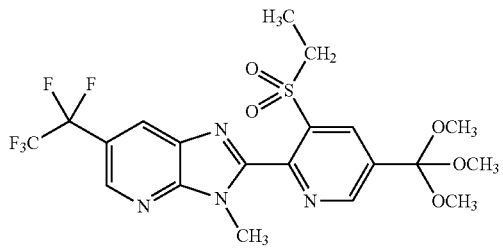 [SMILES: CCS(=O)(=O)c1cc(C(OC)(OC)OC)cnc1-c1nc2cc(C(F)(F)C(F)(F)F)cnc2n1C]

¹H-NMR (CDCl₃) δ: 9.16 (1H, d), 8.74 (1H, d), 8.70 (1H, d), 8.31 (1H, d), 3.93 (3H, s), 3.88 (2H, q), 3.28 (9H, s), 1.38 (3H, t).

Production Example 63

2-(3-Methylsulfonyl-5-trifluoromethylpyridin-2-yl)-3-methyl-6-pentafluoroethyl-3H-imidazo[4,5-b]pyridine (hereinafter referred to as the present fused heterocyclic compound 419) was prepared in a similar manner as described for the preparation of Production example 5 by using 2-(3-methylsulfanyl-5-trifluoromethylpyridin-2-yl)-3-methyl-6-pentafluoroethyl-3H-imidazo[4,5-b]pyridine instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).

Present Fused Heterocyclic Compound 419

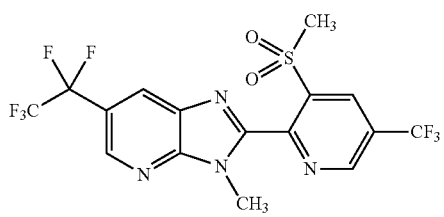 [SMILES: Cn1c(-c2ncc(C(F)(F)F)cc2S(C)(=O)=O)nc2cc(C(F)(F)C(F)(F)F)cnc21]

¹H-NMR (CDCl₃) δ: 9.25 (1H, s), 8.85 (1H, s), 8.75 (1H, s), 8.32 (1H, s), 3.96 (3H, s), 3.73 (3H, s)

Production Example 64

2-(3-Propylsulfonyl-5-trifluoromethylpyridin-2-yl)-3-methyl-6-pentafluoroethyl-3H-imidazo[4,5-b]pyridine (hereinafter referred to as the present fused heterocyclic compound 421) was prepared in a similar manner as described for the preparation of Production example 5 by using 2-(3-propylsulfanyl-5-trifluoromethylpyridin-2-yl)-3-methyl-6-pentafluoroethyl-3H-imidazo[4,5-b]pyridine instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).

Present Fused Heterocyclic Compound 421

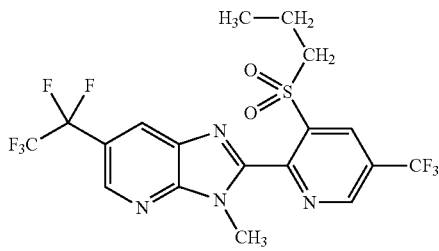 [SMILES: CCCS(=O)(=O)c1cc(C(F)(F)F)cnc1-c1nc2cc(C(F)(F)C(F)(F)F)cnc2n1C]

¹H-NMR (CDCl₃) δ: 9.24 (1H, s), 8.79 (1H, s), 8.74 (1H, s), 8.31 (1H, s), 3.95-3.88 (5H, m), 1.92-1.81 (2H, m), 1.13 (3H, t)

Production Example 65

2-(3-Isopropylsulfonyl-5-trifluoromethylpyridin-2-yl)-3-methyl-6-pentafluoroethyl-3H-imidazo[4,5-b]pyridine (hereinafter referred to as the present fused heterocyclic compound 423) was prepared in a similar manner as described for the preparation of Production example 5 by using 2-(3-isopropylsulfanyl-5-trifluoromethylpyridin-2-yl)-3-methyl-6-pentafluoroethyl-3H-imidazo[4,5-b]pyridine instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).

Present Fused Heterocyclic Compound 423

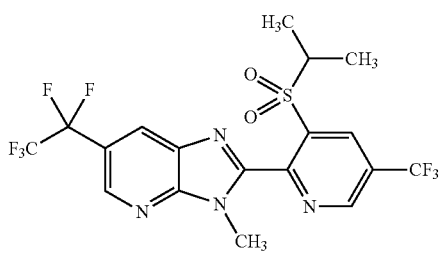 [SMILES: CC(C)S(=O)(=O)c1cc(C(F)(F)F)cnc1-c1nc2cc(C(F)(F)C(F)(F)F)cnc2n1C]

¹H-NMR (CDCl₃) δ: 9.24 (1H, s), 8.75 (2H, d), 8.31 (1H, s), 4.71-4.60 (1H, m), 3.93 (3H, s), 1.39 (6H, d)

Production Example 66

2-(3-Ethylsulfonylpyridin-2-yl)-6-pentafluoroethyl-oxazolo[5,4-b]pyridine (hereinafter referred to as the present fused heterocyclic compound 464) was prepared in a similar manner as described for the preparation of Production example 5 by using 2-(3-ethylsulfanylpyridin-2-yl)-6-pentafluoroethyl-oxazolo[5,4-b]pyridine instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).

Present Fused Heterocyclic Compound 464

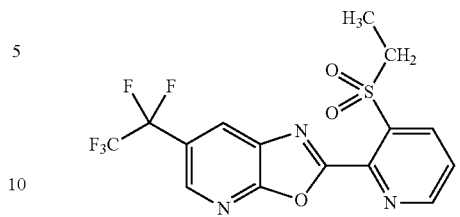

¹H-NMR (CDCl₃) δ: 9.07 (1H, dd), 8.74 (1H, d), 8.59 (1H, dd), 8.41 (1H, d), 7.80 (1H, dd), 3.91 (2H, q), 1.45 (3H, t).

Production Example 67

2-(3-Ethylsulfonylpyridin-2-yl)-5-pentafluoroethyl-benzoxazole (hereinafter referred to as the present fused heterocyclic compound 467) was prepared in a similar manner as described for the preparation of Production example 5 by using 2-(3-ethylsulfanylpyridin-2-yl)-5-pentafluoroethyl-benzoxazole instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).

Present Fused Heterocyclic Compound 467

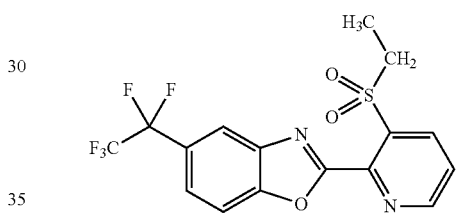

¹H-NMR (CDCl₃) δ: 9.04 (1H, dd), 8.61 (1H, dd), 8.12 (1H, d), 7.82 (1H, d), 7.75 (1H, dd), 7.72 (1H, dd), 4.04 (2H, q), 1.44 (3H, t).

Production Example 68(1)

A mixture of 2 amino-4-(trifluoromethylsulfanyl)phenol 1.0 g, 3-ethylsulfanylpicolinic acid 0.87 g, EDC hydrochloride 1.10 g, and chloroform 10 mL was stirred at RT for 30 min. To the reaction mixture was added water, and the resulting mixture was extracted with ethyl acetate. The organic layer was washed with saturated aqueous sodium bicarbonate and brine, dried over anhydrous magnesium sulfate, and then concentrated under reduced pressure. The resultant residue was treated with silica gel column chromatography to give 3-ethylsulfanyl-N-[2-hydroxy-5-(trifluoromethylsulfanyl)phenyl]picolinamide 1.32 g.

3-Ethylsulfanyl-N-[2-hydroxy-5-(trifluoromethylsulfanyl)phenyl]picolinamide

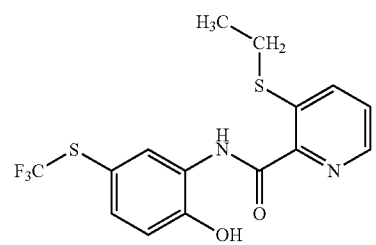 [SMILES: CCSc1cccnc1C(=O)Nc1cc(SC(F)(F)F)ccc1O]

$^1$H-NMR (CDCl$_3$) δ: 10.40 (1H, brs), 9.63 (1H, s), 8.36 (1H, dd), 7.75 (1H, dd), 7.53 (1H, d), 7.45 (1H, dd), 7.41 (1H, dd), 7.08 (1H, d), 2.97 (2H, q), 1.44 (3H, t).

Production Example 68(2)

A mixture of 3-ethylsulfanyl-N-[2-hydroxy-5-(trifluoromethylsulfanyl)phenyl]picolinamide 1.23 g, di-2-methoxyethyl azodicarboxylate (hereinafter referred to as DMEAD) 1.28 g, triphenylphosphine 1.39 g, and THF 30 mL was stirred at RT for 1 hr and at 50° C. for 1 hr. The reaction mixture allowed to cool to RT was concentrated under reduced pressure, and to the mixture was added water. The resulting mixture was extracted with ethyl acetate. The organic layer was washed with saturated aqueous sodium bicarbonate and brine, dried over anhydrous magnesium sulfate, and then concentrated under reduced pressure. The resultant residue was treated with silica gel column chromatography to give 2-(3-ethylsulfanylpyridin-2-yl)-5-(trifluoromethylsulfanyl)benzoxazole (hereinafter referred to as the present fused heterocyclic compound 441) 1.21 g.
Present Fused Heterocyclic Compound 441

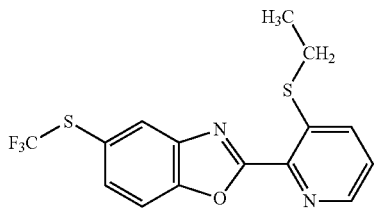 [SMILES: CCSc1cccnc1-c1nc2cc(SC(F)(F)F)ccc2o1]

$^1$H-NMR (CDCl$_3$) δ: 8.59 (1H, dd), 8.27 (1H, s), 7.78 (1H, dd), 7.75-7.69 (2H, m), 7.42 (1H, dd), 3.07 (2H, q), 1.47 (3H, t).

Production Example 69

To a mixture of the present fused heterocyclic compound 441 (1.06 g) and chloroform 30 mL at ice temperature was added m-chloroperbenzoic acid (65% or more purity) 1.47 g, and then the mixture was stirred at RT for 6 hr. To the reaction mixture was added aqueous 10 sodium sulfite, and the reaction mixture was extracted with chloroform. The organic layer was washed with saturated aqueous sodium bicarbonate, and dried over anhydrous magnesium sulfate, and then concentrated under reduced pressure. The resultant residue was treated with silica gel column chromatography to give 2-(3-ethylsulfonylpyridin-2-yl)-5-(trifluoromethylsulfanyl)benzoxazole (hereinafter referred to as the present fused heterocyclic compound 443) 0.87 g and 2-(3-ethylsulfonylpyridin-2-yl)-5-(trifluoromethylsulfinyl)benzoxazole (hereinafter referred to as the present fused heterocyclic compound 444) 0.17 g.
Present Fused Heterocyclic Compound 443

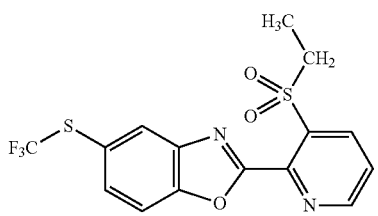 [SMILES: CCS(=O)(=O)c1cccnc1-c1nc2cc(SC(F)(F)F)ccc2o1]

$^1$H-NMR (CDCl$_3$) δ: 9.03 (1H, dd), 8.60 (1H, dd), 8.19 (1H, d), 7.80-7.71 (3H, m), 4.02 (2H, q), 1.43 (3H, t).
Present Fused Heterocyclic Compound 444

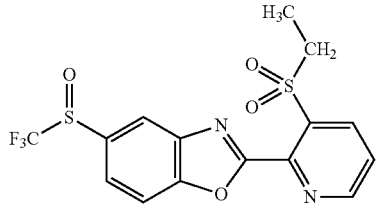 [SMILES: CCS(=O)(=O)c1cccnc1-c1nc2cc(S(=O)C(F)(F)F)ccc2o1]

$^1$H-NMR (CDCl$_3$) δ: 9.04 (1H, dd), 8.61 (1H, dd), 8.35 (1H, d), 7.96-7.86 (2H, m), 7.77 (1H, dd), 4.01 (2H, q), 1.44 (3H, t).

Production Example 70

To a mixture of the present fused heterocyclic compound 443 (0.35 g) and chloroform 8 mL at ice temperature was added m-chloroperbenzoic acid (65% or more purity) 0.43 g, and then the mixture was stirred at 40° C. for 6 hr. The reaction mixture was allowed to cool to RT, and to the mixture was added aqueous 10% sodium sulfite, and the reaction mixture was extracted with chloroform. The organic layer was washed with saturated aqueous sodium bicarbonate, and dried over anhydrous magnesium sulfate, and then concentrated under reduced pressure. To the resultant residue was added acetonitrile 4 mL, sodium tungstate dihydrate 30 mg, and aqueous hydrogen peroxide (30%) 4 mL, and the mixture was stirred at 80° C. for 6 hr. The reaction mixture was allowed to cool to RT, and to the mixture was added water. The precipitated solid was removed by filtration, and to the filtrate was added aqueous 10% sodium sulfite. The resulting mixture was extracted with ethyl acetate. The organic layer was washed with water and brine, dried over anhydrous magnesium sulfate, and then concentrated under reduced pressure. The resultant residue was treated with silica gel column chromatography to give 2-(3-ethylsulfonylpyridin-2-yl)-5-(trifluoromethylsulfonyl)benzoxazole (hereinafter referred to as the present fused heterocyclic compound 445) 0.35 g.
Present Fused Heterocyclic Compound 445

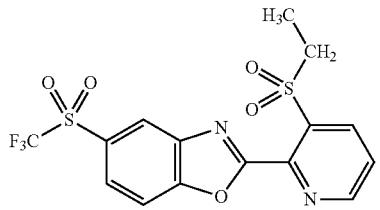 [SMILES: CCS(=O)(=O)c1cccnc1-c1nc2cc(S(=O)(=O)C(F)(F)F)ccc2o1]

$^1$H-NMR (CDCl$_3$) δ: 9.05 (1H, dd), 8.61 (1H, dd), 8.59 (1H, d), 8.17 (1H, dd), 7.96 (1H, d), 7.80 (1H, dd), 3.98 (2H, q), 1.45 (3H, t).

Production Example 71 (1)

A mixture of 2-amino-4-(trifluoromethylsulfanyl)phenol 1.0 g, 3-chloro-5-trifluoromethylpicolinic acid 1.08 g, EDC hydrochloride 1.10 g, and chloroform 10 mL, was stirred at RT for 1 hr. To the reaction mixture was added water, and the resulting mixture was extracted with ethyl acetate. The organic layer was washed with saturated aqueous sodium bicarbonate, water, and brine, dried over anhydrous magnesium sulfate, and then concentrated under reduced pressure to give 3-chloro-5-trifluoromethyl-N-[2-hydroxy-5-(trifluoromethylsulfanyl)phenyl]picolinamide 1.94 g.

3-chloro-5-trifluoromethyl-N-[2-hydroxy-5-(trifluoromethylsulfanyl)phenyl]picolinamide

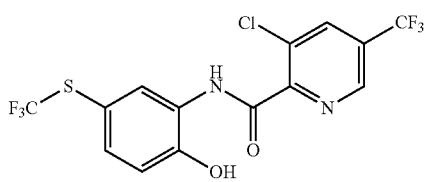 [SMILES: O=C(Nc1cc(SC(F)(F)F)ccc1O)c1ncc(C(F)(F)F)cc1Cl]

$^1$H-NMR (CDCl$_3$) δ: 8.78 (1H, d), 8.15 (1H, d), 8.09 (1H, d), 7.37 (1H, dd), 7.04 (1H, d).

Production Example 71 (2)

To a mixture of 3-chloro-5-trifluoromethyl-N-[2-hydroxy-5-(trifluoromethylsulfanyl)phenyl]picolinamide 1.93 g, DMF 6 mL, THF 1 mL, and ethyl mercaptan 0.38 mL at ice temperature was added potassium tert-butoxide 0.62 g, and the mixture was stirred at RT for 2 hr. To the reaction mixture was added water, and the resulting mixture was extracted with ethyl acetate. The organic layer was washed with water and brine, dried over anhydrous magnesium sulfate, and then concentrated under reduced pressure. The resultant residue was treated with silica gel column chromatography to give 3-ethylsulfanyl-5-trifluoromethyl-N-[2-hydroxy-5-(trifluoromethylsulfanyl)phenyl]picolinamide 1.45 g.

3-Ethylsulfanyl-5-trifluoromethyl-N-[2-hydroxy-5-(trifluoromethylsulfanyl)phenyl]picolinamide

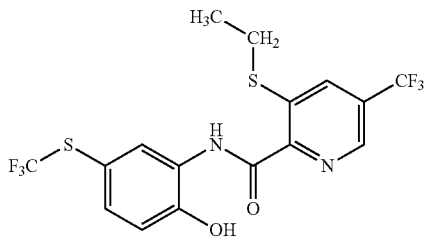 [SMILES: CCSc1cc(C(F)(F)F)cnc1C(=O)Nc1cc(SC(F)(F)F)ccc1O]

$^1$H-NMR (CDCl$_3$) δ: 10.31 (1H, s), 8.96 (1H, brs), 8.58 (1H, d), 7.91 (1H, d), 7.70 (1H, d), 7.43 (1H, dd), 7.07 (1H, d), 3.00 (2H, q), 1.47 (3H, t).

Production Example 71 (3)

A mixture of 3-ethylsulfanyl-5-trifluoromethyl-N-[2-hydroxy-5-(trifluoromethylsulfanyl)phenyl]picolinamide 1.45 g, DMEAD 1.19 g, triphenylphosphine 1.29 g, and THF 30 mL was stirred at RT for 1 hr and at 50° C. for 1 hr. The reaction mixture allowed to cool to RT was concentrated under reduced pressure, and then to the residue was added water, the resulting mixture was extracted with ethyl acetate. The organic layer was washed with saturated aqueous sodium bicarbonate and brine, dried over anhydrous magnesium sulfate, and then concentrated under reduced pressure. The resultant residue was treated with silica gel column chromatography to give 2-(3-ethylsulfanyl-5-trifluoromethylpyridin-2-yl)-5-(trifluoromethylsulfanyl)benzoxazole (hereinafter referred to as the present fused heterocyclic compound 451) 1.31 g.

Present Fused Heterocyclic Compound 451

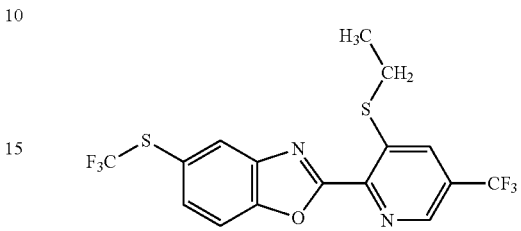

$^1$H-NMR (CDCl$_3$) δ: 8.78 (1H, d), 8.30 (1H, s), 7.94 (1H, d), 7.77-7.75 (2H, m), 3.11 (2H, q), 1.51 (3H, t).

Production Example 72

To a mixture of the present fused heterocyclic compound 451 (1.13 g) and chloroform 25 mL at ice temperature was added m-chloroperbenzoic acid (65% or more purity) 0.56 g, and then the mixture was stirred at 0° C. for 40 min. To the reaction mixture was added aqueous 10% sodium sulfite, and the reaction mixture was extracted with chloroform. The organic layer was washed with saturated aqueous sodium bicarbonate, and dried over anhydrous magnesium sulfate, and then concentrated under reduced pressure. The resultant residue was treated with silica gel column chromatography to give 2-(3-ethylsulfinyl-5-trifluoromethylpyridin-2-yl)-5-(trifluoromethylsulfanyl)benzoxazole (hereinafter referred to as the present fused heterocyclic compound 452) 1.01 g.

Present Fused Heterocyclic Compound 452

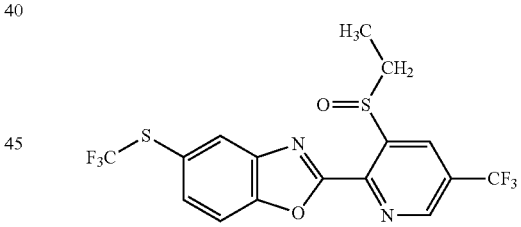

$^1$H-NMR (CDCl$_3$) δ: 9.13 (1H, d), 8.91 (1H, d), 8.25 (1H, s), 7.85-7.79 (2H, m), 3.60-3.49 (1H, m), 3.13-3.02 (1H, m), 1.44 (3H, t).

PRODUCTION EXAMPLE 73

To a mixture of the present fused heterocyclic compound 452 (1.01 g) and chloroform 20 mL at ice temperature was added m-chloroperbenzoic acid (65% or more purity) 0.56 g, and then the mixture was stirred at RT for 6 hr. To the reaction mixture was added m-chloroperbenzoic acid (65% or more purity) 0.20 g, and then the reaction mixture was stirred at RT for 3 hr. To the reaction mixture was added aqueous 10% sodium sulfite, and the reaction mixture was extracted with chloroform. The organic layer was washed with saturated aqueous sodium bicarbonate, and dried over anhydrous magnesium sulfate, and then concentrated under reduced pressure. The resultant residue was treated with silica gel column chromatography to give 2-(3-ethylsulfonyl-5-trifluoromethylpyridin-2-yl)-5-(trifluoromethylsulfanyl)benzoxazole (hereinafter referred to as the present fused heterocyclic compound 453) 0.53 g and 2-(3-ethylsulfonyl-5-trifluoromethylpyridin-2-yl)-5-(trifluoromethylsulfinyl)benzoxazole (hereinafter referred to as the present fused heterocyclic compound 454) 0.48 g.

Present Fused Heterocyclic Compound 453

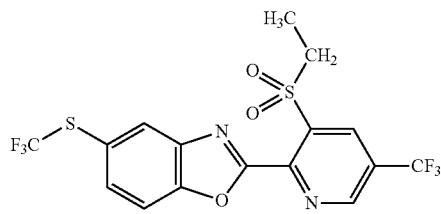 [SMILES: CCS(=O)(=O)c1cc(C(F)(F)F)cnc1-c1nc2cc(SC(F)(F)F)ccc2o1]

$^1$H-NMR (CDCl$_3$) δ: 9.25 (1H, d), 8.84 (1H, d), 8.22 (1H, d), 7.82 (1H, dd), 7.77 (1H, d), 4.11 (2H, q), 1.47 (3H, t).

Present Fused Heterocyclic Compound 454

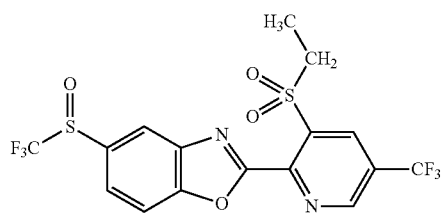 [SMILES: CCS(=O)(=O)c1cc(C(F)(F)F)cnc1-c1nc2cc(S(=O)C(F)(F)F)ccc2o1]

$^1$H-NMR (CDCl$_3$) δ: 9.27 (1H, d), 8.85 (1H, d), 8.39 (1H, s), 7.96 (1H, d), 7.92 (1H, d), 4.09 (2H, q), 1.48 (3H, t).

Production Example 74

The present fused heterocyclic compound 454 (0.26 g), acetonitrile 4 mL, sodium tungstate dihydrate 18 mg, and aqueous hydrogen peroxide (30%) 3.5 mL was mixed, and the mixture was stirred at 85° C. for 5 hr. The reaction mixture was allowed to cool to RT, and to the mixture was added aqueous hydrogen peroxide (30%) 0.5 mL, and the mixture was stirred at 85° C. for 3 hr. The reaction mixture was allowed to cool to RT, and to the mixture was added water. The precipitated solid was removed by filtration, and to the filtrate was added aqueous 10% sodium sulfite. The resulting mixture was extracted with ethyl acetate. The organic layer was washed with water and brine, dried over anhydrous magnesium sulfate, and then concentrated under reduced pressure. The resultant residue was treated with silica gel column chromatography to give 2-(3-ethylsulfonyl-5-trifluoromethylpyridin-2-yl)-5-(trifluoromethylsulfonyl)benzoxazole (hereinafter referred to as the present fused heterocyclic compound 455) 0.24 g.

Present Fused Heterocyclic Compound 455

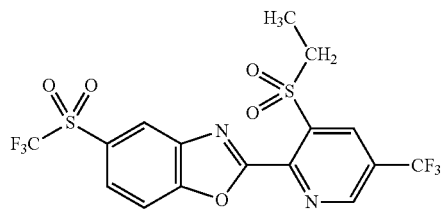 [SMILES: CCS(=O)(=O)c1cc(C(F)(F)F)cnc1-c1nc2cc(S(=O)(=O)C(F)(F)F)ccc2o1]

$^1$H-NMR (CDCl$_3$) δ: 9.28 (1H, d), 8.84 (1H, d), 8.62 (1H, d), 8.21 (1H, dd), 8.00 (1H, d), 4.05 (2H, q), 1.49 (3H, t).

Production Example 75 (1)

A mixture of tert-butanol 27 mL and potassium hydroxide 3.15 g was stirred with heating to reflux for 1 hr. To the mixture was added 2-chloro-5-trifluoromethylsulfanylpyridine 6.0 g and tert-butanol 3 mL with dropping funnel, and the mixture was stirred with heating to reflux for 5 hr. The reaction mixture was allowed to cool to RT, and to the mixture was added concentrated hydrochloric acid. The precipitated solid was removed by filtration and washed with ethanol. The resulting filtrate was concentrated under reduced pressure. To the residue was added 1 N hydrochloric acid. The precipitated solid was collected by filtration and washed with water, and then with hexane, and dried to give 2-hydroxy-5-trifluoromethylsulfanylpyridine 4.42 g.

2-Hydroxy-5-trifluoromethylsulfanylpyridine

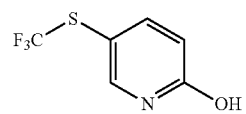

$^1$H-NMR (CDCl$_3$) δ: 7.73 (1H, d), 7.62 (1H, dd), 6.61 (1H, d).

Production Example 75 (2)

To a mixture of 2-hydroxy-5-trifluoromethylsulfanylpyridine 2 g and concentrated sulfuric acid 10 mL at ice temperature was added fuming nitric acid 0.74 mL, and the mixture was stirred at 60° C. for 2 hr. The reaction mixture was allowed to cool to RT, and then to ice water 50 mL was poured the mixture, and then the resulting mixture was extracted with ethyl acetate. The organic layer was washed with brine, and dried over anhydrous sodium sulfate, and concentrated under reduced pressure. The resulting solid was washed with tert-butyl methyl ether to give 2-hydroxy-3-nitro-5-trifluoromethylsulfinylpyridine 2.13 g.

2-Hydroxy-3-nitro-5-trifluoromethylsulfinylpyridine

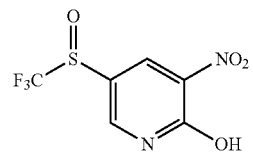 [SMILES: O=[N+]([O-])c1cc(S(=O)C(F)(F)F)cnc1O]

$^1$H-NMR (DMSO-D$_6$) δ: 8.67 (1H, brs), 8.59 (1H, brs).

Production Example 75 (3)

A mixture of iron powder 4.6 g, acetic acid 0.5 mL, ethanol 20 mL, and water 15 mL was stirred at 70° C. To the mixture was added 2-hydroxy-3-nitro-5-trifluoromethylsulfinylpyridine 2 g, and the mixture was stirred at 70° C. for 2 hr. The reaction mixture was allowed to cool to RT and filtrated through Celite (Trademark). The residual mixture was concentrated under reduced pressure, and to the resultant residue was added saturated aqueous sodium bicarbonate. The resulting mixture was extracted with ethyl acetate. The organic layer was dried over anhydrous sodium sulfate, and concentrated under reduced pressure. The resulting solid was washed with tert-butyl methyl ether to give 3-amino-2-hydroxy-5-trifluoromethylsulfinylpyridine 1.45 g.

3-Amino-2-hydroxy-5-trifluoromethylsulfinylpyridine

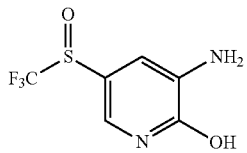

$^1$H-NMR (DMSO-D$_6$) δ: 12.23 (1H, brs), 7.49 (1H, s), 6.68 (1H, s), 5.72 (2H, brs).

Production Example 75 (4)

A mixture of 3-amino-2-hydroxy-5-trifluoromethylsulfinylpyridine 0.63 g, 3-ethylsulfanylpicolinic acid 0.55 g, EDC hydrochloride 0.68 g and pyridine 20 ml was stirred at RT 3 hr. To the reaction mixture was added water, the mixture was stirred at RT for 30 min. The precipitated solids were collected by filtration, and concentrated under reduced pressure to give 3-ethylsulfanyl-N-[2-hydroxy-5-trifluoromethylsulfinylpyridin-3-yl]picolinamide 0.73 g.

3-Ethylsulfanyl-N-[2-hydroxy-5-trifluoromethylsulfinylpyridin-3-yl]picolinamide

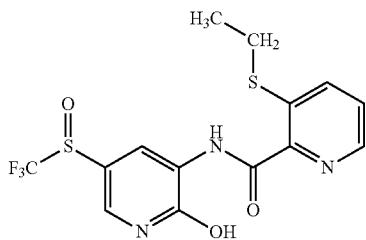 [SMILES: CCSc1cccnc1C(=O)Nc1cc(S(=O)C(F)(F)F)cnc1O]

$^1$H-NMR (DMSO-D$_6$) δ: 10.83 (1H, s), 8.71 (1H, s), 8.48 (1H, dd), 8.09 (1H, d), 7.98 (1H, d), 7.65 (1H, dd), 2.99 (2H, q), 1.31 (3H, t).

Production Example 75 (5)

A mixture of 3-ethylsulfanyl-N-[2-hydroxy-5-trifluoromethylsulfinylpyridin-3-yl]picolinamide 0.67 g, DMEAD 0.64 g, triphenylphosphine 0.68 g, and THF 40 mL was stirred at 50° C. for 3 hr. The reaction mixture allowed to cool to RT was concentrated under reduced pressure, and to the mixture was added water, and the mixture was extracted with ethyl acetate. The organic layer was washed with saturated aqueous ammonium chloride and brine, dried over anhydrous sodium sulfate, and concentrated under reduced pressure. The resultant residue is treated with silica gel column chromatography to give 2-(3-ethylsulfanylpyridin-2-yl)-6-(trifluoromethylsulfinyl)oxazolo[5,4-b]pyridine 0.59 g (hereinafter referred to as the present fused heterocyclic compound 474).

Present Fused Heterocyclic Compound 474

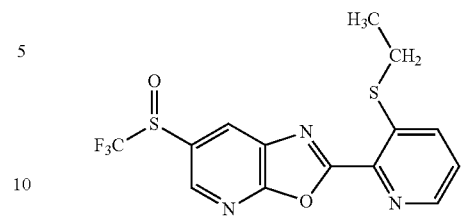

$^1$H-NMR (CDCl$_3$) δ: 8.76 (1H, d), 8.70 (1H, d), 8.64 (1H, dd), 7.82 (1H, dd), 7.47 (1H, dd), 3.09 (2H, q), 1.47 (3H, t).

Production Example 76

To a mixture of the present fused heterocyclic compound 474 (0.43 g) and chloroform 30 mL at ice temperature was added m-chloroperbenzoic acid (65% or more purity) 0.53 g, and then the mixture was stirred at RT for 5 hr. To the reaction mixture was added aqueous 10% sodium sulfite, and the mixture was extracted with chloroform. The organic layer was washed with saturated aqueous sodium bicarbonate, dried over anhydrous sodium sulfate, and then concentrated under reduced pressure. The resultant residue was treated with silica gel column chromatography to give 2-(3-ethylsulfonylpyridin-2-yl)-6-(trifluoromethylsulfinyl)oxazolo[5,4-b]pyridine (hereinafter referred to as the present fused heterocyclic compound 439) 0.34 g.

Present Fused Heterocyclic Compound 439

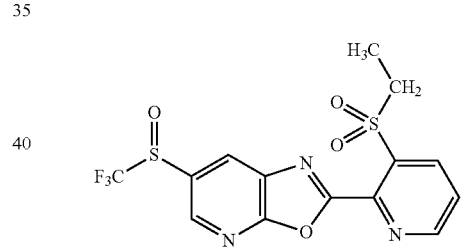

$^1$H-NMR (CDCl$_3$) δ: 9.08 (1H, dd), 8.80 (1H, d), 8.69 (1H, d), 8.60 (1H, dd), 7.81 (1H, dd), 3.91 (2H, q), 1.45 (3H, t).

Production Example 77

The present fused heterocyclic compound 439 (0.17 g), acetonitrile 4 mL, sodium tungstate dihydrate 14 mg, and aqueous hydrogen peroxide (30%) 4 mL was mixed, and the mixture was stirred at 80° C. for 4 hr. To the reaction mixture allowed to cool to RT was added water, and the precipitated solid was collected by filtration, and the solids and aqueous 10% sodium sulfite were mixed, and the mixture was extracted with ethyl acetate. The organic layer was washed with water and brine, dried over anhydrous sodium sulfate, and concentrated under reduced pressure. The resultant residue is treated with silica gel column chromatography to give 2-(3-ethylsulfonylpyridin-2-yl)-6-(trifluoromethylsulfonyl)oxazolo[5,4-b]pyridine (hereinafter referred to as the present fused heterocyclic compound 440) 0.09 g.

Present Fused Heterocyclic Compound 440

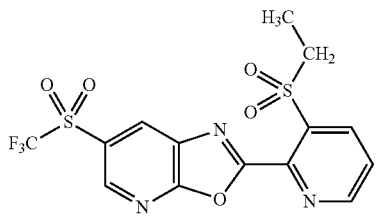 [SMILES: CCS(=O)(=O)c1cccnc1-c1nc2cc(S(=O)(=O)C(F)(F)F)cnc2o1]

¹H-NMR (CDCl₃) δ: 9.13 (1H, dd), 9.09 (1H, dd), 8.79 (1H, d), 8.60 (1H, dd), 7.83 (1H, dd), 3.88 (2H, q), 1.46 (3H, t).

Production Example 78 (1)

A mixture of 3-amino-2-hydroxy-5-trifluoromethylsulfinylpyridine 0.67 g, 3-ethylsulfanyl-5-trifluoromethylpicolinic acid 0.75 g, EDC hydrochloride 0.68 g and pyridine 20 mL was stirred at RT for 1.5 hr. To the reaction mixture was added water, and the mixture was stirred at RT for 30 min. The precipitated solids were collected by filtration and dried under reduced pressure to give 3-ethylsulfanyl-5-trifluoromethyl-N-[2-hydroxy-5-trifluoromethylsulfinylpyridin-3-yl]picolinamide.

3-Ethylsulfanyl-5-trifluoromethyl-N-[2-hydroxy-5-trifluoromethylsulfinylpyridin-3-yl]picolinamide 1.28 g

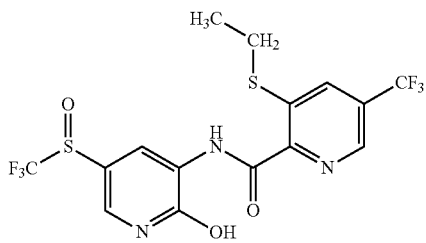 [SMILES: CCSc1cc(C(F)(F)F)cnc1C(=O)Nc1cc(S(=O)C(F)(F)F)cnc1O]

¹H-NMR (CDCl₃) δ: 10.99 (1H, dd), 8.90 (1H, s), 8.68 (1H, 5), 7.91 (1H, s), 7.81 (1H, s), 3.02 (2H, q), 1.48 (3H, t).

Production Example 78 (2)

A mixture of 3-ethylsulfanyl-5-trifluoromethyl-N-[2-hydroxy-5-trifluoromethylsulfinylpyridin-3-yl]picolinamide (1.24 g), DMEAD 1.01 g, triphenylphosphine 1.06 g, and THF 40 mL was stirred at 50° C. for 3 hr. The reaction mixture allowed to cool to RT was concentrated under reduced pressure, and to the mixture is added water, and the mixture was extracted with ethyl acetate. The organic layer was washed with saturated aqueous ammonium chloride and brine, dried over anhydrous magnesium sulfate, and concentrated under reduced pressure. The resultant residue was treated with silica gel column chromatography to give 2-(3-ethylsulfanyl-5-trifluoromethylpyridin-2-yl)-6-(trifluoromethylsulfinyl)oxazolo[5,4-b]pyridine (hereinafter referred to as the present fused heterocyclic compound 478) 0.94 g.

Present Fused Heterocyclic Compound 478

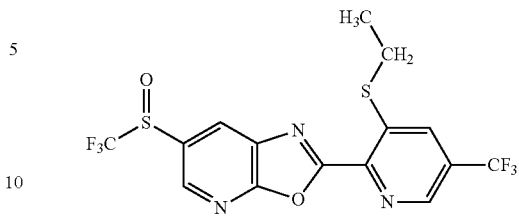

¹H-NMR (CDCl₃) δ: 8.83 (1H, d), 8.81 (1H, d), 8.75 (1H, d), 7.97 (1H, d), 3.13 (2H, q), 1.51 (3H, t).

Production Example 79

To a mixture of the present fused heterocyclic compound 478 (0.74 g) and chloroform 30 mL at ice temperature was added m-chloroperbenzoic acid (65% or more purity) 0.77 g, and then the mixture was stirred at RT 4 hr. To the reaction mixture was added aqueous 10% sodium sulfite, and the mixture was extracted with chloroform. The organic layer was washed with saturated aqueous sodium bicarbonate, dried over anhydrous sodium sulfate, and concentrated under reduced pressure. The resultant residue was treated with silica gel column chromatography to give 2-(3-ethylsulfonyl-5-trifluoromethylpyridin-2-yl)-6-(trifluoromethylsulfinyl)oxazolo[5,4-b]pyridine (hereinafter referred to as the present fused heterocyclic compound 449) 0.75 g.

Present Fused Heterocyclic Compound 449

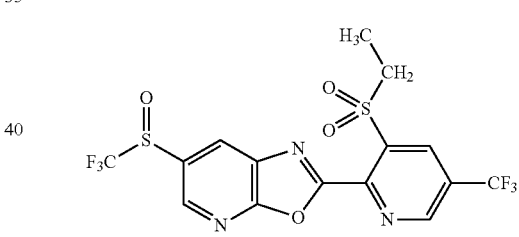

¹H-NMR (CDCl₃) δ: 9.31 (1H, d), 8.84-8.81 (2H, m), 8.73 (1H, d), 3.98 (2H, q), 1.49 (3H, t).

Production Example 80

The present fused heterocyclic compound 449 (0.14 g), acetonitrile 4 mL, sodium tungstate dihydrate 27 mg, and aqueous hydrogen peroxide (30%) 4 mL were mixed, and the mixture was stirred at 80° C. for 5 hr. To the reaction mixture allowed to cool to RT was added water, and the precipitated solids were collected by filtration. The solids and aqueous 10% sodium sulfite were mixed and the mixture was extracted with ethyl acetate. The organic layer was washed with water and brine, dried over anhydrous sodium sulfate, and concentrated under reduced pressure. The resultant residue was treated with silica gel column chromatography to give 2-(3-ethylsulfonyl-5-trifluoromethylpyridin-2-yl)-6-(trifluoromethylsulfonyl)oxazolo[5,4-b]pyridine (hereinafter referred to as the present fused heterocyclic compound 450) 0.21 g.

Present Fused Heterocyclic Compound 450

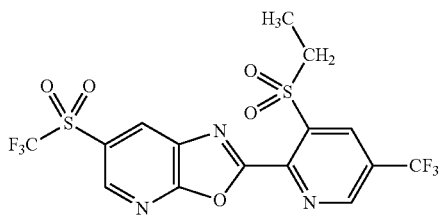 [SMILES: CCS(=O)(=O)c1cc(C(F)(F)F)cnc1-c1nc2cc(S(=O)(=O)C(F)(F)F)cnc2o1]

$^1$H-NMR (CDCl$_3$) δ: 9.32 (1H, d), 9.17 (1H, d), 8.85-8.82 (2H, m), 3.95 (2H, q), 1.50 (3H, t).

Production Example 81

To a mixture of the present fused heterocyclic compound 440 (1 mmol) and chloroform 10 mL at ice temperature is added m-chloroperbenzoic acid (65% or more purity) 5 mmol, and then the mixture is stirred with heating to reflux for 6 hr. To the reaction mixture allowed to cool to RT is added m-chloroperbenzoic acid (65% or more purity) 5 mmol, and then the mixture is stirred with heating to reflux for 6 hr. To the reaction mixture allowed to cool to RT is added aqueous 10% sodium sulfite, and the mixture is extracted with chloroform. The organic layer is washed with saturated aqueous sodium bicarbonate, dried over anhydrous magnesium sulfate, and concentrated under reduced pressure. The resultant residue is treated with silica gel column chromatography to give 2-(3-ethylsulfonylpyridin-2-yl)-6-(trifluoromethylsulfonyl)oxazolo[5,4-b]pyridine 4-oxide (hereinafter referred to as the present fused heterocyclic compound 456) and 2-(3-ethylsulfonyl-1-oxy-pyridin-2-yl)-6-(trifluoromethylsulfonyl)oxazolo[5,4-b]pyridine (hereinafter referred to as the present fused heterocyclic compound 458).

Present Fused Heterocyclic Compound 456

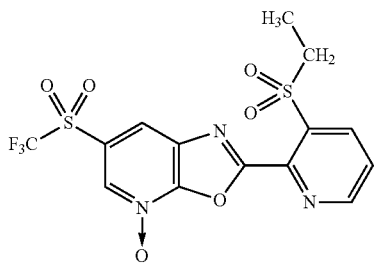 [SMILES: CCS(=O)(=O)c1cccnc1-c1nc2cc(S(=O)(=O)C(F)(F)F)c[n+]([O-])c2o1]

Present Fused Heterocyclic Compound 458

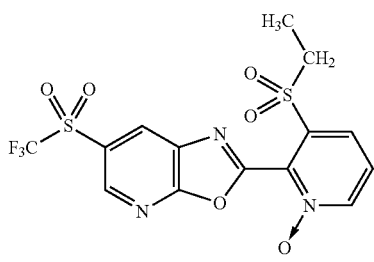 [SMILES: CCS(=O)(=O)c1ccc[n+]([O-])c1-c1nc2cc(S(=O)(=O)C(F)(F)F)cnc2o1]

Compounds as described in the above Production example, and compounds which are prepared in a similar manner as described for the preparation of the above Production examples are listed in the following tables.

Examples of the combinations of $R^1$, $R^2$, $R^3$, $R^4$, $R^5$, $R^6$, $A^1$, $A^2$, and n in the compound represented by the formula (1):

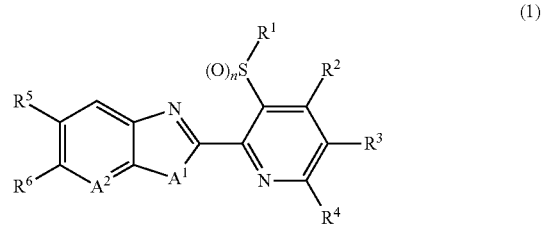

(1)

are shown below in [Table 1] to [Table 20].

TABLE 1

| No. | $R^1$ | $R^2$ | $R^3$ | $R^4$ | $R^5$ | $R^6$ | $A^1$ | $A^2$ | n |
|---|---|---|---|---|---|---|---|---|---|
| 1 | Et | H | H | H | CF$_3$ | H | NMe | N | 0 |
| 2 | Et | H | H | H | CF$_3$ | H | NMe | N | 1 |
| 3 | Et | H | H | H | CF$_3$ | H | NMe | N | 2 |
| 4 | Et | H | CF$_3$ | H | CF$_3$ | H | NMe | N | 0 |
| 5 | Et | H | CF$_3$ | H | CF$_3$ | H | NMe | N | 2 |
| 6 | Et | H | H | H | CF$_2$CF$_3$ | H | NMe | N | 0 |
| 7 | Et | H | H | H | CF$_2$CF$_3$ | H | NMe | N | 1 |
| 8 | Et | H | H | H | CF$_2$CF$_3$ | H | NMe | N | 2 |
| 9 | Et | H | H | H | I | H | NMe | N | 0 |
| 10 | Et | H | CF$_3$ | H | CF$_3$ | H | S | N | 0 |
| 11 | Et | H | CF$_3$ | H | CF$_3$ | H | S | N | 2 |
| 12 | Et | H | H | H | CF$_3$ | H | S | N | 2 |
| 13 | Et | H | H | H | SCF$_3$ | H | NMe | N | 0 |
| 14 | Et | H | H | H | SCF$_3$ | H | NMe | N | 1 |
| 15 | Et | H | H | H | SCF$_3$ | H | NMe | N | 2 |
| 16 | Et | H | H | H | SO$_2$CF$_3$ | H | NMe | N | 2 |
| 17 | Et | H | CF$_3$ | H | CF$_2$CF$_3$ | H | NMe | N | 0 |
| 18 | Et | H | CF$_3$ | H | CF$_2$CF$_3$ | H | NMe | N | 1 |
| 19 | Et | H | CF$_3$ | H | CF$_2$CF$_3$ | H | NMe | N | 2 |
| 20 | Et | H | H | H | SOCF$_3$ | H | NMe | N | 2 |
| 21 | Et | H | H | H | I | H | NMe | CH | 0 |
| 22* | Et | H | H | H | CF$_3$ | H | S | N | 2 |
| 23 | Et | H | H | H | SF$_5$ | H | NMe | CH | 0 |
| 24 | Et | H | H | H | SF$_5$ | H | NMe | CH | 2 |
| 25 | Et | H | CF$_3$ | H | SO$_2$CF$_3$ | H | NMe | N | 2 |

TABLE 2

| No. | $R^1$ | $R^2$ | $R^3$ | $R^4$ | $R^5$ | $R^6$ | $A^1$ | $A^2$ | n |
|---|---|---|---|---|---|---|---|---|---|
| 26 | Et | H | H | H | CF$_2$CF$_3$ | H | NMe | CH | 0 |
| 27 | Et | H | H | H | CF$_2$CF$_3$ | H | NMe | CH | 2 |
| 28 | Et | H | CF$_3$ | H | SCF$_3$ | H | NMe | N | 0 |
| 29 | Et | H | CF$_3$ | H | SCF$_3$ | H | NMe | N | 1 |
| 30 | Et | H | H | H | CF$_3$ | H | NMe | CH | 0 |
| 31 | Et | H | H | H | CF$_3$ | H | NMe | CH | 1 |
| 32 | Et | H | H | H | CF$_3$ | H | NMe | CH | 2 |
| 33 | Et | H | CF$_3$ | H | CF$_3$ | H | NMe | CH | 0 |
| 34 | Et | H | CF$_3$ | H | CF$_3$ | H | NMe | CH | 1 |
| 35 | Et | H | CF$_3$ | H | CF$_3$ | H | NMe | CH | 2 |
| 36* | Et | H | H | H | CF$_3$ | H | NMe | N | 2 |
| 37* | Et | H | H | H | CF$_3$ | H | NMe | N | 2 |
| 38 | Et | H | CF$_3$ | H | CF$_2$CF$_3$ | H | NMe | CH | 0 |
| 39 | Et | H | CF$_3$ | H | CF$_2$CF$_3$ | H | NMe | CH | 1 |
| 40 | Et | H | CF$_3$ | H | CF$_2$CF$_3$ | H | NMe | CH | 2 |
| 41 | Et | H | H | H | CF3 | H | S | N | 0 |
| 42 | Et | H | CF$_3$ | H | I | H | NMe | N | 0 |
| 43 | Et | H | CF$_3$ | H | SH | H | NMe | N | 0 |
| 44 | Et | H | CF$_3$ | H | SCF$_3$ | H | NMe | N | 2 |
| 45 | Et | H | CF$_3$ | H | I | H | NMe | CH | 0 |
| 46 | Et | H | H | H | CF$_3$ | H | NMe | CBr | 2 |
| 47* | Et | H | H | H | CF$_2$CF$_3$ | H | NMe | CH | 2 |

TABLE 2-continued

| No. | R¹ | R² | R³ | R⁴ | R⁵ | R⁶ | A¹ | A² | n |
|---|---|---|---|---|---|---|---|---|---|
| 48* | Et | H | CF₃ | H | CF₃ | H | NMe | N | 2 |
| 49 | Et | H | H | H | OCF₃ | H | NMe | CH | 0 |
| 50 | Et | H | H | H | OCF₃ | H | NMe | CH | 2 |

TABLE 3

| No. | R¹ | R² | R³ | R⁴ | R⁵ | R⁶ | A¹ | A² | n |
|---|---|---|---|---|---|---|---|---|---|
| 51* | Et | H | CF₃ | H | CF₃ | H | NMe | N | 2 |
| 52 | Et | H | H | H | CF₃ | H | S | CH | 0 |
| 53 | Et | H | H | H | CF₃ | H | S | CH | 2 |
| 54 | Et | H | CF₃ | H | CF₃ | H | S | CH | 0 |
| 55 | Et | H | CF₃ | H | CF₃ | H | S | CH | 2 |
| 56 | Et | H | H | H | CF₃ | OMe | NMe | CH | 2 |
| 57 | Et | H | H | H | C(OH)₂CF₃ | H | NMe | N | 0 |
| 58 | Et | H | H | H | C(OH)₂CF₃ | H | NMe | N | 2 |
| 59 | Et | H | CF₃ | H | CO₂Me | H | NMe | N | 0 |
| 60 | Et | H | CF₃ | H | SOCF₃ | H | NMe | N | 2 |
| 61 | Et | H | H | H | SCF₃ | H | NMe | CH | 0 |
| 62 | Et | H | H | H | SCF₃ | H | NMe | CH | 1 |
| 63 | Et | H | H | H | SCF₃ | H | NMe | CH | 2 |
| 64 | Et | H | H | H | SO₂CF₃ | H | NMe | CH | 2 |
| 65 | Et | H | H | H | CF₃ | H | NCH₂CF₃ | N | 0 |
| 66 | Et | H | CF₃ | H | CF₃ | H | NCH₂CF₃ | N | 0 |
| 67 | Et | H | H | H | CF₃ | H | NCH₂CF₃ | N | 2 |
| 68 | Et | H | CF₃ | H | CF₃ | H | NCH₂CF₃ | N | 2 |
| 69 | Et | H | CF₃ | H | CO₂Me | H | NMe | N | 2 |
| 70* | Et | H | CF₃ | H | CO₂Me | H | NMe | N | 2 |
| 71 | Et | H | CF₂CF₃ | H | CF₃ | H | NMe | N | 0 |
| 72 | Et | H | CF₂CF₃ | H | CF₃ | H | NMe | N | 2 |
| 73 | Et | H | CF₂CF₃ | H | CF₂CF₃ | H | NMe | N | 0 |
| 74 | Et | H | CF₂CF₃ | H | CF₂CF₃ | H | NMe | N | 2 |
| 75 | Et | H | H | H | CF₃ | H | NMe | CBr | 0 |

TABLE 4

| No. | R¹ | R² | R³ | R⁴ | R⁵ | R⁶ | A¹ | A² | n |
|---|---|---|---|---|---|---|---|---|---|
| 76 | Et | H | H | H | CF₃ | H | NH | N | 0 |
| 77 | Et | H | H | H | CF₃ | H | NH | N | 2 |
| 78 | Et | H | CF₃ | H | CF₃ | H | NH | N | 0 |
| 79 | Et | H | CF₃ | H | CF₃ | H | NH | N | 2 |
| 80 | Et | H | H | H | CF₃ | H | O | N | 0 |
| 81 | Et | H | H | H | CF₃ | H | O | N | 2 |
| 82 | Et | H | CF₃ | H | CF₃ | H | O | N | 0 |
| 83 | Et | H | CF₃ | H | CF₃ | H | O | N | 2 |
| 84 | Et | H | H | H | CF₃ | H | O | CH | 0 |
| 85 | Et | H | H | H | CF₃ | H | O | CH | 2 |
| 86 | Et | H | CF₃ | H | CF₃ | H | O | CH | 0 |
| 87 | Et | H | CF₃ | H | CF₃ | H | O | CH | 2 |
| 88 | Et | H | H | H | CF₃ | Cl | NMe | N | 2 |
| 89 | Et | H | CF₃ | H | CF₃ | Cl | NMe | N | 2 |
| 90 | Et | H | H | H | CF₃ | OC(O)Me | NMe | N | 2 |
| 91 | Et | H | CF₃ | H | CF₃ | OC(O)Me | NMe | N | 2 |
| 92 | Et | H | H | H | CF₃ | OH | NMe | N | 2 |
| 93 | Et | H | CF₃ | H | CF₃ | OH | NMe | N | 2 |
| 94 | Et | H | H | H | CF₃ | OMe | NMe | N | 2 |
| 95 | Et | H | CF₃ | H | CF₃ | OMe | NMe | N | 2 |
| 96 | Et | H | H | H | CF₃ | SMe | NMe | N | 2 |
| 97 | Et | H | CF₃ | H | CF₃ | SMe | NMe | N | 2 |
| 98 | Et | H | H | H | CF₃ | NMe₂ | NMe | N | 2 |
| 99 | Et | H | CF₃ | H | CF₃ | NMe₂ | NMe | N | 2 |
| 100 | CH₂CycPr | H | H | H | CF₃ | H | NMe | N | 2 |

TABLE 5

| No. | R¹ | R² | R³ | R⁴ | R⁵ | R⁶ | A¹ | A² | n |
|---|---|---|---|---|---|---|---|---|---|
| 101 | CH₂CycPr | H | CF₃ | H | CF₃ | H | NMe | N | 2 |
| 102 | CF₃ | H | H | H | CF₃ | H | NMe | N | 2 |
| 103 | CF₃ | H | CF₃ | H | CF₃ | H | NMe | N | 2 |
| 104 | CH₂CF₃ | H | H | H | CF₃ | H | NMe | N | 2 |
| 105 | CH₂CF₃ | H | CF₃ | H | CF₃ | H | NMe | N | 2 |
| 106 | Et | Cl | H | H | CF₃ | H | NMe | N | 2 |
| 107 | Et | H | Cl | H | CF₃ | H | NMe | N | 2 |
| 108 | Et | H | H | Cl | CF₃ | H | NMe | N | 2 |
| 109 | Et | H | OCF₃ | H | CF₃ | H | NMe | N | 2 |
| 110 | Et | H | SCF₃ | H | CF₃ | H | NMe | N | 2 |
| 111 | Et | H | SOCF₃ | H | CF₃ | H | NMe | N | 2 |
| 112 | Et | H | SO₂CF₃ | H | CF₃ | H | NMe | N | 2 |
| 113 | Et | H | CF(CF₃)₂CF₃ | H | CF₃ | H | NMe | N | 2 |
| 114 | Et | H | CF₂CF₂CF₃ | H | CF₃ | H | NMe | N | 2 |

TABLE 5-continued

| No. | R¹ | R² | R³ | R⁴ | R⁵ | R⁶ | A¹ | A² | n |
|---|---|---|---|---|---|---|---|---|---|
| 115 | Et | H | Br | H | $CF_3$ | H | NMe | N | 2 |
| 116 | Et | H | I | H | $CF_3$ | H | NMe | N | 2 |
| 117 | Et | H | Me | H | $CF_3$ | H | NMe | N | 2 |
| 118 | Et | H | OMe | H | $CF_3$ | H | NMe | N | 2 |
| 119 | Et | H | H | H | $CF(CF_3)_2$ | H | NMe | N | 2 |
| 120 | Et | H | $CF_3$ | H | $CF(CF_3)_2$ | H | NMe | N | 2 |
| 121 | Et | H | $CF_3$ | H | $SF_5$ | H | NMe | N | 2 |
| 122 | Et | H | H | H | $CF_2CF_2CF_3$ | H | NMe | N | 2 |
| 123 | Et | H | $CF_3$ | H | $CF_2CF_2CF_3$ | H | NMe | N | 2 |
| 124 | Et | H | H | H | $SCF_2CF_3$ | H | NMe | N | 2 |
| 125 | Et | H | $CF_3$ | H | $SCF_2CF_3$ | H | NMe | N | 2 |

TABLE 6

| No. | R¹ | R² | R³ | R⁴ | R⁵ | R⁶ | A¹ | A² | n |
|---|---|---|---|---|---|---|---|---|---|
| 126 | Et | H | H | H | $SO_2CF_2CF_3$ | H | NMe | N | 2 |
| 127 | Et | H | $CF_3$ | H | $SO_2CF_2CF_3$ | H | NMe | N | 2 |
| 128 | Et | H | H | H | $CF_3$ | H | $NCH_2OMe$ | N | 2 |
| 129 | Et | H | $CF_3$ | H | $CF_3$ | H | $NCH_2OMe$ | N | 2 |
| 130 | Et | H | H | H | $CF_3$ | H | NMe | CCN | 2 |
| 131 | Et | H | $CF_3$ | H | $CF_3$ | H | NMe | CCN | 2 |
| 132 | Et | H | H | H | $CF_3$ | H | NMe | CF | 2 |
| 133 | Et | H | $CF_3$ | H | $CF_3$ | H | NMe | CF | 2 |
| 134 | Et | H | H | H | $CF_3$ | H | NMe | CMe | 2 |
| 135 | Et | H | $CF_3$ | H | $CF_3$ | H | NMe | CMe | 2 |
| 136 | Et | H | H | H | $CF_3$ | H | NMe | COMe | 2 |
| 137 | Et | H | $CF_3$ | H | $CF_3$ | H | NMe | COMe | 2 |
| 138 | Et | H | H | H | $CF_3$ | H | NMe | $CSCH_2CH_3$ | 2 |
| 139 | Et | H | $CF_3$ | H | $CF_3$ | H | NMe | $CSCH_2CH_3$ | 2 |
| 140 | Et | H | H | H | $CF_3$ | H | NMe | $CSO_2CH_2CH_3$ | 2 |
| 141 | Et | H | $CF_3$ | H | $CF_3$ | H | NMe | $CSO_2CH_2CH_3$ | 2 |
| 142 | Me | H | H | H | $CF_3$ | H | NMe | N | 0 |
| 143 | Me | H | H | H | $CF_3$ | H | NMe | N | 1 |
| 144 | Me | H | H | H | $CF_3$ | H | NMe | N | 2 |
| 145 | Pr | H | H | H | $CF_3$ | H | NMe | N | 0 |
| 146 | Pr | H | H | H | $CF_3$ | H | NMe | N | 1 |
| 147 | Pr | H | H | H | $CF_3$ | H | NMe | N | 2 |
| 148 | iPr | H | H | H | $CF_3$ | H | NMe | N | 0 |
| 149 | iPr | H | H | H | $CF_3$ | H | NMe | N | 1 |
| 150 | iPr | H | H | H | $CF_3$ | H | NMe | N | 2 |

TABLE 7

| No. | R¹ | R² | R³ | R⁴ | R⁵ | R⁶ | A¹ | A² | n |
|---|---|---|---|---|---|---|---|---|---|
| 151 | tBu | H | H | H | $CF_3$ | H | NMe | N | 0 |
| 152 | tBu | H | H | H | $CF_3$ | H | NMe | N | 1 |
| 153 | tBu | H | H | H | $CF_3$ | H | NMe | N | 2 |
| 154 | $CF_3$ | H | H | H | $CF_3$ | H | NMe | N | 0 |
| 155 | $CF_3$ | H | H | H | $CF_3$ | H | NMe | N | 1 |
| 156 | Et | H | H | H | $CF_3$ | H | NEt | N | 0 |
| 157 | Et | H | H | H | $CF_3$ | H | NEt | N | 1 |
| 158 | Et | H | H | H | $CF_3$ | H | NEt | N | 2 |
| 159 | Et | H | H | H | $CF_3$ | H | NPr | N | 0 |
| 160 | Et | H | H | H | $CF_3$ | H | NPr | N | 1 |
| 161 | Et | H | H | H | $CF_3$ | H | NPr | N | 2 |
| 162 | Et | H | H | H | $CF_3$ | H | NiPr | N | 0 |
| 163 | Et | H | H | H | $CF_3$ | H | NiPr | N | 1 |
| 164 | Et | H | H | H | $CF_3$ | H | NiPr | N | 2 |
| 165 | Et | H | H | H | $CF_3$ | H | NCycPr | N | 0 |
| 166 | Et | H | H | H | $CF_3$ | H | NCycPr | N | 1 |
| 167 | Et | H | H | H | $CF_3$ | H | NCycPr | N | 2 |
| 168 | Et | H | H | H | $CF_3$ | H | $NCH_2OEt$ | N | 0 |
| 169 | Et | H | H | H | $CF_3$ | H | $NCH_2OEt$ | N | 1 |
| 170 | Et | H | H | H | $CF_3$ | H | $NCH_2OEt$ | N | 2 |
| 171 | Et | H | H | H | $CF_3$ | H | $NCH_2OMe$ | N | 0 |
| 172 | Et | H | H | H | Me | H | NMe | N | 0 |
| 173 | Et | H | H | H | Me | H | NMe | N | 1 |
| 174 | Et | H | H | H | Me | H | NMe | N | 2 |
| 175 | Et | H | H | H | Br | H | NMe | N | 0 |

TABLE 8

| No. | R¹ | R² | R³ | R⁴ | R⁵ | R⁶ | A¹ | A² | n |
|---|---|---|---|---|---|---|---|---|---|
| 176 | Et | H | H | H | Br | H | NMe | N | 1 |
| 177 | Et | H | H | H | Br | H | NMe | N | 2 |
| 178 | Et | H | H | H | I | H | NMe | N | 1 |
| 179 | Et | H | H | H | I | H | NMe | N | 2 |
| 180 | Et | H | H | H | CN | H | NMe | N | 0 |
| 181 | Et | H | H | H | CN | H | NMe | N | 1 |
| 182 | Et | H | H | H | CN | H | NMe | N | 2 |
| 183 | Et | H | H | H | CHO | H | NMe | N | 0 |
| 184 | Et | H | H | H | $CF_2H$ | H | NMe | N | 0 |
| 185 | Et | H | H | H | $CF_2H$ | H | NMe | N | 1 |
| 186 | Et | H | H | H | $CF_2H$ | H | NMe | N | 2 |
| 187 | Me | H | H | H | $CF_3$ | H | NMe | CH | 0 |
| 188 | Et | H | H | H | $CF_3$ | H | NMe | CCl | 0 |
| 189 | Et | H | H | H | $CF_3$ | H | NMe | CCl | 1 |
| 190 | Et | H | H | H | $CF_3$ | H | NMe | CCl | 2 |
| 191 | Et | H | H | H | $CF_3$ | H | NMe | CBr | 1 |
| 192 | Me | H | H | H | $CF_3$ | H | O | CH | 0 |
| 193 | Et | H | H | H | $CF_3$ | H | O | CH | 1 |
| 194 | Et | H | H | H | $CF_3$ | H | O | N | 1 |
| 195 | Me | H | H | H | $CF_3$ | H | S | CH | 0 |
| 196 | Et | H | H | H | $CF_3$ | H | S | CH | 1 |
| 197 | Et | Cl | H | H | $CF_3$ | H | NMe | N | 0 |
| 198 | Et | Cl | H | H | $CF_3$ | H | NMe | N | 1 |
| 199 | Et | H | H | H | $COCF_3$ | H | NMe | N | 0 |
| 200 | Et | H | H | H | Cl | H | NMe | N | 0 |

TABLE 9

| No. | R¹ | R² | R³ | R⁴ | R⁵ | R⁶ | A¹ | A² | n |
|---|---|---|---|---|---|---|---|---|---|
| 201 | Et | H | H | H | Cl | H | NMe | N | 1 |
| 202 | Et | H | H | H | Cl | H | NMe | N | 2 |
| 203 | Et | H | H | H | Br | H | NMe | N | 0 |
| 204 | Et | H | H | SEt | CF₃ | H | NMe | N | 0 |
| 205 | Et | H | H | H | CF₃ | H | NCH₂OEt | CH | 0 |
| 206 | Et | H | H | H | CF₃ | H | NCH₂CO₂Me | N | 0 |
| 207 | Et | H | H | H | CF₃ | H | NCH₂CO₂Et | N | 0 |
| 208 | Et | H | H | H | CF₃ | H | N(CH₂)₂OMe | N | 0 |
| 209 | Et | H | H | H | CF₃ | H | NBu | N | 0 |
| 210 | Et | H | H | H | CF₃ | H | NCO₂tBu | N | 0 |
| 211 | Et | H | H | H | CH(OH)CF₃ | H | NMe | N | 0 |
| 212 | Et | H | H | H | CHFCF₃ | H | NMe | N | 0 |
| 213 | Et | H | F | H | CF₃ | H | NMe | N | 0 |
| 214 | Et | H | F | H | CF₃ | H | NMe | N | 1 |
| 215 | Et | H | F | H | CF₃ | H | NMe | N | 2 |
| 216 | Et | OMe | H | H | CF₃ | H | NMe | N | 0 |
| 217 | Et | OMe | H | H | CF₃ | H | NMe | N | 1 |
| 218 | Et | H | OMe | H | CF₃ | H | NMe | N | 0 |
| 219 | Et | H | OMe | H | CF₃ | H | NMe | N | 1 |
| 220 | Et | H | OH | H | CF₃ | H | NMe | N | 0 |
| 221 | Et | H | H | H | NH₂ | H | NMe | N | 0 |
| 222 | Et | H | H | H | CHFCF₃ | H | NMe | N | 1 |
| 223 | Et | H | H | H | CHFCF₃ | H | NMe | N | 2 |
| 224 | Et | H | H | H | CF₂CF₂CF₃ | H | NMe | N | 0 |
| 225 | Et | H | H | H | CF₂CF₂CF₃ | H | NMe | N | 1 |

TABLE 10

| No. | R¹ | R² | R³ | R⁴ | R⁵ | R⁶ | A¹ | A² | n |
|---|---|---|---|---|---|---|---|---|---|
| 226 | Et | Cl | H | H | CF₂CF₃ | H | NMe | N | 1 |
| 227 | Et | Cl | H | H | CF₂CF₃ | H | NMe | N | 2 |
| 228 | Et | H | Cl | H | CF₃ | H | NMe | N | 0 |
| 229 | Et | H | Cl | H | CF₃ | H | NMe | N | 1 |
| 230 | Et | H | Cl | H | CF₂CF₃ | H | NMe | N | 1 |
| 231 | Et | H | H | Cl | CF₃ | H | NMe | N | 0 |
| 232 | Et | H | H | Cl | CF₃ | H | NMe | N | 1 |
| 233 | Et | H | H | OMe | CF₃ | H | NMe | N | 0 |
| 234 | Et | H | H | OMe | CF₃ | H | NMe | N | 1 |
| 235 | Et | H | H | OMe | CF₃ | H | NMe | N | 2 |
| 236 | Et | H | H | H | SH | H | NMe | N | 0 |
| 237 | Et | H | H | H | Et | H | NMe | N | 0 |
| 238 | Et | H | H | H | iPr | H | NMe | N | 0 |
| 239 | Et | H | H | H | NHEt | H | NMe | N | 0 |
| 240 | Et | H | H | H | NEt₂ | H | NMe | N | 0 |
| 241 | Et | H | H | H | tBu | H | NMe | N | 0 |
| 242 | Et | H | H | H | H | CF₃ | NMe | N | 0 |
| 243 | Et | F | H | H | CF₃ | H | NMe | N | 0 |
| 244 | Et | F | H | H | CF₃ | H | NMe | N | 1 |
| 245 | Et | F | H | H | CF₃ | H | NMe | N | 2 |
| 246 | Et | H | H | H | H | CF₃ | NMe | N | 1 |
| 247 | Et | H | H | H | H | CF₃ | NMe | N | 2 |
| 248 | Et | H | H | H | NMe₂ | H | NMe | N | 0 |
| 249 | Et | H | H | H | NHCOMe | H | NMe | N | 0 |
| 250 | Et | H | H | H | CH₂CF₃ | H | NMe | N | 0 |

TABLE 11

| No. | R¹ | R² | R³ | R⁴ | R⁵ | R⁶ | A¹ | A² | n |
|---|---|---|---|---|---|---|---|---|---|
| 251 | Et | H | H | H | NMeCOMe | H | NMe | N | 0 |
| 252 | Et | H | H | H | NH2 | H | NMe | N | 1 |
| 253 | Et | H | CF₃ | H | CF₃ | H | NMe | N | 1 |
| 254 | Et | H | H | H | NHCOCF₃ | H | NMe | N | 0 |
| 255 | Et | H | H | H | NHCOCF₃ | H | NMe | N | 1 |
| 256 | Et | H | H | H | NHCOCF₃ | H | NMe | N | 2 |
| 257 | Et | H | H | H | CF₃ | H | S | N | 1 |
| 258 | CH₂CF₃ | H | H | H | CF₃ | H | NMe | N | 0 |
| 259 | CH₂CF₃ | H | H | H | CF₃ | H | NMe | N | 1 |
| 260 | Et | Me | H | H | CF₃ | H | NMe | N | 0 |
| 261 | Et | Me | H | H | CF₃ | H | NMe | N | 1 |
| 262 | Et | Me | H | H | CF₃ | H | NMe | N | 2 |
| 263 | Et | H | Me | H | CF₃ | H | NMe | N | 0 |
| 264 | Et | H | Me | H | CF₃ | H | NMe | N | 1 |
| 265 | Et | H | H | CF₃ | CF₃ | H | NMe | N | 0 |
| 266 | Et | H | H | CF₃ | CF₃ | H | NMe | N | 1 |
| 267 | Et | H | H | CF₃ | CF₃ | H | NMe | N | 2 |
| 268 | Et | H | Br | H | CF₃ | H | NMe | N | 0 |
| 269 | Et | H | Br | H | CF₃ | H | NMe | N | 1 |
| 270 | Et | H | CN | H | CF₃ | H | NMe | N | 0 |
| 271 | Et | H | CN | H | CF₃ | H | NMe | N | 1 |
| 272 | Et | H | CN | H | CF₃ | H | NMe | N | 2 |
| 273 | Et | H | CF₂CF₃ | H | CF₃ | H | NMe | N | 1 |
| 274 | Et | H | CHO | H | CF₃ | H | NMe | N | 0 |
| 275 | Et | H | H | H | SMe | H | NMe | N | 0 |

TABLE 12

| No. | R¹ | R² | R³ | R⁴ | R⁵ | R⁶ | A¹ | A² | n |
|---|---|---|---|---|---|---|---|---|---|
| 276 | Et | H | H | H | SO₂Me | H | NMe | N | 2 |
| 277 | Et | H | H | H | SEt | H | NMe | N | 0 |
| 278 | Et | H | H | H | SO₂Et | H | NMe | N | 2 |
| 279 | Et | H | H | H | SO₂iPr | H | NMe | N | 2 |
| 280 | Et | H | H | H | SCH₂CF₃ | H | NMe | N | 0 |
| 281 | Et | H | H | H | SO₂CH₂CF₃ | H | NMe | N | 2 |
| 282 | Et | H | H | H | SCF₂CF₃ | H | NMe | N | 0 |
| 283 | Et | H | H | H | SCF₂CF₂CF₃ | H | NMe | N | 0 |
| 284 | Et | H | H | H | SCF(CF₃)₂ | H | NMe | N | 0 |
| 285 | Et | H | H | H | CH(OH)CF₃ | H | NMe | N | 0 |
| 286 | Et | H | H | H | CH(Cl)CF₃ | H | NMe | N | 0 |
| 287 | Et | H | H | H | OH | H | NMe | N | 0 |
| 288 | Et | H | H | H | OH | H | NMe | N | 2 |
| 289 | Et | H | H | H | OCF₂Br | H | NMe | N | 2 |
| 290 | Et | H | H | H | OCF₃ | H | NMe | N | 2 |
| 291 | Et | H | H | H | SCF₂CF₃ | H | NMe | N | 1 |
| 292 | Et | H | H | H | SCF₂CF₃ | H | NMe | N | 1 |
| 293 | Et | H | H | H | SCF₂CF₂CF₃ | H | NMe | N | 2 |
| 294 | Et | H | H | H | StBu | H | NMe | N | 0 |
| 295 | Et | H | H | H | SO₂tBu | H | NMe | N | 2 |
| 296 | Et | H | CF₃ | H | Br | H | NMe | N | 0 |
| 297 | Et | H | CF₃ | H | Br | H | NMe | N | 1 |
| 298 | Et | H | CF₃ | H | Br | H | NMe | N | 2 |
| 299 | Et | H | I | H | CF₂CF₃ | H | NMe | N | 2 |
| 300 | Et | H | NO₂ | H | CF₃ | H | NMe | N | 0 |

TABLE 13

| No. | R¹ | R² | R³ | R⁴ | R⁵ | R⁶ | A¹ | A² | n |
|---|---|---|---|---|---|---|---|---|---|
| 301 | Et | H | NO₂ | H | CF₃ | H | NMe | N | 1 |
| 302 | Et | H | NO₂ | H | CF₃ | H | NMe | N | 2 |
| 303 | Et | H | I | H | SCF₃ | H | NMe | N | 2 |
| 304 | Et | H | I | H | SO₂CF₃ | H | NMe | N | 2 |
| 305 | Et | H | Br | H | CF₂CF₃ | H | NMe | N | 2 |
| 306 | Et | H | Cl | H | CF₃ | H | S | N | 0 |
| 307 | Et | H | Cl | H | CF₃ | H | S | N | 2 |
| 308 | Et | H | H | H | C(OH)(CF₃)₂ | H | NMe | N | 0 |
| 309 | Et | H | H | H | C(Cl)(CF₃)₂ | H | NMe | N | 0 |
| 310 | Et | H | H | H | C(Cl)(CF₃)₂ | H | NMe | N | 1 |
| 311 | Et | H | H | H | C(Cl)(CF₃)₂ | H | NMe | N | 2 |
| 312 | Et | H | Cl | H | CF₂CF₃ | H | NMe | N | 2 |
| 313 | Et | H | H | H | H | CF(CF₃)₂ | NMe | CH | 0 |
| 314 | Et | H | H | H | CF(CF₃)₂ | H | NMe | CH | 0 |
| 315 | Et | H | CF₃ | H | I | H | NMe | N | 2 |
| 316 | Et | H | H | H | CF₂CF₃ | H | NMe | CH | 1 |
| 317 | Et | H | H | H | SF₅ | H | NMe | CH | 1 |
| 318 | Et | H | CF₃ | H | SF₅ | H | NMe | CH | 0 |
| 319 | Et | H | CF₃ | H | SF₅ | H | NMe | CH | 1 |
| 320 | Et | H | Me | H | CF₂CF₃ | H | NMe | N | 0 |
| 321 | Et | H | Me | H | CF₂CF₃ | H | NMe | N | 1 |
| 322 | Et | H | Me | H | CF₂CF₃ | H | NMe | N | 2 |
| 323 | Et | H | H | H | I | H | S | N | 0 |
| 324 | Et | H | CF₃ | H | I | H | S | N | 0 |
| 325 | Et | H | H | H | CF₂CF₃ | H | S | N | 0 |

TABLE 14

| No. | R¹ | R² | R³ | R⁴ | R⁵ | R⁶ | A¹ | A² | n |
|---|---|---|---|---|---|---|---|---|---|
| 326 | Et | H | CF₃ | H | CF₂CF₃ | H | S | N | 0 |
| 327 | Et | H | H | H | CF₂CF₃ | H | S | N | 2 |
| 328 | Et | H | CF₃ | H | CF₂CF₃ | H | S | N | 2 |
| 329 | Et | H | Et | H | CF₃ | H | NMe | N | 2 |
| 330 | Et | H | H | H | SO₂NMe₂ | H | NMe | N | 1 |
| 331 | Et | H | H | H | SO₂NMe₂ | H | NMe | N | 2 |
| 332 | Et | H | H | H | CF₃ | H | NMe | CNH₂ | 0 |
| 333 | Et | H | Br | H | SCF₃ | H | NMe | N | 2 |
| 334 | Et | H | H | H | CF₃ | H | NMe | CNMe₂ | 0 |
| 335 | Et | H | CF₃ | H | CF₃ | H | NMe | CNH₂ | 0 |
| 336 | Et | H | CF₃ | H | CF₃ | H | NMe | CNMe₂ | 0 |
| 337 | Et | H | SF₅ | H | CF₃ | H | NMe | N | 0 |
| 338 | Et | H | SF₅ | H | CF₃ | H | NMe | N | 1 |
| 339 | Et | H | SF₅ | H | CF₃ | H | NMe | N | 2 |
| 340 | Et | H | H | H | CF(CF₃)₂ | H | NH | CH | 0 |
| 341 | Et | H | H | H | Br | H | NMe | N | 0 |
| 342 | Et | H | H | H | Br | H | NMe | N | 1 |
| 343 | Et | H | H | H | Br | H | NMe | N | 2 |
| 344 | Et | H | H | H | Br | H | NMe | N | 2 |
| 345 | Et | H | H | H | CF₃ | H | NH | N | 1 |
| 346 | Et | H | H | H | CF₃ | H | NH | CH | 0 |
| 347 | Et | H | CF₃ | H | CF₃ | H | NEt | N | 2 |
| 348 | Et | H | CF₃ | H | CF₃ | H | NCH₂CN | N | 2 |
| 349 | Et | H | CF₃ | H | CF₃ | H | NCH₂OEt | N | 2 |
| 350 | Et | H | CF₃ | H | CF₃ | H | NPr | N | 2 |

TABLE 15

| No. | R¹ | R² | R³ | R⁴ | R⁵ | R⁶ | A¹ | A² | n |
|---|---|---|---|---|---|---|---|---|---|
| 351 | Et | H | CF₃ | H | CF₃ | H | N(CH₂)₃CH₃ | N | 2 |
| 352 | Et | H | CF₃ | H | CF₃ | H | NCH₂CO₂Me | N | 2 |
| 353 | Et | H | CF₃ | H | CF₃ | H | NCO₂tBu | N | 2 |
| 354 | Et | H | CF₃ | H | CF₃ | H | NCO₂Me | N | 2 |
| 355 | Et | H | CF₃ | H | CF₃ | H | NCOMe | N | 2 |
| 356 | Et | H | OCF₃ | H | CF₃ | H | NMe | N | 0 |
| 357 | Et | H | OCF₃ | H | CF₃ | H | NMe | N | 1 |
| 358 | Et | H | CF₂CF₂CF₂CF₃ | H | CF₃ | H | NMe | N | 2 |
| 359 | Et | H | NH₂ | H | CF₃ | H | NMe | N | 2 |
| 360 | Et | H | NHCOCF₃ | H | CF₃ | H | NMe | N | 2 |
| 361 | Et | H | iPr | H | CF₃ | H | NMe | N | 2 |
| 362 | Et | H | CHO | H | CF₃ | H | NMe | N | 2 |
| 363 | Bu | H | H | H | CF₃ | H | NMe | N | 0 |
| 364 | CH₂CN | H | H | H | CF₃ | H | NMe | N | 0 |
| 365 | CH₂tBu | H | H | H | CF₃ | H | NMe | N | 0 |
| 366 | CH₂CH₂CN | H | H | H | CF₃ | H | NMe | N | 0 |
| 367 | CH₂CycBu | H | H | H | CF₃ | H | NMe | N | 0 |
| 368 | CF₂Br | H | H | H | CF₃ | H | NMe | N | 0 |
| 369 | Et | H | CF₂H | H | CF₃ | H | NMe | N | 2 |
| 370 | Et | H | CH₂OH | H | CF₃ | H | NMe | N | 2 |
| 371 | Bu | H | H | H | CF₃ | H | NMe | N | 2 |
| 372 | CH₂CN | H | H | H | CF₃ | H | NMe | N | 2 |
| 373 | CH₂tBu | H | H | H | CF₃ | H | NMe | N | 2 |
| 374 | CH₂CH₂CN | H | H | H | CF₃ | H | NMe | N | 2 |
| 375 | CH₂CycBu | H | H | H | CF₃ | H | NMe | N | 2 |

TABLE 16

| No. | R¹ | R² | R³ | R⁴ | R⁵ | R⁶ | A¹ | A² | n |
|---|---|---|---|---|---|---|---|---|---|
| 376 | CF₂Br | H | H | H | CF₃ | H | NMe | N | 2 |
| 377 | Et | H | CH₂F | H | CF₃ | H | NMe | N | 2 |
| 378 | Et | H | H | H | H | CF₃ | S | N | 0 |
| 379 | Et | H | H | H | H | CF₃ | S | N | 2 |
| 380 | Et | H | OCF₃ | H | CF₂CF₃ | H | NMe | N | 0 |
| 381 | Et | H | OCF₃ | H | CF₂CF₃ | H | NMe | N | 1 |
| 382 | Et | H | OCF₃ | H | CF₂CF₃ | H | NMe | N | 2 |
| 383 | Et | H | CF₃ | H | CF₃ | H | NMe | CMe | 0 |
| 384 | Et | H | CF₃ | H | CF₃ | H | NMe | CMe | 1 |
| 385 | Et | H | CF₃ | H | CF₃ | H | NMe | CF | 0 |
| 386 | Et | H | CF₃ | H | CF₃ | H | NMe | CF | 1 |

TABLE 16-continued

| No. | R¹ | R² | R³ | R⁴ | R⁵ | R⁶ | A¹ | A² | n |
|---|---|---|---|---|---|---|---|---|---|
| 387 | CH₂CycPr | H | H | H | CF₃ | H | NMe | N | 0 |
| 388 | CH₂CycPr | H | H | H | CF₃ | H | NMe | N | 1 |
| 389 | Et | H | CF₃ | H | CF₃ | H | NMe | CBr | 0 |
| 390 | Et | H | CF₃ | H | CF₃ | H | NMe | CSCH₂CH₃ | 0 |
| 391 | Et | H | OCF₃ | H | SCF₃ | H | NMe | N | 0 |
| 392 | Et | H | OCF₃ | H | SCF₃ | H | NMe | N | 1 |
| 393 | Et | H | OCF₃ | H | SCF₃ | H | NMe | N | 2 |
| 394 | Et | H | CF₃ | H | CF₃ | H | NMe | CBr | 1 |
| 395 | Et | H | CF₃ | H | CF₃ | H | NMe | CBr | 2 |
| 396 | Et | H | H | H | COMe | H | NMe | N | 0 |
| 397 | Et | H | H | H | COMe | H | NMe | N | 2 |
| 398 | Et | H | H | H | CF₃ | CN | NMe | N | 2 |
| 399 | Et | H | CF₃ | H | CF₃ | CN | NMe | N | 2 |
| 400* | Et | H | H | H | CF₃ | H | NMe | N | 2 |

TABLE 17

| No. | R¹ | R² | R³ | R⁴ | R⁵ | R⁶ | A¹ | A² | n |
|---|---|---|---|---|---|---|---|---|---|
| 401* | Et | H | CF₃ | H | CF₃ | H | NMe | N | 2 |
| 402 | Et | H | H | H | CF₃ | H | NMe | COMe | 0 |
| 403 | Et | H | H | H | CF₃ | H | NMe | CSCH₃ | 0 |
| 404 | Et | H | H | H | CF₃ | H | NMe | CSO₂CH₃ | 2 |
| 405 | Et | H | H | H | CF₃ | H | NMe | CSO₂CH₂CF₃ | 2 |
| 406 | Et | H | H | H | CF₃ | H | NMe | CCN | 0 |
| 407 | Et | H | CF₃ | H | CF₃ | COOH | NMe | N | 2 |
| 408 | Et | H | CF₃ | H | CF₃ | CONH₂ | NMe | N | 2 |
| 409* | Et | H | CF₃ | H | CF₂CF₃ | H | NMe | N | 2 |
| 410* | Et | H | CF₃ | H | CF₂CF₃ | H | NMe | N | 2 |
| 411 | Et | H | CF₃ | H | COOH | H | NMe | N | 0 |
| 412 | Et | H | H | H | CF₃ | H | NMe | CCN | 1 |
| 413 | Et | H | H | H | CF₃ | H | NH | CCF₃ | 0 |
| 414 | Et | H | C(OCH₃)₃ | H | CF₂CF₃ | H | NMe | N | 2 |
| 415 | Et | H | H | H | H | CF₃ | NMe | CH | 0 |
| 416 | Et | H | H | H | H | CF₃ | NMe | CH | 2 |
| 417 | Et | H | H | H | CF₃ | H | NMe | CCF₃ | 2 |
| 418 | Me | H | CF₃ | H | CF₂CF₃ | H | NMe | N | 0 |
| 419 | Me | H | CF₃ | H | CF₂CF₃ | H | NMe | N | 2 |
| 420 | Pr | H | CF₃ | H | CF₂CF₃ | H | NMe | N | 0 |
| 421 | Pr | H | CF₃ | H | CF₂CF₃ | H | NMe | N | 2 |
| 422 | iPr | H | CF₃ | H | CF₂CF₃ | H | NMe | N | 0 |
| 423 | iPr | H | CF₃ | H | CF₂CF₃ | H | NMe | N | 2 |
| 424 | Bu | H | CF₃ | H | CF₂CF₃ | H | NMe | N | 0 |
| 425 | Bu | H | CF₃ | H | CF₂CF₃ | H | NMe | N | 2 |

TABLE 18

| No. | R¹ | R² | R³ | R⁴ | R⁵ | R⁶ | A¹ | A² | n |
|---|---|---|---|---|---|---|---|---|---|
| 426 | CH(CH₃)CH₂CH₃ | H | CF₃ | H | CF₂CF₃ | H | NMe | N | 0 |
| 427 | CH(CH₃)CH₂CH₃ | H | CF₃ | H | CF₂CF₃ | H | NMe | N | 2 |
| 428 | CH₂CH(CH₃)₂ | H | CF₃ | H | CF₂CF₃ | H | NMe | N | 0 |
| 429 | CH₂CH(CH₃)₂ | H | CF₃ | H | CF₂CF₃ | H | NMe | N | 2 |
| 430 | tBu | H | CF₃ | H | CF₂CF₃ | H | NMe | N | 0 |
| 431 | tBu | H | CF₃ | H | CF₂CF₃ | H | NMe | N | 2 |
| 432 | CH₂CF₃ | H | CF₃ | H | CF₂CF₃ | H | NMe | N | 0 |
| 433 | CH₂CF₃ | H | CF₃ | H | CF₂CF₃ | H | NMe | N | 2 |
| 434 | Et | H | CF₃ | H | CN | H | NMe | N | 0 |
| 435 | Et | H | H | H | CF₃ | H | NMe | CCF₃ | 0 |
| 436 | Et | H | H | H | SCF₃ | H | O | N | 0 |
| 437 | Et | H | H | H | SCF₃ | H | O | N | 1 |
| 438 | Et | H | H | H | SCF₃ | H | O | N | 2 |
| 439 | Et | H | H | H | S(O)CF₃ | H | O | N | 2 |
| 440 | Et | H | H | H | S(O)₂CF₃ | H | O | N | 2 |
| 441 | Et | H | H | H | SCF₃ | H | O | CH | 0 |
| 442 | Et | H | H | H | SCF₃ | H | O | CH | 1 |
| 443 | Et | H | H | H | SCF₃ | H | O | CH | 2 |
| 444 | Et | H | H | H | S(O)CF₃ | H | O | CH | 2 |
| 445 | Et | H | H | H | S(O)₂CF₃ | H | O | CH | 2 |

TABLE 18-continued

| No. | R¹ | R² | R³ | R⁴ | R⁵ | R⁶ | A¹ | A² | n |
|---|---|---|---|---|---|---|---|---|---|
| 446 | Et | H | CF₃ | H | SCF₃ | H | O | N | 0 |
| 447 | Et | H | CF₃ | H | SCF₃ | H | O | N | 1 |
| 448 | Et | H | CF₃ | H | SCF₃ | H | O | N | 2 |
| 449 | Et | H | CF₃ | H | S(O)CF₃ | H | O | N | 2 |
| 450 | Et | H | CF₃ | H | S(O)₂CF₃ | H | O | N | 2 |

TABLE 19

| No. | R¹ | R² | R³ | R⁴ | R⁵ | R⁶ | A¹ | A² | n |
|---|---|---|---|---|---|---|---|---|---|
| 451 | Et | H | CF₃ | H | SCF₃ | H | O | CH | 0 |
| 452 | Et | H | CF₃ | H | SCF₃ | H | O | CH | 1 |
| 453 | Et | H | CF₃ | H | SCF₃ | H | O | CH | 2 |
| 454 | Et | H | CF₃ | H | S(O)CF₃ | H | O | CH | 2 |
| 455 | Et | H | CF₃ | H | S(O)₂CF₃ | H | O | CH | 2 |
| 456* | Et | H | H | H | S(O)₂CF₃ | H | O | N | 2 |
| 457* | Et | H | CF₃ | H | S(O)₂CF₃ | H | O | N | 2 |
| 458* | Et | H | H | H | S(O)₂CF₃ | H | O | N | 2 |
| 459* | Et | H | H | H | S(O)₂CF₃ | H | O | CH | 2 |
| 460* | Et | H | CF₃ | H | S(O)₂CF₃ | H | O | N | 2 |
| 461* | Et | H | CF₃ | H | S(O)₂CF₃ | H | O | CH | 2 |
| 462 | Et | H | H | H | CF₂CF₃ | H | O | N | 0 |
| 463 | Et | H | H | H | CF₂CF₃ | H | O | N | 1 |
| 464 | Et | H | H | H | CF₂CF₃ | H | O | N | 2 |
| 465 | Et | H | H | H | CF₂CF₃ | H | O | CH | 0 |
| 466 | Et | H | H | H | CF₂CF₃ | H | O | CH | 1 |
| 467 | Et | H | H | H | CF₂CF₃ | H | O | CH | 2 |
| 468 | Et | H | CF₃ | H | CF₂CF₃ | H | O | N | 0 |
| 469 | Et | H | CF₃ | H | CF₂CF₃ | H | O | N | 1 |
| 470 | Et | H | CF₃ | H | CF₂CF₃ | H | O | N | 2 |
| 471 | Et | H | CF₃ | H | CF₂CF₃ | H | O | CH | 0 |
| 472 | Et | H | CF₃ | H | CF₂CF₃ | H | O | CH | 1 |
| 473 | Et | H | CF₃ | H | CF₂CF₃ | H | O | CH | 2 |
| 474 | Et | H | H | H | S(O)CF₃ | H | O | N | 0 |
| 475 | Et | H | H | H | S(O)₂CF₃ | H | O | N | 0 |

TABLE 20

| No. | R¹ | R² | R³ | R⁴ | R⁵ | R⁶ | A¹ | A² | n |
|---|---|---|---|---|---|---|---|---|---|
| 476 | Et | H | H | H | S(O)CF₃ | H | O | CH | 0 |
| 477 | Et | H | H | H | S(O)₂CF₃ | H | O | CH | 0 |
| 478 | Et | H | CF₃ | H | S(O)CF₃ | H | O | N | 0 |
| 479 | Et | H | CF₃ | H | S(O)₂CF₃ | H | O | N | 0 |
| 480 | Et | H | CF₃ | H | S(O)CF₃ | H | O | CH | 0 |
| 481 | Et | H | CF₃ | H | S(O)₂CF₃ | H | O | CH | 0 |

In [Table 1] to [Table 20], the symbol "*" in the leftmost column denotes that the present fused heterocyclic compound is a N-oxide. Specifically, the following compounds are included.

Present Fused Heterocyclic Compound 22

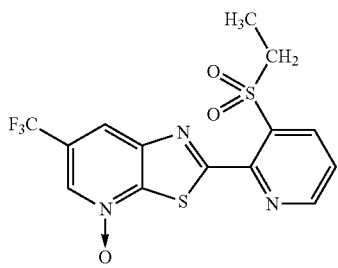 [SMILES: CCS(=O)(=O)c1cccnc1-c1nc2cc(C(F)(F)F)c[n+]([O-])c2s1]

Present Fused Heterocyclic Compound 36

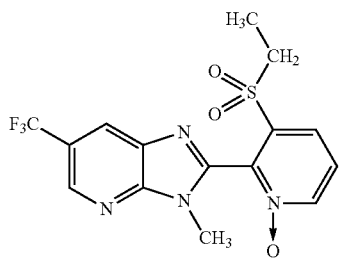 [SMILES: CCS(=O)(=O)c1ccc[n+]([O-])c1-c1nc2cc(C(F)(F)F)cnc2n1C]

Present Fused Heterocyclic Compound 37

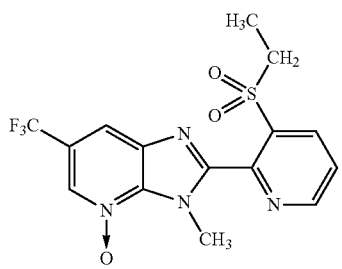 [SMILES: CCS(=O)(=O)c1cccnc1-c1nc2cc(C(F)(F)F)c[n+]([O-])c2n1C]

Present Fused Heterocyclic Compound 47

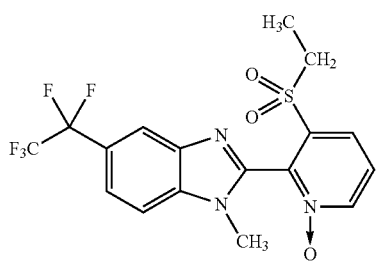 [SMILES: CCS(=O)(=O)c1ccc[n+]([O-])c1-c1nc2cc(C(F)(F)C(F)(F)F)ccc2n1C]

Present Fused Heterocyclic Compound 48

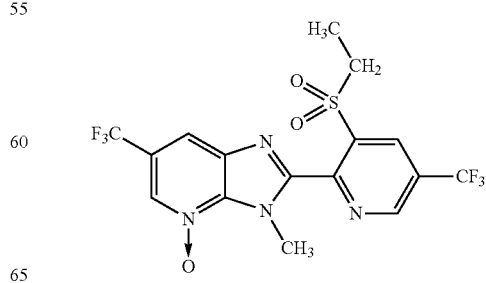

Present Fused Heterocyclic Compound 51
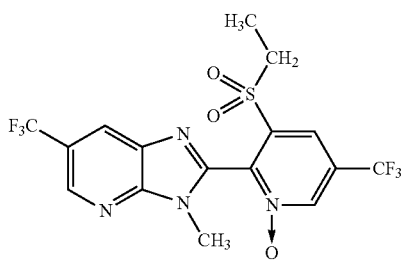 [SMILES: CCS(=O)(=O)c1cc(C(F)(F)F)c[n+]([O-])c1-c1nc2cc(C(F)(F)F)cnc2n1C]
Present Fused Heterocyclic Compound 70
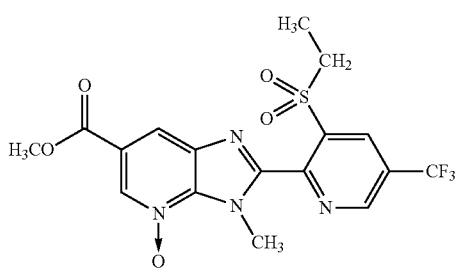 [SMILES: CCS(=O)(=O)c1cc(C(F)(F)F)cnc1-c1nc2cc(C(=O)OC)c[n+]([O-])c2n1C]
Present Fused Heterocyclic Compound 400
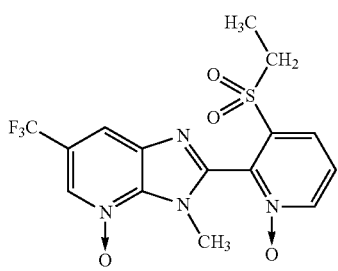 [SMILES: CCS(=O)(=O)c1ccc[n+]([O-])c1-c1nc2cc(C(F)(F)F)c[n+]([O-])c2n1C]
Present Fused Heterocyclic Compound 401
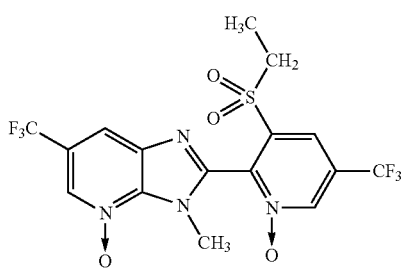 [SMILES: CCS(=O)(=O)c1cc(C(F)(F)F)c[n+]([O-])c1-c1nc2cc(C(F)(F)F)c[n+]([O-])c2n1C]
Present Fused Heterocyclic Compound 409
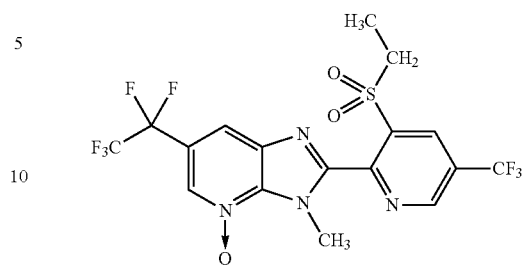
Present Fused Heterocyclic Compound 410
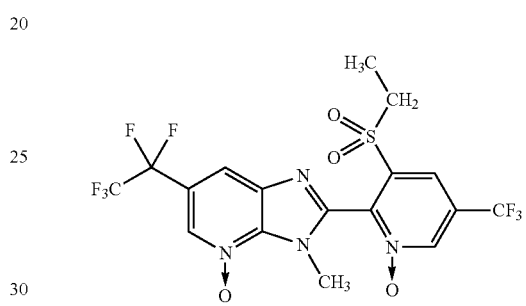
Present Fused Heterocyclic Compound 456
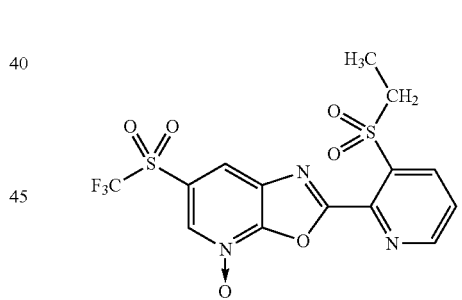
Present Fused Heterocyclic Compound 457
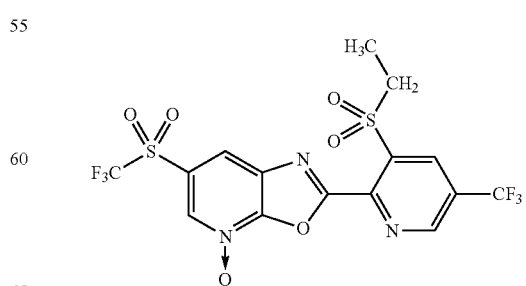

Present Fused Heterocyclic Compound 458

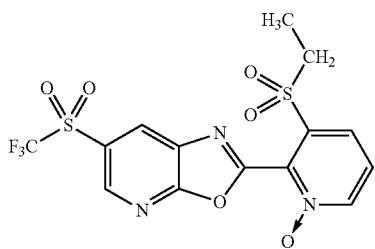 [SMILES: CCS(=O)(=O)c1ccc[n+]([O-])c1-c1nc2cc(S(=O)(=O)C(F)(F)F)cnc2o1]

Present Fused Heterocyclic Compound 459

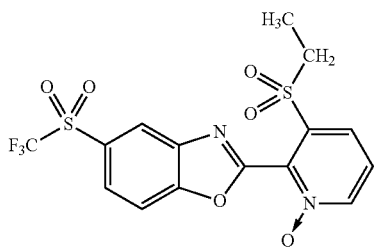 [SMILES: CCS(=O)(=O)c1ccc[n+]([O-])c1-c1nc2cc(S(=O)(=O)C(F)(F)F)ccc2o1]

Present Fused Heterocyclic Compound 460

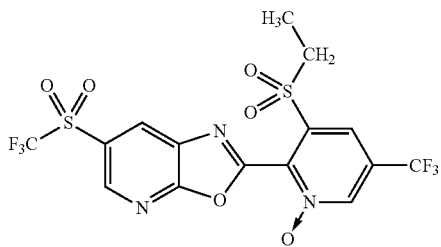 [SMILES: CCS(=O)(=O)c1cc(C(F)(F)F)c[n+]([O-])c1-c1nc2cc(S(=O)(=O)C(F)(F)F)cnc2o1]

Present Fused Heterocyclic Compound 461

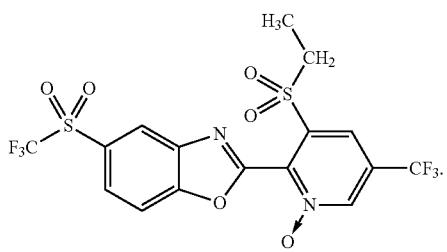 [SMILES: CCS(=O)(=O)c1cc(C(F)(F)F)c[n+]([O-])c1-c1nc2cc(S(=O)(=O)C(F)(F)F)ccc2o1]

In [Table 1] to [Table 20],
Me represents a methyl group;
Et represents an ethyl group;
Pr represents a propyl group;
Bu represents a butyl group;
tBu represents a tertiary butyl group;
iPr represents an isopropyl group;
CycPr represents a cyclopropyl group.
Formulation Examples are shown below.

Formulation Example 1

Twenty (20) parts of one compound selected from the present fused heterocyclic compounds 1 to 481, 35 parts of a mixture (weight ratio 1:1) of white carbon and ammonium polyoxyethylene alkyl ether sulfate are mixed with an appropriate amount of water so as to give a total amount of 100 parts, and then the mixture is finely-ground by a wet grinding method to obtain each formulation.

Formulation Example 2

Forty (40) parts of one compound selected from the present fused heterocyclic compounds 1 to 481, 1.5 parts of sorbitan trioleate, and 28 parts of an aqueous solution containing 2 parts of polyvinyl alcohol are mixed, and then the mixture is finely-ground by a wet grinding method. To this mixture is added an appropriate amount of aqueous solution containing 0.05 parts of xanthane gum and 0.1 parts of magnesium aluminium silicate so as to give a total amount of 90 parts, and then 10 parts of propylene glycol is added thereto. The mixture is stirred to obtain each formulation.

Formulation Example 3

Ten (10) parts of one compound selected from the present fused heterocyclic compounds 1 to 481, 3 parts of calcium lignin sulfonate, 2 parts of sodium lauryl sulfate, and the rest parts of synthetic hydrated silicon oxide are well mixed while grinding to obtain 100 parts of each wettable powder.

Next, treatment examples of the present fused heterocyclic compound to plant seeds are shown below.

Treatment Example 1

Each of the flowable formulation prepared in Formulation example 1 or 2 is used for a smear treatment in an amount of 200 ml per 100 kg of dried sugar cane seeds by using a rotary seed treatment machine (seed dresser, produced by Hans-Ulrich Hege GmbH) to obtain each of seeds of the present invention.

Treatment Example 2

Each of the flowable formulation prepared in Formulation example 1 or 2 is used for a smear treatment in an amount of 10 ml per 10 kg of dried rice seeds by using a rotary seed treatment machine (seed dresser, produced by Hans-Ulrich Hege GmbH) to obtain each of seeds of the present invention.

Treatment Example 3

Each of the flowable formulation prepared in Formulation example 1 or 2 is used for a smear treatment in an amount of 40 ml per 10 kg of dried corn seeds by using a rotary seed treatment machine (seed dresser, produced by Hans-Ulrich Hege GmbH) to obtain each of seeds of the present invention.

Treatment Example 4

Each of the flowable formulation prepared in Formulation example 1 or 2 is used for a smear treatment in an amount of 100 ml per 10 kg of dried corn seeds by using a rotary seed treatment machine (seed dresser, produced by Hans-Ulrich Hege GmbH) to obtain each of seeds of the present invention.

Treatment Example 5

Each of the wettable powder prepared in Formulation example 3 is used for powder coating treatment in an amount of 50 g per 10 kg of dried corn seeds to obtain each of seeds of the present invention.

Treatment Example 6

Each of the flowable formulation prepared in Formulation example 1 or 2 is used for a smear treatment in an amount of 20 ml per 10 kg of dried soybean seeds by using a rotary seed treatment machine (seed dresser, produced by Hans-Ulrich Hege GmbH) to obtain each of seeds of the present invention.

Treatment Example 7

Each of the flowable formulation prepared in Formulation example 1 or 2 is used for a smear treatment in an amount of 100 ml per 10 kg of dried soybean seeds by using a rotary seed treatment machine (seed dresser, produced by Hans-Ulrich Hege GmbH) to obtain each of seeds of the present invention.

Treatment Example 8

Each of the flowable formulation prepared in Formulation example 1 or 2 is used for a smear treatment in an amount of 50 ml per 10 kg of dried cotton seeds by using a rotary seed treatment machine (seed dresser, produced by Hans-Ulrich Hege GmbH) to obtain each of seeds of the present invention.

Treatment Example 9

Each of the flowable formulation prepared in Formulation example 1 or 2 is used for a smear treatment in an amount of 50 ml per 10 kg of dried colza seeds by using a rotary seed treatment machine (seed dresser, produced by Hans-Ulrich Hege GmbH) to obtain each of seeds of the present invention.

Treatment Example 10

Each of the flowable formulation prepared in Formulation example 1 or 2 is used for a smear treatment in an amount of 10 ml per 10 kg of dried colza seeds by using a rotary seed treatment machine (seed dresser, produced by Hans-Ulrich Hege GmbH) to obtain each of seeds of the present invention.

Treatment Example 11

Each of the flowable formulation prepared in Formulation example 1 or 2 is used for a smear treatment in an amount of 100 ml per 10 kg of dried wheat seeds by using a rotary seed treatment machine (seed dresser, produced by Hans-Ulrich Hege GmbH) to obtain each of seeds of the present invention.

Next, the effect of the present invention is shown in Test examples.

Test Example 1

Each of the present fused heterocyclic compounds 3, 4, 5, 9, 15, 16, 17, 18, 19, 20, 22, 25, 72, 74, 85, 130, 399, 409, 414, 419, 443, 444, 445, 464 and 467 was dissolved in acetone (available from Wako Pure Chemical Industries, Ltd.) containing 5% (W/V) SOLGEN TW-20 (available from Daiichi-Kogyo Seiyaku Co. Ltd.) so as to give a prescribed concentration, and to prepare the testing solution.

Nine (9) grains of the Japanese raddish (*Raphanus sativas* var. *longipinnatus*) were placed in a 2 ml volume polypropylene microtube (manufactured by As One Co.) and thereto was added 18 µl of the above testing solution and the seeds in the microtube were shaken and stirred on Stirrer (Trade name: VORTEX-GENIE2, manufactured by Scientific Industries, Inc.). After the testing solution was spread uniformly to the whole seed, the seeds were allowed to air dry.

To a 90 ml volume of plastic cup filled with ten (10) g of culture soil (Trade name: Aisai No. 1; available from Katakura Chikkarin Co., Ltd.) was added water (5 ml) and thereto was seeded three (3) grains of the above seeds.

At four days after the seeding, Diamondback moth (*Plutella xylostella*) at the third instar larval stages were released in a ratio of 10 (ten) heads of insects per the cup, and then the cups were covered with nylon gauze and covered with a lid (hereinafter, referred to as "treated group").

On the other hand, Japanese raddish was seeded by the similar procedures to the treated group except that the present fused heterocyclic compound was not dissolved in acetone (available from Wako Pure Chemical Industries, Ltd.) containing 5% (W/V) SOLGEN TW-20 (available from Daiichi-Kogyo Seiyaku Co. Ltd.), and the larvae were released, and the cups were covered with a lid (hereinafter, referred to as "Untreated group").

At two days after the release, the surviving and death of the larvae were observed and on basis of the results of the observation, the mortalities of both groups were calculated by the following equation 1), respectively. Two replication tests were performed on each group. The average value is shown below.

Mortality (%)=(Total number of Tested insects Number of Surviving insects)/Total number of Tested insects×100    Equation 1)

The results are shown in Tables 21 to 23.

TABLE 21

| Compound | Dose (mg/1 grain of seed) | Mortality (%) |
|---|---|---|
| Present fused heterocyclic compound 3 | 0.01 | 100 |
| Present fused heterocyclic compound 3 | 0.2 | 100 |
| Present fused heterocyclic compound 4 | 0.01 | 100 |
| Present fused heterocyclic compound 4 | 0.2 | 100 |
| Present fused heterocyclic compound 5 | 0.01 | 100 |
| Present fused heterocyclic compound 5 | 0.2 | 100 |
| Present fused heterocyclic compound 9 | 0.01 | 100 |
| Present fused heterocyclic compound 9 | 0.2 | 100 |
| Present fused heterocyclic compound 15 | 0.01 | 100 |
| Present fused heterocyclic compound 15 | 0.2 | 100 |
| Present fused heterocyclic compound 16 | 0.01 | 100 |
| Present fused heterocyclic compound 16 | 0.2 | 100 |
| Present fused heterocyclic compound 17 | 0.01 | 100 |
| Present fused heterocyclic compound 17 | 0.2 | 100 |
| Present fused heterocyclic compound 18 | 0.01 | 100 |
| Present fused heterocyclic compound 18 | 0.2 | 100 |
| Present fused heterocyclic compound 19 | 0.01 | 100 |
| Present fused heterocyclic compound 19 | 0.2 | 100 |
| Present fused heterocyclic compound 20 | 0.01 | 100 |
| Present fused heterocyclic compound 20 | 0.2 | 100 |
| Present fused heterocyclic compound 22 | 0.01 | 100 |
| Present fused heterocyclic compound 22 | 0.2 | 100 |

TABLE 21-continued

| Compound | Dose (mg/1 grain of seed) | Mortality (%) |
| --- | --- | --- |
| Present fused heterocyclic compound 25 | 0.01 | 100 |
| Present fused heterocyclic compound 25 | 0.2 | 100 |
| Untreated group | — | 0 |

TABLE 22

| Compound | Dose (mg/1 grain of seed) | Mortality (%) |
| --- | --- | --- |
| Present fused heterocyclic compound 72 | 0.01 | 100 |
| Present fused heterocyclic compound 72 | 0.2 | 100 |
| Present fused heterocyclic compound 74 | 0.01 | 100 |
| Present fused heterocyclic compound 74 | 0.2 | 100 |
| Present fused heterocyclic compound 85 | 0.01 | 90 |
| Present fused heterocyclic compound 85 | 0.2 | 95 |
| Present fused heterocyclic compound 130 | 0.01 | 100 |
| Present fused heterocyclic compound 130 | 0.2 | 80 |
| Present fused heterocyclic compound 399 | 0.01 | 90 |
| Present fused heterocyclic compound 399 | 0.2 | 95 |
| Present fused heterocyclic compound 409 | 0.01 | 100 |
| Present fused heterocyclic compound 409 | 0.2 | 100 |
| Present fused heterocyclic compound 414 | 0.01 | 95 |
| Present fused heterocyclic compound 414 | 0.2 | 100 |
| Present fused heterocyclic compound 419 | 0.01 | 100 |
| Present fused heterocyclic compound 419 | 0.2 | 100 |
| Present fused heterocyclic compound 443 | 0.01 | 100 |
| Present fused heterocyclic compound 443 | 0.2 | 100 |
| Present fused heterocyclic compound 444 | 0.01 | 100 |
| Present fused heterocyclic compound 444 | 0.2 | 100 |
| Present fused heterocyclic compound 445 | 0.01 | 100 |
| Present fused heterocyclic compound 445 | 0.2 | 100 |
| Present fused heterocyclic compound 464 | 0.01 | 100 |
| Present fused heterocyclic compound 464 | 0.2 | 100 |
| Untreated group | — | 0 |

TABLE 23

| Compound | Dose (mg/1 grain of seed) | Mortality (%) |
| --- | --- | --- |
| Present fused heterocyclic compound 467 | 0.01 | 100 |
| Present fused heterocyclic compound 467 | 0.2 | 100 |
| Untreated group | — | 0 |

Test Example 2

Beet seeds prepared in Treatment Example 1 are seeded. After germination, tabacco cutworm (*Spodoptera litura*) at the second instar larval stages are released and covered with nylon gauze and covered with a lid (hereinafter, referred to as "treated group"). On the other hand, the seeds that are not applied by the present fused heterocyclic compound are seeded by a similar procedure to the treated group, the larvae are released and the cups are covered with a lid (hereinafter, referred to as "Untreated group").

At two days after the release, the surviving and death of the larvae are observed and the mortalities of both groups are calculated by the equation 1), respectively. As a result of the calculation, the mortalities of the treated group are expected to being significantly high compared to those of the untreated group.

Mortality (%)=(Total number of Tested insects−Number of Surviving insects)/Total number of Tested insects×100   Equation 1)

Test Example 3

Rice seeds prepared in Treatment example 2 are seeded. After germination, rice brown planthopper (*Nilaparvata lugens*) at the third instar larval stages are released and covered with nylon gauze and covered with a lid (hereinafter, referred to as "treated group"). On the other hand, the seeds that are not applied by the present fused heterocyclic compound are seeded by a similar procedure to the treated group, the larvae are released and the cups are covered with a lid (hereinafter, referred to as "Untreated group").

At two days after the release, the surviving and death of the larvae are observed and the mortalities of both groups are calculated by the equation 1), respectively. As a result of the calculation, the mortalities of the treated group are expected to being significantly high compared to those of the untreated group.

Mortality (%)=(Total number of Tested insects−Number of Surviving insects)/Total number of Tested insects×100   Equation 1)

Test Example 4

Corn seeds prepared in Treatment Example 3 are seeded. After germination, armyworm (*Mythimna separata*) at the second instar larval stages are released and covered with nylon gauze and covered with a lid (hereinafter, referred to as "treated group"). On the other hand, the seeds that are not applied by the present fused heterocyclic compound are seeded by a similar procedure to the treated group, the larvae are released and the cups are covered with a lid (hereinafter, referred to as "Untreated group").

At two days after the release, the surviving and death of the larvae are observed and the mortalities of both groups are calculated by the equation 1), respectively. As a result of the calculation, the mortalities of the treated group are expected to being significantly high compared to those of the untreated group.

Mortality (%)=(Total number of Tested insects−Number of Surviving insects)/Total number of Tested insects×100   Equation 1)

Test Example 5

Soybean seeds prepared in Treatment Example 6 are seeded. After germination, tabacco cutworm (*Spodoptera litura*) at the second instar larval stages are released and covered with nylon gauze and covered with a lid (hereinafter, referred to as "treated group"). On the other hand, the seeds that are not applied by the present fused heterocyclic compound are seeded by a similar procedure to the treated group, the larvae are released and the cups are covered with a lid (hereinafter, referred to as "Untreated group").

At two days after the release, the surviving and death of the larvae are observed and the mortalities of both groups are calculated by the equation 1), respectively. As a result of the calculation, the mortalities of the treated group are expected to being significantly high compared to those of the untreated group.

Mortality (%)=(Total number of Tested insects−Number of Surviving insects)/Total number of Tested insects×100   Equation 1)

Test Example 6

Cotton seeds prepared in Treatment Example 8 are seeded. After germination, cotton aphid (*Aphis gossypii*) are released and covered with nylon gauze and covered with a lid (hereinafter, referred to as "treated group"). On the other hand, the seeds that are not applied by the present fused heterocyclic compound are seeded by a similar procedure to the treated group, the larvae are released and the cups are covered with a lid (hereinafter, referred to as "Untreated group").

At two days after the release, the surviving and death of the larvae are observed and the mortalities of both groups are calculated by the equation 1), respectively. As a result of the calculation, the mortalities of the treated group are expected to being significantly high compared to those of the untreated group.

Mortality (%)=(Total number of Tested insects−Number of Surviving insects)/Total number of Tested insects×100    Equation 1)

Test Example 7

Colza seeds prepared in Treatment Example 9 are seeded. After germination, Diamondback moth (*Plutella xylostella*) at the third instar larval stages are released and covered with nylon gauze and covered with a lid (hereinafter, referred to as "treated group"). On the other hand, the seeds that are not applied by the present fused heterocyclic compound are seeded by a similar procedure to the treated group, the larvae are released and the cups are covered with a lid (hereinafter, referred to as "Untreated group").

At two days after the release, the surviving and death of the larvae are observed and the mortalities of both groups are calculated by the equation 1), respectively. As a result of the calculation, the mortalities of the treated group are expected to being significantly high compared to those of the untreated group.

Mortality (%)=(Total number of Tested insects−Number of Surviving insects)/Total number of Tested insects×100    Equation 1)

Test Example 8

Wheat seeds prepared in Treatment Example 10 are seeded. After germination, oat bird-cherry aphid (*Rhopalosiphum padi*) are released and covered with nylon gauze and covered with a lid (hereinafter, referred to as "treated group"). On the other hand, the seeds that are not applied by the present fused heterocyclic compound are seeded by a similar procedure to the treated group, the larvae are released and the cups are covered with a lid (hereinafter, referred to as "Untreated group").

At two days after the release, the surviving and death of the larvae are observed and the mortalities of both groups are calculated by the equation 1), respectively. As a result of the calculation, the mortalities of the treated group are expected to being significantly high compared to those of the untreated group.

Mortality (%)=(Total number of Tested insects−Number of Surviving insects)/Total number of Tested insects×100    Equation 1)

INDUSTRIAL APPLICABILITY

A method for controlling pests of the present invention can control pests.

The invention claimed is:

1. A method for controlling pests which comprises applying a compound represented by formula (1) or N-oxide thereof to plant seeds:

the formula (1):

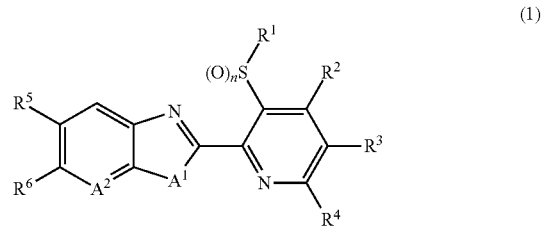

wherein
$A^1$ represents $-NR^7-$, an oxygen atom, or a sulfur atom;
$A^2$ represents a nitrogen atom or $=CR^8-$;
$R^1$ represents a C1-C6 alkyl group which may be substituted with one or more atoms or groups selected from Group X;
$R^2$, $R^3$ and $R^4$ are the same or different to each other and each independently represent a C1-C6 alkyl group which may be substituted with one or more atoms or groups selected from Group X, a $-OR^{10}$ group, a $-C(OR^{10})_3$ group, a $-S(O)_mR^{10}$ group, a $-S(O)_2NR^{10}R^{11}$ group, a $-NR^{10}R^{11}$ group, a $-NR^{10}CO_2R^{11}$ group, a $-NR^{10}C(O)R^{11}$ group, a $-CO_2R^{10}$ group, a $-C(O)R^{10}$ group, a $-C(O)NR^{10}R^{11}$ group, a $-SF_5$ group, a cyano group, a nitro group, a halogen atom, or a hydrogen atom;
$R^5$ and $R^6$ are the same or different to each other and each independently represent a C1-C6 alkyl group which may be substituted with one or more atoms or groups selected from Group X, a $-OR^{10}$ group, a $-S(O)_mR^{10}$ group, a $-S(O)_2NR^{10}R^{11}$ group, a $-NR^{10}R^{11}$ group, a $-NR^{10}CO_2R^{11}$ group, a $-NR^{10}C(O)R^{11}$ group, a $-CO_2R^{10}$ group, a $-C(O)R^{10}$ group, a $-C(O)NR^{10}R^{11}$ group, $-OC(O)R^{10}$, a $-SF_5$ group, a $-SH$ group, a cyano group, a nitro group, a halogen atom, or a hydrogen atom, except for a case in which $R^5$ and $R^6$ are both hydrogen atoms;
$R^7$ represents a C1-C6 alkyl group which may be substituted with one or more atoms or groups selected from Group W, a $-CO_2R^{10}$ group, a $-C(O)R^{10}$ group, a $-CH_2CO_2R^{10}$ group, a C3-C6 cycloalkyl group, or a hydrogen atom;
$R^8$ represents a C1-C6 alkyl group which may be substituted with one or more halogen atoms, a $-OR^{10}$ group, a $-S(O)_mR^{10}$ group, a $-NR^{10}R^{11}$ group, a $-CO_2R^{10}$ group, a $-C(O)R^{10}$ group, a cyano group, a nitro group, a halogen atom, or a hydrogen atom;
$R^{10}$ and $R^{11}$ are the same or different to each other and each independently represent a C1-C6 alkyl group which may be substituted with one or more atoms or groups selected from Group X or a hydrogen atom, except for a $-S(O)_mR^{10}$ group wherein m is 1 or 2 and $R^{10}$ is a hydrogen atom;
m independently represents 0, 1 or 2; and
n represents 0, 1 or 2;

Group X comprising:
a C1-C6 alkoxy group which may be substituted with one or more halogen atoms,
a C3-C6 cycloalkyl group which may be substituted with one or more halogen atoms or one or more C1-C3 alkyl groups,
a cyano group,
a hydroxy group, and
a halogen atom;
Group W comprising:
a C1-C6 alkoxy group which may be substituted with one or more halogen atoms,
a C3-C6 cycloalkyl group which may be substituted with one or more halogen atoms,
a hydroxy group,
a halogen atom, and
a cyano group.

2. The method for controlling pests according to claim 1, in the compound represented by the formula (1) or N-oxide thereof,
$R^1$ is a C1-C6 alkyl group which may be substituted with one or more atoms or groups selected from Group Y;
$R^2$ and $R^4$ are hydrogen atoms;
$R^3$ is a C1-C3 alkyl group which may be substituted with one or more halogen atoms, a —C(OR$^{10}$)$_3$ group, a halogen atom, or a hydrogen atom;
$R^5$ is a C1-C3 alkyl group which may be substituted with one or more halogen atoms, a —OR$^{10}$ group, a —S(O)$_m$ R$^{10}$ group, a —CO$_2$R$^{10}$ group, a —SF$_5$ group, or a halogen atom;
$R^6$ is a —OR$^{10}$ group, a —NR$^{10}$R$^{11}$ group, a —CO$_2$R$^{10}$ group, a —C(O)NR$^{10}$R$^{11}$ group, —OC(O)R$^{10}$, a cyano group, a halogen atom, or a hydrogen atom;
$R^7$ is a C1-C6 alkyl group which may be substituted with one or more halogen atoms, a —CH$_2$CO$_2$R$^{10}$ group, a C3-C6 cycloalkyl group, or a hydrogen atom,
$R^8$ is a C1-C3 alkyl group which may be substituted with one or more halogen atoms, a —OR$^{10}$ group, a —S(O)$_m$ R$^{10}$ group, a cyano group, a halogen atom, or a hydrogen atom;
$R^{10}$ and $R^{11}$ are the same or different to each other and each independently represent a C1-C3 alkyl group which may be substituted with one or more halogen atoms or a hydrogen atom, except for a —S(O)$_m$R$^{10}$ group wherein m is 1 or 2 and R$^{10}$ is a hydrogen atom; and
Group Y comprising:
a C3-C6 cycloalkyl group which may be substituted with one or more halogen atoms and a halogen atom.

3. The method for controlling pests according to claim 1, wherein in the compound represented by the formula (1) or N-oxide thereof,
$R^1$ is a C1-C3 alkyl group which may be substituted with one or more halogen atoms;
$R^2$ and $R^4$ are hydrogen atoms;
$R^3$ is a C1-C3 alkyl group which may be substituted with one or more halogen atoms, a —C(OR$^{10}$)$_3$ group, a halogen atom, or a hydrogen atom;
$R^5$ is a C1-C3 alkyl group which may be substituted with one or more halogen atoms, a —OR$^{10}$ group, a —S(O)$_m$ R$^{10}$ group, or a halogen atom;
$R^6$ is a cyano group, a —NR$^{10}$R$^{11}$ group, a halogen atom, or a hydrogen atom;
$R^7$ is a C1-C6 alkyl group which may be substituted with one or more halogen atoms;
$R^8$ is a —S(O)$_m$R$^{10}$ group, a cyano group, a halogen atom, or a hydrogen atom; and $R^{10}$ and $R^{11}$ are the same or different to each other and each independently represent a C1-C3 alkyl group which may be substituted with one or more halogen atoms.

4. The method for controlling pests according to claim 1, wherein in the compound represented by the formula (1) or N-oxide thereof:
$R^1$ is an ethyl group;
$R^2$ and $R^4$ are hydrogen atoms;
$R^3$ is a C1-C3 alkyl group which may be substituted with one or more halogen atoms, a —C(OR$^{10}$)$_3$ group, a halogen atom, or a hydrogen atom;
$R^5$ is a C1-C3 haloalkyl group, a —OR$^{20}$ group, a —S(O)$_m$ R$^{20}$ group, or a halogen atom;
$R^6$ is a cyano group, a —NR$^{10}$R$^{11}$ group, a halogen atom, or a hydrogen atom;
$R^7$ is a C1-C6 alkyl group which may be substituted with one or more halogen atoms;
$R^8$ is a —S(O)$_m$R$^{10}$ group, a cyano group, a halogen atom, or a hydrogen atom;
$R^{10}$ and $R^{11}$ are the same or different to each other and each independently represent a C1-C3 alkyl group which may be substituted with one or more halogen atoms; and
$R^{20}$ is a C1-C3 haloalkyl group.

5. The method for controlling pests according to claim 1, wherein in the compound represented by the formula (1) or N-oxide thereof,
$A^1$ is —NR$^7$—.

6. The method for controlling pests according to claim 1, wherein in the compound represented by the formula (1) or N-oxide thereof,
$A^1$ is an oxygen atom.

7. The method for controlling pests according to claim 1, wherein in the compound represented by the formula (1) or N-oxide thereof,
$A^1$ is a sulfur atom.

8. The method for controlling pests according to claim 1, wherein the compound represented by the formula (1) or N-oxide thereof is a compound represented by the formula (1-2) or N-oxide thereof;
the formula (1-2):

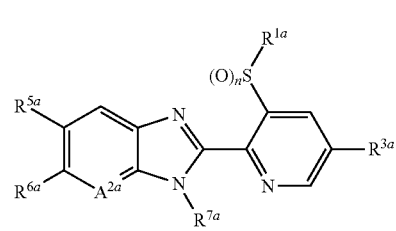

(1-2)

wherein
$R^{1a}$ represents a C1-C3 alkyl group;
$A^{2a}$ represents a nitrogen atom or $=CR^{8a}$—;
$R^{3a}$ represents a C1-C3 alkyl group which may be substituted with one or more halogen atoms, a —C(OR$^{10a}$)$_3$ group, a halogen atom, or a hydrogen atom;
$R^{5a}$ represents a C1-C3 haloalkyl group, a —OR$^{20a}$ group, a —S(O)$_m$R$^{20a}$ group, or a halogen atom;
$R^{6a}$ represents a cyano group, a —NR$^{10a}$R$^{11a}$ group, a halogen atom, or a hydrogen atom;
$R^{7\ a}$ represents a C1-C6 alkyl group which may be substituted with one or more halogen atoms;

$R^{8a}$ represents a —S(O)$_m$R$^{10a}$ group, a cyano group, a halogen atom, or a hydrogen atom;

$R^{10\ a}$ and $R^{11\ a}$ are the same or different to each other and each independently represent a C1-C3 alkyl group which may be substituted with one or more halogen atoms;

$R^{20a}$ represents a C1-C3 haloalkyl group;

m independently represents 0, 1 or 2; and n represents 0, 1 or 2.

9. The method for controlling pests according to claim 1, wherein the compound represented by the formula (1) or N-oxide thereof is a compound represented by the formula (1-3) or N-oxide thereof;

the formula (1-3):

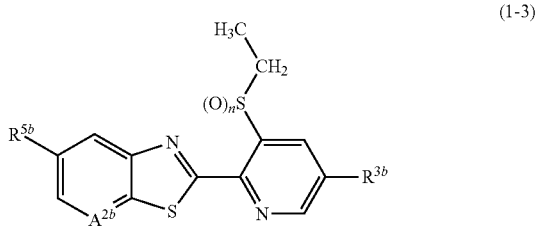

(1-3)

wherein $A^{2b}$ represents a nitrogen atom or =CR$^{8b}$—;

$R^{3b}$ represents a C1-C3 alkyl group which may be substituted with one or more halogen atoms, a —C(OR$^{10b}$)$_3$ group, a halogen atom, or a hydrogen atom;

$R^{5b}$ represents a C1-C3 haloalkyl group, a —OR$^{20b}$ group, a —S(O)$_m$R$^{20b}$ group, or a halogen atom;

$R^{8b}$ represents a —S(O)$_m$R$^{11b}$ group, a cyano group, a halogen atom, or a hydrogen atom;

$R^{10\ b}$ independently represents a C1-C3 alkyl group which may be substituted with one or more halogen atoms;

$R^{20b}$ represents a C1-C3 haloalkyl group;

m independently represents 0, 1 or 2; and n represents 0, 1 or 2.

10. The method for controlling pests according to claim 1, wherein in the compound represented by the formula (1-3) or N-oxide thereof, $R^{3b}$ is a halogen atom or a hydrogen atom;

$R^{5b}$ is a C1-C3 perfluoroalkyl group, a —OR$^{30b}$ group, or a —S(O)$_m$R$^{30b}$ group;

$R^{30b}$ is a C1-C3 perfluoroalkyl group; and $R^{8b}$ is a halogen atom or a hydrogen atom.

11. The method for controlling pests according to claim 1, wherein the compound represented by the formula (1) or N-oxide thereof is a compound represented by the formula (1-4) or N-oxide thereof;

the formula (1-4):

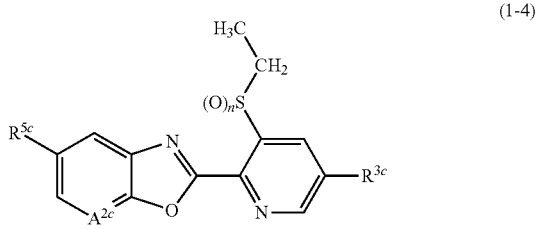

(1-4)

wherein $A^{2c}$ represents a nitrogen atom or =CR$^{8c}$—;

$R^{3c}$ represents a C1-C3 alkyl group which may be substituted with one or more halogen atoms, a —C(OR$^{10c}$)$_3$ group, a halogen atom, or a hydrogen atom;

$R^{5c}$ represents a C1-C3 haloalkyl group, a —OR$^{20c}$ group, a —S(O)$_m$R$^{20c}$ group, or a halogen atom;

$R^{8c}$ represents a —S(O)$_m$R$^{10c}$ group, a cyano group, a halogen atom, or a hydrogen atom;

$R^{10\ c}$ independently represents a C1-C3 alkyl group which may be substituted with one or more halogen atoms;

$R^{20c}$ represents a C1-C3 haloalkyl group;

m independently represents 0, 1 or 2; and n represents 0, 1 or 2.

12. The method for controlling pests according to claim 11, wherein in the compound represented by the formula (1-4) or N-oxide thereof, $R^{3c}$ is a halogen atom or a hydrogen atom;

$R^{5c}$ is a C1-C3 perfluoroalkyl group, a —OR$^{30c}$ group, or a —S(O)$_m$R$^{30c}$ group, $R^{30c}$ is a C1-C3 perfluoroalkyl group, and $R^{8c}$ is a halogen atom or a hydrogen atom.

13. The method for controlling pests according to claim 1 wherein the compound represented by formula (1) or N-oxide thereof is applied in an amount of 0.01 to 1.000 g per 10 kg seeds.

14. The method for controlling pests according to claim 1, wherein the plant seeds is a seed of corn, cotton, soybean, beet, colza, Japanese radish or rice.

15. A plant seed containing an effective amount of a compound represented by formula (1) or N-oxide thereof: the formula (1):

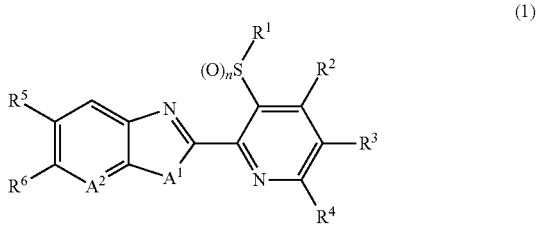

(1)

wherein $A^1$ represents —NR$^7$—, an oxygen atom, or a sulfur atom;

$A^2$ represents a nitrogen atom or =CR$^8$—;

$R^1$ represents a C1-C6 alkyl group which may be substituted with one or more atoms or groups selected from Group X;

$R^2$, $R^3$ and $R^4$ are the same or different to each other and each independently represent a C1-C6 alkyl group which may be substituted with one or more atoms or groups selected from Group X, a —OR$^{10}$ group, a —C(OR$^{10}$)$_3$ group, a —S(O)$_m$R$^{10}$ group, a —S(O)$_2$NR$^{10}$R$^{11}$ group, a —NR$^{10}$R$^{11}$ group, a —NR$^{10}$CO$_2$R$^{11}$ group, a —NR$^{10}$C(O)R$^{11}$ group, a —CO$_2$R$^{10}$ group, a —C(O)R$^{10}$ group, a —C(O)NR$^{10}$R$^{11}$ group, a —SF$_5$ group, a cyano group, a nitro group, a halogen atom, or a hydrogen atom;

$R^5$ and $R^6$ are the same or different to each other and each independently represent a C1-C6 alkyl group which may be substituted with one or more atoms or groups selected from Group X, a —OR$^{10}$ group, a —S(O)$_m$R$^{10}$ group, a —S(O)$_2$NR$^{10}$R$^{11}$ group, a —NR$^{10}$R$^{11}$ group, a —NR$^{10}$CO$_2$R$^{11}$ group, a —NR$^{10}$C(O)R$^{11}$ group, a —CO$_2$R$^{10}$ group, a —C(O)R$^{10}$ group, a —C(O)NR$^{10}$R$^{11}$ group, —OC(O)R$^{10}$, a —SF$_5$ group, a —SH group, a cyano group, a nitro group, a halogen atom, or a hydrogen atom, except for a case in which R$^5$ and R$^6$ are both hydrogen atoms;

R$^7$ represents a C1-C6 alkyl group which may be substituted with one or more atoms or groups selected from Group W, a —CO$_2$R$^0$ group, a —C(O)R$^{10}$ group, a —CH$_2$CO$_2$R$^{10}$ group, a C3-C6 cycloalkyl group, or a hydrogen atom;

R$^8$ represents a C1-C6 alkyl group which may be substituted with one or more halogen atoms, a —OR$^{10}$ group, a —S(O)$_m$R$^{10}$ group, a —NR$^{10}$R$^{11}$ group, a —CO$_2$R$^{10}$ group, a —C(O)R$^{10}$ group, a cyano group, a nitro group, a halogen atom, or a hydrogen atom;

R$^{10}$ and R$^{11}$ are the same or different to each other and each independently represent a C1-C6 alkyl group which may be substituted with one or more atoms or groups selected from Group X or a hydrogen atom, except for a —S(O)$_m$R$^{10}$ group wherein m is 1 or 2 and R$^{10}$ is a hydrogen atom;

m independently represents 0, 1 or 2; and n represents 0, 1 or 2.

Group X comprising:
a C1-C6 alkoxy group which may be substituted with one or more halogen atoms,
a C3-C6 cycloalkyl group which may be substituted with one or more halogen atoms or one or more C1-C3 alkyl groups,
a cyano group,
a hydroxy group, and
a halogen atom;

Group W comprising:
a C1-C6 alkoxy group which may be substituted with one or more halogen atoms,
a C3-C6 cycloalkyl group which may be substituted with one or more halogen atoms,
a hydroxy group,
a halogen atom, and
a cyano group.

16. The plant seed according to claim 15, in the compound represented by the formula (1) or N-oxide thereof,
R$^1$ is a C1-C6 alkyl group which may be substituted with one or more atoms or groups selected from Group Y;
R$^2$ and R$^4$ are hydrogen atoms;
R$^3$ is a C1-C3 alkyl group which may be substituted with one or more halogen atoms, a —C(OR$^{10}$)$_3$ group, a halogen atom, or a hydrogen atom;
R$^5$ is a C1-C3 alkyl group which may be substituted with one or more halogen atoms, a —OR$^{10}$ group, a —S(O)$_m$ R$^{10}$ group, a —CO$_2$R$^{10}$ group, a —SF$_5$ group, or a halogen atom;
R$^6$ is a —OR$^{10}$ group, a —NR$^{10}$R$^{11}$ group, a —CO$_2$R$^{10}$ group, a —C(O)NR$^{10}$R$^{11}$ group, —OC(O)R$^{10}$, a cyano group, a halogen atom, or a hydrogen atom;
R$^7$ is a C1-C6 alkyl group which may be substituted with one or more halogen atoms, a —CH$_2$CO$_2$R$^{10}$ group, a C3-C6 cycloalkyl group, or a hydrogen atom,
R$^8$ is a C1-C3 alkyl group which may be substituted with one or more halogen atoms, a —OR$^{10}$ group, a —S(O)$_m$ R$^{10}$ group, a cyano group, a halogen atom, or a hydrogen atom;

R$^{10}$ and R$^{11}$ are the same or different to each other and each independently represent a C1-C3 alkyl group which may be substituted with one or more halogen atoms or a hydrogen atom, except for a —S(O)$_m$R$^{10}$ group wherein m is 1 or 2 and R$^{10}$ is a hydrogen atom; and Group Y comprising:
a C3-C6 cycloalkyl group which may be substituted with one or more halogen atoms and a halogen atom.

17. The plant seed according to claim 15, wherein in the compound represented by the formula (1) or N-oxide thereof,
R$^1$ is a C1-C3 alkyl group which may be substituted with one or more halogen atoms;
R$^2$ and R$^4$ are hydrogen atoms;
R$^3$ is a C1-C3 alkyl group which may be substituted with one or more halogen atoms, a —C(OR$^{10}$)$_3$ group, a halogen atom, or a hydrogen atom;
R$^5$ is a C1-C3 alkyl group which may be substituted with one or more halogen atoms, a —OR$^{10}$ group, a —S(O)$_m$ R$^{10}$ group, or a halogen atom;
R$^6$ is a cyano group, a —NR$^{10}$R$^{11}$ group, a halogen atom, or a hydrogen atom;
R$^7$ is a C1-C6 alkyl group which may be substituted with one or more halogen atoms;
R$^8$ is a —S(O)$_m$R$^{10}$ group, a cyano group, a halogen atom, or a hydrogen atom; and
R$^{10}$ and R$^{11}$ are the same or different to each other and each independently represent a C1-C3 alkyl group which may be substituted with one or more halogen atoms.

18. The plant seed according to claim 15, wherein in the compound represented by the formula (1) or N-oxide thereof:
R$^1$ is an ethyl group;
R$^2$ and R$^4$ are hydrogen atoms;
R$^3$ is a C1-C3 alkyl group which may be substituted with one or more halogen atoms, a —C(OR$^{10}$)$_3$ group, a halogen atom, or a hydrogen atom;
R$^5$ is a C1-C3 haloalkyl group, a —OR$^{20}$ group, a —S(O)$_m$ R$^{20}$ group, or a halogen atom;
R$^6$ is a cyano group, a —NR$^{10}$R$^{11}$ group, a halogen atom, or a hydrogen atom;
R$^7$ is a C1-C6 alkyl group which may be substituted with one or more halogen atoms;
R$^8$ is a —S(O)$_m$R$^{10}$ group, a cyano group, a halogen atom, or a hydrogen atom;
R$^{10}$ and R$^{11}$ are the same or different to each other and each independently represent a C1-C3 alkyl group which may be substituted with one or more halogen atoms; and
R$^{20}$ is a C1-C3 haloalkyl group.

19. The plant seed according to claim 15, wherein in the compound represented by the formula (1) or N-oxide thereof,
A$^1$ is —NR$^7$—.

20. The plant seed according to claim 15, wherein in the compound represented by the formula (1) or N-oxide thereof,
A$^1$ is an oxygen atom.

21. The plant seeds according to claim 15, wherein in the compound represented by the formula (1) or N-oxide thereof,
A$^1$ is a sulfur atom.

22. The plant seeds according to claim 15, wherein the compound represented by the formula (1) or N-oxide thereof is a compound represented by the formula (1-2) or N-oxide thereof;

the formula (1-2):

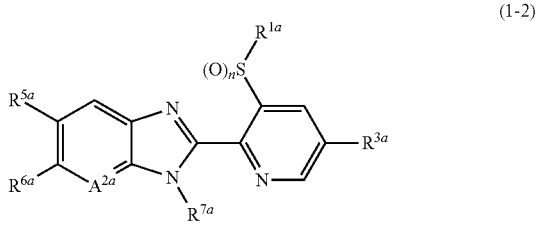

(1-2)

wherein
$R^{1a}$ represents a C1-C3 alkyl group;
$A^{2a}$ represents a nitrogen atom or =CR$^{8a}$—;
$R^{3a}$ represents a C1-C3 alkyl group which may be substituted with one or more halogen atoms, a —C(OR$^{10a}$)$_3$ group, a halogen atom, or a hydrogen atom;
$R^{5a}$ represents a C1-C3 haloalkyl group, a —OR$^{20a}$ group, a —S(O)$_m$R$^{20a}$ group, or a halogen atom;
$R^{6a}$ represents a cyano group, a —NR$^{10a}$R$^{11a}$ group, a halogen atom, or a hydrogen atom;
$R^{7a}$ represents a C1-C6 alkyl group which may be substituted with one or more halogen atoms;
$R^{8a}$ represents a —S(O)$_m$R$^{10a}$ group, a cyano group, a halogen atom, or a hydrogen atom;
$R^{10a}$ and $R^{11a}$ are the same or different to each other and each independently represent a C1-C3 alkyl group which may be substituted with one or more halogen atoms;
$R^{20a}$ represents a C1-C3 haloalkyl group;
m independently represents 0, 1 or 2; and
n represents 0, 1 or 2.

23. The plant seed according to claim 15, wherein the compound represented by the formula (1) or N-oxide thereof is a compound represented by the formula (1-3) or N-oxide thereof;

the formula (1-3):

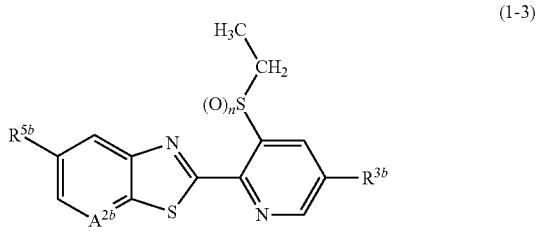

(1-3)

wherein
$A^{2b}$ represents a nitrogen atom or =CR$^{8b}$—;
$R^{3b}$ represents a C1-C3 alkyl group which may be substituted with one or more halogen atoms, a —C(OR$^{10b}$)$_3$ group, a halogen atom, or a hydrogen atom;
$R^{5b}$ represents a C1-C3 haloalkyl group, a —OR$^{20b}$ group, a —S(O)$_m$R$^{20b}$ group, or a halogen atom;
$R^{8b}$ represents a —S(O)$_m$R$^{10b}$ group, a cyano group, a halogen atom, or a hydrogen atom;
$R^{10b}$ independently represents a C1-C3 alkyl group which may be substituted with one or more halogen atoms;
$R^{20b}$ represents a C1-C3 haloalkyl group;
m independently represents 0, 1 or 2; and
n represents 0, 1 or 2.

24. The plant seed according to claim 23, wherein in the compound represented by the formula (1-3) or N-oxide thereof,
$R^{3b}$ is a halogen atom or a hydrogen atom;
$R^{5b}$ is a C1-C3 perfluoroalkyl group, a —OR$^{30b}$ group, or a —S(O)$_m$R$^{30b}$ group;
$R^{30b}$ is a C1-C3 perfluoroalkyl group; and
$R^{8b}$ is a halogen atom or a hydrogen atom.

25. The plant seed according to claim 23, wherein the compound represented by the formula (1) or N-oxide thereof is a compound represented by the formula (1-4) or N-oxide thereof;

the formula (1-4):

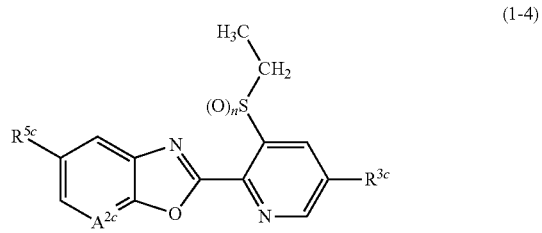

(1-4)

wherein
$A^{2c}$ represents a nitrogen atom or =CR$^{8c}$—;
$R^{3c}$ represents a C1-C3 alkyl group which may be substituted with one or more halogen atoms, a —C(OR$^{10c}$)$_3$ group, a halogen atom, or a hydrogen atom;
$R^{5c}$ represents a C1-C3 haloalkyl group, a —OR$^{20c}$ group, a —S(O)$_m$R$^{20c}$ group, or a halogen atom;
$R^{8c}$ represents a —S(O)$_m$R$^{10c}$ group, a cyano group, a halogen atom, or a hydrogen atom;
$R^{10c}$ independently represents a C1-C3 alkyl group which may be substituted with one or more halogen atoms;
$R^{20c}$ represents a C1-C3 haloalkyl group;
m independently represents 0, 1 or 2; and
n represents 0, 1 or 2.

26. The plant seed according to claim 23, wherein in the compound represented by the formula (1-4) or N-oxide thereof,
$R^{3c}$ is a halogen atom or a hydrogen atom;
$R^{5c}$ is a C1-C3 perfluoroalkyl group, a —OR$^{30c}$ group, or a —S(O)$_m$R$^{30c}$ group,
$R^{30c}$ is a C1-C3 perfluoroalkyl group, and
$R^{8c}$ is a halogen atom or a hydrogen atom.

27. The method for controlling pests according to claim 15, wherein the plant seeds is a seed of corn, cotton, soybean, beet, colza, Japanese radish or rice.

* * * * *